United States Patent
Biggers et al.

(10) Patent No.: US 7,291,619 B2
(45) Date of Patent: *Nov. 6, 2007

(54) MELANOCORTIN RECEPTOR AGONISTS

(75) Inventors: Christopher Kelly Biggers, Clayton, NC (US); Karin Briner, Indianapolis, IN (US); Christopher William Doecke, Indianapolis, IN (US); Matthew Joseph Fisher, Mooresville, IN (US); Larry Wayne Hertel, Indianapolis, IN (US); Vincent Mancuso, Thy-Le Chateau (BE); Michael John Martinelli, Zionsville, IN (US); John Philip Mayer, Indianapolis, IN (US); Paul Leslie Ornstein, Carmel, IN (US); Timothy Ivo Richardson, Indianapolis, IN (US); Jikesh Arvind Shah, Greenwood, IN (US); Qing Shi, Carmel, IN (US); Zhipei Wu, Noblesville, IN (US); Chaoyu Xie, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 258 days.

This patent is subject to a terminal disclaimer.

(21) Appl. No.: 10/466,121

(22) PCT Filed: Jan. 23, 2002

(86) PCT No.: PCT/US02/00517

§ 371 (c)(1),
(2), (4) Date: Jul. 11, 2003

(87) PCT Pub. No.: WO02/059108

PCT Pub. Date: Aug. 1, 2002

(65) Prior Publication Data

US 2004/0092507 A1    May 13, 2004

(51) Int. Cl.
*A61K 31/496* (2006.01)
*C07D 217/26* (2006.01)
*C07D 209/44* (2006.01)

(52) U.S. Cl. .............. 514/253.05; 514/253.09; 544/363; 544/373

(58) Field of Classification Search ............... 544/363, 544/373; 514/233.5, 253.05, 254.09
See application file for complete search history.

(56) References Cited

U.S. PATENT DOCUMENTS

| | | | |
|---|---|---|---|
| 6,294,534 B1 | 9/2001 | Nargund et al. | 514/233.5 |
| 7,115,607 B2 * | 10/2006 | Fotsch et al. | 514/252.13 |
| 7,186,715 B2 * | 3/2007 | Briner et al. | 514/233.5 |
| 2003/0220324 A1 * | 11/2003 | Fotsch et al. | 514/218 |

FOREIGN PATENT DOCUMENTS

| | | |
|---|---|---|
| WO | WO 94 13696 A | 6/1994 |
| WO | WO 99 55679 A | 11/1999 |
| WO | WO 99 64002 A | 12/1999 |
| WO | WO 00 74679 A | 12/2000 |
| WO | WO 01 70337 A | 9/2001 |
| WO | WO 01 70708 A | 9/2001 |
| WO | WO 02 15909 A | 2/2002 |
| WO | WO 02 059095 | 8/2002 |
| WO | WO 02 059107 | 8/2002 |
| WO | WO 02 059117 | 8/2002 |
| WO | WO 02 070511 | 9/2002 |

OTHER PUBLICATIONS

Sebhat et al. Annual Reports in medicinal Chemistry, vol. 38,p. 31-40 (2003).*
Campfield et al. Science, vol. 280, p. 1383-1387 (1998).*

* cited by examiner

*Primary Examiner*—Emily Bernhardt
(74) *Attorney, Agent, or Firm*—Soonhee Jang; James B. Myers

(57) ABSTRACT

The present invention relates to melanocortin receptor agonists of formula (I), which is useful in the treatment of obesity, diabetes and male and/or female sexual dysfunction (I)

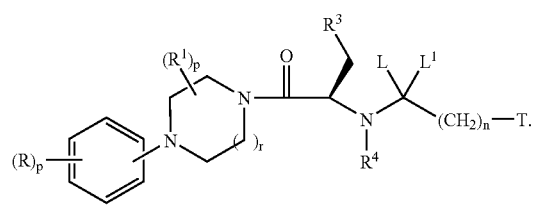

23 Claims, No Drawings

MELANOCORTIN RECEPTOR AGONISTS

FIELD OF THE INVENTION

The present invention relates to melanocortin receptor agonists, and more particularly piperazine derivatives as melanocortin receptor agonists, which are useful for the treatment or prevention of diseases and disorders responsive to the activation of melanocortin receptors.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are targets of POMC derived peptides involved in the control of food intake and metabolism.

Evidence for the involvement of MC-R in obesity includes: i) the agouti ($A^{vy}$) mouse which ectopically expresses an antagonist of the MC-1R, MC-3R and MC-4R is obese, indicating that blocking the action of these three MC-Rs can lead to hyperphagia and metabolic disorders; ii) MC-4R knockout mice (Huszar et al., Cell, 88:131-141, 1997) recapitulate the phenotype of the agouti mouse and these mice are obese; iii) the cyclic heptapeptide MC-1R, MC-3R, MC-4R, and MC-5R agonist melanotanin-II (MT-II) injected intracerebroventricularly (ICV) in rodents, reduces food intake in several animal feeding models (NPY, ob/ob, agouti, fasted) while ICV injected SHU-9119 (MC-3R, MC-4R antagonist; MC-1R and MC-5R agonist) reverses this effect and can induce hyperphagia; and iv) chronic intraperitoneal treatment of Zucker fatty rats with an α-NDP-MASH derivative (HP228) has been reported to activate MC-1R, MC-3R, MC-4R and MC-5R and to attenuate food intake and body weight gain over a 12 week period.

Five MC-Rs have thus far been identified, and these are expressed in different tissues. MC-1R was initially characterized by dominant gain of function mutations at the extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut and placenta and may be involved in the control of food intake and thermogenesis. MC-4R is uniquely expressed in the brain and its inactivation was shown to cause obesity. (A. Kask, et al., "Selective antagonist for the melanocortin-4-receptor (HS014) increases food intake in free-feeding rats, Biochem. Biophys. Res. Commun., 245:90-93, 1998). MC-5R is expressed in many tissues including white fat, placenta and exocrine glands. A low level of expression is also observed in the brain. MC-5R knock out mice reveal reduced sebaceous gland lipid production (Chen et al., Cell, 91:789-798, 1997).

MC-4R appears to play a role in other physiological functions as well, namely controlling grooming behavior, erection and blood pressure. Erectile dysfunction denotes the medical condition of inability to achieve penile erection sufficient for successful intercourse. The term "impotence" is often times employed to describe this prevalent condition. Synthetic melanocortin receptor agonists have been found to initiate erections in men with psychogenic erectile dysfunction (H. Wessells et al., "Synthetic Melanotropic Petide Initiates Erections in Men With Psychogenic Erectile Dysfunction: Double-Blind, Placebo Controlled Crossover Study," J. Urol., 160: 389-393, 1998). Activation of melanocortin receptors of the brain appears to cause normal stimulation of sexual arousal. Evidence for the involvement of MC-R in male and/or female sexual dysfunction is detailed in WO 00/74679.

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes, which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL which are risk factors in cardiovascular diseases. The constellation of symptoms which include hyperinsulemia combined with hypertension, elevated body weight, elevated triglycerides and elevated LDL is known as Syndrome X.

Spiropiperidine and piperidine derivates have been disclosed in U.S. Pat. No. 6,294,534 B1, WO 01/70337, WO 00/74679 and WO 01/70708 as agonists of melanocortin receptor(s), which can be used for the treatment of diseases and disorders, such as obesity, diabetes and sexual dysfunction.

In view of the unresolved deficiencies in treatment of various diseases and disorders as discussed above, it is an object of the present invention to provide novel piperazine derivatives, which are useful as melanocortin receptor agonists to treat obesity, diabetes, and male and female sexual dysfunction.

BRIEF SUMMARY OF THE INVENTION

The present invention relates to a compound of novel piperazine derivatives as melanocortin receptor agonists as shown formula I:

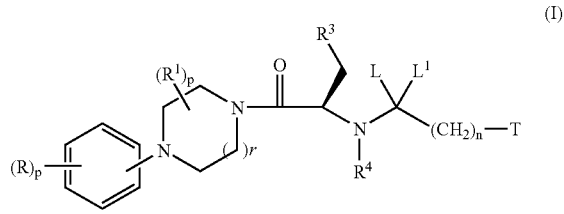

or a pharmaceutically acceptable salts or stereoisomers thereof, wherein

L and $L^1$ are independently: hydrogen or together oxo;

T is:

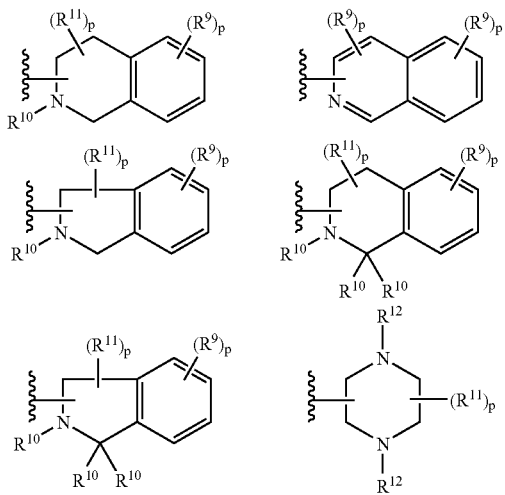

R is independently:
hydrogen,
hydroxy,
cyano,
nitro,
halo,
$C_1$-$C_8$ alkyl,
$C_1$-$C_8$ alkoxy,
$C_1$-$C_4$ haloalkyl,
(D)C(O)$R^9$,
(D)C(O)O$R^9$,
(D)C(O)S$R^9$,
(D)C(O)heteroaryl,
(D)C(O)heterocyclyl,
(D)C(O)N($R^9$)$_2$,
(D)N($R^9$)$_2$,
(D)N$R^9$CO$R^9$,
(D)N$R^9$CON($R^9$)$_2$,
(D)N$R^9$C(O)O$R^9$,
(D)N$R^9$C($R^9$)=N($R^9$),
(D)N$R^9$C(=N$R^9$)N($R^9$)$_2$,
(D)N$R^9$SO$_2$$R^9$,
(D)N$R^9$SO$_2$N($R^9$)$_2$,
(D)N$R^9$(CH$_2$)$_n$heterocyclyl,
(D)N$R^9$(CH$_2$)$_n$heteroaryl,
(D)O$R^9$,
OSO$_2$$R^9$,
(D)[O]$_q$($C_3$-$C_7$ cycloalkyl),
(D)[O]$_q$(CH$_2$)$_n$aryl,
(D)[O]$_q$(CH$_2$)$_n$heteroaryl,
(D)[O]$_q$(CH$_2$)$_n$ heterocyclyl, wherein heterocyclyl excludes a heterocyclyl containing a single nitrogen when q=1,
(D)S$R^9$,
(D)SO$R^9$,
(D)SO$_2$$R^9$, or
(D)SO$_2$N($R^9$)$_2$;
wherein $C_1$-$C_8$ alkyl, $C_1$-$C_8$ alkoxy, $C_3$-$C_7$ cycloalkyl, aryl, heterocyclyl and heteroaryl are optionally substituted with one to five substituents independently selected from $R^8$;

$R^1$ is independently:
hydrogen, CONH($C_1$-$C_8$ alkyl), $C_1$-$C_8$ alkyl, (D)phenyl, (D)$C_3$-$C_7$ cycloalkyl or oxo, provided that oxo is not attached to provide a secondary amide moiety;
$R^3$ is independently: aryl or thienyl;
wherein aryl and thienyl are optionally substituted with one to three substituents selected from the group consisting of: cyano, halo, $C_1$-$C_8$ alkyl, (D)$C_3$-$C_7$ cycloalkyl, $C_1$-$C_4$ alkoxy, $C_1$-$C_4$ haloalkyl and $C_1$-$C_4$ haloalkyloxy;
$R^4$ is independently:
hydrogen, $C_1$-$C_8$ alkyl, C(O)$R^9$, C(O)O$R^9$, $C_3$-$C_7$ cycloalkyl or (CH$_2$)$_n$O($C_1$-$C_8$ alkyl), wherein n is 2-8;
each $R^8$ is independently:
hydrogen,
halo,
oxo
N($R^{10}$)$_2$
$C_1$-$C_8$ alkyl,
(D)$C_3$-$C_7$ cycloalkyl,
$C_1$-$C_4$ haloalkyl,
$C_1$-$C_4$ alkoxy,
heteroaryl,
hydroxy,
heterocyclyl, wherein heterocyclyl excludes a heterocyclyl containing a single
nitrogen,
phenyl,
(D)CO$R^9$,
(D)C(O)O$R^9$
(D)O$R^9$,
(D)OCO$R^9$,
(D)OCO$_2$$R^9$,
(D)S$R^9$,
(D)SO$R^9$, or
(D)SO$_2$$R^9$;
wherein aryl, heteroaryl, heterocyclyl, alkyl or cycloalkyl is optionally substituted with one to three substituents selected from the group consisting of oxo, $C_1$-$C_8$ alkyl, N($R^{10}$)$_2$, O$R^{10}$, S$R^{10}$ and CO$_2$$R^{10}$;
each $R^9$ is independently:
hydrogen,
$C_1$-$C_8$ alkyl,
$C_1$-$C_4$ haloalkyl,
(D)$C_3$-$C_7$ cycloalkyl,
(D)aryl, wherein aryl being phenyl or naphthyl,
(D)heteroaryl or
(D)heterocyclyl; wherein heterocyclyl excludes a heterocyclyl containing a single nitrogen; and
wherein aryl, heteroaryl, heterocyclyl, alkyl or cycloalkyl is optionally substituted with one to three substituents selected from the group consisting of oxo, $C_1$-$C_8$ alkyl, N($R^{10}$)$_2$, O$R^{10}$, S$R^{10}$ and CO$_2$$R^{10}$;
each $R^{10}$ is independently:
hydrogen, ($C_1$-$C_8$)alkyl, C(O)$C_1$-$C_8$ alkyl, aryl or $C_3$-$C_7$ cycloalkyl;
each $R^{11}$ is independently:
hydrogen,
$C_1$-$C_8$ alkyl,
(D)aryl,
(D)heteroaryl
(CH$_2$)$_n$N($R^8$)$_2$,
(CH$_2$)$_n$N$R^8$C(O)$C_1$-$C_4$ alkyl,
(CH$_2$)$_n$N$R^8$SO$_2$$C_1$-$C_4$ alkyl,
(CH$_2$)$_n$SO$_2$N($R^8$)$_2$,
(CH$_2$)$_n$[O]$_q$$C_1$-$C_8$ alkyl,
(CH$_2$)$_n$[O]$_q$(CH$_2$)$_n$N$R^8$CO$R^8$,
(CH$_2$)$_n$[O]$_q$(CH$_2$)$_n$N$R^8$SO$_2$$R^8$, (CH$_2$)$_n$[O]$_q$-heterocyclyl or
(CH$_2$)$_n$[O]$_q$(C$_1$-C$_8$ alkyl)-heterocyclyl; and
wherein n is 2-8;
each R$^{12}$ is independently:
hydrogen,
C$_1$-C$_8$ alkyl,
(D)phenyl
C(O)C$_1$-C$_8$ alkyl,
C(O)phenyl,
SO$_2$C$_1$-C$_8$ alkyl or
SO$_2$-phenyl;
D is a bond or —(CH$_2$)$_n$—;
n is 0-8;
p is 0-5;
q is 0-1; and
r is 1-2.

The compounds of the present invention are useful in preventing or treating obesity or diabetes mellitus in a mammal comprising the administration of a therapeutically effective amount of the compound of formula I.

The compounds of the present invention are also useful in preventing or treating male or female sexual dysfunction in mammal, more specifically erectile dysfunction, comprising the administration of a therapeutically effective amount of the compound of formula I.

Also within the scope of the present invention is a pharmaceutical composition or formulation which comprises a pharmaceutical carrier and at least one compound of formula I or its pharmaceutically acceptable salts or stereoisomers thereof.

The present invention further includes a process of making a pharmaceutical composition or formulation comprising a compound of formula I or its pharmaceutically acceptable salt or stereoisomers thereof and a pharmaceutically acceptable carrier.

The present invention further includes a process of preparing a compound of formula I.

DETAILED DESCRIPTION OF THE INVENTION

The present invention relates to melanocortin receptor agonists, and more particularly piperazine derivatives as melanocortin receptor agonists. The compounds of present invention are useful for the treatment or prevention of diseases and disorders responsive to the activation of melanocortin receptors, such as obesity, diabetes and sexual dysfunction including erectile dysfunction and female sexual dysfunction.

An embodiment of the present invention is a compound of formula I:

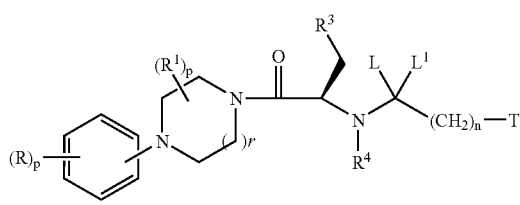

(I)

or a pharmaceutically acceptable salts or stereoisomers thereof, wherein
L and L$^1$ are independently: hydrogen or together oxo;

T is:

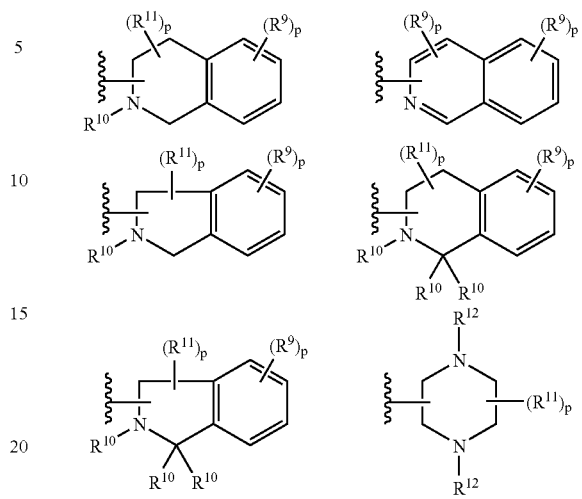

R is independently:
hydrogen,
hydroxy,
cyano,
nitro,
halo,
C$_1$-C$_8$ alkyl,
C$_1$-C$_8$ alkoxy,
C$_1$-C$_4$ haloalkyl,
(D)C(O)R$^9$,
(D)C(O)OR$^9$,
(D)C(O)SR$^9$,
(D)C(O)heteroaryl,
(D)C(O)heterocyclyl,
(D)C(O)N(R$^9$)$_2$,
(D))N(R$^9$)$_2$,
(D)NR$^9$COR$^9$,
(D)NR$^9$CON(R$^9$)$_2$,
(D)NR$^9$C(O)OR$^9$,
(D)NR$^9$C(R$^9$)=N(R$^9$),
(D)NR$^9$C(=NR$^9$)N(R$^9$)$_2$,
(D)NR$^9$SO$_2$R$^9$,
(D)NR$^9$SO$_2$N(R$^9$)$_2$,
(D)NR$^9$(CH$_2$)$_n$heterocyclyl,
(D)NR$^9$(CH$_2$)$_n$heteroaryl,
(D)OR$^9$,
OSO$_2$R$^9$,
(D)[O]$_q$(C$_3$-C$_7$ cycloalkyl),
(D)[O]$_q$(CH$_2$)$_n$aryl,
(D)[O]$_q$(CH$_2$)$_n$heteroaryl,
(D)[O]$_q$(CH$_2$)$_n$ heterocyclyl, wherein heterocyclyl excludes a heterocyclyl containing a single nitrogen when q=1,
(D)SR$^9$,
(D)SOR$^9$,
(D)SO$_2$R$^9$, or
(D)SO$_2$N(R$^9$)$_2$;
wherein C$_1$-C$_8$ alkyl, C$_1$-C$_8$ alkoxy, C$_3$-C$_7$ cycloalkyl, aryl, heterocyclyl and heteroaryl are optionally substituted with one to five substituents independently selected from R$^8$;
R$^1$ is independently:
hydrogen, CONH(C$_1$-C$_8$ alkyl), C$_1$-C$_8$ alkyl, (D)phenyl, (D)C$_3$-C$_7$ cycloalkyl or oxo, provided that oxo is not attached to the same carbon that attached to nitrogen which forms an amide bond;

$R^3$ is independently: aryl or thienyl;

wherein aryl and thienyl are optionally substituted with one to three substituents selected from the group consisting of: cyano, halo, $C_1$-$C_8$ alkyl, (D)$C_3$-$C_7$ cycloalkyl, $C_1$-$C_4$ alkoxy, $C_1$-$C_4$ haloalkyl and $C_1$-$C_4$ haloalkyloxy;

$R^4$ is independently:
hydrogen, $C_1$-$C_8$ alkyl, $C(O)R^9$, $C(O)OR^9$, $C_3$-$C_7$ cycloalkyl or $(CH_2)_nO(C_1$-$C_8$ alkyl), wherein n is 2-8;

each $R^8$ is independently:
hydrogen,
halo,
oxo
$N(R^{10})_2$
$C_1$-$C_8$ alkyl,
(D)$C_3$-$C_7$ cycloalkyl,
$C_1$-$C_4$ haloalkyl,
$C_1$-$C_4$ alkoxy,
heteroaryl,
hydroxy,
heterocyclyl, wherein heterocyclyl excludes a heterocyclyl containing a single nitrogen,
phenyl,
(D)$COR^9$,
(D)$C(O)OR^9$
(D)$OR^9$,
(D)$OCOR^9$,
(D)$OCO_2R^9$,
(D)$SR^9$,
(D)$SOR^9$, or
(D)$SO_2R^9$;

wherein aryl, heteroaryl, heterocyclyl, alkyl or cycloalkyl is optionally substituted with one to three substituents selected from the group consisting of oxo, $C_1$-$C_8$ alkyl, $N(R^{10})_2$, $OR^{10}$, $SR^{10}$ and $CO_2R^{10}$;

each $R^9$ is independently:
hydrogen,
$C_1$-$C_8$ alkyl,
$C_1$-$C_4$ haloalkyl,
(D)$C_3$-$C_7$ cycloalkyl,
(D)aryl, wherein aryl being phenyl or naphthyl,
(D)heteroaryl or
(D)heterocyclyl; wherein heterocyclyl excludes a heterocyclyl containing a single nitrogen; and
wherein aryl, heteroaryl, heterocyclyl, alkyl or cycloalkyl is optionally substituted with one to three substituents selected from the group consisting of oxo, $C_1$-$C_8$ alkyl, $N(R^{10})_2$, $OR^{10}$, $SR^{10}$ and $CO_2R^{10}$;

each $R^{10}$ is independently:
hydrogen, $(C_1$-$C_8)$alkyl, $C(O)C_1$-$C_8$ alkyl, aryl or $C_3$-$C_7$ cycloalkyl;

each $R^{11}$ is independently:
hydrogen,
$C_1$-$C_8$ alkyl,
(D)aryl,
(D)heteroaryl
$(CH_2)_nN(R^8)_2$,
$(CH_2)_nNR^8C(O)C_1$-$C_4$ alkyl,
$(CH_2)_nNR^8SO_2C_1$-$C_4$ alkyl,
$(CH_2)_nSO_2N(R^8)_2$,
$(CH_2)_n[O]_qC_1$-$C_8$ alkyl,
$(CH_2)_n[O]_q(CH_2)_nNR^8COR^8$,
$(CH_2)_n[O]_q(CH_2)_nNR^8SO_2R^8$,
$(CH_2)_n[O]_q$-heterocyclyl or
$(CH_2)_n[O]_q(C_1$-$C_8$ alkyl)-heterocyclyl; and
wherein n is 2-8;

each $R^{12}$ is independently:
hydrogen,
$C_1$-$C_8$ alkyl,
(D)phenyl
$C(O)C_1$-$C_8$ alkyl,
$C(O)$phenyl,
$SO_2C_1$-$C_8$ alkyl or
$SO_2$-phenyl;

D is a bond or —$(CH_2)_n$—;

n is 0-8;

p is 0-5;

q is 0-1; and r is 1-2.

The compound of the present invention as recited above, wherein $R^3$ is phenyl optionally para-substituted with chloro, bromo, fluoro, iodo, methoxy, benzyloxy or methyl. The preferred $R^3$ is phenyl para-substituted with chloro, fluoro or methoxy.

The compound of the present invention as recited above, wherein $R^4$ is hydrogen.

The compound of the present invention as recited above, wherein —$(CH_2)_n$-T is:

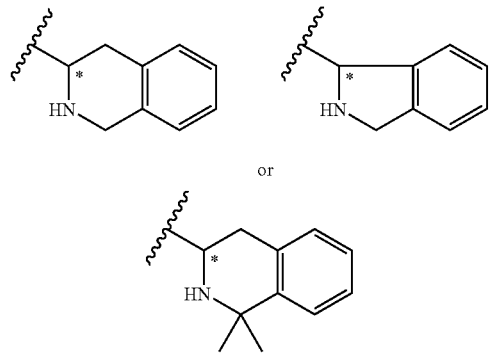

where * denotes a chiral carbon atom having a R or S configuration.

The compound of the present invention as recited above, wherein L and $L^1$ are together oxo and the chiral carbon has R configuration.

The preferred embodiment of the present invention provides a compound of formula II,

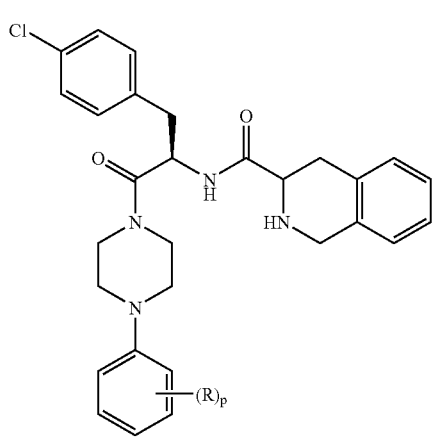

(II)

or a pharmaceutically acceptable salts or stereoisomers thereof.

Yet another preferred embodiment of the present invention provides a compound of formula III,

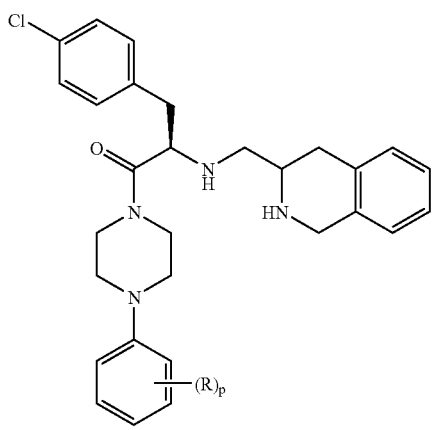

(III)

or a pharmaceutically acceptable salts or stereoisomers thereof.

Yet another preferred embodiment of the present invention provides a compound of formula IV,

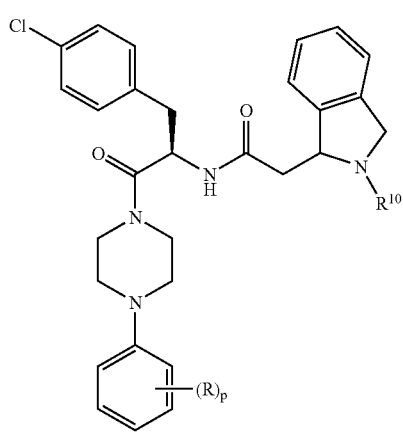

(IV)

or a pharmaceutically acceptable salts or stereoisomers thereof.

Yet another preferred embodiment of the present invention provides a compound of formula V,

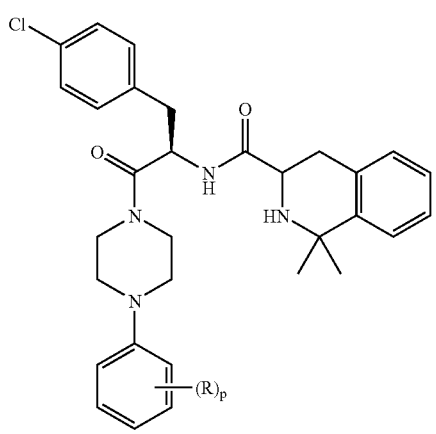

(V)

or a pharmaceutically acceptable salts or stereoisomers thereof.

The compound of the present invention as recited above in formula II to V wherein, P is 0-5;
n is 0-8;
q is 0-1;
D is a bond or —$(CH_2)_n$—;
R is independently:
  hydrogen,
  hydroxy,
  cyano,
  nitro,
  halo,
  $C_1$-$C_8$ alkyl,
  $C_1$-$C_8$ alkoxy,
  $C_1$-$C_4$ haloalkyl,
  $(D)C(O)R^9$,
  $(D)C(O)OR^9$,
  $(D)C(O)SR^9$,
  $(D)C(O)$heteroaryl,
  $(D)C(O)$heterocyclyl,
  $(D)C(O)N(R^9)_2$,
  $(D)N(R^9)_2$,
  $(D)NR^9COR^9$,
  $(D)NR^9CON(R^9)_2$,
  $(D)NR^9C(O)OR^9$,
  $(D)NR^9C(R^9)=N(R^9)$,
  $(D)NR^9C(=NR^9)N(R^9)_2$,
  $(D)NR^9SO_2R^9$,
  $(D)NR^9SO_2N(R^9)_2$,
  $(D)NR^9(CH_2)_n$heterocyclyl,
  $(D)NR^9(CH_2)_n$heteroaryl,
  $(D)OR^9$,
  $OSO_2R^9$,
  $(D)[O]_q(C_3$-$C_7$ cycloalkyl),
  $(D)[O]_q(CH_2)_n$aryl,
  $(D)[O]_q(CH_2)_n$heteroaryl,
  $(D)[O]_q(CH_2)_n$ heterocyclyl, wherein heterocyclyl excludes a heterocyclyl containing a single nitrogen when q=1,
  $(D)SR^9$,
  $(D)SOR^9$,
  $(D)SO_2R^9$, or
  $(D)SO_2N(R^9)_2$;
wherein $C_1$-$C_8$ alkyl, $C_1$-$C_8$ alkoxy, $C_3$-$C_7$ cycloalkyl, aryl, heterocyclyl and heteroaryl are optionally substituted with one to five substituents independently selected from $R^8$;
each $R^8$ is independently:
  hydrogen,
  halo,
  oxo
  $N(R^{10})_2$
  $C_1$-$C_8$ alkyl,
  $(D)C_3$-$C_7$ cycloalkyl,
  $C_1$-$C_4$ haloalkyl,
  $C_1$-$C_4$ alkoxy,
  heteroaryl,
  hydroxy,
  heterocyclyl, wherein heterocyclyl excludes a heterocyclyl containing a single nitrogen,
  phenyl,
  $(D)COR^9$,
  $(D)C(O)OR^9$
  $(D)OR^9$,
  $(D)OCOR^9$,
  $(D)OCO_2R^9$,
  $(D)SR^9$, (D)SOR$^9$, or
(D)SO$_2$R$^9$;
wherein aryl, heteroaryl, heterocyclyl, alkyl or cycloalkyl is optionally substituted with one to three substituents selected from the group consisting of oxo, C$_1$-C$_8$ alkyl, N(R$^{10}$)$_2$, OR$^{10}$, SR$^{10}$ and CO$_2$R$^{10}$;

each R$^9$ is independently:
hydrogen,
C$_1$-C$_8$ alkyl,
C$_1$-C$_4$ haloalkyl,
(D)C$_3$-C$_7$ cycloalkyl,
(D)aryl, wherein aryl being phenyl or naphthyl
heteroaryl or heterocyclyl; wherein heterocyclyl excludes a heterocyclyl containing a single nitrogen; and
wherein aryl, heteroaryl, heterocyclyl, alkyl or cycloalkyl is optionally substituted with one to three substituents selected from the group consisting of oxo, C$_1$-C$_8$ alkyl, N(R$^{10}$)$_2$, OR$^{10}$, SR$^{10}$ and CO$_2$R$^{10}$; and each R$^{10}$ is independently:
hydrogen, (C$_1$-C$_8$)alkyl, C(O)C$_1$-C$_8$ alkyl, aryl or C$_3$-C$_7$ cycloalkyl.

The compound of the present invention as recited above in formula IV, wherein R$^{10}$ is hydrogen or (C$_1$-C$_8$)alkyl.

The most preferred compound of the present invention is the compound listed below:

| Name of Compounds | Structure of Compounds |
|---|---|
| 1-(D-Tic-4-Cl-D-Phe)-4-(2-methanesulfonylamino-phenyl)-piperazine | |
| 1-(D-Tic-4-Cl-D-Phe)-4-(2-dimethylaminomethyl-phenyl)-piperazine | |

| Name of Compounds | Structure of Compounds |
|---|---|
| 3-(4-chloro-phenyl)-2-[(1,2,3,4-tetrahydro-isoquinolin-3-ylmethyl)-amino]-1-[4-(2-[1,2,4]triazol-1-ylmethyl-phenyl)-piperazin-1-yl]-propan-1-one | |
| N-(1-(4-chloro-benzyl)-2-{4-[2-(isobutyl-methanesulfonyl-amino)-phenyl]-piperazin-1-yl}-2-oxo-ethyl)-2-(2,3-dihydro-1H-isoindol-1-yl)-acetamide | |

Also encompassed by the present invention is a pharmaceutical composition or formulation, which comprises a pharmaceutical carrier and at least one compound of formula I or its pharmaceutically acceptable salts or stereoisomers thereof. The pharmaceutical composition and or formulation may optionally further include a second active ingredient selected from the group consisting of an insulin sensitizer, insulin mimetic, sulfonylurea, alpha-glucosidase inhibitor, HMG-CoA reductase inhibitor, sequestrant cholesterol lowering agent, beta 3 adrenergic receptor agonist, neuropeptide Y antagonist, phosphodiester V inhibitor, and an alpha 2 adrenergic receptor antagonist.

Yet another aspect of the present invention is a process of making a pharmaceutical composition comprising a compound of formula I or its pharmaceutically acceptable salt or stereoisomers thereof as recited above and a pharmaceutically acceptable carrier.

Yet another aspect of the present invention is a method of preventing or treating obesity or diabetes mellitus in mammal comprising the administration of a therapeutically effective amount of the compound of formula I.

Yet anther aspect of the present invention is a method of preventing or treating male or female sexual dysfunction in mammal, more specifically the male or female sexual dysfunction, comprising the administration of a therapeutically effective amount of the compound of formula I.

Yet anther aspect of the present invention is a process for preparing a compound of formula I,

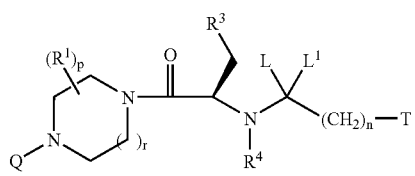

(I)

or a pharmaceutically acceptable salts or stereoisomers thereof, wherein

—CLL$^1$—(CH$_2$)$_n$-T is:

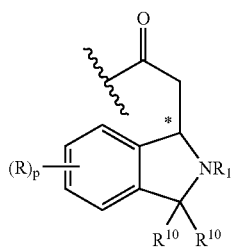

wherein R$_1$ is hydrogen, C$_1$-C$_8$ alkyl, Boc, CBZ, phenyl, FMOC or (C$_1$-C$_8$ alkyl)phenyl;

Q represents a moiety:

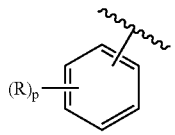

R is independently:
hydrogen,
hydroxy,
cyano,
nitro,
halo,
$C_1$-$C_8$ alkyl,
$C_1$-$C_8$ alkoxy,
$C_1$-$C_4$ haloalkyl,
(D)C(O)$R^9$,
(D)C(O)O$R^9$,
(D)C(O)S$R^9$,
(D)C(O)heteroaryl,
(D)C(O)heterocyclyl,
(D)C(O)N($R^9$)$_2$,
(D)N($R^9$)$_2$,
(D)N$R^9$CO$R^9$,
(D)N$R^9$CON($R^9$)$_2$,
(D)N$R^9$C(O)O$R^9$,
(D)N$R^9$C($R^9$)=N($R^9$),
(D)N$R^9$C(=N$R^9$)N($R^9$)$_2$,
(D)N$R^9$SO$_2$$R^9$,
(D)N$R^9$SO$_2$N($R^9$)$_2$,
(D)N$R^9$(CH$_2$)$_n$heterocyclyl,
(D)N$R^9$(CH$_2$)$_n$heteroaryl,
(D)O$R^9$,
OSO$_2$$R^9$,
(D)[O]$_q$($C_3$-$C_7$ cycloalkyl),
(D)[O]$_q$(CH$_2$)$_n$aryl,
(D)[O]$_q$(CH$_2$)$_n$heteroaryl,
(D)[O]$_q$(CH$_2$)$_n$ heterocyclyl, wherein heterocyclyl excludes a heterocyclyl containing a single nitrogen when q=1,
(D)S$R^9$,
(D)SO$R^9$,
(D)SO$_2$$R^9$, or
(D)SO$_2$N($R^9$)$_2$;
wherein $C_1$-$C_8$ alkyl, $C_1$-$C_8$ alkoxy, $C_3$-$C_7$ cycloalkyl, aryl, heterocyclyl and heteroaryl are optionally substituted with one to five substituents independently selected from $R^8$;

$R^1$ is independently:
hydrogen, CONH($C_1$-$C_8$ alkyl), $C_1$-$C_8$ alkyl, (D)phenyl, (D)$C_3$-$C_7$ cycloalkyl or oxo, provided that oxo is not attached to the same carbon that attached to nitrogen which forms an amide bond;

$R^3$ is independently: aryl or thienyl;
wherein aryl and thienyl are optionally substituted with one to three substituents selected from the group consisting of: cyano, halo, $C_1$-$C_8$ alkyl, (D)$C_3$-$C_7$ cycloalkyl, $C_1$-$C_4$ alkoxy, $C_1$-$C_4$ haloalkyl and $C_1$-$C_4$ haloalkyloxy;

$R^4$ is independently:
hydrogen, $C_1$-$C_8$ alkyl, C(O)$R^9$, C(O)O$R^9$, $C_3$-$C_7$ cycloalkyl or (CH$_2$)$_n$O($C_1$-$C_8$ alkyl), wherein n is 2-8;

each $R^8$ is independently:
hydrogen,
halo,
oxo
N($R^{10}$)$_2$
$C_1$-$C_8$ alkyl,
(D)$C_3$-$C_7$ cycloalkyl,
$C_1$-$C_4$ haloalkyl,
$C_1$-$C_4$ alkoxy,
heteroaryl,
hydroxy,
heterocyclyl, wherein heterocyclyl excludes a heterocyclyl containing a single nitrogen,
phenyl,
(D)CO$R^9$,
(D)C(O)O$R^9$
(D)O$R^9$,
(D)OCO$R^9$,
(D)OCO$_2$$R^9$,
(D)S$R^9$,
(D)SO$R^9$, or
(D)SO$_2$$R^9$;
wherein aryl, heteroaryl, heterocyclyl, alkyl or cycloalkyl is optionally substituted with one to three substituents selected from the group consisting of oxo, $C_1$-$C_8$ alkyl, N($R^{10}$)$_2$, O$R^{10}$, S$R^{10}$ and CO$_2$$R^{10}$;

each $R^9$ is independently:
hydrogen,
$C_1$-$C_8$ alkyl,
$C_1$-$C_4$ haloalkyl,
(D)$C_3$-$C_7$ cycloalkyl,
(D)aryl, wherein aryl being phenyl or naphthyl,
(D)heteroaryl or
(D)heterocyclyl; wherein heterocyclyl excludes a heterocyclyl containing a single nitrogen; and
wherein aryl, heteroaryl, heterocyclyl, alkyl or cycloalkyl is optionally substituted with one to three substituents selected from the group consisting of oxo, $C_1$-$C_8$ alkyl, N($R^{10}$)$_2$, O$R^{10}$, S$R^{10}$ and CO$_2$$R^{10}$;

each $R^{10}$ is independently:
hydrogen, ($C_1$-$C_8$)alkyl, C(O)$C_1$-$C_8$ alkyl, aryl or $C_3$-$C_7$ cycloalkyl;

D is a bond or —(CH$_2$)$_n$—;
n is 0-8;
p is 0-5;
q is 0-1; and
r is 1-2;
comprising the steps of:
a) reacting a compound having a structural formula 1,

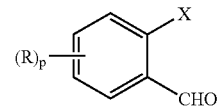

(1)

with CH$_2$CH=C(O)O$R^a$ wherein $R^a$ is hydrogen or $C_1$-$C_8$ alkyl and X is halo, in the presence of a catalyst and a base in a suitable organic solvent to give the compound of formula 2,

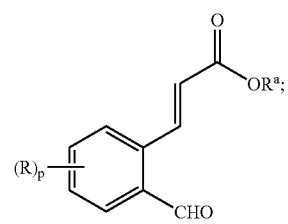

(2)

b) reductively aminating the compound of formula 2 in the presence of amine in an acidic condition to give a compound of formula 3,

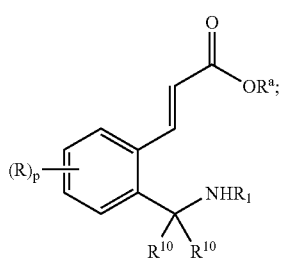
(3)

c) cyclizing the compound of formula 3 by Michael addition to give a compound of formula 4 or stereoisomers thereof,

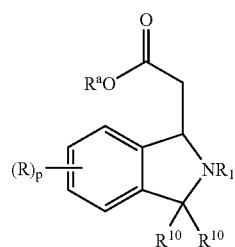
(4)

d) coupling the compound of formula 4 or stereoisomers thereof, wherein $R^a$ of compound 4 is H, with a compound of formula 5,

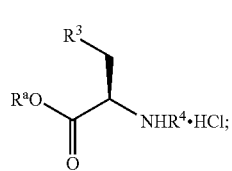
(5)

wherein $R^a$ of compound 5 is $C_1$-$C_8$ alkyl, to give a compound of formula 6;

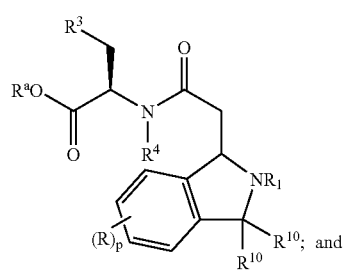
(6)

e) coupling the compound of formula 6, wherein $R^a$ is H, with a compound having a structural,

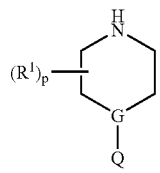

to afford the compound of formula 1.

The process of the present invention as recited above, wherein

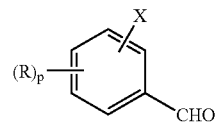

in Step (a) is 2-boromobenzaldehydes.

The process of the present invention as recited above, wherein $CH_2CH{=}C(O)OR$ in Step (a) is methylacrylate.

The process of the present invention as recited above, wherein the catalyst in Step (a) is selected from the group consisting of: $Pd(Ph_3P)_2Cl_2$, $Pd(Ph_3P)_4Cl_2$, $Pd(Ph_3P)_4$, $Pd(Ph_3P)_2Cl_2/CuI$, $Pd(OAc)_2/Ph_3P$-$Bu_4NBr$, $Pd(Ph_3P)_4Cl_2/H_2$ and $Pd(OAc)_2/P(O\text{-tol})_3$; and wherein the base in Step (a) is $NR_3$ wherein R is hydrogen or $C_1$-$C_8$ alkyl.

The process of the present invention as recited above, wherein the amine in Step (b) is selected from the group consisting of: benzylamine, alpha-methylbenzylamine and $BocNH_2$.

The process of the present invention as recited above, wherein the Step (b) further comprises reducing of intermediate imine compound in the presence of reducing agent, the reducing agent being selected from the group consisting of: $NaCNBH_3$, $Na(OAc)_3BH$, $NaBH_4/H+$, and a combination of $Et_3SiH$ and TFA in $CH_3CN$ or $CH_2Cl_2$.

The process of the present invention as recited above, wherein the stereoisomer of compound of formula 4 in Step (c) is a compound of formula 4a.

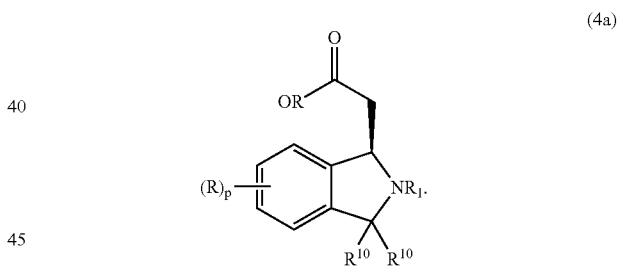
(4a)

The process of the present invention as recited above, wherein the compound of formula 4a is prepared by asymmetric hydrogenation of a compound having structural formula,

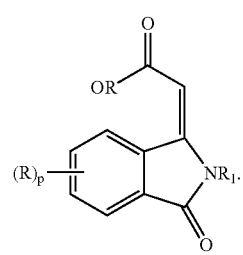

The process of the present invention as recited above, wherein the Michael addition in Step (c) is carried out in a basic workup condition.

The process of the present invention as recited above, wherein the Step (e) further comprises deprotecting or protecting of the compound of formula (4) at $NR_1$.

Yet another aspect of the present invention is a process for preparing a compound of formula I,

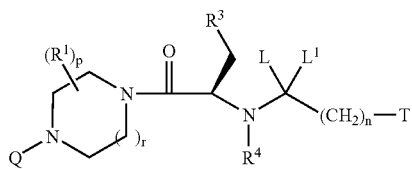

(I)

or a pharmaceutically acceptable salts or stereoisomers thereof, wherein
—CLL$^1$—(CH$_2$)$_n$-T is:

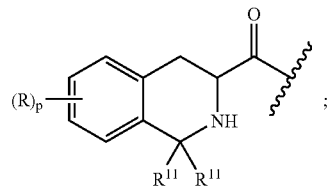

Q represents a moiety:

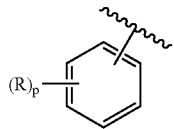

R is independently:
hydrogen,
hydroxy,
cyano,
nitro,
halo,
$C_1$-$C_8$ alkyl,
$C_1$-$C_8$ alkoxy,
$C_1$-$C_4$ haloalkyl,
(D)C(O)R$^9$,
(D)C(O)OR$^9$,
(D)C(O)SR$^9$,
(D)C(O)heteroaryl,
(D)C(O)heterocyclyl,
(D)C(O)N(R$^9$)$_2$,
(D)N(R$^9$)$_2$,
(D)NR$^9$COR$^9$,
(D)NR$^9$CON(R$^9$)$_2$,
(D)NR$^9$C(O)OR$^9$,
(D)NR$^9$C(R$^9$)=N(R$^9$),
(D)NR$^9$C(=NR$^9$)N(R$^9$)$_2$,
(D)NR$^9$SO$_2$R$^9$,
(D)NR$^9$SO$_2$N(R$^9$)$_2$,
(D)NR$^9$(CH$_2$)$_n$heterocyclyl,
(D)NR$^9$(CH$_2$)$_n$heteroaryl,
(D)OR$^9$,
OSO$_2$R$^9$,
(D)[O]$_q$(C$_3$-C$_7$ cycloalkyl),
(D)[O]$_q$(CH$_2$)$_n$aryl,
(D)[O]$_q$(CH$_2$)$_n$heteroaryl,
(D)[O]$_q$(CH$_2$)$_n$ heterocyclyl, wherein heterocyclyl excludes a heterocyclyl containing a single nitrogen when q=1,
(D)SR$^9$,
(D)SOR$^9$,
(D)SO$_2$R$^9$, or
(D)SO$_2$N(R$^9$)$_2$;
wherein $C_1$-$C_8$ alkyl, $C_1$-$C_8$ alkoxy, $C_3$-$C_7$ cycloalkyl, aryl, heterocyclyl and heteroaryl are optionally substituted with one to five substituents independently selected from R$^8$;
R$^1$ is independently:
hydrogen, CONH($C_1$-$C_8$ alkyl), $C_1$-$C_8$ alkyl, (D)phenyl, (D)$C_3$-$C_7$ cycloalkyl or oxo, provided that oxo is not attached to the same carbon that attached to nitrogen which forms an amide bond;
R$^3$ is independently: aryl or thienyl;
wherein aryl and thienyl are optionally substituted with one to three substituents selected from the group consisting of: cyano, halo, $C_1$-$C_8$ alkyl, (D)$C_3$-$C_7$ cycloalkyl, $C_1$-$C_4$ alkoxy, $C_1$-$C_4$ haloalkyl and $C_1$-$C_4$ haloalkyloxy;
R$^4$ is independently:
hydrogen, $C_1$-$C_8$ alkyl, C(O)R$^9$, C(O)OR$^9$, $C_3$-$C_7$ cycloalkyl or (CH$_2$)$_n$O($C_1$-$C_8$ alkyl), wherein n is 2-8;
each R$^8$ is independently:
hydrogen,
halo,
oxo
N(R$^{10}$)$_2$
$C_1$-$C_8$ alkyl,
(D)$C_3$-$C_7$ cycloalkyl,
$C_1$-$C_4$ haloalkyl,
$C_1$-$C_4$ alkoxy,
heteroaryl,
hydroxy,
heterocyclyl, wherein heterocyclyl excludes a heterocyclyl containing a single nitrogen,
phenyl,
(D)COR$^9$,
(D)C(O)OR$^9$,
(D)OR$^9$,
(D)OCOR$^9$,
(D)OCO$_2$R$^9$,
(D)SR$^9$,
(D)SOR$^9$, or
(D)SO$_2$R$^9$;
wherein aryl, heteroaryl, heterocyclyl, alkyl or cycloalkyl is optionally substituted with one to three substituents selected from the group consisting of oxo, $C_1$-$C_8$ alkyl, N(R$^{10}$)$_2$, OR$^{10}$, SR$^{10}$ and CO$_2$R$^{10}$;
each R$^9$ is independently:
hydrogen,
$C_1$-$C_8$ alkyl,
$C_1$-$C_4$ haloalkyl,
(D)$C_3$-$C_7$ cycloalkyl,
(D)aryl, wherein aryl being phenyl or naphthyl,
(D)heteroaryl or
(D)heterocyclyl; wherein heterocyclyl excludes a heterocyclyl containing a single nitrogen; and
wherein aryl, heteroaryl, heterocyclyl, alkyl or cycloalkyl is optionally substituted with one to three substituents selected from the group consisting of oxo, $C_1$-$C_8$ alkyl, N(R$^{10}$)$_2$, OR$^{10}$, SR$^{10}$ and CO$_2$R$^{10}$;

each $R^{10}$ is independently:
hydrogen, $(C_1-C_8)$alkyl, $C(O)C_1-C_8$ alkyl, aryl or $C_3-C_7$ cycloalkyl;

each $R^{11}$ is independently: hydrogen or $(C_1-C_8)$alkyl;

D is a bond or $-(CH_2)_n-$;

n is 0-8;

p is 0-5;

q is 0-1; and r is 1-2;

comprising the steps of:

a) esterifying a compound of formula 1,

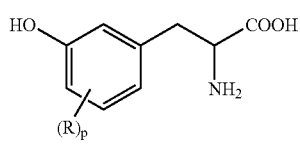
(1)

with an alcohol $R^aOH$ to form a compound of formula 2,

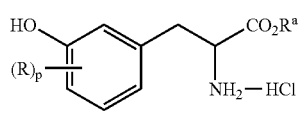
(2)

wherein $R^a$ is $C_1-C_4$ alkyl or (D)phenyl;

b) reacting a compound of formula 2 with $R^{11}COR^{11}$ to form a compound of formula 3,

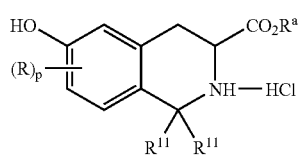
(3)

wherein $R^{11}$ is independently hydrogen or $C_1-C_4$ alkyl;

c) reacting a compound of formula 3 with an activating group to form a compound of formula 4,

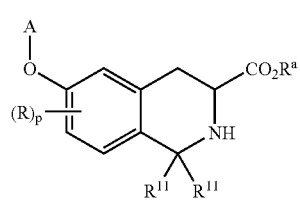
(4)

wherein A is an activating group;

d) deoxygenating the compound of formula 4 by hydrogenation to afford a compound of formula 5,

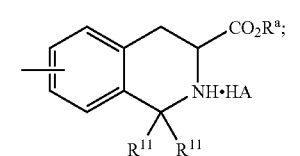
(5)

e) optionally reacting the compound of formula 5 with an inorganic base to form a compound of formula 6,

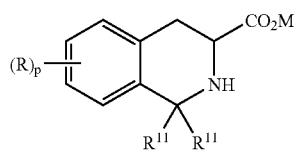
(6)

wherein HA is an acidic and M is a univalent cation;

f) resolving the compound of formula 5 or formula 6 to afford a chiral compound of formula 7,

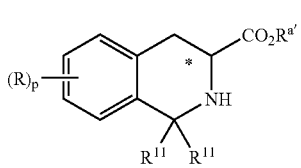
(7)

wherein M is hydrogen and $R^{a'}$ is H or $R^a$;

g) coupling the compound of formula 7 with a compound of formula 8,

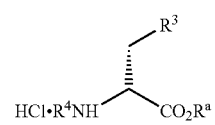
(8)

to afford a compound of formula 9,

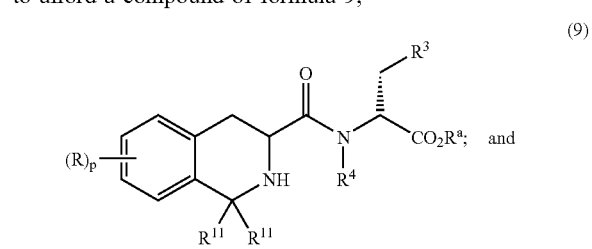
(9)

h) coupling the compound of formula 9 with a compound having a formula,

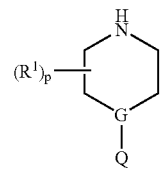

to afford a compound of formula I.

Yet another aspect of the present invention is a process for preparing a compound of formula I,

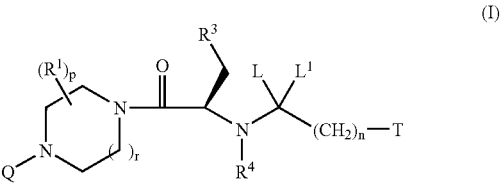
(I)

or a pharmaceutically acceptable salts or stereoisomers thereof, wherein
—CLL$^1$—(CH$_2$)$_n$-T is:

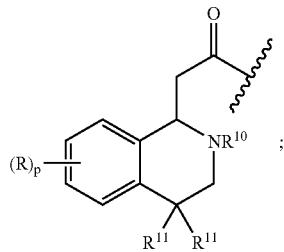

Q represents a moiety:

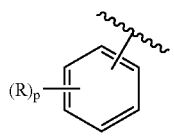

R is independently:
  hydrogen,
  hydroxy,
  cyano,
  nitro,
  halo,
  C$_1$-C$_8$ alkyl,
  C$_1$-C$_8$ alkoxy,
  C$_1$-C$_4$ haloalkyl,
  (D)C(O)R$^9$,
  (D)C(O)OR$^9$,
  (D)C(O)SR$^9$,
  (D)C(O)heteroaryl,
  (D)C(O)heterocyclyl,
  (D)C(O)N(R$^9$)$_2$,
  (D)N(R$^9$)$_2$,
  (D)NR$^9$COR$^9$,
  (D)NR$^9$CON(R$^9$)$_2$,
  (D)NR$^9$C(O)OR$^9$,
  (D)NR$^9$C(R$^9$)=N(R$^9$),
  (D)NR$^9$C(=NR$^9$)N(R$^9$)$_2$,
  (D)NR$^9$SO$_2$R$^9$,
  (D)NR$^9$SO$_2$N(R$^9$)$_2$,
  (D)NR$^9$(CH$_2$)$_n$heterocyclyl,
  (D)NR$^9$(CH$_2$)$_n$heteroaryl,
  (D)OR$^9$,
  OSO$_2$R$^9$,
  (D)[O]$_q$(C$_3$-C$_7$ cycloalkyl),
  (D)[O]$_q$(CH$_2$)$_n$aryl,
  (D)[O]$_q$(CH$_2$)$_n$heteroaryl,
  (D)[O]$_q$(CH$_2$)$_n$ heterocyclyl, wherein heterocyclyl excludes a heterocyclyl containing a single nitrogen when q=1,
  (D)SR$^9$,
  (D)SOR$^9$,
  (D)SO$_2$R$^9$, or
  (D)SO$_2$N(R$^9$)$_2$;
wherein C$_1$-C$_8$ alkyl, C$_1$-C$_8$ alkoxy, C$_3$-C$_7$ cycloalkyl, aryl, heterocyclyl and heteroaryl are optionally substituted with one to five substituents independently selected from R$^8$;

R$^1$ is independently:
  hydrogen, CONH(C$_1$-C$_8$ alkyl), C$_1$-C$_8$ alkyl, (D)phenyl, (D)C$_3$-C$_7$ cycloalkyl or oxo, provided that oxo is not attached to the same carbon that attached to nitrogen which forms an amide bond;
R$^3$ is independently: aryl or thienyl;
  wherein aryl and thienyl are optionally substituted with one to three substituents selected from the group consisting of: cyano, halo, C$_1$-C$_8$ alkyl, (D)C$_3$-C$_7$ cycloalkyl, C$_1$-C$_4$ alkoxy, C$_1$-C$_4$ haloalkyl and C$_1$-C$_4$ haloalkyloxy;
R$^4$ is independently:
  hydrogen, C$_1$-C$_8$ alkyl, C(O)R$^9$, C(O)OR$^9$, C$_3$-C$_7$ cycloalkyl or (CH$_2$)$_n$O(C$_1$-C$_8$ alkyl), wherein n is 2-8;
each R$^8$ is independently:
  hydrogen,
  halo,
  oxo
  N(R$^{10}$)$_2$
  C$_1$-C$_8$ alkyl,
  (D)C$_3$-C$_7$ cycloalkyl,
  C$_1$-C$_4$ haloalkyl,
  C$_1$-C$_4$ alkoxy,
  heteroaryl,
  hydroxy,
  heterocyclyl, wherein heterocyclyl excludes a heterocyclyl containing a single nitrogen,
  phenyl,
  (D)COR$^9$,
  (D)C(O)OR$^9$
  (D)OR$^9$,
  (D)OCOR$^9$,
  (D)OCO$_2$R$^9$,
  (D)SR$^9$,
  (D)SOR$^9$, or
  (D)SO$_2$R$^9$;
  wherein aryl, heteroaryl, heterocyclyl, alkyl or cycloalkyl is optionally substituted with one to three substituents selected from the group consisting of oxo, C$_1$-C$_8$ alkyl, N(R$^{10}$)$_2$, OR$^{10}$, SR$^{10}$ and CO$_2$R$^{10}$;
each R$^9$ is independently:
  hydrogen,
  C$_1$-C$_8$ alkyl,
  C$_1$-C$_4$ haloalkyl,
  (D)C$_3$-C$_7$ cycloalkyl,
  (D)aryl, wherein aryl being phenyl or naphthyl,
  (D)heteroaryl or
  (D)heterocyclyl; wherein heterocyclyl excludes a heterocyclyl containing a single nitrogen; and
  wherein aryl, heteroaryl, heterocyclyl, alkyl or cycloalkyl is optionally substituted with one to three substituents selected from the group consisting of oxo, C$_1$-C$_8$ alkyl, N(R$^{10}$)$_2$, OR$^{10}$, SR$^{10}$ and CO$_2$R$^{10}$;
each R$^{10}$ is independently:
  hydrogen, (C$_1$-C$_8$)alkyl, C(O)C$_1$-C$_8$ alkyl, aryl or C$_3$-C$_7$ cycloalkyl;
each R$^{10}$ is independently: hydrogen or (C$_1$-C$_8$)alkyl;
D is a bond or —(CH$_2$)$_n$—;
n is 0-8;
p is 0-5;
q is 0-1; and
r is 1-2;

comprising the steps of:

a) reacting a compound formula 1:

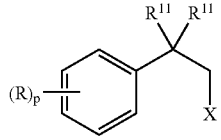
(1)

wherein X is halo, and $R^{11}$ is independently, hydrogen or $C_1$-$C_4$ alkyl, with $CNCH_2CO_2R^a$ wherein $R^a$ is $C_1$-$C_8$ alkyl or benzyl to afford a compound of formula 2:

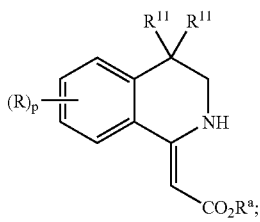
(2)

b) protecting the compound of formula 2 to form the compound of formula 3:

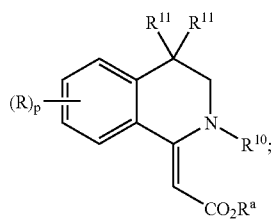
(3)

c) hydrogenating the compound of formula 3 to afford a compound of formula 4:

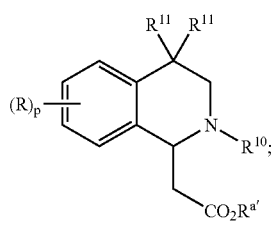
(4)

d) coupling the compound of formula 4 wherein $R^{a'}$ is hydrogen or $R^a$, with a compound of formula 5,

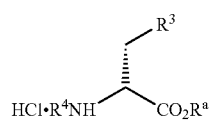
(5)

to afford a compound of formula 6,

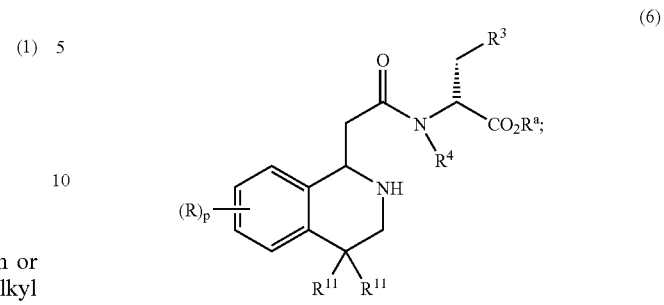
(6)

e) coupling the compound of formula 6 with a compound having a formula,

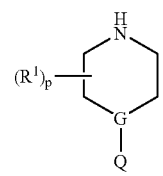

to afford a compound of formula I.

Throughout the instant application, the following terms have the indicated meanings:

The term "alkyl," unless otherwise indicated, refers to those alkyl groups of a designated number of carbon atoms of either a straight or branched saturated configuration. Examples of "alkyl" includes, but are not limited to methyl, ethyl, n-propyl, isopropyl, n-butyl, isobutyl, sec-butyl and t-butyl, pentyl, hexyl, neopenyl, isopentyl and the like. Alkyl as defined above may be optionally substituted with a designated number of substituents as set forth in the embodiment recited above.

The term "alkenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with designated number of substituents as set forth in the embodiment recited above.

The term "haloalkyl" is an alkyl group of indicated number of carbon atoms, which is substituted with one to five halo atoms selected from F, Br, Cl and I. An example of a haloalkyl group is trifluoromethyl.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "cycloalkyl" refers to a ring composed of 3 to 7 methylene groups, each of which may be optionally substituted with other hydrocarbon substituents. Examples of cycloalkyl includes, but are not limited to: cyclopropyl, cyclobutyl, cyclopentyl, cyclohexyl and cycloheptyl, and the like. Cycloalkyl as defined above may be optionally substituted with a designated number of substituents as set forth in the embodiment recited above.

The term "halo" refers to fluoro, chloro, bromo and iodo.

The term "haloalkyloxy" represents a haloalkyl group of indicated number of carbon atoms attached through an oxygen bridge, such as $OCF_3$. "Haloalkyloxy" as defined above may be optionally substituted with a designated number of substituents as set forth in the embodiment recited above.

The term "aryl" refers to phenyl, naphthyl, anthracenyl, phenanthrenyl and the like which is optionally substituted with a designated number of substituents as set forth in the embodiment recited above.

The term "heteroaryl" refers to monocyclic or bicyclic aromatic ring of 5- to 10-carbon atoms containing from one to four heteroatoms selected from O, N, or S, and the heteroaryl being optionally substituted with a designated number of substituents as set forth in the embodiment recited above. Examples of heteroaryl are, but are not limited to furanyl, thienyl, thiazolyl, imidazolyl, isoxazoyl, oxazoyl, pyrazoyl, pyrrolyl, pyrazinyl, pyridyl, pyrimidyl, and purinyl, cinnolinyl, benzothienyl, benzotriazolyl, benzoxazolyl, quinoline, isoquinoline and the like.

The "heterocyclyl" is defined as a monocyclic, bicyclic, or tricyclic ring of 5 to 14 carbon atoms which are saturated or partially saturated containing from one to four heteroatoms selected from N, O or S. The "heterocycly" includes "nitrogen containing heterocyclyl," which contains from one to four nitrogen atoms and optionally further contains one other heteroatom selected from O or S. Heterocyclyl as defined above may be optionally substituted with a designated number of substituents as set forth in the embodiment recited above.

A mammal as used in here includes a human and a warm-blooded animal such as a cat, a dog and the like.

The term "composition" or "formulation", as in pharmaceutical composition or formulation, is intended to encompass a product comprising the active ingredient(s), and the inert ingredient(s) that make up the carrier. Accordingly, the pharmaceutical compositions of the present invention encompass any composition made by admixing a compound of the present invention (a compound of formula I) and a pharmaceutically acceptable carrier.

The term "pharmaceutical" when used herein as an adjective means substantially non-deleterious to the recipient mammal.

The term "unit dosage form" refers to physically discrete units suitable as unitary dosages for human subjects and other non-human animals such as warm-blooded animals each unit containing a predetermined quantity of active ingredient (a compound of formula I) calculated to produce the desired therapeutic effect in association with a suitable pharmaceutical carrier.

The term "treating" or "preventing" as used herein includes its generally accepted meanings, i.e., preventing, prohibiting, restraining, alleviating, ameliorating, slowing, stopping, or reversing the progression or severity of a pathological condition, or sequela thereof as described herein.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, inability to achieve an orgasm. An increase in erectile dysfunction is often associated with age and is generally caused by a physical disease or as a side effect of drug treatment.

"Female sexual dysfunction" encompasses, without limitation, conditions such as a lack of sexual desire and related arousal disorders, inhibited orgasm, lubrication difficulties, and vaginismus.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I can also exist as a pharmaceutical acid addition salt Such salts include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, beta-hydroxybutyrate, glycollate, maleate, tartrate, methanesulfonate, propanesulfonate, naphthalene-1-sulfonate, naphthalene-2-sulfonate, mandelate and the like salts. Preferred salt form of compound of formula I is an acid addition salts, more specifically hydrochloride salt.

Some of the compounds described herein may exist as tautomers such as ketoenol tautomers. The individual tautomers as well as mixtures thereof are encompassed within the scope of the present invention.

Utility

Compounds of formula I are effective as melanocortin receptor modulators, particularly as agonists of the human MC-4 receptor. As melanocortin receptor agonists, the compounds of formula I are useful in the treatment of diseases, disorders or conditions responsive to the activation of one or more of the melanocortin receptors including, but not limited to, MC-1, MC-2, MC-3, MC-4, and MC-5. Diseases, disorders or conditions receptive to treatment with a MC-4 agonist include those mentioned above and those described in WO 00/74679, the teachings of which are herein incorporated by reference. In particular diseases, disorders or conditions receptive to treatment with a MC-4 agonist include obesity or diabetes mellitus, male or female sexual dysfunction, more specifically erectile dysfunction.

When describing various aspects of the present compounds of formula I, the terms "A domain", "B domain" and "C domain" are used below. This domain concept is illustrated below:

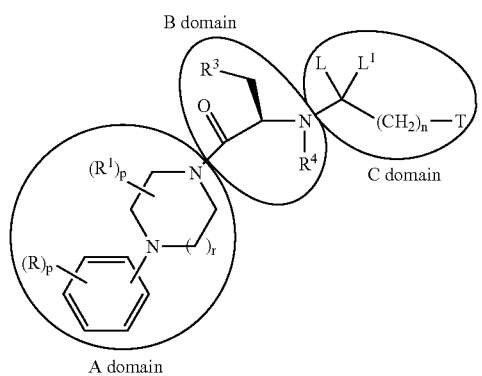
A domain
The following listing provides some of examples "A domain", "B domain" and "C domain" of the compound of formula I. These listings are provided as illustrative purposes and as such are not meant to be limiting.
Examples of A Domain:
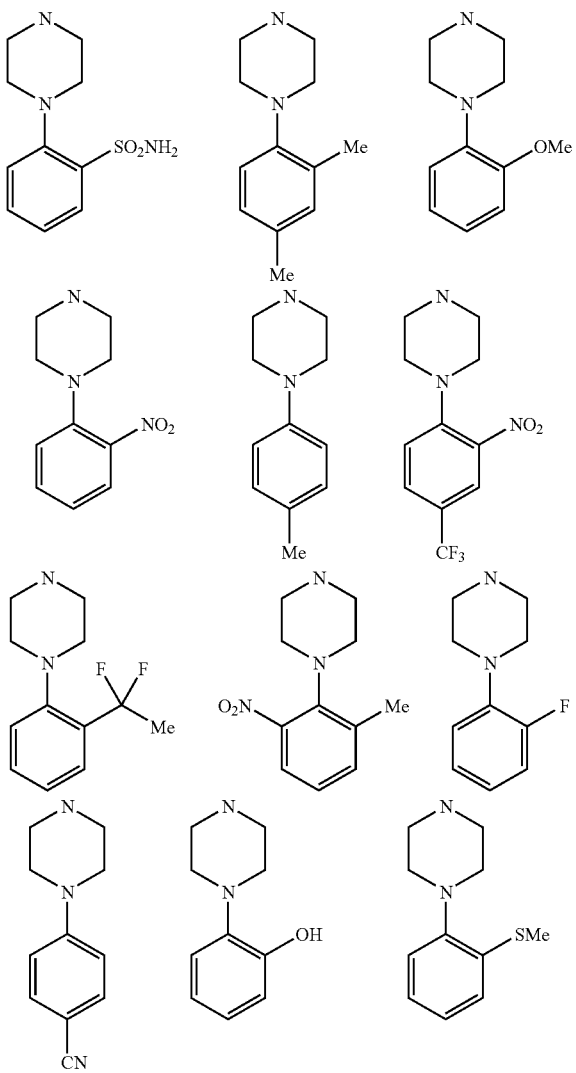
Examples of B Domain:
-continued
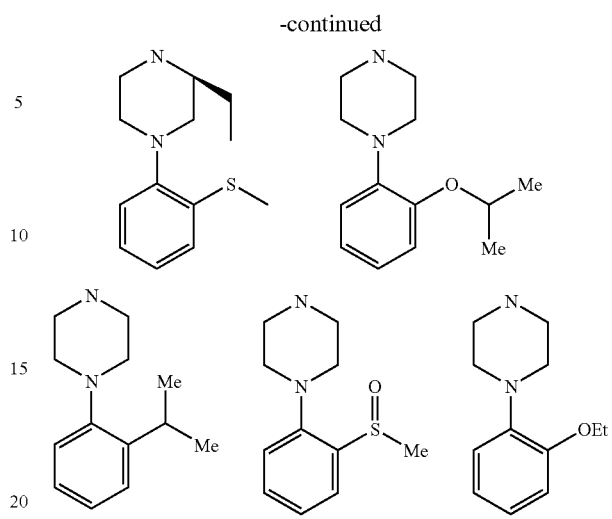
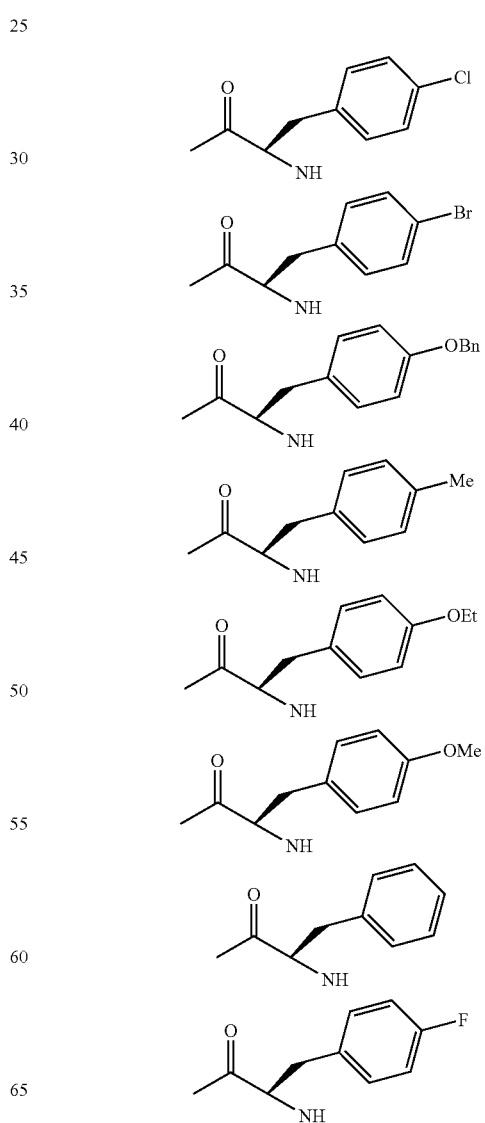

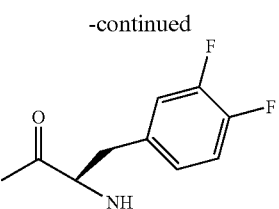

Examples of C Domain:

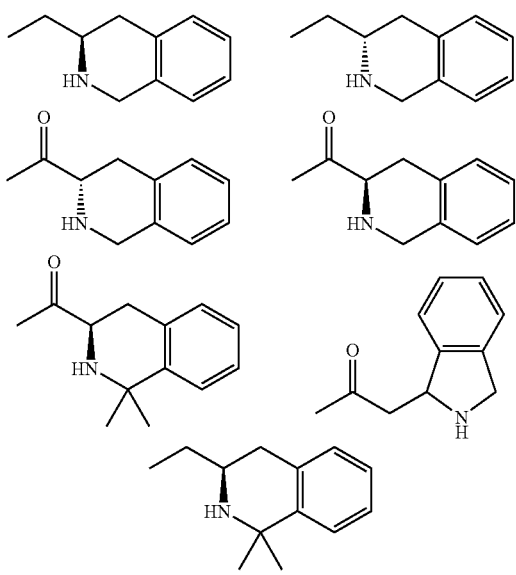

Formulation

The compound of formula I is preferably formulated in a unit dosage form prior to administration. Accordingly the present invention also includes a pharmaceutical composition comprising a compound of formula I and a suitable pharmaceutical carrier.

The present pharmaceutical compositions are prepared by known procedures using well-known and readily available ingredients. In making the formulations of the present invention, the active ingredient (a compound of formula I) is usually be mixed with a carrier, or diluted by a carrier, or enclosed within a carrier, which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

Dosage:

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. Additionally, it would be understood that the therapeutic dosage administered can be determined by the physician in the light of the relevant circumstances.

Generally, an effective minimum daily dose of a compound of formula I is about 1, 5, 10, 15, or 20 mg. Typically, an effective maximum dose is about 500, 100, 60, 50, or 40 mg. The suitable dose may be determined in accordance with the standard practice in the medical arts of "dose titrating" the recipient, which involves administering a low dose of the compound initially and then gradually increasing the does until the desired therapeutic effect is observed.

Route of Administration

The compounds may be administered by a variety of routes including the oral, rectal, transdermal, subcutaneous, topical, intravenous, intramuscular or intranasal routes.

Combination Therapy

Compounds of formula I may be used in combination with other drugs that are used in the treatment of the diseases or conditions for which compounds of formula I are useful. Such other drugs may be administered by a route and in an amount commonly used therefor, contemporaneously or sequentially with a compound of formula I. When a compound of formula I is used contemporaneously with one or more other drugs, a pharmaceutical composition containing such other drugs in addition to the compound of formula I is preferred. Accordingly, the pharmaceutical compositions of the present invention include those that also contain one or more other active ingredients in addition to a compound of formula I. Examples of other active ingredients that may be combined with a compound of formula I, either administered separately or in the same pharmaceutical compositions, include but are not limited to:

(a) insulin sensitizers including (i) PPARγ agonists such as the glitazones (e.g., troglitazone, pioglitazone, englitazone, MCC-555, BRL49653 and the like) and compounds disclosed in WO97/27857, WO 97/28115, WO 97/28137 and WO97/27847; (ii) biguanides such as metformin and phenformin;

(b) insulin or insulin mimetics;

(c) sulfonylureas such as tolbutamide and glipizide;

(d) α-glucosidase inhibitors (such as acarbose), (e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (iii) nicotinyl alcohol nicotinic acid or a salt thereof, (iv) proliferator-activater receptor α-agonists such as fenofibric acid derivatives (gemfibrozil, clofibrat, fenofibrate and benzafibrate), (v) inhibitors of cholesterol absorption such as β-sitosterol and acyl CoA:cholesterol acyltransferase inhibitors such as melinamide, (vi) probucol, (vii) vitamin E, and (viii) thyromimetics;

(f) PPARδ agonists such as those disclosed in WO97/28149;
(g) antiobesity compounds such as fenfluramine, dexfenfluramine, phentermine, sibutramine, orlistat, and β-3 adrenergic receptor agonists;
(h) feeding behavior modifying agents such as neuropeptide Y antagonists (e.g., neuropeptide Y5) as disclosed in WO 97/19682, WO 97/20820, WO 97/20821, WO 97/20822 and WO 97/20823;
(i) PPARα agonists as described in WO 97/36579;
(j) PPARγ antagonists as described in WO97/10813;
(k) serotonin reuptake inhibitors, such as fluoxetine and sertraline;
(l) growth hormone secretagogues such as MK-0677; and
(m) agents useful in the treatment of male and/or female sexual dysfunction, such as phosphodiester V inhibitors including sildenafil and ICI-351, and α-2 adrenergic receptor antagonists including phentolamine mesylate; and dopamine-receptor agonists, such as apomorphine.

Biological Assays

A. Binding Assay:

The radioligand binding assay is used to identify competitive inhibitors of $^{125}$I-NDP-α-MSH binding to cloned human MCRs using membranes from stably transfected human embryonic kidney (HEK) 293 cells.

HEK 293 cells transfected with human or rat melanocortinin receptors are grown either as adherent monolayers or suspension culture. Monolayer cells are grown in roller bottle cultures at 37° C. and 5% $CO_2$/air atmosphere in a 3:1 mixture of Dulbecco's modified Eagle medium (DMEM) and Ham's F12 containing 25 mM L-glucose, 100 units/ml penicillin G, 100 microgram/ml streptomyocin, 250 nanogram/ml amphoterin B, 300 microgram/ml genticin and supplemented with 5% fetal bovine serum. Monolayer cells are adapted to suspension culture (Berg et al., *Biotechniques* Vol. 14, No. 6, 1993) and are grown in either spinner or shaker flasks (37° C. and 7.5% $CO_2$/air overlay) in a modified DME/F12 medium containing 0.1 mM $CaCl_2$, 2% equine serum and 100 microgram/ml sodium heparin to prevent cell-cell aggregation. Cells are harvested by centrifugation, washed in PBS, and pellets are stored frozen at −80° C. until membrane preparations.

The cell pellets are resuspended in 10 volumes of membrane preparation buffer (i.e., 1 g pellet to 10 ml buffer) having the following composition: 50 mM Tris pH 7.5 @ 4° C., 250 mM sucrose, 1 mM $MgCl_2$, Complete® EDTA-free protease inhibitor tablet (Boehringer Mannheim), and 24 micrograms/ml DNase I (Sigma, St. Louis, Mo.). The cells are homogenized with a motor-driven dounce using 20 strokes, and the homogenate is centrifuged at 38,000×g at 4° C. for 40 minutes. The pellets are resuspended in membrane preparation buffer at a concentration of 2.5-7.5 mg/ml and 1 milliliter aliquots of membrane homogenates are quickly frozen in liquid nitrogen and then stored at −80° C.

Solutions of a compound of formula I (300 picomolar to 30 micromolar) or unlabelled NDP-α-MSH (1 picomolar to 100 nanomolar) are added to 150 microliters of membrane binding buffer to yield final concentrations (listed in parantheses). The membrane binding buffer has the following composition: 25 mM HEPES pH 7.5; 10 mM $CaCl_2$; 0.3% BSA). One hundred fifty microliters of membrane binding buffer containing 0.5-5.0 microgram membrane protein is added, followed by 50 nanomolar $^{125}$I-NDP-α-MSH to final concentration of 100 picomolar. Additionally, fifty microliters of SPA beads (5 mg/ml) are added and the resulting mixture is agitated briefly and incubated for 10 hours at r.t. The radioactivity is quantified in a Wallac Trilux Microplate Scintillation counter. $IC_{50}$ values obtained in competition assays are converted to affinity constants ($K_i$ values) using the Cheng-Prusoff equation: $K_i = IC_{50}/(1+D/K_d)$.

B. Functional Assay:

Functional cell based assays are developed to discriminate agonists and antagonists.

Agonist Assay: HEK 293 cells stably expressing a human melanocortin receptor (see e.g., Yang, et al., *Mol-Endocrinol.*, 11(3): 274-80, 1997) are dissociated from tissue culture flasks using a trypsin/EDTA solution(0.25%; Life Technologies, Rockville, Md.). Cells are collected by centrifugation and resuspended in DMEM (Life Technologies, Rockville, Md.) supplemented with 1% L-glutamine and 0.5% fetal bovine serum. Cells are counted and diluted to $4.5 \times 10^5$/ml.

A compound of formula I is diluted in dimethylsulfoxide (DMSO) ($3 \times 10^{-5}$ to $3 \times 10^{31\ 10}$ M final concentrations) and 0.05 volume of compound solution is added to 0.95 volumes of cell suspension; the final DMSO concentration is 0.5%. After incubation at 37° C./5% $CO_2$ for 5 hours, cells are lysed by addition of luciferin solution (50 mM Tris, 1 mM $MgCl_2$, 0.2% Triton-X100, 5 mM DTT, 500 micromolar Coenzyme A, 150 micromolar ATP, and 440 micromolar luciferin) to quantify the activity of the reporter gene luciferase, an indirect measurement of intracellular cAMP production.

Luciferase activity is measured from the cell lysate using a Wallac Victor 2 luminometer. The amount of lumen production which results from a compound of formula I is compared to that amount of lumens produced in response to NDP-α-MSH, defined as a 100% agonist, to obtain the relative efficacy of a compound. The $EC_{50}$ is defined as the compound concentration that results in half maximal stimulation, when compared to its own maximal level of stimulation.

Antagonist assay: Antagonist activity is defined as the ability of a compound to block lumen production in response to NDP-α-MSH. Concentration-response curves are generated for NDP-α-MSH in the absence and presence of a fixed concentration of a solution of a compound of formula I (10×$K_i$ from binding assays). Suspensions of MCR-expressing cells are prepared and are incubated with NDP-α-MSH and compound solutions for 5 hours as described above. The assay is terminated by the addition of luciferin reagent and lumen production is quantified. Antagonist potency is determined from the rightward shift of the $EC_{50}$ value in the absence of a compound of formula I using the equation: $K_b$=Concentration of Antagonist/[($EC_{50}'/EC_{50}$)−1].

Whole Cell cAMP Accumulation Assay

Compound Preparation

In the agonist assay, the compounds are prepared as 10 mM and NDP-alpha-MSH (control) as 33.3 μM stock solutions in 100% DMSO. These are serially diluted in 100% DMSO. The compound plate is further diluted 1:200 in compound dilution buffer (HBSS-092, 1 mM Ascorbic Acid, 1 mM IBMX, 0.6% DMSO, 0.1% BSA). The final concentration range being 10 μM-100 pM for compound and 33.33 nM-0.3 pM for control in 0.5% DMSO. Transfer 20 μl from this plate into four PET 96-well plates (all assays are performed in duplicate for each receptor).

Cell Culture and Cell Stimulation

HEK 293 cells stably transfected with the MC3R and MC4R were grown in DMEM containing 10% FBS and 1% Antibiotic/Antimycotic Solution. On the day of the assay the cells were dislodged with enzyme free cell dissociation solution and resuspended in cell buffer (HBSS-092, 0.1% BSA, 10 mM HEPES) at 1×e6 cells/ml. Add 40 µl of cells/well to the PET 96-well plates containing 20 microliter diluted compound and control. Incubate @ 37° C. in a waterbath for 20 minutes. Stop the assay by adding 50 µl Quench Buffer (50 mM Na Acetate, 0.25% Triton X-100).

Radioligand Binding Assays

Radioligand binding assays were run in SPA buffer (50 mM Sodium Acetate, 0.1% BSA). The beads, antibody and radioligand were diluted in SPA buffer to provide sufficient volume for each 96-well plate. To each quenched assay well was added 100 microliter cocktail containing 33.33 microliter of beads, 33.33 microliter antibody and 33.33 microliter $^{125}$I-cAMP. This was based on a final concentration of 6.3 mg/ml beads, 0.65% anti-goat antibody and 61 pM of $^{125}$I-cAMP (containing 25000-30000 CPM) in a final assay volume of 210 microliter. The plates were counted in a Wallac MicroBeta counter after a 12-hour incubation.

The data was converted to pmoles cAMP using a standard curve assayed under the same conditions. The data was analyzed using Activity Base software to generate agonist potencies (EC50) and percent relative efficacy data to NDP-alpha-MSH.

C. In Vivo Food Intake Models:

1) Daily food intake. Male Long-Evans rats are injected intracerebroventricularly (ICV) with a test compound in 5 microliters of 50% propylene glyco/artificial cerebrospinal fluid one hour prior to onset of dark cycle (12 hours). Food intake is determined by subtracting the food weight remaining after 24 hours from food weight just prior to ICV injection.

2) Acute Calorimetry. Male Long-Evans rats are administered test compound by subcutaneous injection, intramuscular injection, intravenous injection, intraperitoneal injection, ICV injection or by oral gavage between 0 and 5 hours after the onset of the dark cycle. Rats are placed into a calorimetry chamber and the volume of oxygen consumed and volume or carbon dioxide exhaled are measured each hour for 24 hours. Food intake is measured for the 24 hour period as described in C.1). Locomoter activity is measured when the rat breaks a series of infrared laser beams when in the calorimeter. These measurements permit calculation of energy expenditure, respiratory quotient and energy balance.

3) Food intake in diet induced obese mice. Male C57/B16J mice maintained on a high fat diet (60% fat calories) for 6.5 months from 4 weeks of age are dosed intraperitoneally with a compound of formula I. Food intake and body weight are measured over an eight day period. Biochemical parameters relating to obesity, including leptin, insulin, triglyceride, free fatty acid, cholesterol and serum glucose levels are determined.

D. Rat Ex Copula Assay:

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes about 4 days. Day 1, the animals are placed in a darkened restrainer and left for 15-30 minutes. Day 2, the animals are restrained in a supine position in the restrainer for 15-30 minutes. Day 3, the animals are restrained in the supine position with the penile sheath retracted for 15-30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation, animals are given a treat to ensure positive reinforcement.

2) Ex Copula Reflex Tests. Rats are gently restrained in a supine position with their anterior torso placed inside a cylinder of adequate size to allow for normal head and paw grooming. For a 400-500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copulu genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and/or vehicle evaluations are conducted to determine how and if an animal will respond. Some animals have a long duration until the first response while others are non-responders altogether. During this baseline evaluation, latency to first response time, number and type of responses are recorded. The testing time frame is 15 minutes after the first response.

After a minimum of 1 day between evaluations, these same animals are administered a compound of formula I at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction:

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna, et al., *Am. J. Physiol.*, (Regulatory Integrative Comp. Physiol 30):R1276-R1285, 1991; McKenna, et al., *Pharm. Bioch. Behav.*, 40:151-156, 1991; and Takahashi, et al., *Brain Res.*, 359:194-207, 1985.

Preparation of the Compounds of the Invention

Preparation of the compounds of the present invention may be carried out via sequential or convergent synthetic routes. The skilled artisan will recognize that, in general, the three domains of a compound of formula I are connected via amide bonds. The B and C domains are optionally connected via a reduced or partially reduced amide bond (e.g., via reductive amination). The skilled artisan can, therefore, readily envision numerous routes and methods of connecting the three domains via standard peptide coupling reaction conditions.

The phrase "standard peptide coupling reaction conditions" means coupling a carboxylic acid with an amine using an acid activating agent such as EDC, dicyclohexylcarbodiimide, and benzotriazol-1-yloxytris(dimethylamino)phosphonium hexafluorophosphate in a inert solvent such as DCM in the presence of a catalyst such as HOBT. The uses of protective groups for amine and carboxylic acids to facilitate the desired reaction and minimize undesired reactions are well documented. Conditions required to remove protecting groups which may be present can be found in Greene, et al., *Protective Groups in Organic Synthesis*, John Wiley & Sons, Inc., New York, N.Y. 1991.

CBZ, Boc and FMOC protecting groups are used extensively in the synthesis, and their removal conditions are well known to those skilled in the art. For example, removal of CBZ groups can he achieved by catalytic hydrogenation with hydrogen in the presence of a noble metal or its oxide such as palladium on activated carbon in a protic solvent such as ethanol. In cases where catalytic hydrogenation is contraindicated by the presence of other potentially reactive functionality, removal of CBZ can also be achieved by treatment with a solution of hydrogen bromide in acetic acid, or by treatment with a mixture of TFA and dimethylsulfide. Removal of Boc protecting groups is carried out in a solvent such as methylene chloride, methanol or ethyl acetate with a strong acid, such as TFA or HCl or hydrogen chloride gas.

The compounds of formula I, when exist as a diastereomeric mixture, may be separated into diastereomeric pairs of enantiomers by fractional crystallization from a suitable solvent such as methanol, ethyl acetate or a mixture thereof. The pair of enantiomers thus obtained may be separated into individual stereoisomers by conventional means by using an optically active acid as a resolving agent. Alternatively, any enantiomer of a compound of the formula I may be obtained by stereospecific synthesis using optically pure starting materials or reagents of known configuration.

The compounds of the present invention can be prepared according to the procedure of the following schemes and examples, which may further illustrate details for the preparation of the compounds of the present invention. The compounds illustrated in the examples are, however, not to be construed as forming the only genus that is considered as the present invention.

In the Schemes, Preparations and Examples below, various reagent symbols and abbreviations have the following meanings:

| | |
|---|---|
| BINAP | 2,2'-Bis(diphenylphosphino)-1,1'-binaphthyl |
| Boc | t-butoxycarbonyl |
| CBZ | benzyloxycarbonyl |
| DCM | dichloromethane |
| DEAD | diethyl azodicarboxylate |
| DIAD | diisopropyl azodicarboxylate |
| DIPEA | diisopropylethylamine |
| DMAP | 4-dimethylamino pyridine |
| DMF | N,N-dimethylformamide |
| DMSO | dimethylsulfoxide |
| eq. | equivalent(s) |
| EDC | 1-(3-dimethylaminopropyl)-3-ethylcarbodiimide HCl |
| ESI-MS | electron spray ion-mass spectroscopy |
| Et | ethyl |
| EtOAc | ethyl acetate |
| FMOC | 9-Flurorenylmethyl carbamate |
| HATU | O-(7-azabenzotriazol-1-yl)-N,N,N',N'-tetramethyluronium hexafluorophosphate |
| HOAT | 1-hydroxy-7-azabenzotriazole |
| HOBT | 1-hydroxybenzotriazole hydrate |
| HPLC | high performance liquid chromatography |
| HRMS | high resolution mass spectroscopy |
| h (hr) | hour(s) |
| LRMS | low resolution mass spectroscopy |
| Me | methyl |
| Ms | methanesulfonyl |
| NMM | 4-methyl morpholine |
| Pd$_2$(dba)$_3$ | tris(dibenzylideneacetone) dipalladium(0) |
| Ph | phenyl |
| Phe | phenylalanine |
| Pr | propyl |
| r.t. | room temperature |
| TBAF | tetrabutylammonium fluoride |
| TBS | tertbutyldimethylsilyl |
| TFA | trifluoroacetic acid |
| TEA | triethylamine |
| THF | tetrahydrofuran |
| Tic | 1,2,3,4-tetrahydroisoquinoline-3-carboxylic acid |
| TLC | thin-layer chromatography |

Reaction Scheme 1:
Coupling Procedures

Procedure 1

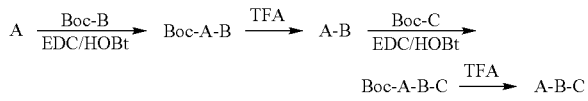

Procedure 2

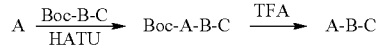

Procedure 3

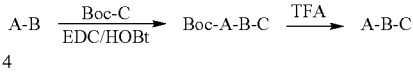

Procedure 4

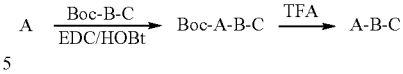

Procedure 5

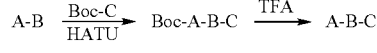

In coupling procedure 1, an appropriate A domain (e.g., piperazine) is coupled to B domain (e.g., D-Boc-p-Cl-Phe-OH) in the presence of EDC/HOBt followed by Boc deprotection. The coupled AB compound is then coupled to an appropriate C domain followed by deprotection of Boc group and salt formation. Alternatively, when C domain is not protected with Boc group, the final compound can be obtained without the deprotection step.

In coupling procedure 2, an appropriate A domain (e.g., piperazine) is coupled to an appropriate BC domain in the presence of HATU followed by deprotection of Boc group and salt formation. Alternatively, when BC domain is not protected with Boc group, the final compound can be obtained without the deprotection step.

In coupling procedure 3, an appropriate AB domain is coupled to an appropriate C domain in the presence of EDC/HOBt followed by deprotection of Boc group and salt formation.

In coupling procedure 4, an appropriate BC domain is coupled to an appropriate A domain in the presence of EDC/HOBT followed by deprotection of Boc group and salt formation. Alternatively, when C domain is not protected with Boc group, the final compound can be obtained without the deprotection step.

In coupling procedure 5, an appropriate AB domain is coupled to an appropriate C domain in the presence of HATU followed by deprotection of Boc group salt formation.

For coupling of A with Boc-B, EDC/HOAT, EDC/HOBT or DCC/HOBT can be used.

Generally, the starting material of Boc-protected piperazine (A domain) can be deprotected in the presence of TFA/CH$_2$Cl$_2$, HCl/EtOAc, HCl/dioxane, or HCl in MeOH/Et$_2$O with or without a cation scavenger, such as dimethyl sulfide (DMS) before being subjected to the coupling procedure. It can be freebased before being subjected to the coupling procedure or in some cases used as the salt.

A suitable solvent such as CH$_2$Cl$_2$, DMF, THF or a mixture of the above solvents can be used for the coupling procedure. Suitable base includes triethyl amine (TEA), diisopropyethyl amine (DIPEA), N-methymorpholine, collidine, or 2,6-lutidine. Base may not be needed when EDC/HOBt is used.

Generally after the reaction is completed, the reaction mixture can be diluted with an appropriate organic solvent, such as EtOAc, CH$_2$Cl$_2$, or Et$_2$O, which is then washed with aqueous solutions, such as water, HCl, NaHSO$_4$, bicarbonate, NaH$_2$PO$_4$, phosphate buffer (pH 7), brine or any combination thereof. The reaction mixture can be concentrated and then be partitioned between an appropriate organic solvent and an aqueous solution. The reaction mixture can be concentrated and subjected to chromatography without aqueous workup.

Protecting group such as Boc or CBZ, FMOC, CF$_3$CO and H$_2$/Pd—C can be deprotected in the presence of TFA/CH$_2$Cl$_2$, HCl/EtOAc, HCl/dioxane, HCl in MeOH/Et$_2$O, NH3/MeOH, or TBAF with or without a cation scavenger, such as thioanisole, ethane thiol and dimethyl sulfide (DMS). The deprotected amines can be used as the resulting salt or are freebased by dissolving in CH$_2$Cl$_2$ and washing with aqueous bicarbonate or aqueous NaOH. The deprotected amines can also be freebased by ion exchange chromatography.

The compounds of the present invention can be prepared as salt, such as TFA, hydrochloride or succinate salts by using known standard methods.

Reaction Scheme for Preparation of "A Domain"

The A domains of the present invention, in general, may be prepared from commercially available starting materials via known chemical transformations. The preparation of A domain of the compound of the present invention is illustrated in the reaction scheme below.

Reaction Schemes of "A Domain"

Reaction Scheme 2:
Buchwald

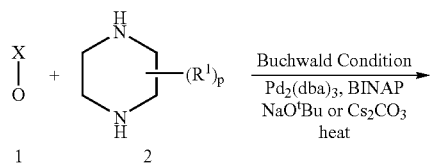

1    2

-continued

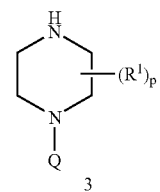

3

X= halo; and Q = aryl

As shown in Reaction Scheme 2, the "A domain" of the compounds of the present invention can be prepared by coupling halo-substituted aryl 1 (X-Q) with piperazines 2 in the presence of tris(dibenzylideneacetone) dipalladium (Pd$_2$(dba)$_3$), 1,1'-Bi[(2-diphenylphosphines) naphthalene] (BI-NAP) and sodium t-butoxide (NaO$^t$Bu) or cesium carbonate (Cs$_2$CO$_3$) in an organic solvent such as toluene at a suitable temperature. More detailed examples of A Domain preparation are described below.

Reaction Scheme 3:
SNAr

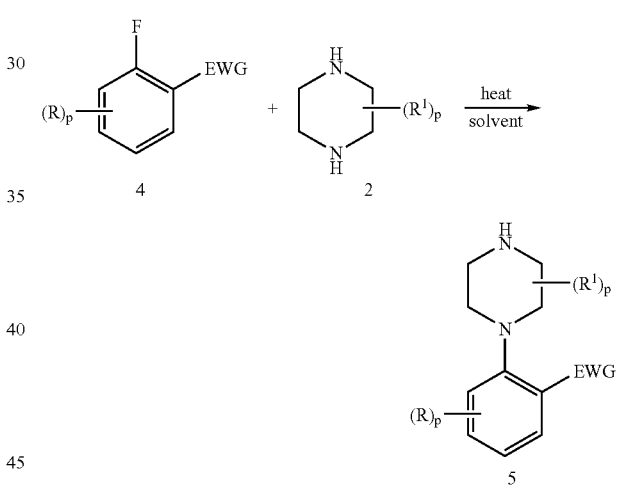

EWG = electron withdrawing group

As shown in Reaction Scheme 3, the "A domain" of the compounds of the present invention can be prepared by heating appropriately substituted fluoro-aryl compounds 4 and piperazines 2 neat or with an appropriate solvent and with or without an appropriate base.

Reaction Scheme 4:
SNAr followed by Buchwald

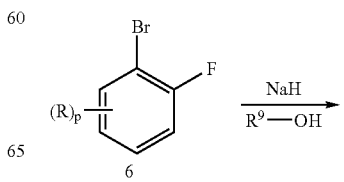

6

-continued

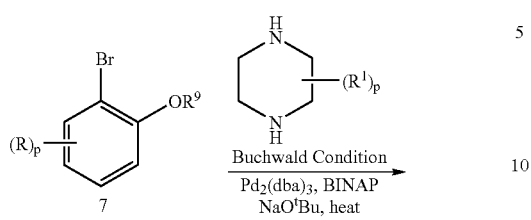

As shown in Reaction Scheme 4, the "A domain" of the compounds of the present invention can be prepared by heating 1-bromo-2-fluoro-benzene 6 with various alcohols (R⁹—OH) in the presence of NaH to give ortho-substituted bromobenzenes 7 which can then be subjected to Buchwald conditions as shown in Reaction Scheme 4 above.

Reaction Scheme 5:
Copper mediated O-arylation of 2-bromophenol with aryl boronic acids followed by Buchwald.

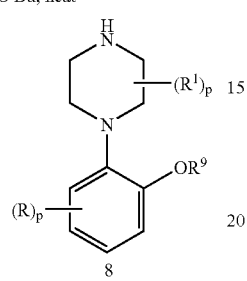

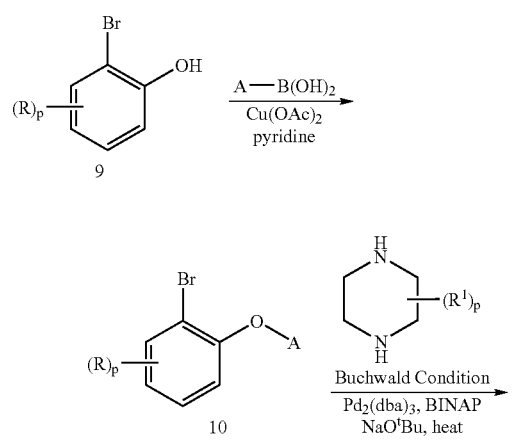

A is aryl or heteroaryl.

As shown in Reaction Scheme 5, the "A domain" of the compounds of the present invention can be prepared by heating 2-bromophenol 9 with various aryl and heteroaryl boronates (X-OH) in the presence of $Cu(OAc)_2$ and pyridine to give ortho-substituted bromobenzenes 10 which can then be subjected to Buchwald conditions.

Reaction Scheme 6:
Benzylamines
6A. Nitrile reduction

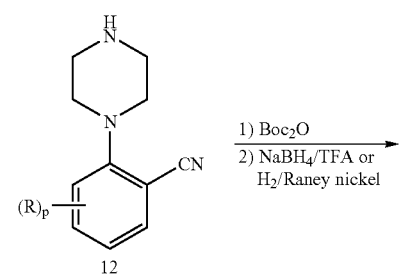

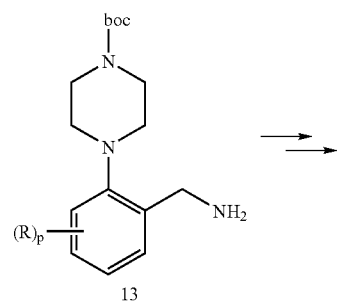

$A = SO_2R^9, SO_2N(R^9)_2, C(O)R^9, C(O)OR^9, C(O)SR^9, C(O)N(R^9)_2$ and etc.

As shown in Reaction Scheme 6A, the "A domain" of the compounds of present invention can be prepared by reducing the nitrile of (2-cyano-phenyl)-piperazine 12 to the corresponding benzyl amine 13 with either $NaBH_4$ and TFA or $H_2$ and Raney nickel. Benzyl amine 13 can be transformed to other benzyl amine derivatives 14 using various methods known to the skilled artisan.

6B. From benzylic alcohol via Mitsunobu or via mesylate

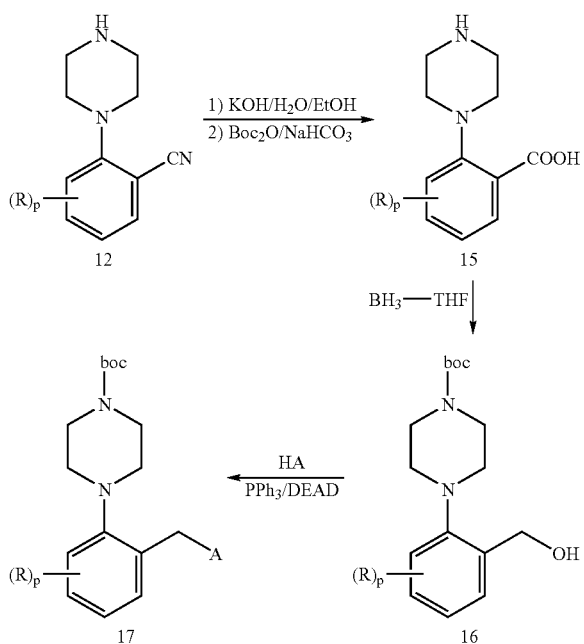

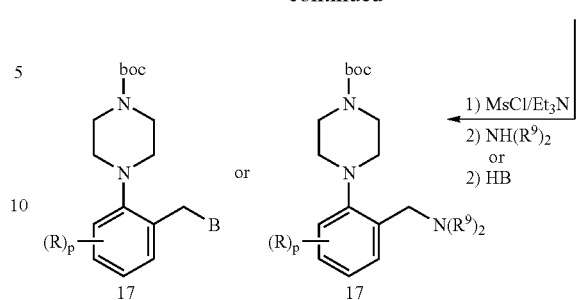

A = acidic heteroaryl, azide, imide and etc.
B = basic heteroaryl, heterocyclyl and etc.

As shown in Reaction Scheme 6B, the "A domain" of the compounds of present invention can be prepared by hydrolyzing the nitrile of (2-cyano-phenyl)-piperazine 12 to the corresponding carboxylic acid 15 with KOH followed by reduction to benzyl alcohol 16 with $BH_3$-ThF. Benzyl alcohol 16 can be transformed to benzyl amines 17 either using Mitsunobu conditions or by activating the alcohol as the mesylate followed by nucleophilic displacement.

Reaction Scheme 7:
Derivatives of 1-Boc-4-(2-amino-phenyl)-piperazine

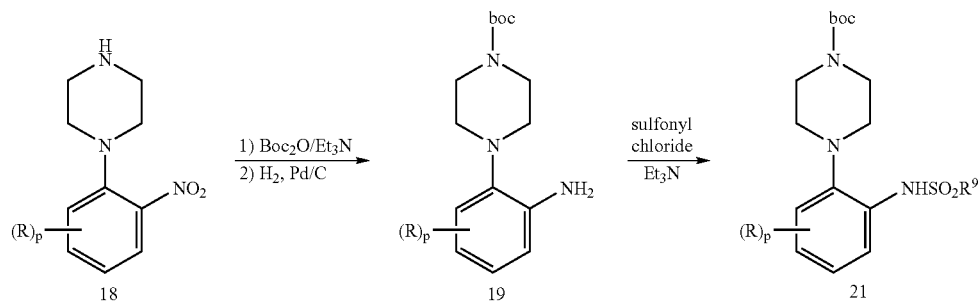

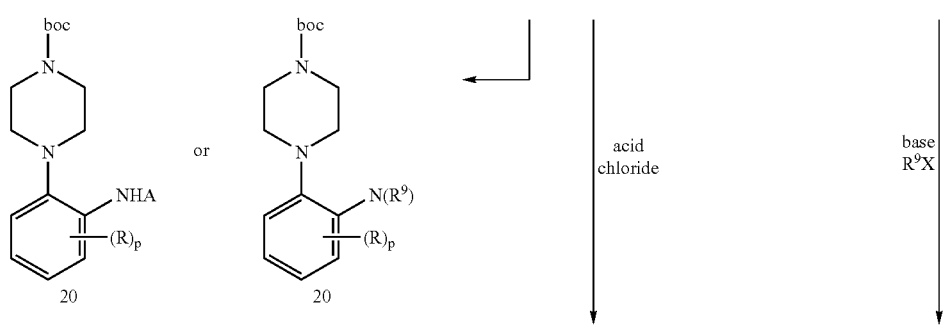

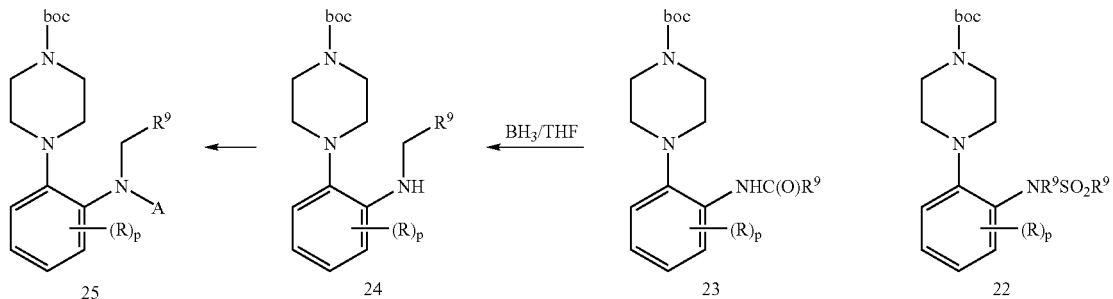

A = SO₂R⁹, SO₂N(R⁹)₂, C(O)R⁹, C(O)OR⁹, C(O)SR⁹, C(O)N(R⁹)₂ and etc.

As shown in Reaction Scheme 7, the "A domain" of the compounds of present invention can be prepared from 1-Boc-4-(2-amino-phenyl)-piperazine 19 which is prepared from 4-(2-nitro-phenyl)-piperazine 18 by Boc protection followed by nitro reduction. 1-Boc-4-(2-amino-phenyl)-piperazine 19 can be transformed to other aniline derivatives 20 using various methods known to the skilled artisan. Sulfonamides 21 could be prepared from 1-Boc-4-(2-amino-phenyl)-piperazine 19 by reaction with various sulfonyl chlorides. The resulting sulfonamides 21 could then be deprotonated with NaH or K₂CO₃ in DMF followed by alkylation with various alkyl halides (R⁹X) to afford alkylated sulfonamides 22. 1-Boc-4-(2-amino-phenyl)-piperazine could also be acylated with various acid chlorides to give acetamides 23. The acetamides 23 could be reduced with BH₃-THF to give alkyl amines 24 which can be transformed to other amine derivatives 25 using various methods known to the skilled artisan.

Reaction Scheme 8:
Derivatives of 2-(N-Boc-piperazin-1-yl)-benzaldehyde

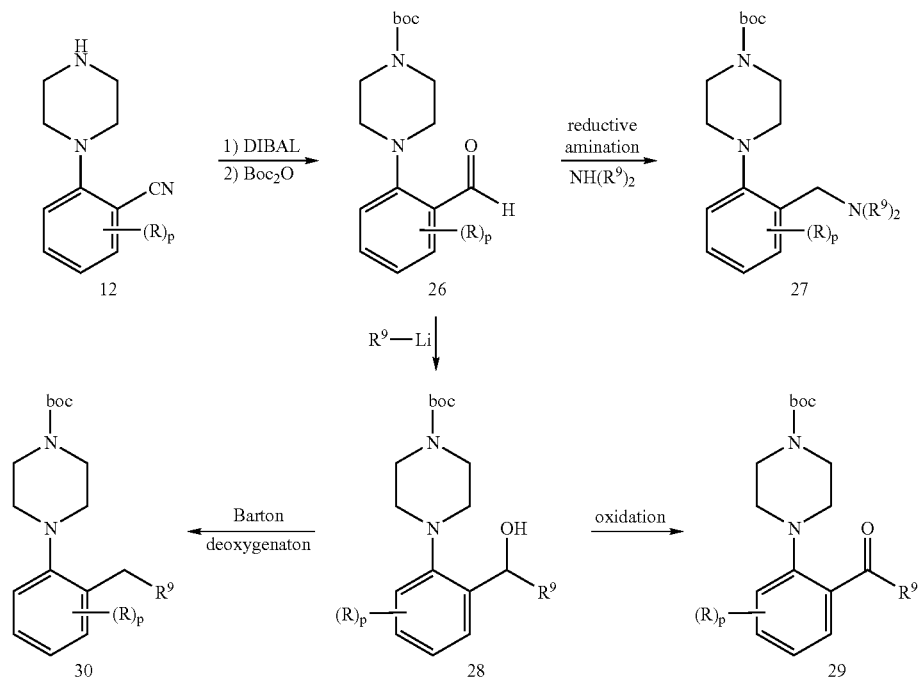

As shown in Reaction Scheme 8, the "A domain" of the compounds of present invention can be prepared by reducing the nitrile of (2-cyano-phenyl)-piperazine 12 to the corresponding aldehyde 26 with DIBAL. Aldehyde 26 can be transformed to benzyl amines 27 by reductive amination with various amines including nitrogen containing heterocycles. These benzyl amines 27 can be transformed to other amine derivatives using various methods known to the skilled artisan.

Aldehyde 26 can also be reacted with various organolithium reagents (including lithiated aryl and heteroaryl groups) to give alcohols 28. The alcohol can be oxidized to give ketones 29 or removed by Barton deoxygenation to give 30.

Reaction Scheme 9:
Derivatives of 1-Boc-4-(2-hydroxy-phenyl)-piperazine

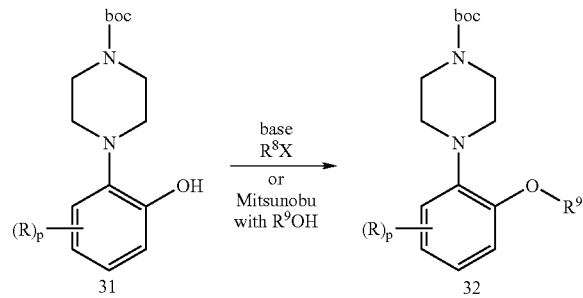

As shown in Reaction Scheme 9, "A domain" of the compounds of present invention can be prepared by treating 1-Boc-(2-hydroxy-phenyl)-piperazine 31 with a base and an alkyl halide (RX) or subjected to Mitsunobu conditions with $R^9OH$ to give ortho-substituted aryl piperazines 32.

Reaction Scheme 10:
Derivatives of 1-Boc-4-(2-carboxy-phenyl)-piperazine

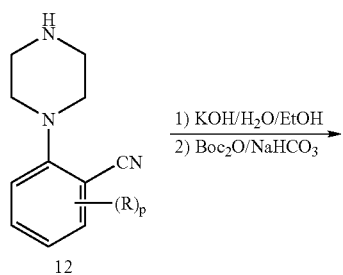

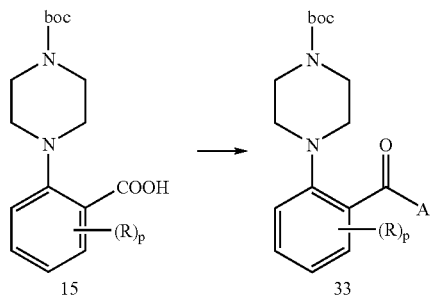

A = heterocyclyl, $N(R^9)_2$, $OR^9$ or $SR^9$ and etc.

As shown in Reaction Scheme 10, "A domain" of the compounds of present invention can be prepared by hydrolyzing the nitrite of (2-cyano-phenyl)-piperazine 12 to the corresponding carboxylic acid 15 with KOH followed by transformation to other carboxylic acid derivatives 33 using various methods known to the skilled artisan.

Reaction Scheme 11:
Tetrazoles

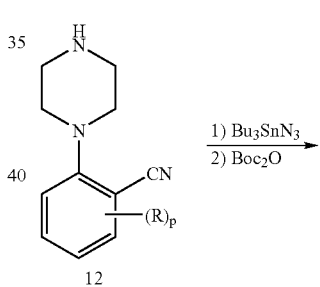

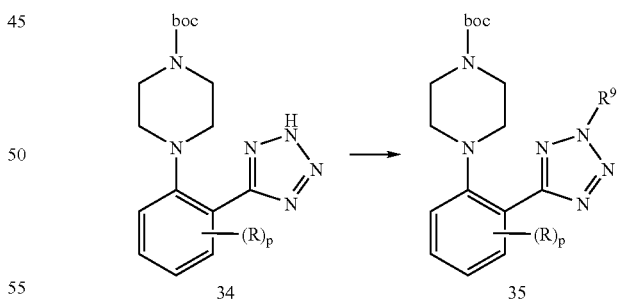

As shown in Reaction Scheme 11, "A domain" of the compounds of present invention can be prepared by reacting the nitrile of (2-cyano-phenyl)-piperazine 12 with tributyltin azide to give tetrazoles 34. The tetrazoles can be further transformed to 35 using various methods known to the skilled artisan.

The present invention also provides a novel process for preparing certain intermediates and/or compounds of the invention as shown in Reaction Schemes 12-14.

Reaction Scheme 12:

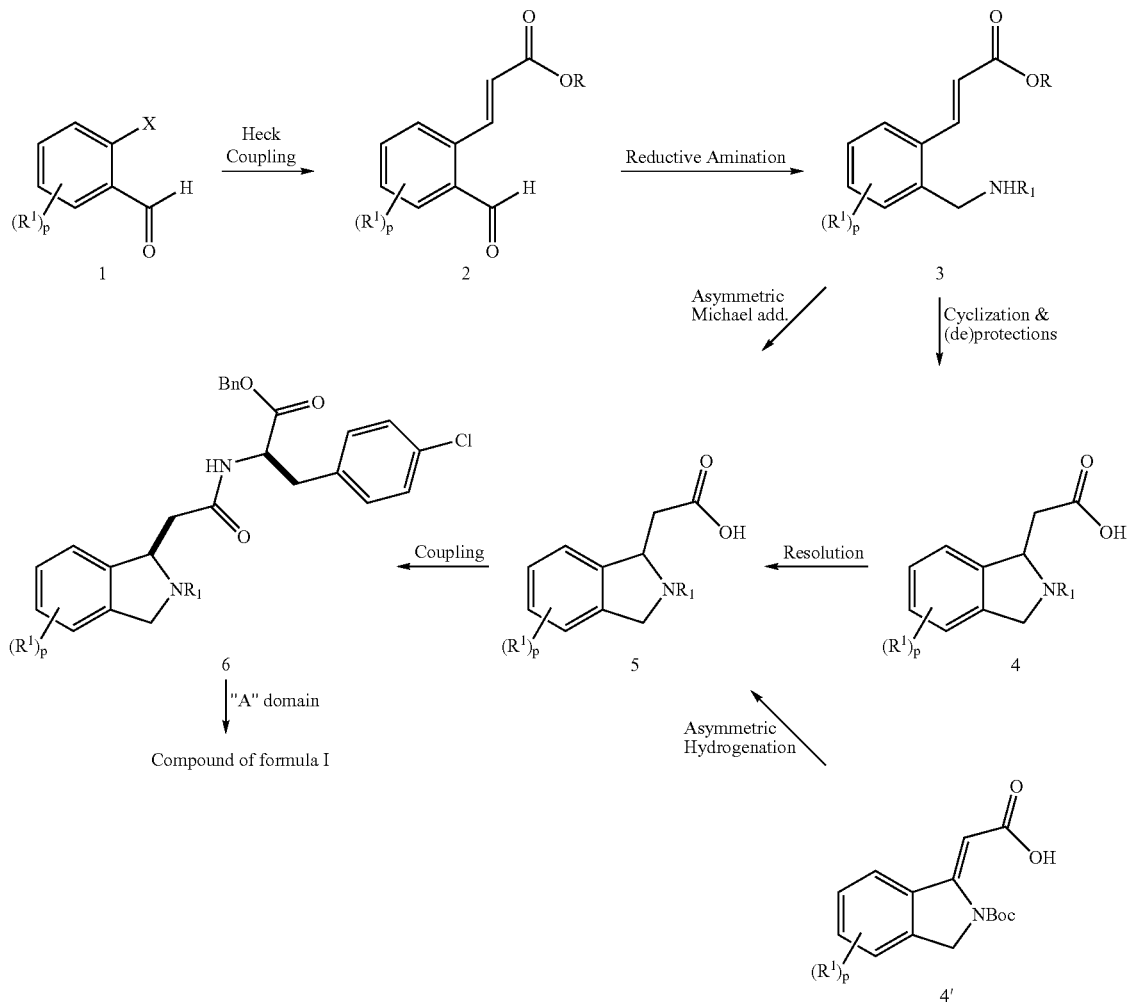

AS shown in Reaction Scheme 12, a convergent synthesis of a key intermediate isoindoline (5) via a Heck coupling, followed by a reductive amination, a ring cyclization and a resolution has been developed. Also, alternate asymmetric approaches including asymmetric Michael addition and asymmetric hydrogenation have also been developed to prepare compounds of the invention and/or intermediates thereof.

As shown in Reaction Scheme 12, the isoindoline compounds of the present invention may be prepared from 2-halobenzaldehyde 1 or substituted analog thereof. Preferred starting material is 2-bromobenzaldehyde or substituted analog thereof. Pd-mediated Heck coupling of 2-bromobenzaldehydes 1 with for example, methyl acrylate, provided alpha, beta-unsaturated methyl esters 2, which undergoes reductive amination to give amines, 3 (or carbamates where $R_1$ is for example, Boc). Various Heck coupling reagents and conditions were found suitable to effect the coupling reaction. Suitable catalysts and ligands include $Pd(OAc)_2/PPh_3$, $Pd(OAc)PPh_3/BU_4NBr$, $Pd(PPH_3)_2Cl_2/CUI$, $Pd(OAC)_2/P(O-Tol)_3$. Suitable solvent or solvent systems for the Heck coupling reaction include DMF, toluene and ethyl acetate. More preferred base is triethylamine.

Reductive amination of the aldehyde functionality of 2 to amines is accomplished in good yields by reaction with benzylamine or alpha-methylbenzylamine in acidic conditions, followed by in situ reduction of the incipient imines with $NaCNBH_3$ at about pH 5. Other reducing agents including $Na(OAc)_3BH$ and $NaBH_4/H$ may also be used to effect reduction of the incipient imines. Interestingly, the resulting amines immediately cyclized to the isoindoline compounds under the same acidic conditions for the reduction. Direct preparation of compound 4 may also be effected by use of $BocNH_2$ instead of benzylamine in the reductive amination step. Screening of various reducing agents demonstrated that the combination of $Et_3SiH$ and TFA in $CH_3CN$ represents the preferred method for effecting reductive amination using $BocNH_2$.

The N-Boc isoindolinecarboxylic acid 5 may also be prepared from 3 as the carbamate, by an intra-molecular Michael addition and ester hydrolysis. The resolution of the isoindolinecarboxylic acids 4 by crystallization afforded enantio-pure compounds 5.

Two alternate asymmetric approaches have also been developed for the synthesis of isoindolinecarboxylic acid 5 i.e., asymmetric Michael additions and asymmetric hydrogenation. In the asymmetric Michael addition approach, alpha-methylbenzyl amine is used as a chiral auxiliary to induce the enantio-selectivity. In the asymmetric hydrogenation approach, compound 4' could be converted to 5 stereoselectively in the presence of chiral ligands.

Finally the coupling of the isoindolines 5 with the "B" domain piece, i.e., D-Cl-Phe to afford compound 6 ("BC" piece) is accomplished by standard amino acid coupling reactions such as, for example, by the use of EDC or EDCI or other activating agents in the presence of suitable is dimethylaminopyridine (DMAP). The product (6) is then coupled with an "A" domain piece to afford the target MC4R agonist compound of formula I by coupling reactions known to one of skill in the art.

Preferably, the isoindole or other "C" domain piece is coupled to an "AB" coupled domain piece to form the compound of formula I.

Reaction Scheme 13:

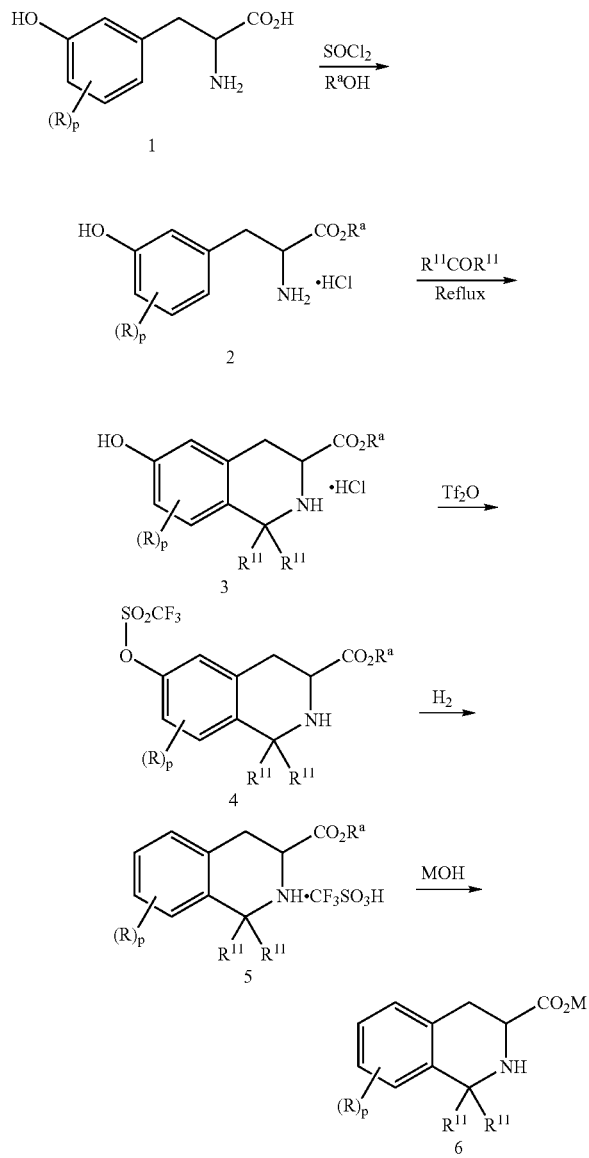

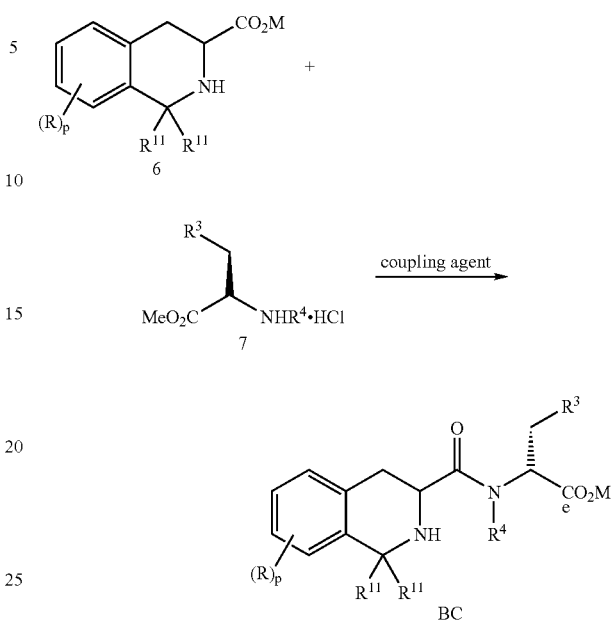

$M = Li^+, K^+, Na^+$

As shown in Reaction Scheme 13, m-tyrosine ester or analogs, including substituted analogs thereof, may be esterified by forming the acid halide followed by nucleophilic displacement of halide by the alkoxy group from an alcohol, i.e., methanol or ethanol. Where thionyl chloride or other halide source is used the product may be isolated as the acid addition salt (2). The resulting ester (2) is subjected to a Pictet-Spengler reaction by heating with a suitable ketone or aldehyde in refluxing conditions. For example, an unsubstituted isoquinoline backbone (3) may be formed by employing formaldehyde in the pictet-Spengler reaction. On the other hand, a gem-dimethyl substituted isoquinoline wherein $R^{11}$ is methyl, may be formed by using acetone as the ketone source and solvent. Other less reactive substituents may be substituted as the $R^{11}$ group for the practice of the present invention.

The product isoquinoline (3) may be isolated preferably as the acid addition salt. Where m-tyrosine is used as the starting material, the free hydroxyl group is removed first by protection/activation with a good leaving group such as, for example, reaction with triflic anhydride (trifluoromethane sulfonic anhydride) or methanesulfonic acid to form the triflate or mesylate in the presence of a base. The triflate is a preferred group used to set up the compound (3) for deoxygenation because of the extra electron withdrawing effect of the trifluoromethane substituent. The deoxygenation reaction is effected by hydrogenation at pressures of about 50 psi. The product (4) may be isolated as the acid addition salt. The product (4) is hydrolyzed under basic conditions to afford the acid salt. Suitable bases for the above hydrolysis include aqueous sodium hydroxide, potassium hydroxide and sodium lithium hydroxide. The reaction is preferably performed in a mixture of aqueous and organic solvents. An exotherm during addition of base may be regulated (i.e., less than about 35° C.) to avoid overheating or "runaway reactions." The reaction product may be isolated by aqueous work up. Alternatively, the entire mixture may be concentrated and washed with organic solvents to afford the desired product (6) after crystallization.

The product (6) is then reacted with a "B" domain substrate such as, for example, 4-chloro-D-phenylalanine as described previously and in the experimental section. The resulting "BC" combination product is then reacted with an "A" domain piece to form the respective compound of formula I. Alternatively, the product (6) may be reacted with an "AB" domain combination product to afford a compound of formula I.

One of skill is aware that certain protections and deprotections of intermediates in Reaction Scheme 13, to form the carbamate, substituted amine or free amine at the isoquinolinyl nitrogen are possible and contemplated as within the scope of this invention. Unless otherwise specified, reagents and procedures for effecting the reactions described herein are known to one of skill in the art and may be found in general reference texts such as *Advanced Organic Chemistry* by J. March, 5$^{th}$ edition, Wiley Interscience Publishers, New York, N.Y., and references therein.

In an alternate procedure, the isoquinoline product i.e., compound (3) or (5) including their N-protected analogs may be resolved by reaction with a resolving agent such as for example, L-tartaric acid, dehydroabietylamine or other resolving agents known to one of skill in the art.

Alternatively, asymmetric analogs of product (6) may be prepared by using asymmetric starting materials. For example, L-DOPA may be used in place of m-tyrosine ester in reactions essentially similar to those described and illustrated in Reaction Scheme 13, and in the examples, to afford the asymmetric analog of compound (6).

Tetrahydroisoquinoline acetic acid derivatives may be prepared and utilized as shown in Reaction Scheme 14 below:

As shown in Reaction Scheme 14, a compound of formula 10a wherein X is halogen, preferably bromo or chloro, and R and $R^{11}$ are as defined previously, and which is obtained commercially or prepared from commercial starting materials is reacted with cyanomethylethylacetate to afford a compound of formula 10b. The compound of formula 10b may be protected as the compound 10c with a suitable protecting group (Pg) and then subjected to hydrogenation conditions including for example asymmetric hydrogenation to form a compound of formula 10d, which may be chiral (depending on hydrogenation conditions, i.e., asymmetric versus non-asymmetric hydrogenation). The compound of formula 10d or stereoisomer thereof, is reacted with a B-domain piece such as, for example, 4-chloro-D-phe to afford a BC piece (10e). The compound of formula 10e is then reacted with an A-domain piece to afford a compound of formula I. The details of the specific reaction steps are similar to or analogous to reactions taught herein, and in the experimental section. Furthermore, one of skill in the art is aware of that such intermediate reactions as hydrolysis and deprotection may be necessary to achieve optimum yields in certain steps of the scheme as shown. One of skill in the art is also aware of further common manipulations such as N-alkylation, or N-acylation, and alkylations on the benzene ring to afford other compounds of formula I.

The following describes the detailed examples of A Domain preparation.

Reaction Scheme 14:

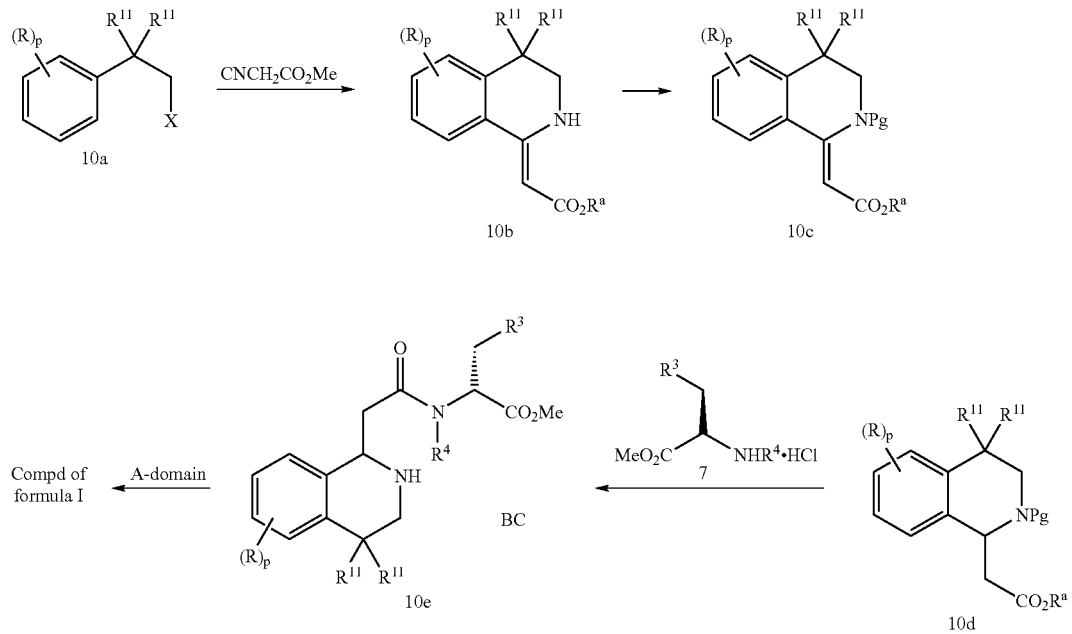

Preparation 1A (Buchwald Using NaOtBu)

(3R)-3-methyl-(2-methylthiophenyl)piperazine

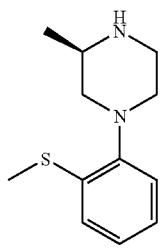

2-Bromothioanisole (300 mg, 1.48 mmol), (R)-2-methylpiperazine (185 mg, 1.85 mmol), Pd$_2$(dba)$_3$ (32 mg, 0.35 mmol), BINAP (41 mg, 0.66 mmol), sodium t-butoxide (200 mg, 2.08 mmol) and anhydrous toluene (3 ml) were combined in a 15 ml round-bottomed flask. The atmosphere in the flask was evacuated and flushed with nitrogen (3×). The mixture was lowered into an oil bath heated to 100° C. After heating for about 1.2 hours, the mixture was cooled, diluted with ethyl acetate (100 ml), filtered through Celite, and concentrated to a crude oil (285 mg). The oil was loaded onto an cation exchange column, and the column was flushed with methanol (100 ml), and then with 2 M ammonia/methanol (100 ml). The basic methanol solution was concentrated to an oil (250 mg). The oil was further purified by flash chromatography using 19:1 dichloromethane: 0.5 M ammonia/methanol as eluent to yield the final product (160 mg, 58%) as an oil. LRMS (ESI+): 223.0 (M+1)

Preparation 2A (Buchwald Using CsCO$_3$)

4-(2-diethylcarbamoyl-phenyl)-piperazine

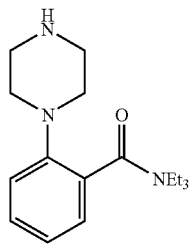

HOBT (2.72 g, 10.08 mmol), DIPEA (3.52 mL, 20.16 mmol), 2-bromo benzoic acid (4.08 g, 10.08 mmol), and diethyl amine (2.08 mL, 10.08 mmol) were dissolved in DCM (100 mL) and stirred at r.t. for about 30 minutes. EDCI (3.86 g, 10.08 mmol) was added, and the mixture was stirred at r.t. for about 16 hours. The reaction was concentrated to an oil, and the oil was purified via column chromatography to give 2-bromo-N,N-diethyl-benzamide (3.35 g, 68%) as a yellow oil.

Piperazine (489 mg, 4.8 mmol), 2-bromo-N,N-diethyl-benzamide (1 g, 3.95 mmol), Pd$_2$(dba)$_3$ (235 mg, 0.2 mmol), BINAP (442 mg, 0.6 mmol), and cesium carbonate (3 g, 5.53 mmol) were mixed together in toluene (20 mL). The mixture was degassed and heated to 100° C. for about 72 hours. The mixture was diluted with ether (100 mL) and filtered over celite. The filtrate was concentrated and then subjected to chromatography on silica gel to give the title compound (480 mg, 47%) as a brown oil. LRMS (ESI+): 262.2 (M+1)

Preparation 3A

1-Boc-4-(2-piperazin-1-yl-benzoyl)-piperazine

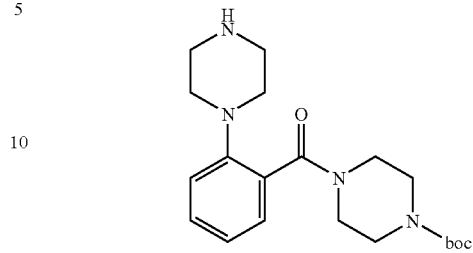

Boc protected piperazine (849 mg, 4.56 mmol) was dissolved in DCM (20 mL) and triethyl amine (2.54 mL, 18.2 mmol) was added. To the stirred solution, ortho-bromo benzoyl chloride (2 g, 9.11 mmol) was added via syringe under nitrogen. The system was stirred for about 12 hours at r.t. The reaction was washed with water, dried, filtered, and concentrated. The residue was subjected to chromatography on silica gel to give 1-Boc-4-(2-bromo-)-piperazine (1.48 g, 8.85 mmol) as a white foam. 1-Boc-4-(2-bromo-benzoyl)-piperazine was coupled to piperazine in a manner similar to Preparation 1A. LRMS (ESI+): 375.2 (M+1)

Preparation 4A 1-(2-Methoxy-5-nitro-phenyl)-piperazine

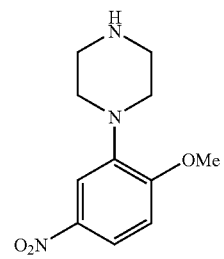

1-(2-Methoxy-5-nitro-phenyl]piperazine was prepared in a manner similar to Preparation 1A except that piperazine was coupled to 2-bromo-1-methoxy-4-nitro-benzene. LRMS (ESI+): 238.4 (M+1)

Preparation 5A 1-(2-Methyl-6-nitro-phenyl)-piperazine

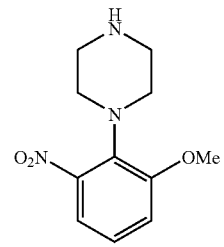

1-(2-Methyl-6-nitrophenyl]piperazine was prepared in a manner similar to Preparation 1A except that piperazine was coupled to 2-bromo-1-methyl-3-nitro-benzene. LRMS (ESI+): 222.4 (M+1)

Preparation 6A 1-(2-isopropoxy-phenyl)-piperazine

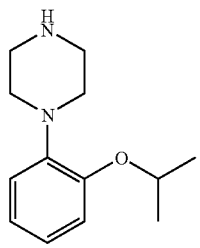

The title compound was prepared in a manner similar to Preparation 1A except that piperazine was coupled to 1-bromo-2-isopropoxy-benzene. LRMS (ESI+): 221.4 (M+1)

Preparation 7A 1-(2-isopropyl-phenyl)piperazine

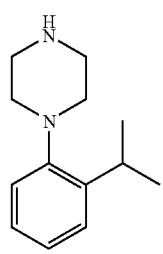

The title compound was prepared in a manner similar to Preparation 1A except that piperazine was coupled to 1-bromo-2-isopropyl-benzene. LRMS (ESI+): 205.4 (M+1)

Preparation 8A 1-(2-isopropyl-5-methyl-phenyl)piperazine

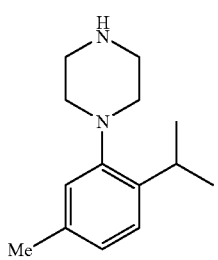

The title compound was prepared in a manner similar to Preparation 1A except that piperazine was coupled to 1-bromo-5-methyl-2-isopropyl-benzene.

$^1$H NMR (CDCl$_3$) δ7.05-7.00 (m, 1H), 6.85-6.75 (m, 2H), 3.95 (s, 1H), 3.10-3.00 (m, 4H), 2.95-2.90 (m, 4H) 2.30 (s, 3H,), 1.25-1.20 (m, 6H).

Preparation 9A 1-(2-cyclohexyl-phenyl)piperazine

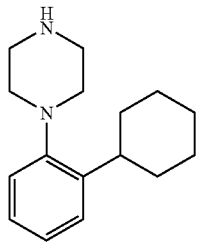

The title compound was prepared in a manner similar to Preparation 1A except that piperazine was coupled to 1-bromo-2-cyclohexyl-benzene.
LRMS (ESI+): 245.1 (M+1)

Preparation 10A

1-[2-(1,1-Difluoro-ethyl)-phenyl]-piperazine

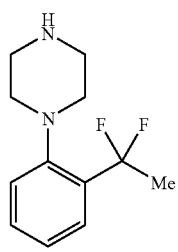

A solution of diethylaminosulfur trifluoride (560 mg, 3.47 mmol, 3 eq) and 2-bromoacetophenone (230 mg, 1.16 mmol, 1.0 eq) was heated to 40° C. for about 72 hours. The solution was diluted with CH$_2$Cl$_2$ and washed with saturated sodium bicarbonate, water, brine, dried over Na$_2$SO$_4$, filtered, and concentrated. Purification by flash chromatography (35 g SiO$_2$, linear gradient 0-10% ethyl acetate/Hexanes, 30 mL/minute, over 30 minutes) afforded about 125 mg (0.57 mmol, 49%) of 2-(1,1-difluoroethyl)-1-bromobenzene. GC/MS (EI): 220 (M+H). 2-(1,1-Difluoroethyl)-1-bromobenzene was coupled to piperazine in a manner similar to Preparation 1A. LRMS (ESI+): 227.2 (M+1)

Preparation 11A (S)-1-{2-[1-(tert-Butyl-dimethyl-silanyloxy)-ethyl]-phenyl}-piperazine

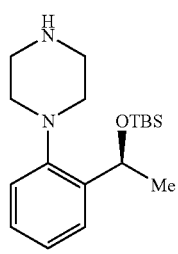

To a 25 mL flask containing (S)-(−)-2-bromo-alpha-methylbenzyl alcohol (200 mg, 1.0 mmol), tert-butyldimethylsilyl chloride (165 mg, 1.1 mmol), and imidazole (203 mg, 3.0 mmol) flushed with nitrogen was added 5 mL of dimethylformamide. After stirring overnight, the mixture was quenched with saturated sodium bicarbonate, diluted with ethyl acetate, washed with $NaH_2PO_4$, saturated aqueous sodium bicarbonate, water, brine, dried ($Na_2SO_4$), filtered, and concentrated. Purification by flash chromatography (10 g $SiO_2$, linear gradient 0-10% ethyl acetate/Hexanes, 30 mL/minute, over 30 minutes) gave about 260 mg (0.82 mmol, 82%) of (5)-[1-(2-Bromo-phenyl)-ethoxy]-tert-butyl-dimethyl-silane as a colorless oil. GC/MS (EI): 315 (M). The (5)-[1-(2-Bromo-phenyl)-ethoxy]-tert-butyl-dimethyl-silane was coupled to piperazine in a manner similar to Preparation 1A. LRMS (ESI+): 321.5 (M+1)

Preparation 12A (R)-1-{2-[1-(tert-Butyl-dimethyl-silanyloxy)-ethyl]-phenyl}-piperazine

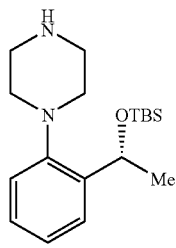

The title compound was prepared in a manner similar to Preparation 11A except that (R)-(−)-2-bromo-alpha-methyl-benzyl alcohol was used. LRMS (ESI+): 321.3 (M+1)

Preparation 13A (2R)-3-Ethyl-1-(2-methylthiophenyl)piperazine

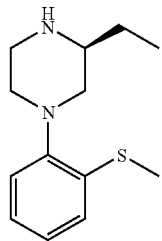

The title compound was prepared in a manner similar to Preparation 1A. LRMS (ESI+): 237.1 (M+1)

Preparation 14A (3S)-3-Methyl-1-(2-methylthiophenyl)piperazine

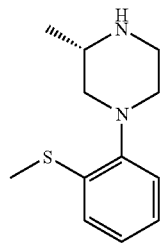

The title compound was prepared in a manner similar to Preparation 1A.

Preparation 15A 1-(2-Ethylphenyl)piperazine

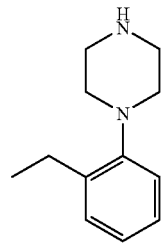

The title compound was prepared in a manner similar to Preparation 1A. LRMS (ESI+): 191.2 (M+1)

Preparation 16A (2R)-2-methyl-1-(2-methylthophenyl)piperazine

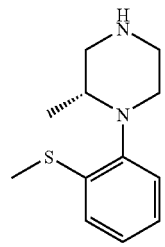

(2R)-4-Benzyl-2-methyl-1-(2-methylthiophenyl) piperazine was prepared in 26% yield from ortho-bromothioanisole and (R)-3-methyl-1-benzylpiperazine in a manner similar to Preparation 1A. LRMS (ESI+): 223.2 (M+1)

(2R)-4-Benzyl-2-methyl-1-(2-thiomethylphenyl) piperazine (24 mg, 0.077 mmol) was dissolved in 1,2-dichloroethane (4 ml) and cooled in an ice bath. To the chilled solution was added 1-chloroethyl chloroformate (38 microliters, 50 mg, 0.35 mmol) in one portion. The solution was covered with a nitrogen atmosphere and then heated to 50° C. After stirring at 50° C. for about 1.25 hours, the solution was concentrated under reduced pressure and then dissolved in methanol (6 ml). The methanolic solution was covered with a nitrogen atmosphere and allowed to stir overnight at r.t. The solution was concentrated to give about 21 mg of crude oil. Flash chromatography (10% 0.5 M $NH_3$/methanol in DCM as eluent) yielded the final compound (14 mg, 82%). LRMS (ESI+): 223.2 (M+1)

Preparation 17A (2S)-2-Methyl-1-(2-methylthiophenyl)piperazine

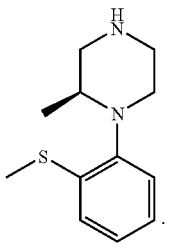

The title compound was prepared in a manner similar to Preparation 16A. LRMS (ESI+): 223.2 (M+1)

Preparation 18A

1-[2-(2-Methyl-propane-1-sulfonyl)-phenyl]-piperazine

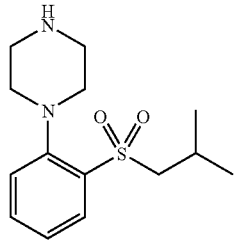

To a solution of 2-bromobenzene thiol (10.0 g, 52.8 mmol, 1.0 eq.) in DMF (250 mL) was added K₂CO₃ (17.5 g, 126.7 mmol, 2.4 eq.) and isobutyl iodide (7.3 mL, 63.36 mmol, 1.2 eq). The reaction was warmed to about 40° C. and stirred overnight. The mixture was diluted with EtOAc (300 mL) and washed with water (100 mL) and brine (100 mL). The organic layer was extracted with EtOAc(2×). The combined organic extracts were dried (Na₂SO₄), filtered and concentrated to afford 1-bromo-2-isobutylsulfanyl-benzene (12.94 g, 52.8 mmol, 100%), which is then taken to the next step without any further purification. GCMS (EI): 244.0

To a solution of 1-bromo-2-isobutylsulfanyl-benzene (8.0 g, 32.6 mmol, 1.0 eq) in DCM (100 mL) at 0° C. was added CaCO₃ (13.05 g, 130.4 mmol, 4.0 eq.) and MCPBA (28.1 g, 81.5 mmol, 2.5 eq.). The mixture was stirred for about 30 minutes and filtered through a pad of celite. The solution was washed with sodium bisulfite (2×) and 5N NaOH (2×). The organic layer was dried (Na₂SO₄), filtered and concentrated. Purification by flash chromatography (250 g SiO₂, linear gradient, 40 mL/min, 10%-40% EtOAC/hexane for about 33 minutes) afforded 1-bromo-2-(2-methyl-propane-1-sulfonyl)-benzene (7.4 g, 26.6 mmol, 82%). GCMS (EI): 276.0. 1-bromo-2-(2-methyl-propane-1-sulfonyl)-benzene was coupled to piperazine in a manner similar to Preparation 1A. LRMS (ESI+): 283.06 (M+1)

Preparation 19A (SNAr)

1-(2-aminosulfonyl-phenyl)piperazine

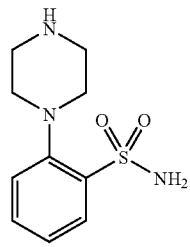

To a 50 mL flask containing 2-flourobenzene sulfonamide (200 mg, 1.14 mmol, 1 eq.) and piperazine (245 mg, 2.84 mmol, 2.5 eq) was added 20 mL of dioxane. The solution was heated to 100° C. for about 4 hours. More piperazine (200 mg, 2.32 mmol, 2 eq.) was added and the solution was heated to 100° C. for another 72 hours. The solution was concentrated to an oil and dissolved in 30 mL of 0.1 M pH 7.0 phosphate buffer. The aqueous solution was extracted with CH₂Cl₂ (3×30 mL). The combined organic extracts were dried over Na₂SO₄ and concentrated to yield about 275 mg (1.14 mmol, 100%) of the title compound. LRMS (ESI+): 242.1 (M+H).

Preparation 20A

1-Boc-4-(3-Chloro-2-cyano-phenyl)-piperazine

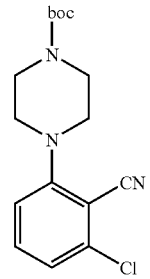

To a solution of N-Boc-piperazine (2.02 g, 11.0 mmol) in DMSO (20 mL) was added 2-fluoro-6-chlorobenzonitrile (1.55 g, 10 mmol) and potassium carbonate (1.52 g, 11 mmol). The mixture was stirred at 80° C. for about 48 hours. The mixture was cooled to r.t. and diluted with diethyl ether (200 mL). The solution was washed with 1N HCl (2×20 mL), H₂O (3×20 mL) and brine (20 mL) and then dried over sodium sulfate and concentrated to a yellow oil. Purification by flash chromatography (4:1 hexanes/ethyl acetate) gave the title compound (2.5 g, 86%) as a colorless oil.

¹H NMR (CDCl₃) δ7.40-7.50 (m, 1H,), 7.10-7.20 (m, 1H), 6.80-6.90 (m, 1H), 3.70 (s, 4H), 3.20 (s, 4H), 1.48 (s, 9H). TLC (SiO₂): 0.48 (4:1 hexanes/ethyl acetate)

Preparation 21A

1-Boc-4-(3-Chloro-2-dimethylaminomethyl-phenyl)-piperazine

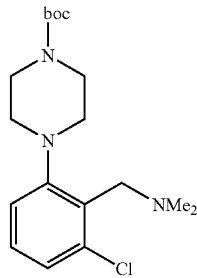

Sodium borohydride (1.2 g, 31.4 mmol) was dissolved in THF (20 mL) and TFA (2.42 mL, 31.4 mmol) in THF (20 mL) was added dropwise at 0° C., and the reaction was stirred for about 30 minutes. 1-Boc-4-(3-Chloro-2-cyano-phenyl)-piperazine (2.0 g, 6.3 mmol) was dissolved in ThF (20 mL) and added dropwise to the solution at 0° C., and the reaction was stirred for about 24 hours. The reaction was carefully quenched with H₂O and ethyl acetate (200 mL) was added. The mixture was washed with H₂O (3×25 mL), brine (25 mL) and dried over MgSO₄. The solvents were removed in vacuo and the crude reaction mixture was dissolved into acetonitrile (7 mL). Formalin (1.6 mL, 59.2 mmol) was added, followed by sodium cyanoborohydride (0.26 g, 7.4 mmol) at 0° C. The reaction was warmed to r.t. and stirred for about one hour. The reaction was quenched with H₂O and ethyl acetate (100 mL) was added. The solution was washed with saturated NaHCO₃ (2×10 mL) and dried over MgSO₄. Purification by silica gel chromatography (1:1 hexanes/ethyl acetate) gave the title compound as a yellow oil (180 mg, 13%).

¹H NMR (CDCl₃) δ7.10-7.15 (m, 2H,), 6.92-6.98 (m, 1H), 3.68 (s, 2H), 3.50-3.60 (m, 4H), 2.90-2.97 (m, 4H), 2.25 (s, 6H), 1.48 (s, 9H). TLC (SiO₂): 0.28 (1:1 hexanes/ethyl acetate)

Preparation 22A

1-Boc-4-(2-cyano-phenyl)-[1,4]diazepane

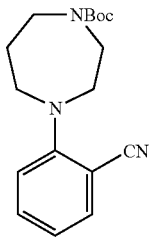

To a solution of 1-Boc-homopiperazine(2.18 g, 11.0 mmol) in DMSO (20 mL) was added 2-fluorobenzonitrile (1.21 g, 1.08 mL, 10 mmol) and potassium carbonate (1.52 g, 11 mmol). The mixture was stirred at 80° C. for about 48 hours. The mixture was cooled to r.t. and diluted with diethyl ether (200 mL). The solution was washed with 1N HCl (2×20 mL), H₂O (3×20 mL) and brine (20 mL), dried over sodium sulfate and concentrated to a yellow oil. Purification by flash chromatography (3:1 hexanes/ethyl acetate) gave the title compound (1.1 g, 36%) as a colorless oil.

¹H NMR (CDCl₃) δ7.49 (dd, J=6.7, 1.7 Hz, 1H), 7.38 (td, J=7.3, 1.7 Hz, 1H), 6.92 (d, J=8.5 Hz, 1H), 6.83 (t, J=7.4 Hz, 1H), 3.63-3.66 (m, 2H), 3.46-3.57 (m, 6H), 2.01-2.10 (m, 2H), 1.40-1.45 (m, 9H). TLC (SiO₂): R_f=0.38 (3:1 hexanes/ethyl acetate)

Preparation 23A

1-Boc-4-(2-dimethylaminomethyl-phenyl)-[1,4]diazepane

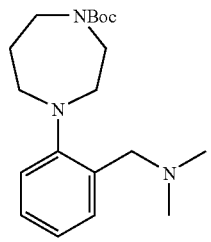

A solution of 1-Boc-4-(2-Cyano-phenyl)-[1,4]diazepane (600 mg, 2.0 mmol) and Raney nickel (50% dispersion in H₂O, 1 mL) in methanol (50 mL) was stirred under hydrogen (1 atm) for about 16 hours. Formalin (2 mL) was added and the solution was stirred a further 24 hours. The mixture was filtered through celite. The filter cake was rinsed with methanol (100 mL) and the filtrate was concentrated to a clear oil. Purification by flash chromatography (1% methanol/ethyl acetate) gave the title compound (285 mg, 55%) as a colorless oil.

¹H NMR (CDCl₃) δ7.39 (d, J=7.4 Hz, 1H), 7.19 (t, J=7.4 Hz, 1H), 7.03-7.10 (m, 2H), 3.53-64 (m, 4H), 3.52 (s, 2H), 3.04-3.08 (m, 4H), 2.25 (s, 6H), 1.88-1.94 (m, 2H), 1.49 (s, 9H). TLC (SiO₂): R_f=0.40 (ethyl acetate)

Preparation 24A (SNAr then Buchwald)

1-(2-cyclohexyloxy-phenyl)-piperazine

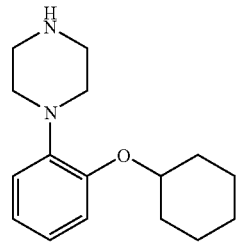

NaH (8.4 g, 210 mmol, 60% in mineral oil) was slurred in DMF (40 mL) and heated to about 65° C. To the slurry was added cyclohexanol (7 g, 69.9 mmol) dissolved in DMF (50 mL). The mixture was stirred at 65° C. for about 1 hour. Ortho-fluoro bromobenzene (9.2 mL, 83.9 mmol) was added dropwise in DMF (10 mL) and the mixture was stirred at 65° C. for about 16 hours, and quenched with water and diluted with DCM. The mixture was concentrated to an oily solid and extracted between water and 1/1 EtOAc/hex. The organic layer was dried, filtered and concentrated. Chromatography on silica gel (EtOAc/hexanes) gave 1-bromo-2-cyclohydroxy-benzene (6.13 g, 34%) as a yellow oil. 1-Bromo-2-cyclohexyloxy-benzene was coupled to piperazine using the Buchwald chemistry described in preparation 1A. LRMS (ESI+): 261.1 (M+1)

Preparation 25A 1-(2-cycloheptyloxy-phenyl)-piperazine

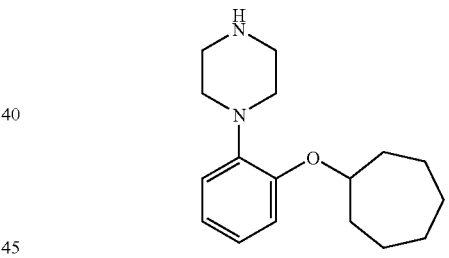

The title compound was prepared in a manner similar to preparation 24A except that cycloheptanol was used. LRMS (ESI+): 275.2 (M+1)

Preparation 26A

1-[2-(3,3-dimethyl-cyclohexyloxy-phenyl)]-piperazine

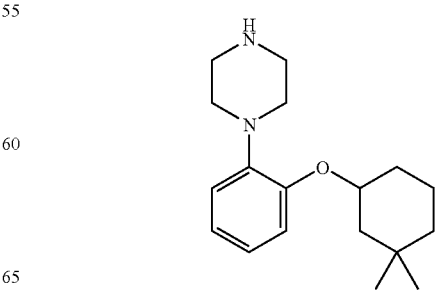

The title compound was prepared in a manner similar to preparation 24A except that 3,3-Dimethyl-cyclohexanol was used. LRMS (ESI+): 289.2 (M+1)

Preparation 27A 1-(2-cyclopentyloxy-phenyl)-piperazine

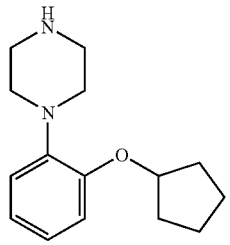

The title compound was prepared in a manner similar to preparation 24A except that cyclopentanol was used. LRMS (ESI+): 247.1 (M+1)

Preparation 28A

1-[2-(tetrahydro-thiopyran-3-yloxy)-phenyl]-piperazine

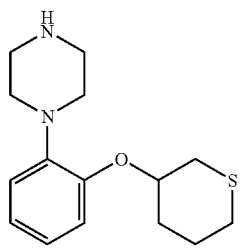

The title compound was prepared in a manner similar to preparation 24A except that tetrahydro-thiopyran-3-ol was used. LRMS (ESI+): 279.2 (M+1)

Preparation 29A

1-[2-(tetrahydro-pyran-3-yloxy)-phenyl]-piperazine

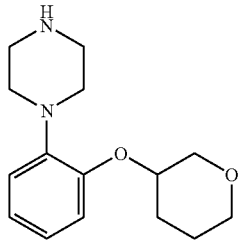

3-hydroxy-tetrahydro pyrane was prepared according to Brown, Herbert C.; Prasad, J. V. N. Vara; Zee, Sheng-Hsu; J.Org.Chem. 50 (10), 1985, 1582-1589. The compound was reacted with ortho-fluoro bromobenzene followed by Buchwald coupling in a manner similar to preparation 24A to afford the title compound. LRMS (ESI+): 263.1 (M+1)

Preparation 30A

1-[2-(1,1-Dioxo-hexahydro-1λ$^6$-thiopyran-4-yloxy)-phenyl]piperazine

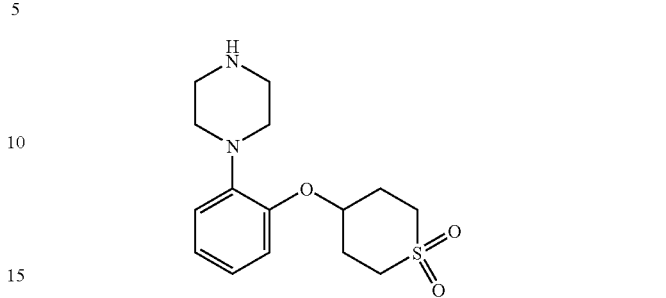

Ortho-fluoro bromobenzene was reacted with tetrahydro-thiopyran-3-ol to give 4-(2-Bromo-phenoxy)-tetrahydro-thiopyran in a manner similar to preparation 24A. 4-(2-Bromo-phenoxy)-tetrahydro-thiopyran (1.94 g, 7.10 mmol) is placed in DCM (70 mL) and calcium carbonate (2.84 g, 28.41 mmol) was added. To this mixture cooled to 0° C. in an ice bath was added meta-chloro peroxy-benzoic acid (6.13 g, 17.75 mmol 50%) in portions while monitoring the temperature. The mixture was allowed to warm to r.t and stirred for about 15 minutes. The mixture was filtered over celite, and washed with sodium bisulfite solution (2×250 mL) and sodium bicarbonate (2×250 mL). The mixture was then concentrated to an oil. Chromatography (EtOAc/hexanes) provided 4-(2-Bromo-phenoxy)-tetrahydro-thiopyran 1,1-dioxide (2.2 g, quant.) as a yellow solid. 4-(2-Bromo-phenoxy)-tetrahydro-thiopyran 1,1-dioxide was coupled to piperazine using the Buchwald chemistry described in preparation 1A to afford the title compound. LRMS (ESI+): 311.1 (M+1)

Preparation 31A (o-arylation of 2-bromophenol Followed by Buchwald)

1-[2-(Pyridin-3-yloxy)-phenyl]-piperazine

2-Bromophenol (355 mg, 2.05 mmol), 3-pyridyl-boronic acid (500 mg, 4.1 mmol), copper acetate (745 mg, 4.1 mmol) and pyridine (3.3 mL, 41 mmol) were added to dichloromethane (41 mL) and stirred for about 48 hours under air. The reaction was diluted with water (50 mL) and the layers separated. The organic layer was washed with 5N NaOH. The organic layer was concentrated, and chromatographed on silica gel (MeOH/dichloromethane) to yield 3-(2-bromo-phenoxy)-pyridine (30 mg, 6%) as a yellow oil. MS found 249.1 M+1. 3-(2-Bromo-phenoxy)-pyridine was coupled to piperazine using the Buchwald chemistry described in preparation 1A to afford the title compound. LRMS (ESI+): 256.1 (M+1)

Preparation 32A 1-(2-Phenoxy-phenyl)-piperazine

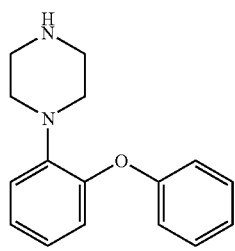

A mixture of phenylboronic acid (5.12 g, 42 mmol), 2-bromophenol (3.55 g, 21 mmol), Cu(OAc)$_2$ (7.63 g, 42 mmol), pyridine (8 ml, 103 mmol) and 4 Å molecular sieves (2.1 g) in CH$_2$Cl$_2$ was stirred at r.t. overnight. The mixture was diluted with CH$_2$Cl$_2$, filtered through celite, washed with 1M NaOH, brine and dried. Removal of solvent gave 1-bromo-2-phenoxybenzene, crystals (1.40 g, 27%). LRMS (ESI$^+$): 248 (M+1). 1-Bromo-2-phenoxybenzene was coupled to piperazine using the Buchwald chemistry described in preparation 1A to afford the title compound. LRMS (ESI+) 255 (M+1)

Preparation 33A 1-(2-m-tolyloxy-phenyl)-piperazine

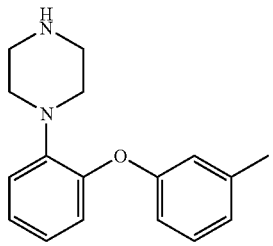

The title compound was prepared in a manner similar to Preparation 32A except that 3-methylphenyl boronic acid was used. LRMS (ESI+) 269 (M+1)

Preparation 34A 1-(2-p-tolyloxy-phenyl)-piperazine

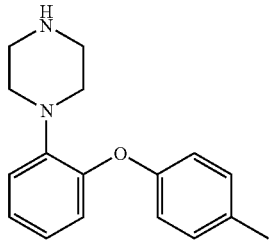

The title compound was prepared in a manner similar to Preparation 32A except that 4-methylphenylboronic acid was used. LRMS (ESI+) 269 (M+1)

Preparation 35A

1-[2-(3-chloro-phenoxy)-phenyl]-piperazine

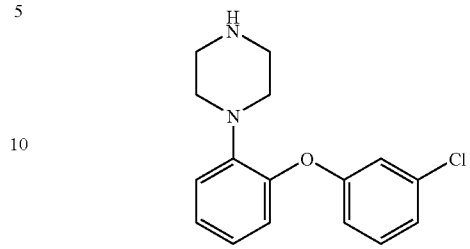

The title compound was prepared in a manner similar to Preparation 32A except that 3-chlorophenylboronic acid was used. LRMS (ESI+) 289 (M+1)

Preparation 36A

1-[2-(3-methoxy-phenoxy)-phenyl]-piperazine

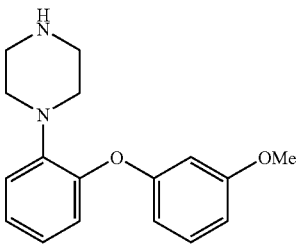

The title compound was prepared in a manner similar to Preparation 32A except that 3-methoxyphenylboronic acid was used. LRMS (ESI+) 285 (M+1)

Preparation 37A (Benzylamine from Nitrile Reduction)

1-Boc-4-(2-aminomethyl-phenyl)-piperazine

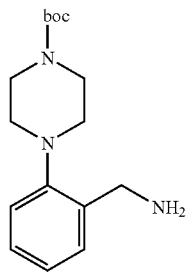

To a solution of (2-cyano-phenyl)-piperazine (2.4 g, 12.78 mmol) in THF and H$_2$O (25 mL, 1:1) was added K$_2$CO$_3$ (3.9 g, 28.12 mmol). The solution was allowed to stir for about 10 minutes at r.t. Boc-anhydride (3.1 g, 14.06 mmol) was then added and reaction was allowed to stir for 1 h. The reaction mixture was diluted with EtOAc (100 mL) and washed with sat. NaHCO$_3$ (100 mL) and brine (100 mL). The organic phase was concentrated to dryness yielding 3.2 g of 1-Boc-4-(2-cyano-phenyl)-piperazine (88%). To a solution of sodium borohydride (2.1 g, 56.03 mmol) in THF (25 mL) at 0° C. was added TFA (4.3 mL, 56.03 mmol) dropwise. 1-Boc-4-(2-cyano-phenyl)-piperazine (3.2 g, 11.21 mmol) was then added slowly at r.t. The reaction was allowed to stir for about 12 hours at r.t. The reaction was quenched with H₂O, diluted five-fold with EtOAc and washed with brine. The organic phase was concentrated to dryness yielding about 1.0 g of 1-Boc-4-(2-aminomethyl-phenyl)-piperazine (30%). MS (ESI+) 292.1 (M+1)

Preparation 38A

1-Boc-4-(2-dimethylaminomethyl-phenyl)-piperazine

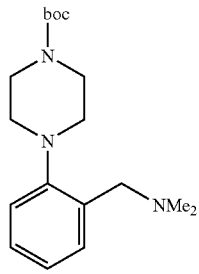

1-Boc-4-(2-aminomethyl-phenyl)-piperazine (2.0 g, 6.86 mmol) was dissolved in CH₃CN (15 mL) and cooled to about 0° C. Aqueous formaldehyde (37% wt. in H₂O) (7.56 mL) was added to the cold solution followed by the addition of sodium cyanoborohydride (2.15 g, 34.32 mmol). The reaction mixture was allowed to stir at 0° C. for about 5 minutes and then allowed to naturally warm to room temperature. The mixture was then concentrated to dryness. The resulting residue was taken up in EtOAc (100 mL) and washed with saturated NaHCO₃ solution (100 mL) and brine (100 mL). The organic phase was concentrated to dryness to afford about 2.2 g of crude material. MS (ESI+) 320.2 [M+1]

Preparation 39A

1-Boc-4-[2-(methanesulfonylamino-methyl)-phenyl]-piperazine

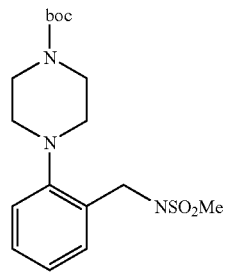

1-Boc-4-(2-aminomethyl-phenyl)-piperazine (2.09 g, 7.18 mmol) was dissolved in methylene chloride (50 mL), cooled to 0° C. and treated with triethylamine (1.5 mL, 10.8 mmol) followed by methanesulfonyl chloride (0.67 mL, 8.61 mmol). The resulting mixture was stirred for about 3 hours at r.t., and then diluted with ether (200 mL) and washed with water (50 mL), saturated aqueous sodium bicarbonate (50 mL) and brine (50 mL), which is then dried over anhydrous magnesium sulfate. Concentration under reduced pressure followed by silica gel chromatography (30% ethyl acetate in hexanes) afforded the title compound (2.07 g, 78%) as a clear oil.
¹H NMR (CDCl₃) δ7.25-7.40 (m, 2H), 7.00-7.15 (m, 2H), 4.40 (s, 1H), 3.55-3.65 (m, 4H), 2.80-2.95 (m, 4H), 2.75 (s, 3H), 1.60 (s, 9H). TLC (SiO₂): $R_f$=0.50 (50% EtOAc/hexanes)

Preparation 40A

1-Boc-4-[2-(acetylamino-methyl)-phenyl]-piperazine

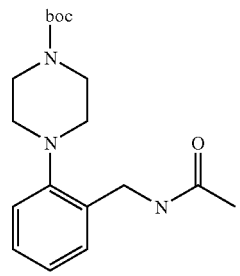

The title compound was Prepared in a similar manner to Preparation 39A except that acetic anhydride was used instead of methanesulfonyl chloride.
¹H NMR (CDCl₃) δ7.45-7.55 (m, 2H), 7.05-7.15 (m, 2H), 6.20 (s, 1H), 4.45-4.50 (m, 2H), 3.55-3.65 (m, 4H), 2.75-2.90 (m, 4H), 2.05 (s, 3H), 1.60 (s, 9H). TLC (SiO₂): $R_f$=0.15 (50% EtOAc/hexanes)

Preparation 41A

1-Boc-4-[2-(bezenesulfonylamino-methyl)-phenyl]-piperazine

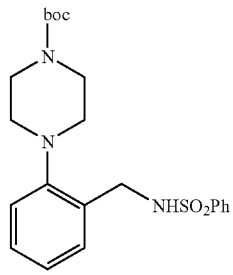

The title compound was Prepared in a similar manner to Preparation 39A except that benzenesulfonyl chloride was used instead of methanesulfonyl chloride.
¹H NMR (CDCl₃) δ6.90-7.90 (m, 9H), 5.75-5.85 (m, 1H), 4.15-4.25 (m, 2H), 3.50-3.60 (m, 4H), 2.60-2.75 (m, 4H), 1.20-1.55 (m, 9H). TLC (SiO₂): $R_f$=0.85 (100% EtOAc)

Preparation 42A

1-Boc-4-[2-(ethanesulfonylamino-methyl)-phenyl]-piperazine

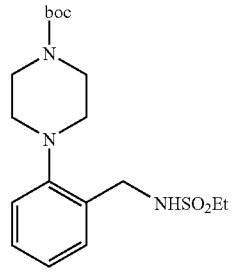

The title compound as Prepared in a similar manner to Preparation 39A except that ethanesulfonyl chloride was used instead of methanesulfonyl chloride.

¹H NMR (CDCl₃) δ7.05-7.35 (m, 4H), 4.35-4.45 (m, 2H), 3.70-3.80 (m, 5H) 2.85-2.90 (m, 6H), 1.25-1.50 (m, 12H). TLC (SiO₂): R$_f$=0.85 (100% EtOAc)

Preparation 43A

1-Boc-4-[2-(propane-2-sulfonylamino-methyl)-phenyl]-piperazine

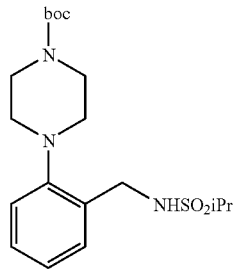

The title compound was Prepared in a similar manner to Preparation 39A except that isopropylsulfonyl chloride was used instead of methanesulfonyl chloride.

¹H NMR (CDCl₃) δ7.00-7.35 (m, 4H), 4.45-4.50 (m, 1H), 3.75-3.85 (m, 4H), 2.90-3.00 (m, 4H), 1.95-2.25 (m, 8H), 1.20-1.55 (m, 10H)

Preparation 44A

1-Boc-4-[2-(isobutyrylamino-methyl)-phenyl]-piperazine

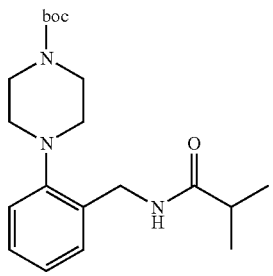

The title compound was Prepared in a similar manner to Preparation 39A except isobutyryl chloride was used instead of methanesulfonyl chloride and diisopropylethylamine was used as the base.

¹H NMR (CDCl₃) δ7.34-7.41 (m, 2H) 7.14-7.22 (m, 2 H), 6.39-6.47 (m, 1 H), 4.53-4.58 (m, 2 H), 2.78-2.95 (m, 4 H), 2.76-2.87 (m, 4 H), 1.43-1.54 (s, 9H) 1.15-1.21 (m, 6H)

Preparation 45A

[2-(propionylamino-methyl)-phenyl]-piperazine

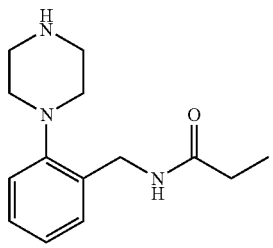

1-Boc-4-(2-aminomethyl-phenyl)-piperazine (0.75 g, 2.6 mmol) was dissolved in methylene chloride (20 mL), treated with DIPEA (2.3 mL, 13 mmol), and cooled to about 0° C. Propionyl chloride (0.20 mL, 2.34 mmol) was added and the mixture was stirred for about 1 hour at 0° C. and subsequently stirred overnight at r.t. The mixture is diluted with ethyl acetate (400 mL), washed with water (45 mL), saturated aqueous sodium bicarbonate (45 mL) and brine (45 mL), and then dried over anhydrous sodium sulfate. Concentration under reduced pressure followed by silica gel chromatography (50% ethyl acetate in hexanes) gave an oil, which was dissolved in methylene chloride (10 mL). The mixture was stirred with TFA (10 mL) for about 1.5 hours. The mixture was concentrated under reduced pressure, and the residue taken up in water (25 mL). Sodium hydroxide (1.0 g, 25 mmol) and ethyl acetate (25 mL) were added and the mixture was stirred for about 45 minutes. The organic phase was collected and the aqueous phase was extracted with ethyl acetate (45 mL). The combined organic fractions were washed with water (20 mL) and brine (20 mL) and then dried over anhydrous sodium sulfate. The solvent was concentrated under reduced pressure to yield the title compound (0.26 g, 40%) as a clear oil.

¹H NMR (CDCl₃) δ6.99-7.43 (m, 5 H), 6.46-6.71 (bs, 1 H), 4.46-4.72 (s, 2 H), 2.79-3.23 (m, 8 H), 2.14-2.43 (m, 2 H), 1.07-1.38 (m, 3 H).

Alternatively, the title compound was prepared in the following procedure: About 0.40 g (1.37 mmol) of 1-Boc-4-(2-aminomethyl-phenyl)-piperazine, 0.11 ml of (1.51 mmol) propionic acid, 0.22 g (1.64 mmol) of HOBt, 0.31 g (1.64 mmol) of EDC, and 0.24 ml (1.37 mmol) of DIEA were mixed in 30 ml THF under nitrogen and stirred overnight at r.t. The reaction was concentrated to dryness and ethyl acetate was added. The mixture was washed with saturated bicarbonate and brine, and then dried with sodium sulfate. The residue was purified by flash chromatography eluting with 1:1 hexane/ethyl acetate giving about 0.4 g (86% yield). The material was deprotected using TFA/DCM to give 4-[2-(propionylamino-methyl)-phenyl]-piperazine. LRMS (ESI+): 248 (M+1)

Preparation 46A

4-{2-[(2,2-Dimethyl-propionylamino)-methyl]-phenyl}-piperazine

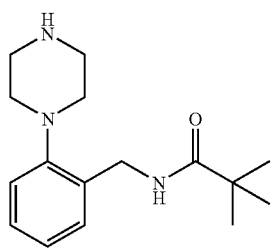

1-Boc-4-(2-Aminomethyl-phenyl)-piperazine (0.75 g, 2.6 mmol) was dissolved in methylene chloride (20 mL). DIPEA (2.3 mL, 13 mmol) was added, and the mixture was cooled to about 0° C. The solution was treated with trimethylacetyl chloride (0.28 g, 0.28 mL, 2.3 mmol) and stirred for about 1 hour at 0° C. The solution was warmed to r.t. and stirred overnight. The mixture was diluted with ethyl acetate (400 mL), washed with water (60 mL), saturated aqueous sodium bicarbonate (60 mL) and brine (60 mL) and then dried over anhydrous sodium sulfate. The solution was concentrated under reduced pressure and purified via silica gel chromatography (80% ethyl acetate in hexanes) to afford a clear oil, which was subsequently stirred in neat TFA (5 mL) for about 1 hours. The solvent was evaporated under reduced pressure and the residue taken up in water (30 mL). Sodium hydroxide (1 g, 25 mmol) and ethyl acetate (30 mL) were added, and the mixture was stirred for about 45 minutes. The organic phase was collected and the aqueous phase was extracted with ethyl acetate (60 mL). The combined organic fractions were washed with water (45 mL) and brine (30 mL) and then dried over anhydrous sodium sulfate. Concentration under reduced pressure afforded the title compound (0.54 g, 75%) as a clear oil.

$^1$H NMR (CDCl$_3$) δ6.97-7.36 (m, 4H), 6.63-6.86 (bs, 1H), 4.47-4.65 (m, 2H), 2.66-3.24 (m, 8H), 1.18 (s, 9H).

Preparation 47A

4-[2-(benzoylamino-methyl)-phenyl]-piperazine

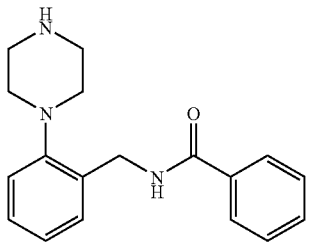

1-Boc-4-(2-Aminomethyl-phenyl)-piperazine (0.47 g, 1.6 mmol) was dissolved in methylene chloride (20 mL). DIPEA (1.5 mL, 8.5 mmol) was added, and the mixture was cooled to about 0° C. The mixture was treated with benzoyl chloride (0.20 g, 0.16 mL, 1.4 mmol). The resulting mixture was stirred for about 1 hour at 0° C., and then warmed to r.t. and stirred overnight. The mixture was diluted with ethyl acetate (500 mL), washed with water (45 mL), saturated aqueous sodium bicarbonate (45 mL) and brine (45 mL) and then dried over anhydrous sodium sulfate. The solution was concentrated under reduced pressure and purified via silica gel chromatography (50% ethyl acetate in hexanes) to afford a clear oil, which was subsequently stirred in neat TFA (5 mL) for about 1 hour. The solvent was evaporated under reduced pressure to afford the title compound as a clear oil (0.30 g, 100%).

$^1$H NMR (CDCl$_3$) δ7.32-7.84 (m, 9H), 4.71-4.86 (m, 2H), 3.42-3.65 (m, 4H), 3.24-3.42 (m, 4H).

Preparation 48A

1-Boc-4-{2-[(methanesulfonyl-methyl-amino)-methyl]-phenyl}-piperazine

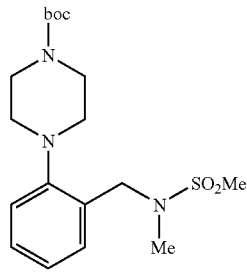

To a stirred suspension of sodium hydride (60% in oil, 113 mg, 2.82 mmol) in THF (20 mL) at 0° C. under nitrogen was added a solution of 1-Boc-4-[2-(methanesulfonylamino-methyl)-phenyl]-piperazine (0.99 g, 2.68 mmol) in THF (5 mL). The mixture was stirred for about 1 hour at room temperature. It then was cooled back to 0° C. and treated with methyl iodide (0.184 mL, 2.95 mmol). After stirring for about 20 hours, the reaction mixture was diluted with ether (150 mL) and then quenched by addition of saturated aqueous ammonium chloride (50 mL). The organic phase was separated, washed with water (50 mL) and brine (50 mL) and then dried over magnesium sulfate. Concentration under reduced pressure followed by silica gel chromatography (30% ethyl acetate in hexanes) afforded the title compound (0.96 g, 94%) as a clear oil.

$^1$H NMR (CDCl$_3$) δ7.45-7.55 (m, 1H), 6.95-7.35 (m, 3H), 4.45 (s, 2H), 3.45-3.60 (m, 4H), 3.05 (s, 3H), 2.75-2.90 (m, 4H), 2.75 (s, 3H), 1.60 (s, 9H). TLC (SiO$_2$): R$_f$=0.70 (50% EtOAc/hexanes).

Preparation 49A

1-Boc-4-{2-[(benzyl-methanesulfonyl-amino)-methyl]-phenyl}-piperazine

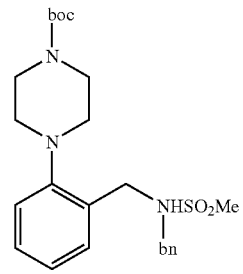

The title compound was prepared in a similar manner to Preparation 48A except that benzyl bromide was used.

$^1$H NMR (CDCl$_3$) δ7.70-7.75 (m, 1H), 7.25-7.55 (m, 8H), 4.75 (s, 2H), 4.50 (s, 2H), 3.45-3.60 (m, 4H), 3.05 (s, 3H), 2.75-2.90 (m, 4H), 1.65 (s, 9H). TLC (SiO$_2$): R$_f$=0.70 (50% EtOAc/hexanes).

Preparation 50A

1-Boc-4-{2-[(ethyl-methanesulfonyl-amino)-methyl]-phenyl}-piperazine

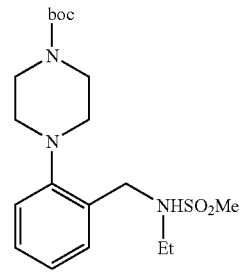

The title compound was prepared in a similar manner to Preparation 48A except that ethyl iodide was used. TLC (SiO$_2$): R$_f$=0.25 (30% EtOAc/hexanes).

Preparation 51A

1-Boc-4-{2-[(Acetyl-methyl-amino)-methyl]-phenyl}-piperazine

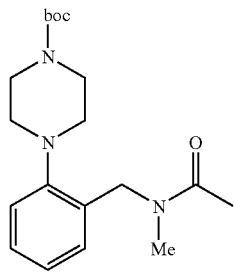

The title compound was prepared in a similar manner to Preparation 48A starting with 1-Boc-4-[2-(acetylamino-methyl)-phenyl]-piperazine (0.58 g, 1.7 mmol). The title compound was obtained (0.36 g, 60%) as a clear oil. TLC (SiO$_2$): R$_f$=0.33 (66% ethyl acetate in hexanes).

Preparation 52A

1-Boc-4-{2-[(Acetyl-benzyl-amino)-methyl]-phenyl}-piperazine

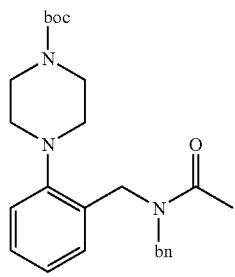

The title compound was prepared in a similar manner to Preparation 51A except that benzyl bromide was used. TLC (SiO$_2$): R$_f$=0.20 (66% ethyl acetate in hexanes)

Preparation 53A

1-Boc-4-{2-[(Acetyl-ethyl-amino)-methyl]-phenyl}-piperazine

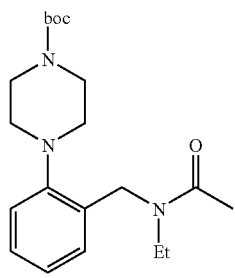

The title compound was prepared in a similar manner to Preparation 51A except that ethyl iodide was used. TLC (SiO$_2$): R$_f$=0.35 (66% ethyl acetate in hexanes).

Preparation 54A (Benzylamine from Benzylic Alcohol Via Mitsunobu)

1-Boc-4-(2-[1,2,4]triazol-1-ylmethyl-phenyl)-piperazine

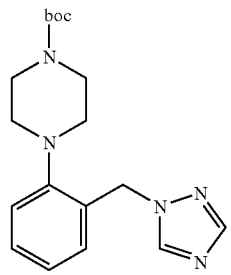

Step 1: 1-Boc-4-(2-carboxy-phenyl)-piperazine

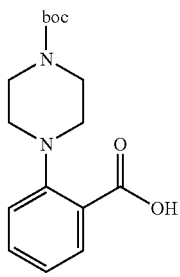

To a solution of 1-(2-cyanophenyl)-piperazine (7.5 g, 40 mmol) in 100 mL of absolute ethanol was added 200 mL of 25% aqueous KOH. The solution was heated to reflux for about 48 hours and then cooled to about 0° C. The solution was acidified with 180 mL of 5 M HCl and then solid NaHCO$_3$ was added to bring the pH of the solution to about 10. After concentration in vacuo to remove 60 mL of solvent, dioxane (300 mL), NaHCO$_3$ (12.7 g, 120 mmol) and Boc$_2$O (11.4 g, 52.2 mmol) were added. The solution was stirred overnight and then acidified with 5 M HCl to about pH 1. After separation, the aqueous solution was extracted with EtOAc (3x). The combined organic solutions were washed with water (2x), brine and then dried (Na$_2$SO$_4$), filtered and concentrated to give the title compound. LRMS (ES–): 305.2 (M–1)

Step 2: 1-Boc-4-(2-hydroxymethyl-phenyl)-piperazine

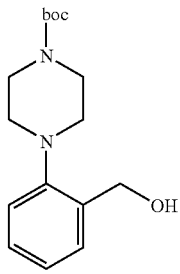

To a solution of 1-Boc-4-(2-carboxy-phenyl)-piperazine from Step 1 in 340 mL of THF at 0° C. was added BH$_3$-THF (120 mL of a 1 M solution in THF). The cold bath was removed, and the solution stirred overnight. The solution was cooled to about 0° C. and then 60 mL of 2 M NaOH was added followed by EtOAc and brine. After separation, the aqueous solution was extracted with EtOAc (3×). The combined organic solutions were washed with water (2×) and brine, and then dried (Na₂SO₄), filtered and concentrated to give about 11.2 g (38.3 mmol, 96%) of the title compound. LRMS (ESI+): 393.2 [M+1]

Step 3: To a solution of 1-Boc-4-(hydroxymethyl-phenyl)-piperazine (300 mg, 1.02 mmol, 1.0 eq.), 1,2,4 triazole (104 mg, 1.53 mmol, 1.5 eq.), triphenylphosphine (535 mg, 2.04 mmol, 2.0 eq.) and THF at 0° C. under nitrogen was added DEAD (0.321 mL, 2.04 mmol, 2.0 eq.) slowly so that temperature of reaction does not rise above 10° C. After addition was completed, the ice bath was removed and the reaction mixture was stirred at r.t. overnight. Methanol was added and the mixture was stirred for about 15 minutes. The mixture was then concentrated. Purification by flash chromatography (35 g SiO₂, linear gradient 50-70% EtOAc/Hexane for 15 minutes and 70% EtOAc for 18 minutes) afforded Boc protected title compound (200 mg, 0.5 mmol, 57%). LRMS (ESI+): 344.1 (M+1)

Preparation 55A

1-Boc-4-(2-tetrazol-2-ylmethyl-phenyl)-piperazine

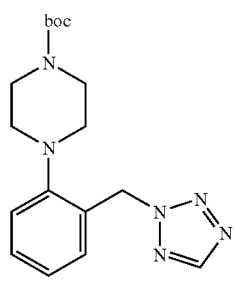

The title compound was prepared in a manner similar to Preparation 54A except that tetrazole was used. LRMS (ESI+): 289.1 (M-Boc).

Preparation 56A

1-Boc-4-(2-imidazol-1-ylmethyl-phenyl)-piperazine

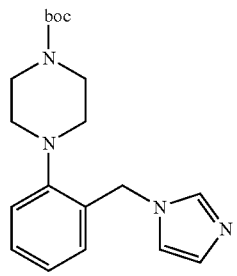

The title compound was prepared in a manner similar to Preparation 54A except that imidazole was used. LRMS (ESI+): 343.2 (M+1)

Preparation 57A

1-Boc-4-(2-azidomethyl-phenyl)-piperazine

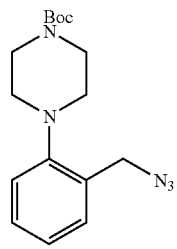

1-Boc-4-(2-Hydroxymethyl-phenyl)-piperazine (4.59 g, 15.7 mmol) was dissolved in toluene (75 mL). Triphenylphosphine (8.3 g, 31.6 mmol) was added followed by zinc azide pyridine salt (3.61 g, 11.72 mmol). Diisopropyl azodicarboxylate (6.27 mL, 31.6 mmol) was added dropwise, and the solution was stirred at r.t. for about 12 hours. The mixture was concentrated under reduced pressure and purified using silica chromatography (12% ethyl acetate in hexanes) to give the title compound (1.89 g, 51%) as an oil.

¹H NMR (CDCl₃) δ7.35-7.05 (m, 4H), 4.45 (s, 2H), 3.60-3.50 (m, 4H), 2.85-2.75 (m, 4H), 1.50 (s, 9H).

Preparation 58A

1-Boc-4-[2-(4-Methoxycarbonyl-[1,2,3]triazol-1-ylmethyl)-phenyl]-piperazine

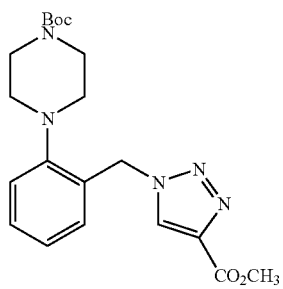

1-Boc-4-(2-Azidomethyl-phenyl)-piperazine (0.25 g, 0.79 mmol) was dissolved in deuterated chloroform (3 mL). Methyl propiolate (0.35 mL, 3.9 mmol) was added, and the mixture was heated to reflux for about 4 hours and then cooled to r.t. The mixture was concentrated under reduced pressure and purified using silica chromatography (50% ethyl acetate in hexanes) to give the title compound (0.155 g, 49%) as an oil.

¹H NMR (CDCl₃) δ7.35-7.05 (m, 4H), 5.75 (s, 2H), 3.95 (s, 3H), 3.55-3.45 (m, 4H), 2.80-2.70 (m, 4H), 3.80-3.85 (m, 1H), 1.50 (s, 9H).

Preparation 59A

1-Boc-4-[2-(4-tert-Butyl-[1,2,3]triazol-1-ylmethyl)-phenyl]-piperazine

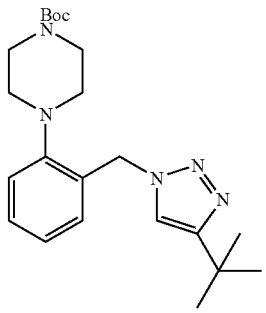

In a sealed tube, 4-(2-Azidomethyl-phenyl)-piperazine-1-carboxylic acid tert-butyl ester (0.366 g, 1.15 mmol) was dissolved in toluene (5 mL). 3,3-dimethyl-1-butyne (0.7 mL, 5.64 mmol) was added and the mixture was heated to reflux for about 48 hours and then cooled to r.t. The mixture was concentrated under reduced pressure and purified using silica chromatography (50% ethyl acetate in hexanes) to give the title compound (0.212 g, 60%) as an oil.

$^1$H NMR (CDCl$_3$) δ7.35-7.05 (m, 4H), 5.75 (s, 2H), 3.60-3.45 (m, 4H), 2.80-2.70 (m, 4H), 1.50 (s, 9H), 1.35 (s, 9H).

Preparation 60A (Benzylamine from Benzylic Alcohol Via Mesylate)

1-Boc-4-[2-(3R-dimethylamino-pyrrolidin-1-ylmethyl)-phenyl-piperazine

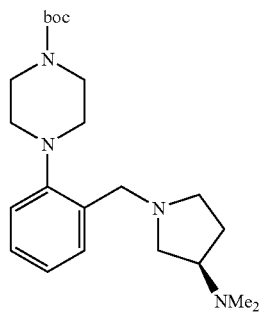

To a solution of 1-Boc-4-(2-hydroxymethyl-phenyl)piperazine (300 mg, 1.03 mmol, 1.0 eq.), triethylamine (0.17 mL, 1.2 mmol, 1.2 eq.), DMAP (6 mg, 0.05 mmol, 0.05 eq.) in CH$_2$Cl$_2$ (10 mL) was added methanesulfonyl chloride (0.085 mL, 1.1 mmol, 1.1 eq.). The solution was stirred at r.t. under N$_2$ for about 2 hours. A solution of 3R-3-(dimethylamino)pyrrolidine (0.63 mL, 5.0 mmol, 5.0 eq.) in THF (3 mL) was added, and the mixture was allowed to stir at r.t. overnight. The mixture was diluted with CH$_2$C$_2$ (10 mL) and washed with saturated aqueous NaHCO$_3$ (15 mL) and brine (15 mL). The aqueous layers were extracted with CH$_2$Cl$_2$ (3×). The combined organic extracts were dried (Na$_2$SO$_4$), filtered and concentrated. Purification by flash chromatography (35 g SiO$_2$, 40 ml/min, linear gradient 0-10% 2.0 M NH$_3$ in MeOH/CH$_2$Cl$_2$ for 25 minutes and 10% 2.0M NH$_3$ in MeOH/CH$_2$Cl$_2$ for 7 minutes) afforded the title compound as a white solid (280 mg, 0.72 mmol, 72%). LRMS (ESI+): 389.2 [M+1]

Preparation 61A

1-Boc-4-[2-(3S-dimethylamino-pyrrolidin-1-ylmethyl)-phenyl-piperazine

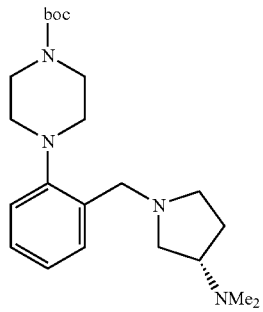

The title compound was prepared in a manner similar to Preparation 60A except that 3S-3-(dimethylamino)pyrrolidine was used. LRMS (ESI+): 389.2 (M+1)

Preparation 62A

1-Boc-4-(2-pyrrolidin-1-ylmethyl-phenyl)-piperazine

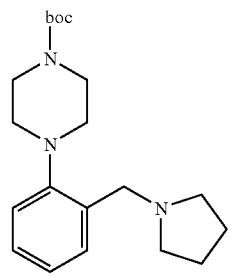

The title compound was prepared in a manner similar to Preparation 60A except that pyrrolidine was used. LRMS (ESI+): 246.1 (M+1)

Preparation 63A

1-Boc-4-[2-(2-methyl-imidazol-1-ylmethyl)-phenyl]-piperazine

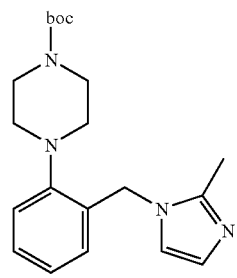

The title compound was prepared in a manner similar to Preparation 60A except that 2-methyl-imidazole was used. LRMS (ESI+): 357.2 (M+1)

Preparation 64A

1-Boc-4-[2-(2-ethyl-imidazol-1-ylmethyl)-phenyl]-piperazine

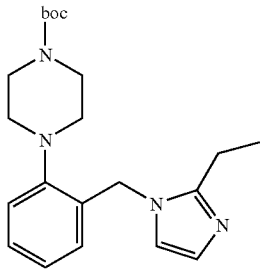

The title compound was prepared in a manner similar to Preparation 60A except that 2-isopropyl-imidazole was used. LRMS (ESI+): 371.3 (M+1)

Preparation 65A

1-Boc-4-[2-(2-ethyl-imidazol-1-ylmethyl)-phenyl]-piperazine

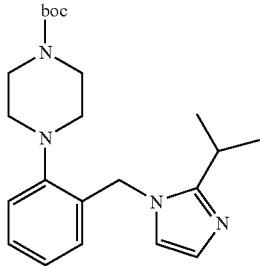

The title compound was prepared in a manner similar to Preparation 60A except that 2-ethyl-imidazole was used. LRMS (ESI+): 385.2 (M+1)

Preparation 66A

1-Boc-4-[2-(2-methylsulfanyl-imidazol-1-ylmethyl)-phenyl]-piperazine

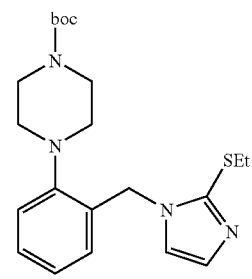

The title compound was prepared in a manner similar to Preparation 60A except that 2-ethylsulfanyl-1H-imidazole was used. LRMS (ESI+): 403.3 (M+1)

Preparation 67A

1-Boc-4-(5-methyl-2-pyrrolidin-1-ylmethyl-phenyl)-piperazine

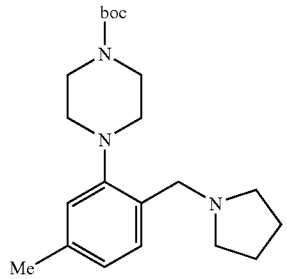

To a solution of 2-bromo-4-methylaniline (558 mg, 3.0 mmol) in 30 mL of acetbnitrile was added tetrafluoroborate (600 μL of a 54% solution in Et$_2$O, 4.35 mmol). The solution was cooled to about 0° C. and t-butyl nitrite (55 uL, 4.62 mmol) was added. After stirring for about 45 minutes, the solution was transferred to a solution of CuCN (800 mg, 8.93 mmol) and NaCN (1.47 g, 30 mmol) in 30 mL, of water cooled to 0° C. via cannula. The cold bath was removed. After stirring overnight, the aqueous solution was extracted with Et$_2$O (2×). The combined organic solutions were washed with 1 M HCl, saturated sodium bicarbonate, water and brine, and then dried (Na$_2$SO$_4$), filtered and concentrated. The material was adsorbed onto 3 g of silica gel and purified by silica gel flash chromatography (4×15 cm column, 5-20 Et$_2$O/pentane, over 48 min at 35 mL/min) to afford about 320 mg (1.63 mmol, 54%) of 2-bromo-4-methyl-benzonitrile as a colorless oil. GC/MS (EI): 195.

2-Bromo-4-methyl-benzonitrile was coupled to piperazine using Preparation 1A Buchwald chemistry to afford 4-(2-cyano-5-methyl-phenyl)-piperazine. 4-(2-cyano-5-methyl-phenyl)-piperazine is converted to 4(2-hydroxymethyl-5-methyl-phenyl)-piperazine in a manner similar to preparation 54A Steps 1 and 2.4-(2-Hydroxymethyl-5-methyl-phenyl)-piperazine was converted to the title compound in a manner similar to Preparation 60A except that pyrrolidine was used to displace the mesylate. LRMS (ESI+): 360.3 (M+1)

Preparation 68A

1-Boc-4-(5-isopropyl-2-pyrrolidin-1-ylmethyl-phenyl)-piperazine

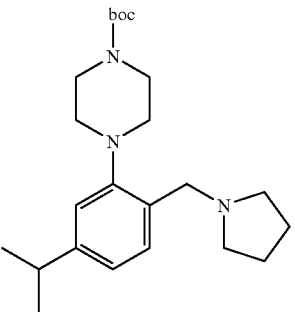

The title compound was prepared in a manner similar to the Preparation 67A except that 2-bromo-4-isopropylaniline was used as the starting material. LRMS (ESI+): 388.3 (M+1)

Preparation 69A

1-Boc-4-(2-dimethylaminomethyl-5-trifluoromethyl-phenyl)piperazine

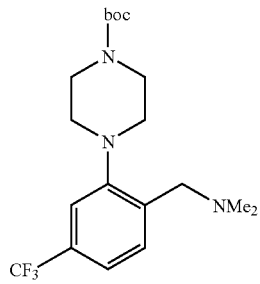

To a solution of piperazine (13.7 g, 159 mmol) in 20 mL DMSO was added 2-fluoro-4-trifluoromethylbenzonitrile (10 g, 52.9 mmol). After stirring overnight, the solution was diluted with 200 mL of EtOAc, washed with water and brine, and then dried ($Na_2SO_4$), filtered and concentrated to afford about 13.0 g (51.1 mmol, 96%) of 4-(2-cyano-5-trifluoromethyl-phenyl)piperazine. LRMS (ESI+): 256.1 [M+1]. The tide compound was prepared from 4-(2-cyano-5-trifluoromethyl-phenyl)piperazine in the same manner as described in Preparation 67A except that dimethyl amine was used to displace the mesylate. LRMS (ESI+): 388.1 [M+1]

Preparation 70A

1-Boc-4-(2-pyrrolidin-1-ylmethyl-5-trifluoromethyl-phenyl)-piperazine

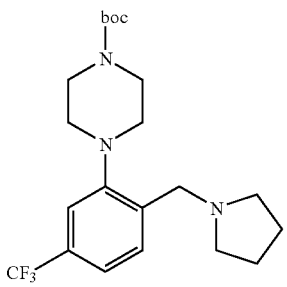

The title compound was synthesized in similar manner as described in Preparation 69A except that pyrrolidine was used to displace the mesylate. LRMS (ESI+): 414.3 (M+1)

Preparation 71A

1-Boc-4-(2-pyrrolidin-1-ylmethyl-4-trifluoromethyl-phenyl)-piperazine

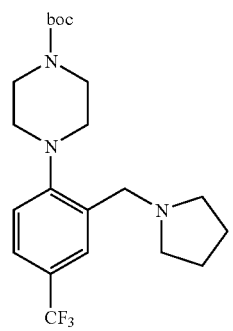

The title compound was synthesized in similar manner as described in Preparation 70A except that 2-fluoro-5-trifluoromethylbenzonitrile was used as the starting material. LRMS (ESI+): 414.3 (M+1)

Preparation 72A

1-Boc-4-(2-pyirrolidin-1-ylmethyl-6-trifluoromethyl-phenyl)-piperazine

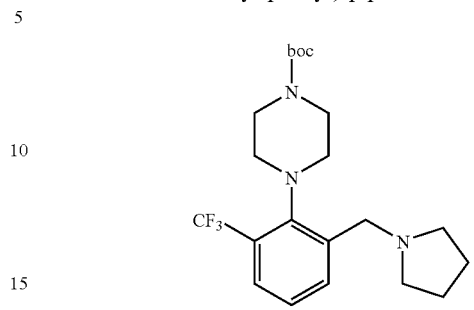

The title compound was synthesized in similar manner as described in Preparation 70A except that 2-fluoro-3-trifluoromethylbenzonitrile was used as the starting material. LRMS (ESI+): 414.3 (M+1)

Preparation 73A

1-Boc-4-(2-pyrrolidin-1-ylmethyl-3-trifluoromethyl-phenyl)-piperazine

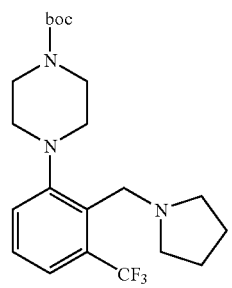

4-(2-cyano-3-trifluoromethyl-phenyl)piperazine was prepared in a manner similar to 4-(2-cyano-5-trifluoromethyl-phenyl)piperazine described above except that 2-fluoro-6-trifluoromethylbenzonitrile was used as the starting material. To a solution of 4-(2-cyano-3-trifluoromethyl-phenyl)piperazine (1.35 g, 5.29 mmol, 1.0 eq.) in dioxane (40 mL) was added a solution of DIBAL in heptane (1.0 M in heptane, 13.2 mL, 13.22 mmol, 2.5 eq.). The resulting mixture was stirred at r.t. for about 3 days. The mixture was transferred via cannula to 0.5 M Rochelle salt and stirred for about 2 hours. $NaHCO_3$ (1.3 g, 15.9 mmol, 3.0 eq) and di-tert-butyl dicarbonate (1.7 g, 7.29 mmol, 1.5 eq.) were added and the mixture was stirred at r.t. overnight. The mixture was partitioned between EtOAc (100 mL) and brine (50 mL). The organic layer was separated, and aqueous layer was extracted with EtOAc (2×). The combined organic extracts were washed with $H_2O$ and brine, and then dried ($Na_2SO_4$), filtered and concentrated. Purification by flash chromatography (120 g $SiO_2$, 40 mL/min, linear gradient 0-25% EtOAc/Hexane for 10 minutes and 25% EtOAc/Hexane for 23 minutes) afforded N-boc-4-(2-formyl-3-trifluoromethyl-phenyl)piperazine (637 mg, 1.77 mmol, 35%). LRMS (ESI+): 359.1 [M+1]

To a solution of N-boc-4-(2-formyl-3-trifluoromethyl-phenyl)piperazine (358 mg, 1 mmol, 1.0 eq.) in MeOH (10 mL) was added pyrrolidine (0.093 mL, 1.1 mmol, 1.1 eq.). The mixture was refluxed overnight. The reaction was cooled to about 0° C., and $NaBH_4$ on alumina (10 wt % on basic alumina, 570 mg, 1.5 mmol, 1.5 eq.) was added. After the addition was compete, the ice bath was removed, and the mixture was stirred at r.t. for about 2 hours. The mixture was filtered through celite, washed with methanol and concentrated. The solution was diluted with EtOAc (50 mL) and washed with saturated NaHCO₃ and brine. The aqueous layers were extracted with EtOAc (2×). The combined organic extracts were dried (Na₂SO₄), filtered and concentrated. Purification by flash chromatography (35 g SiO₂, 40 mL/min, linear gradient 0-10% MeOH/CH₂Cl₂ for 25 minutes and 10% MeOH/CH₂Cl₂ for 7 minutes) gave the title compound (298 mg, 0.72 mmol, 72%). LRMS (ESI+): 414.3 (M+1)

Preparation 74A (Derivatives of 1-Boc-4-(2-amino-phenyl)-piperazine)

1-Boc-4-(2-amino-phenyl)-piperazine

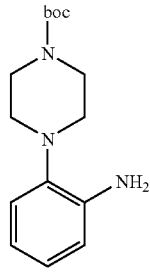

To a solution of N-(2-nitrophenyl)-piperazine (30 g, 145 mmol) and triethylamine (28.3 mL, 203 mmol) in 600 mL of CH₂Cl₂ was added Boc₂O (38 g, 174 mmol). After stirring overnight, the solution was washed with saturated aqueous sodium bicarbonate and brine, and then dried (Na₂SO₄), filtered and concentrated to afford an orange oil. To a solution of the oil in 2 L of ethanol was added 6 g of 5% Pd/C. After shaking under 60 psi H₂ overnight, the solution was filtered and concentrated to afford about 39 g (140 mmol, 97%) of 1-boc-4-(2-aminophenyl)-piperazine as abrown solid. LRMS: 278.1 (M+1)

Preparation 75A

1-Boc-4-(2-dimethylaminophenyl)piperazine

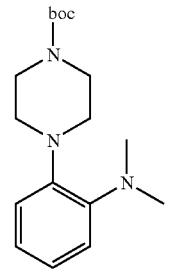

To a solution of 1-boc-4-(2-nitrophenyl) piperazine (500 mg, 1.63 mmol, 1.0 eq) in IPA (20 mL) was added formaldehyde (3.3 mL 37% solution in H₂O, 4.07 mmol, 2.5 eq) and 10% Pd/C (125 mg, 25 wt %). The mixture was shaken under hydrogen at 60-psi overnight. The mixture was filtered and diluted with CH₂Cl₂. The aqueous solution was separated, and the organic solution was dried (Na₂SO₄), filtered through a pad of celite and concentrated. Purification by flash chromatography (35 g SiO₂, 40 ml/min, linear gradient 0-15% EtOAc/hexane for 20 minutes and 15% EtOAc/hexane for 13 minutes) gave about 480 mg (1.57 mmol, 97%) of the title compound as a solid. LRMS (ESI+): 306.2 (M+1)

Preparation 76A

1-Boc-4-[2-(isobutylamido)-phenyl]-piperazine

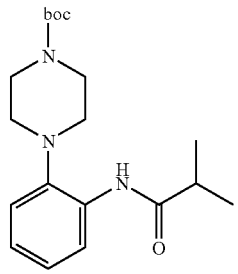

To a solution of 1-Boc-4-(2-amino-phenyl)-piperazine (2.77 g, 10 mmol), triethyl amine (2.8 mL, 20 mmol), and DMAP (70 mg, 0.57 mmol) in 50 mL of CH₂Cl₂ was added isobutyryl chloride (1.15 mL, 11 mmol). After stirring overnight, saturated aqueous sodium bicarbonate was added and the solution was concentrated. The solution was diluted with EtOAc, washed with 1 M HCl, water, saturated aqueous sodium bicarbonate and brine, and then dried (Na₂SO₄), filtered and concentrated to afford about 3.29 g (9.4 mmol, 94%) of the title compound. LRMS: 348.2 (M+1)

Preparation 77A

1-Boc-4-[2-(3-methyl-butyrylamino)-phenyl]-piperazine

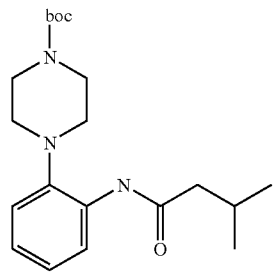

The title compound was prepared in a manner similar to Preparation 76A except that isovaleryl chloride was used instead of isobutyryl chloride. LRMS (ESI+): 362.2 (M+1)

Preparation 78A

1-Boc-4-(2-isobutylamino-phenyl)-piperazine

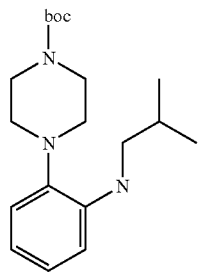

To a solution of 1-Boc-4-(2-isobutylamino-phenyl)-piperazine (2.72 g, 7.8 mmol) in 50 mL of THF was added BH$_3$-THF (24 mL of 1 M solution in THF, 24 mmol). After stirring for about 1 hour at 60° C., the solution was cooled to r.t. and then 25 mL of 1 M NaOH was added. After stirring for about 2 hours, brine and EtOAc were added. The organic solution was washed with water (2×) and brine, and then dried (Na$_2$SO$_4$), filtered and concentrated. Purification by flash chromatography (Biotage 40L column, 0 to 30% EtOAc/Hex linear gradient over 48 min at 35 mL/min) afforded about 2.35 g (7.05 mmol, 90%) of the title compound. LRMS: 334.2 (M+1)

Preparation 79A

1-Boc-4-(2-methanesulfonylamino-phenyl)-piperazine

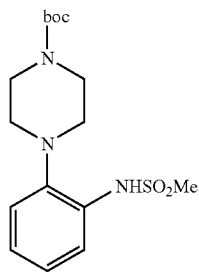

To a solution of 1-boc-4-(2-aminophenyl)-piperazine (5.55 g, 20 mmol) and triethyamine (5.6 mL, 40 mmol) in 200 mL of CH$_2$Cl$_2$ was added methanesulfonyl chloride (1.55 mL, 20 mmol). After stirring for about 4 hours, the solution was concentrated, and the residue dissolved in 200 mL of EtOAc. The solution was washed with 1 M HCl (2×), water and brine, and then dried (Na$_2$SO$_4$), filtered and concentrated to afford about 6.68 g (18.8 mmol, 94%) of the title compound as a brown solid. LRMS: 356.1 (M+1)

Preparation 80A

1-Boc-4-[2-(3,3-Dimethyl-ureido)-phenyl]-piperazine

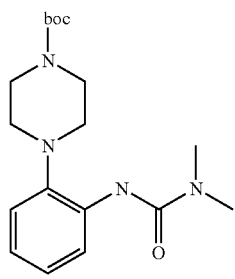

To a solution of 1-Boc-4-(2-aminophenyl)-piperazine (270 mg, 1.0 mmol) and Et$_3$N (400 microliter, 2.89 mmol) in 10 mL of CH$_2$Cl$_2$ was added dimethylcarbamyl chloride (135 microliter, 1.48 mmol). After stirring for about 1 hour, DMAP (10 mg) was added. After stirring for about 3 days, another 800 microliter of Et$_3$N and 270 microliter of dimethylcarbamyl chloride were added. After stirring overnight, the solution was diluted with EtOAc, washed with 1 M HCl (2×), saturated sodium bicarbonate, water and brine, and then dried (Na$_2$SO$_4$), filtered and concentrated. Purification by silica gel chromatography (35 g SiO$_2$, 20 to 50% EtOAc/hexanes, over 30 minutes at 35 mL/min) afforded about 20 mg (0.057 mmol, 6%) of the tide compound as a white solid. LRMS: 349.2 (M+1)

Preparation 81A

1-Boc-4-[2-(3-isopropyl-ureido)-phenyl]-piperazine

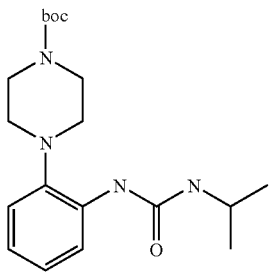

To a solution of 1-Boc-4-(2-aminophenyl)-piperazine (270 mg, 1.0 mmol) in 10 mL of THF was added isopropyl isocyanate (90 uL, 1.46 mmol). After stirring for about 1 hour, another 90 microliter of isopropyl isocyanate was added. After stirring for about 3 days, another 290 microliter of isopropyl isocyanate was added. After stirring overnight, the solution was concentrated. Purification by silica gel chromatography (35 g SiO$_2$, 20 to 50% EtOAc/hexanes, over 30 minutes at 35 mL/min) afforded about 240 mg (0.66 mmol, 66%) of the title compound as a white solid. LRMS: 363.2 (M+1)

Preparation 82A

1-Boc-4-[2-(isobutyl-methanesulfonyl-amino)-phenyl]-piperazine

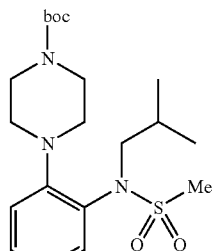

To a solution of 1-boc-4-(2-methanesulfonylamino-phenyl)-piperazine (1.07 g, 3.0 mmol) in 50 mL of DMF was added NaH (240 mg of a 60% dispersion in oil, 6 mmol). After stirring for about 15 minutes at r.t., isobutyl iodide (420 □L, 3.65 mmol) was added and the solution warmed to 60° C. After stirring at 60° C. overnight, the reaction was quenched with saturated aqueous ammonium chloride and diluted with EtOAc. The solution was washed twice with water and brine, and then dried (Na$_2$SO$_4$), filtered and concentrated. Purification by flash chromatography (40M Biotage column, 10-30% linear gradient EtOAc/Hex, over 45 min at 35 mL/min) afforded about 1.07 g (2.6 mmol, 87%) of the title compound as a white foam. LRMS: 412.3 (M+1)

Preparation 83A

1-Boc [2-(methyl-methanesulfonyl-amino)-phenyl]-piperazine

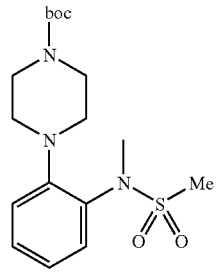

The title compound was prepared in a manner similar to Preparation 82A except that methyl iodide was used and K₂CO₃ instead of NaH as the base. LRMS (ESI+): 370.2 (M+1)

Preparation 84A

1-Boc-4-[2-(ethyl-methanesulfonyl-amino)-phenyl]-piperazine

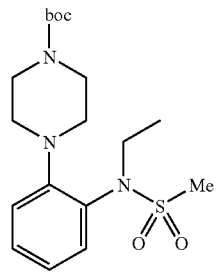

The title compound was prepared in a manner similar to Preparation 82A except that ethyl iodide was used and K₂CO₃ instead of NaH as the base. LRMS (ESI+): 384.2 (M+1)

Preparation 85A

1-Boc-4-[2-(n-butyl-methanesulfonyl-amino)-phenyl]-piperazine

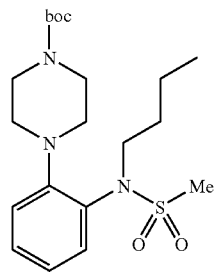

The title compound was prepared in a manner similar to Preparation 82A except that n-butyl iodide was used. LRMS (ESI+): 412.2 (M+1)

Preparation 86A

1-Boc-4-{2-[(2-ethyl-butyl)-methanesulfonyl-amino]-phenyl}-piperazine

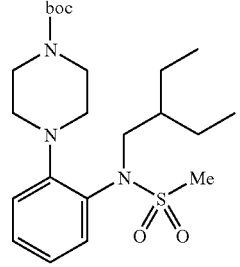

The tide compound was prepared in a manner similar to Preparation 82A except that 1-bromo-2-ethylbutane was used. LRMS (ESI+): 440.2 (M+1)

Preparation 87A

1-Boc-4-[2-(cyclohexylmethyl-methanesulfonyl-amino)-phenyl]-piperazine

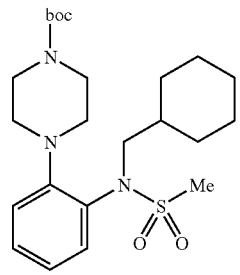

The tide compound was prepared in a manner similar to Preparation 82A except that bromomethyl cyclohexane was used. LRMS: 452.2(M+1)

Preparation 88A

1-Boc-4-[2-(cyclobutylmethyl-methanesulfonyl-amino)-phenyl]-piperazine

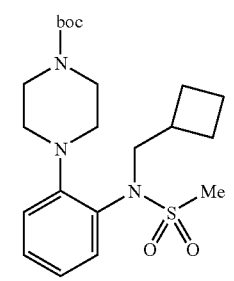

The title compound was prepared in a manner similar to Preparation 82A except that bromomethyl cyclobutane was used. LRMS (ESI+): 424.1 (M+1)

Preparation 89A

1-Boc-4-[2-(cyclopropylmethyl-methanesulfonyl-amino)-phenyl]-piperazine

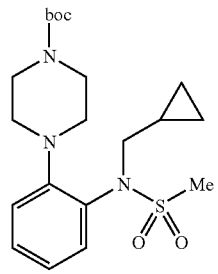

The title compound was prepared in a manner similar to Preparation 82A except that bromomethyl cyclopropane was used. LRMS (ESI+): 410.1 (M+1)

Preparation 90A

1-Boc-4-{2-[methanesulfonyl-(3-methyl-butyl)-amino]-phenyl}-piperazine

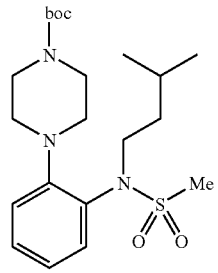

The title compound was prepared in a manner similar to Preparation 82A except that 1-iodo-3-methyl butane was used. LRMS (ESI+): 426.2 (M+1)

Preparation 91A

1-Boc-4-[2-(1,1-dioxo-2-isothiazolidinyl)-phenyl]-piperazine

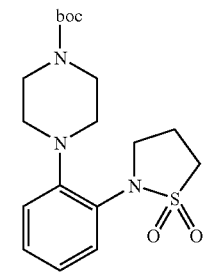

To a solution of N-boc-4-(2-amino-phenyl)-piperazine (555 mg, 2.0 mmol) and Et$_3$N (837 uL, 6 mmol) in 20 mL of CH$_2$Cl$_2$ was added 3-chloropropanesulfonyl chloride (255 uL, 2.1 mmol). After stirring for about 30 minutes, the mixture was quenched with saturated aqueous sodium bicarbonate, diluted with EtOAc, washed with 1 M HCl, water and brine, and then dried (Na$_2$SO$_4$), filtered and concentrated. Purification by silica gel chromatography (35 g SiO$_2$, 10 to 30% EtOAc/hexanes, over 30 min at 35 mL/min) afforded about 781 mg (1.87 mmol, 93%) of N-boc-4-[2-(3-chloro-propane-1-sulfonylamino)-phenyl]-piperazine as a white solid. LRMS (ESI+): 418.1 [M+1]

To a solution of N-boc-4-[2-(3-chloro-propylamino)-phenyl]-piperazine (593 mg, 1.42 mmol) in 140 mL of DMF was added NaH (567 mg of a 60% dispersion in oil, 14 mmol). After stirring for about 1 hour, the mixture was quenched with saturated aqueous sodium bicarbonate, diluted with EtOAc, washed with water and brine, and then dried (Na$_2$SO$_4$), filtered and concentrated to afford about 740 mg of N-boc4-[2-(1,1-dioxo-isothiazolidin-2-yl)-phenyl]-piperazine. LRMS (ESI+): 382.1 [M+1]

Preparation 92A

1-Boc-4-(2-ethanesulfonylamino-phenyl)-piperazine

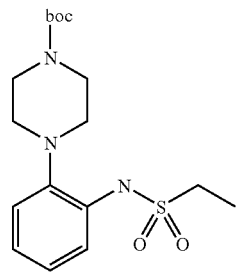

To a solution of 1.0 g (4.4 mmol) of 1-Boc-4-(2-amino-phenyl)-piperazine and 1.1 mL (6.6 mmol) of triethylamine in 12 mL of DCM was added 0.63 mL (6.6 mmol) of ethanesulfonyl chloride, and the mixture was stirred at r.t. for about 16 hours. The mixture was diluted with ethyl acetate and washed once with 10% aqueous sodium bisulfate and then once with saturated aqueous sodium bicarbonate. The organic portion was dried (Na$_2$SO$_4$), filtered and concentrated in vacuo. Silica gel chromatography (3iotage, 40% ethyl acetate/hexanes) of the residue afforded about 0.73 g (45%) of the title compound. LRMS (ESI-): 368 (M-1)

Preparation 93A

1-Boc-4-(2-n-butanesulfonylamino-phenyl)-piperazine

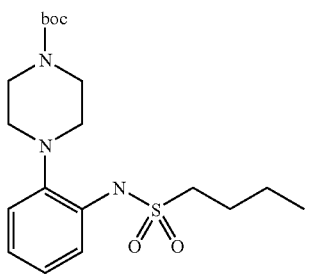

The title compound was prepared in a manner similar to Preparation 92A except that n-butanesulfonyl chloride was used. LRMS (ESI+): 398 (M+1)

Preparation 94A

1-Boc-4-[2-(propane-2-sulfonylamino)-phenyl]-piperazine

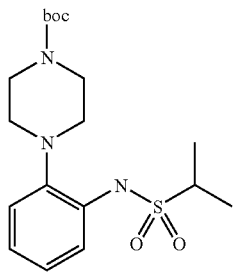

The tide compound was prepared in a manner similar to Preparation 92A except that propane-2-sulfonyl chloride was used and DBU was used as the base. LRMS (ESI+): 384.3 (M+1)

Preparation 95A

1-Boc4-(2-benzenesulfonylamino-phenyl)-piperazine

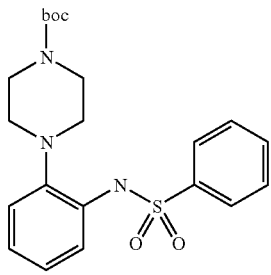

The title compound was prepared in a manner similar to Preparation 92A except that benzenesulfonyl chloride was used. LRMS (ESI+): 418.1 (M+1)

Preparation 96A

1-Boc4-(2-Phenylmethanesulfonylamino-phenyl)piperazine

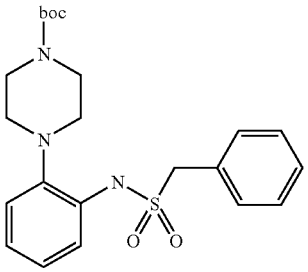

The title compound was prepared in a manner similar to Preparation 92A except that α-toluenesulfonyl chloride was used. LRMS (ESI+): 432 (M+1)

Preparation 97A

1-Boc-(2-piperazin-1-yl-phenyl)-N,N-dimethylsulfonimide

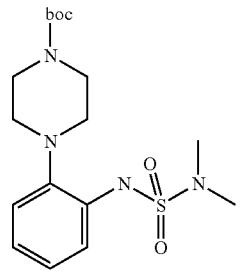

To a 0° C. anhydrous methylene chloride (10 mL) solution of 1-Boc-4-(2-amino-phenyl)-piperazine (1.0 gm, 3.61 mmol), and TEA (0.60 mL, 4.33 mmol) was added dimethylsulfamoyl chloride (0.46 mL, 4.33 mmol). The bath was removed after 5 minutes, and the reaction was stirred under a nitrogen atmosphere for about 3 days and refluxed for 1 day. The mixture was diluted with methylene chloride and 1N HCl. The separated aqueous layer was extracted with methylene chloride (2×). The combined organics were dried (sodium sulfate), filtered, and concentrated to afford crude oil. Silica gel chromatography (0 to 5% methanol in methylene chloride) gave about 0.2 g (14%) of the final product. LRMS (ESI+): 385.3

Preparation 98A

1-Boc-4-[2-(acetyl-isobutyl-amino)-phenyl]-piperazine

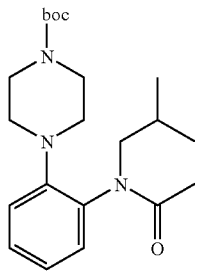

To a solution of N-boc-4-(2-isobutylamino-phenyl)-piperazine (333 mg, 1.0 mmol, 1.0 eq), Et$_3$N (0.42 mL, 3.0 mmol, 3.0 eq) and DMAP (6 mg, 0.05 mmol, 0.05 eq) in DCM (10 mL) was added acetic anhydride (0.14 mL, 1.5 mmol, 1.5 eq). The mixture was stirred at r.t. overnight. The reaction was diluted with DCM (50 mL) and washed with saturated aqueous NaHCO$_3$ (25 mL) and brine (25 mL). The organic layer was separated and aqueous layer was extracted with DCM (2×). The combined organic extracts were dried (Na$_2$SO$_4$), filtered and concentrated to afford the title compound (375 mg, 1.0 mmol, 100%). LRMS (ESI+): 376.18 (M+1)

Preparation 99A

1-Boc-4-[2-(isobutyl-methoxycarbonyl-amino)-phenyl]-piperazine

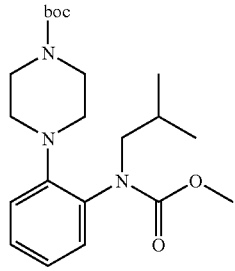

The title compound was prepared in a manner similar to Preparation 98A except that methyl chloroformate was used instead of acetic anhydride. LRMS (ESI+): 392.2 (M+1)

Preparation 100A

1-Boc-4-[2-(isobutyl-isopropoxycarbonyl-amino)-phenyl]-piperazine

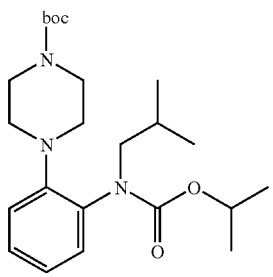

The title compound was prepared in a manner similar to Preparation 98A except that isopropyl chloroformate was used instead of acetic anhydride. LRMS (ESI+): 420.26 (M+1).

Preparation 101A

1-Boc-4-[2-(isobutyl-isobutoxycarbonyl-amino)-phenyl]-piperazine

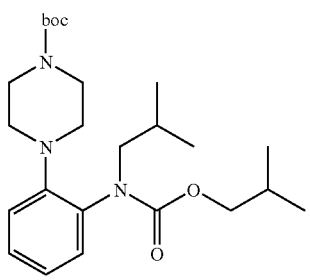

The title compound was prepared in a manner similar to Preparation 98A except that isobutyl chloroformate was used instead of acetic anhydride. LRMS (ESI+): 434.27 (M+1).

Preparation 102A

1-Boc-4-{2-[(2,2-dimethyl-propoxycarbonyl)-isobutyl-amino]-phenyl}-piperazine

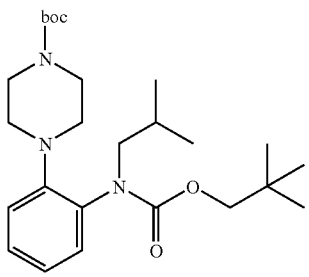

The title compound was prepared in a manner similar to Preparation 98A except that neopentyl chloroformate was used instead of acetic anhydride. LRMS (ESI+): 448.32 (M+1).

Preparation 103A

4-{2-[(1-methyl-1H-imidazol-ylmethyl)-amino]-phenyl}piperazine

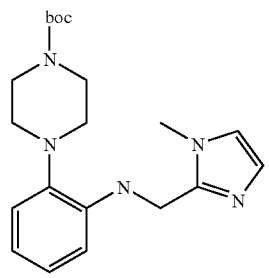

To a solution of 1-boc-4-(2-aminophenyl) piperazine (554 mg, 2.0 mmol, 1.0 eq.) in methanol was added (1-methyl-1H-imidazole-2-carbaldehyde (220 mg, 2.0 mmol, 1.0 eq.). The mixture was reflux for about 1 hour and then cool to about 0° C. Sodium borohydride on alumina (10 wt % on basic alumina, 1.13 g, 3.0 mmol, 1.5 eq.) was added. The solution was warmed to r.t. and then stirred overnight. The reaction mixture was filtered through celite and then concentrated. Purification by flash chromatography (35 g SiO$_2$, 40 mL/min, linear gradient, 0-8% MeOH/CH$_2$Cl$_2$ for 25 minutes and then 8% MeOH for 7 minutes) afforded Boc protected title compound (176 mg, 0.47 mmol, 24%). LRMS (ESI+): 372.3 [M+1].

Preparation 104A 2-(N-Boc-piperazin-1-yl)-benzaldehyde

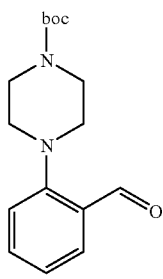

To a solution of 1-(2-cyanophenyl)-piperazine (375 mg, 2.0 mmol) in 15 mL of dioxane was added DIBAL-H (6 mL of a 1 M solution in heptane, 6 mmol). After stirring at r.t. for about 48 hours, the solution was transferred via cannula into 20 mL of 0.5 M Rochelle salt After stirring for about 2 hours, NaHCO$_3$ (636 mg, 6 mmol) and Boc$_2$O (567 mg, 2.6 mmol) were added. After stirring overnight, EtOAc and brine were added. After separation, the aqueous solution was extracted with EtOAc (3×). The combined organic layers were washed with water and brine, and then dried (Na$_2$SO$_4$), filtered and concentrated. Purification by flash chromatography (35 g SiO$_2$, linear gradient 10-20% EtOAc/Hex over 30 min at 35 mL/min) afforded about 436 mg (1.50 mmol, 75%) of the title compound as a yellow oil. LRMS (ESI+): 291.1 (M+1)

Preparation 105A

1-Boc-4-(2-pyrrolidin-1-ylmethyl-phenyl)-piperazine

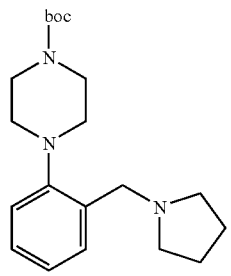

To a solution of 2-(N-Boc-piperazin-1-yl)-benzaldehyde (400 mg, 1.4 mmol) in pyrrolidine (0.33 mL, 4 mmol) was added titanium isopropoxide (1.2 mL, 4 mmol), and the mixture was stirred at r.t. under a nitrogen atmosphere. After about 30 minutes, the mixture was diluted with ethanol (4 mL). Sodium borohydride (106 mg, 2.8 mmol) was added and the mixture was stirred for about 16 hours. Water (2 mL) was added, and the resulting suspension was filtered. The filter cake was washed with methanol (5 mL), and the filtrate was concentrated to dryness. Purification by flash chromatography (1:1 hexanes/ethyl acetate) gave the title compound (470 mg, 96%) as a colorless oil.

$^1$H NMR (CDCl$_3$) δ 7.40-7.44 (m, 1H), 7.19-7.26 (m, 1H), 7.01-7.08 (m, 2H), 3.68 (s, 2H), 3.55 (t, J=4.5 Hz, 4H), 2.92-2.95 (m, 4H), 2.53 (m, 4H), 1.75 (m, 4H), 1.49 (s, 9H). TLC (SiO$_2$): R$_f$=0.28 (50% EtOAc/hexanes).

Preparation 106A

1-Boc-4-(2-piperidin-1-ylmethyl-phenyl)-piperazine

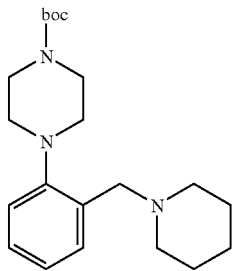

The title compound was prepared in the same manner as described in Preparation 105A except that piperidine was used.

$^1$H NMR (CDCl$_3$) δ 7.38 (d, J=7.6 Hz, 1H), 7.20-7.26 (m, 1H), 7.03-7.08 (m, 2H), 3.54-3.57 (m, 4H), 3.50 (s, 2H), 2.92-2.95 (m, 4H), 2.40 (m, 4H), 1.23-1.59 (m, 15H). TLC (SiO$_2$): R$_f$=0.52 (50% EtOAc/hexanes)

Preparation 107A

1-Boc-4-(2-diethylaminomethyl-phenyl)-piperazine

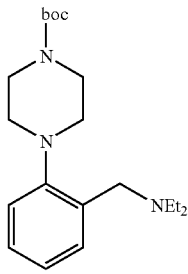

The title compound was prepared in the same manner as described in Preparation 105A except that diethyl amine was used.

$^1$H NMR (CDCl$_3$) δ 7.54 (d, J=7.3 Hz, 1H), 7.19-7.26 (m, 1H), 7.03-7.11 (m, 2H), 3.63 (s, 2H), 3.56 (t, J=4.4 Hz, 4H), 2.88 (t, J=4.6 Hz, 4H), 2.54 (q, J=7.2 Hz, 4H), 1.49 (s, 9H), 1.03 (t, J=7.2 Hz, 6H). TLC (SiO$_2$): R$_f$=0.36 (50% EtOAc/hexanes)

Preparation 108A

1-Boc-4-(2-di-n-butylaminomethyl-phenyl)-piperazine

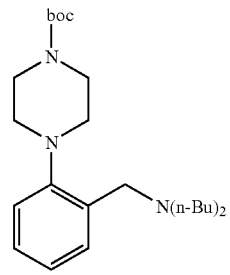

The title compound was prepared in the same manner as described in Preparation 105A except that dibutyl amine was used.

$^1$H NMR (CDCl$_3$) δ 7.54-7.57 (m, 1H), 7.01-7.26 (m, 3H), 3.58 (s, 2H), 3.49-3.53 (m, 4H), 2.85-2.90 (m, 4H), 2.38 (t, J=7.3 Hz, 4H), 1.40-1.50 (m, 13H), 0.84 (t, J=7.3 Hz, 6H). TLC (SiO$_2$): R$_f$=0.70 (80% EtOAc/hexanes).

Preparation 109A

1-Boc-4-(2-morpholin-4-ylmethyl-phenyl)-piperazine

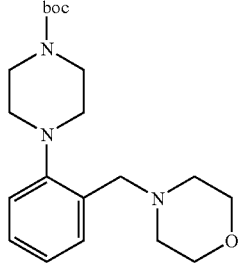

To a solution of 1-Boc-4-(2-formyl-phenyl)-piperazine (500 mg, 1.7 mmol) in methanol (10 mL) was added morpholine (348 mg, 4.0 mmol) and sodium cyanoborohydride (315 mg, 5 mmol) and the mixture was stirred for about 24 hours. The mixture was diluted with ethyl acetate (100 mL), washed with saturated NaHCO$_3$ solution (10 ml), water (10 mL) and brine (10 mL). The organic phase was dried over anhydrous sodium sulfate and concentrated. Silica gel chromatography (1:1 hexanes/ethyl acetate) afforded the title compound as a colorless oil (182 mg, 30%).

$^1$H NMR (CDCl$_3$) δ7.38-7.40 (m, 1H), 7.21-7.27 (m, 1H), 7.04-7.09 (m, 2H), 3.67 (t, J=4.4 Hz, 4H), 3.53-3.55 (s, 6H), 2.92-2.95 (m, 4H), 2.46-2.49 (m, 4H), 1.49 (s, 9H). TLC (SiO$_2$): R$_f$=0.44 (50% EtOAc/hexanes).

Preparation 110A

1-Boc-4-[2-(isopropylamino-methyl)-phenyl]-piperazine

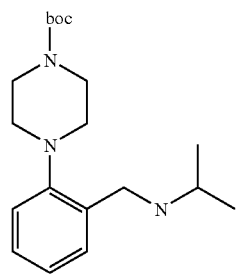

The title compound was prepared in the same manner as described in Preparation 105A except that isopropylamine was used.

$^1$H NMR (CDCl$_3$) δ7.30-7.00 (m, 4H), 3.80 (s, 2H), 3.60-3.45 (m, 4H), 2.95-2.85 (m, 4H), 2.85-2.80 (m, 1H), 1.50 (m, 9H), 1.10-1.00 (m, 6H). TLC (SiO$_2$): R$_f$=0.10 (25% ethyl acetate/hexanes).

Preparation 111A

1-Boc-4-{2-[(Acetyl-isopropyl-amino)-methyl]-phenyl}-piperazine

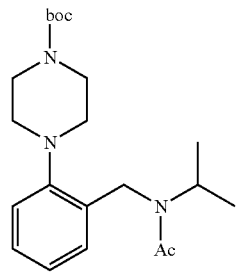

1-Boc-4-[2-(isopropylamino-methyl)-phenyl]-piperazine (0.325 g, 0.975 mmol) was dissolved in tetrahydrofuran (5 mL) and cooled to about 0° C. TEA (0.54 mL, 3.9 mmol) was added followed by dropwise addition of acetyl chloride (0.2 mL, 2.93 mmol). The solution was allowed to warm to r.t. The solvents were removed under reduced pressure, and the resulting oil was purified using silica chromatography (ethyl acetate) to afford the title compound (0.650 g, 82%) as an oil.

$^1$H NMR (CDCl$_3$) δ7.25-6.95 (m, 4H), 4.65 (s, 1H), 4.45 (s, 1H), 3.70-3.50 (m, 4H), 2.90-2.80 (m, 4H), 1.50 (s, 9H), 1.30-1.20 (m, 1H), 1.10-1.00 (m, 6H).

Preparation 112A

1-Boc-4-[2-(isopropyl-methanesulfonyl-amino-methyl)-phenyl]-piperazine

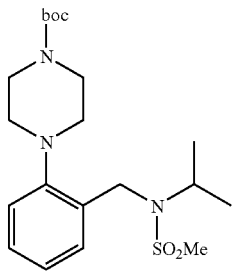

The title compound was prepared in the same manner as described in Preparation 111A except that methanesulfonyl chloride was used instead of acetyl chloride.

$^1$H NMR (CDCl$_3$) δ7.70-7.60 (m, 1H), 7.25-6.95 (m, 3H), 4.45 (s, 2H), 3.65 (s, 2H), 3.65 (s, 3H), 2.95-2.80 (m, 8H), 1.50 (s, 9H), 1.30-1.15 (m, 1H), 1.10-1.00 (m, 6H).

Preparation 113A

1-Boc-4-{2-[Hydroxy-(1-methyl-1H-imidazol-2-yl)-methyl]-phenyl}-piperazine

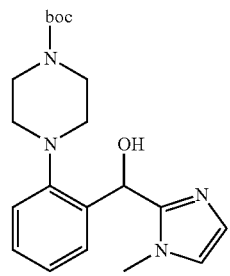

To a solution of 1-methyl imidazole (350 uL, 4.4 mmol) in 15 mL of THF at −78° C. was added n-BuLi (1.5 mL of a 1.6 M solution in hexane, 2.4 mmol). After stirring for about 30 minutes, the solution was warmed to about 0° C. and then stirred for about 15 minutes. The mixture was then cooled to about −78° C. A solution of N-Boc-4-(2-formylphenyl)-piperazine (580 mg, 1.0 mmol) in 5 mL of THF was added via cannula The solution was allowed to warm slowly to r.t. overnight. After addition of saturated aqueous NH$_4$Cl and brine, the solution was extracted with EtOAc (2×). The combined organic solutions were dried (Na$_2$SO$_4$), filtered and concentrated. Purification by silica gel chromatography (35 g SiO$_2$, 0 to 10% 0.2 M NH$_3$ in MeOH/CH$_2$Cl$_2$ over 30 min at 35 mL/min) afforded about 592 mg (1.59 mmol, 79%) of the alcohol as a colorless oil. LRMS (ESI+): 373.2 (M+1)

Preparation 114A

1-Boc-4-[2-(1-Methyl-1H-imidazole-2-carbonyl)-phenyl]-piperazine and 1-Boc-4-{2-[acetoxy-(1H-imidazol-2-yl)-methyl]-phenyl}-piperazine

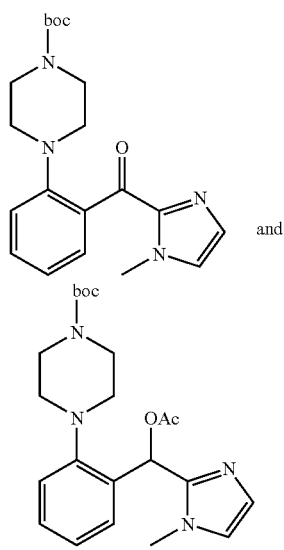
and

To a solution of 1-Boc-4-{2-[hydroxy-(1H-imidazol-2-yl)-methyl]-phenyl}-piperazine (200 mg, 0.734 mmol) and sodium bicarbonate (185 mg, 2.2 mmol) in 8 mL of CH$_2$Cl$_2$ was added Dess-Martin periodane (467 mg, 1.1 mmol). After stirring for about 1 hour, 2 mL of saturated aqueous sodium bicarbonate and 2 mL 0.5 M Na$_2$S$_2$O$_3$ were added. After stirring for about 1 hour, the solution was diluted with CH$_2$Cl$_2$ and washed with water and brine, and then dried (Na$_2$SO$_4$), filtered and concentrated. Purification by silica gel flash chromatography (35 g SiO$_2$, 0-5% 0.2 M NH$_3$ in MeOH/CH$_2$Cl$_2$ linear gradient over 30 min at 35 mL/min) afforded about 53 mg (0.14 mmol, 19%) of the ketone {LRMS (ESI+): 371.2 [M+1]} and about 114 mg (0.28 mmol, 37%) of the acetate {LRMS (ESI+): 415.2 [M+1]}.

Preparation 115A

1-Boc-4-[2-(1-methyl-1H-imidazol-2-ylmethyl)-phenyl]-piperazine

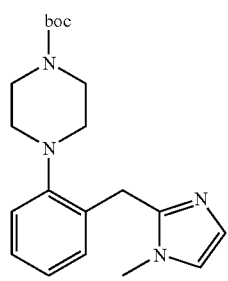

To a solution of 1-Boc-4-{2-[hydroxy-(1H-imidazol-2-yl)-methyl]-phenyl}-piperazine (93 mg, 0.25 mmol) in 5 mL of THF was added NaH (30 mg, 0.75 mmol). After stirring for about 45 minutes, CS$_2$ (75 uL, 1.25 mmol) was added. After stirring for about 30 minutes, 5 mL of THF was added followed by MeI (78 uL, 1.25 mmol). After stirring for about 1 hour, saturated aqueous NH$_4$Cl and brine were added. The solution was extracted EtOAc (2×). The combined organic solutions were dried (Na$_2$SO$_4$), filtered and concentrated. Purification by silica gel chromatography (35 g SiO$_2$, 0 to 5% MeOH/CH$_2$Cl$_2$ over 30 minutes at 35 mL/min) afforded about 97 mg (0.21 mmol, 84%) of the xanthate as a yellow oil. LRMS (ESI+): 463.2 (M+1)

To a solution of the xanthate (90 mg, 0.195 mmol) and Bu$_3$SnH (260 uL, 0.967 mmol) in 2 mL of toluene at 80° C. was added AIBN (50 uL of a 0.4 M solution in toluene, 0.02 mmol). Another 50 uL of the AIBN solution was added every 2 to 3 hours for 8 hours. After stirring overnight another 50 uL of the AIBN solution was added. After stirring for about 8 more hours, the solution was concentrated and filtered through celite with CH$_2$Cl$_2$. Purification by silica gel chromatography (35 g SiO$_2$, 0 to 5% 0.2 M NH$_3$ in MeOH/CH$_2$Cl$_2$ over 30 minutes at 35 mL/min) afforded about 46 mg (0.13 mmol, 66%) of the deoxygenated product as a colorless oil. LRMS (ESI+): 357.2 (M+1)

Preparation 116A

1-Boc-4-(2-thiazol-2-ylmethyl-phenyl)-piperazine

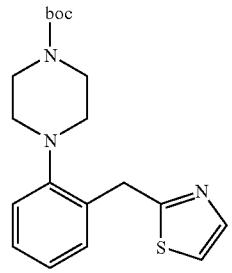

Thiazole was lithiated with n-butyllithium and reacted with N-Boc-4-(2-formylphenyl)-piperazine in a manner similar to preparation 113A. The resulting alcohol was deoxygenated in a manner similar to preparation 115A to afford the final compound. LRMS (ESI+): 360.1 (M+1)

Preparation 117A

1-Boc-4-[2-(2-methyl-2H-[1,2,4]triazol-3-ylmethyl)-phenyl]-piperazine

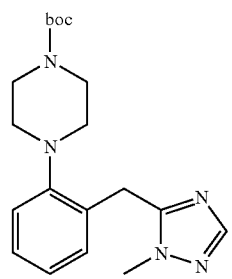

1-methyltetrazole was lithiated with n-butyllithium and reacted with N-Boc-4-(2-formylphenyl)-piperazine in a manner similar to preparation 113A. The resulting alcohol was deoxygenated in a manner similar to preparation 115A to afford the final compound. LRMS (ESI+): 358.3 (M+1)

Preparation 118A

1-Boc-4-(2-isobutoxy-phenyl)-piperazine

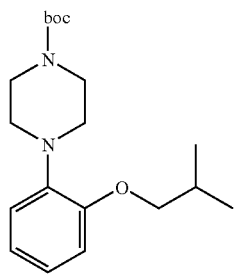

To a solution of 1-Boc-4-(2-hydroxy-phenyl)-piperazine (560 mg, 2.0 mmol) in 10 mL of DMF was added K$_2$CO$_3$ (835 mg, 6 mmol). After stirring for about 5 minutes, isobutyl iodide (350 uL, 3 mmol) was added. After stirring overnight at 60° C., the solution was warmed to about 80° C. After stirring for about 4 hours, the solution was cooled to r.t. diluted with EtOAc, washed with water and brine, and then dried (Na$_2$SO$_4$), filtered and concentrated. Purification by silica gel chromatography (35 g SiO$_2$, 10 to 30% EtOAc/hexanes, over 45 minutes at 35 mL/min) afforded about 418 mg (1.25 mmol, 62%) of N-Boc-4-(2-isobutoxy-phenyl)-piperazine as a colorless oil. LRMS (ESI+): 335.1 [M+1].

Preparation 119A

1-Boc-4-[2-(1-methyl-1H-imidazol-2-ylmethoxy)-phenyl]piperazine

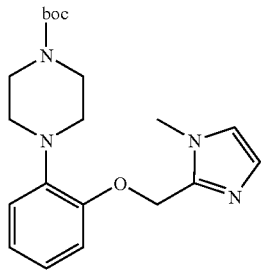

To a solution of 1-Boc-4-(2-hydroxy-phenyl)-piperazine (556 mg, 2.0 mmol, 1.0 eq.), (1-methyl-1H-imidazol-2-yl)-methanol (448 mg, 4.0 mmol, 2.0 eq.), triphenylphosphine (1.04 g mg, 4.0 mmol, 2.0 eq.) and THF at 0° C. under nitrogen was added DEAD (0.629 mL, 4.0 mmol, 2.0 eq.) slowly so that temperature of the reaction does not rise above 10° C. After addition was complete, the ice bath was removed and the mixture was stirred at r.t. overnight. Methanol was added, and the mixture was stirred for about 15 minutes and then concentrated. Purification by flash chromatography (35 g SiO$_2$, 40 mL/min, linear gradient 0-8% 2.0 M NH$_3$ in MeOH/CH$_2$Cl$_2$ for 25 minutes and 8% 2.0 M NH$_3$ in MeOH for 7 minutes) afforded the title compound (279 mg, 0.75 mmol, 37%). LRMS (ESI+): 373.3 (M+1).

Preparation 120A

1-Boc-4-(2-benzyloxy-phenyl)-piperazine

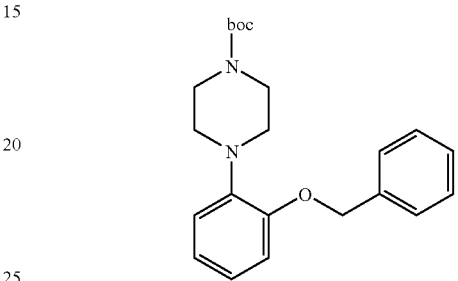

The title compound was prepared in a manner similar to Preparation 118A except that benzyl bromide was used. LRMS (ESI+): 369.1 (M+1).

Preparation 121A

1-Boc-4-(2-carboxy-phenyl)-piperazine

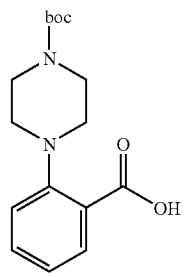

To a solution of 1-(2-cyanophenyl)-piperazine (37.45 g, 200 mmol) in 500 mL of absolute ethanol was added 1000 mL of 25% aqueous KOH. The solution was heated to reflux for about 72 hours and then cooled to about 0° C. The solution was acidified with 890 mL of 5 M HCl, and then solid NaHCO$_3$ was added to bring the pH of the solution to about 8. NaHCO$_3$ (12.7 g, 120 mmol) and Boc$_2$O (11.4 g, 52.2 mmol) were added and the mixture was stirred overnight, which was then acidified with 5 M HCl to about pH 1. After addition of EtOAc and brine, the aqueous solution was separated and extracted with EtOAc (2×). The combined organic solutions were washed with water (2×) and brine, and then dried (Na$_2$SO$_4$), filtered, and concentrated. The material was purified by recrystallization from EtOAc/hexanes to afford about 49.8 g (162 mmol, 81%) of the title compound. LRMS (ESI−): 305.2 (M−1)

Preparation 122A (2-piperazin-1-yl-phenyl)-piperadin-1-yl-methanone

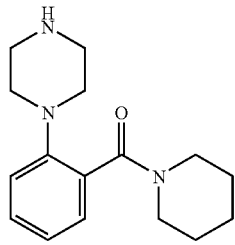

The 1-Boc-4-(2-carboxy-phenyl)-piperazine (1 g, 3.26 mmol), piperidine (278 mg, 3.26 mmol), EDCI (625 mg, 3.26 mmol) and DMAP (50 mg, catalytic) were dissolved in DCM (20 mL) and stirred at r.t. for about 12 hours. The mixture was washed with water, dried, filtered, and concentrated. The resultant foam was taken up in DCM (10 mL) and TPA (5 mL) was added, and the mixture stirred at r.t. for about 2 hours. The reaction was concentrated and subjected to SCX ion exchange chromatography followed by silica gel chromatography to afford the final product (868 mg, 71%) as a white foam. LRMS (ESI+): 274.1 (M+1).

Preparation 123A

1-Boc-4-[2-(2H-tetrazol-5-yl)-phenyl]-piperazine

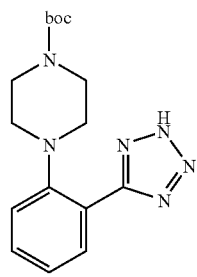

A solution of 4-(2-cyano-phenyl)-piperazine (1.7 g, 9.0 mmol, 1.0 eq) in azidotributyltin (5.0 g, 15 mmol, 1.5 eq.) was stirred at 80° C. for about 5 days. Purification by SCX (10 g) ion exchange chromatography afforded crude 4-(2-tetrazole-5-yl-phenyl)-piperazine. LRMS (ESI+): 231.0 (M+1).

To a solution of 4-[2-(2H-tetrazole-5-yl-phenyl)-piperazine 1.8 g, 7.7 mmol, 1.0 eq.), NaHCO₃ (978 mg, 9.2 mmol, 1.2 eq), DMAP (94 mg, 0.77 mmol, 0.1 eq.) in H₂O:Dioxane (1:1) was added (Boc)2O (1.6 g, 7.7 mmol, 1.0 eq.). The resulting mixture was stirred at r.t. overnight, and then neutralized with 1.0 M HCl and extracted with EtOAc (3x). The combined organic extracts were dried (Na₂SO₄), filtered and concentrated. Purification by flash chromatography (35 g SiO₂, linear gradient, 40 mL/min , 0%-10% 2.0 M NH₃ in MeOH/CH₂Cl₂ for 20 minutes and 10% 2.0 M NH₃ in MeOH /CH₂Cl₂ for 13 minutes) afforded the title compound (798 mg, 2.41 mmol, 32%). LRMS (ESI+): 331.1 (M+1).

Preparation 124A

4-[2-(2-isobutyl-2H-tetrazol-5-yl)-phenyl]piperazine and 4-[2-(1-isobutyl-1H-tetrazol-5-phenyl]piperazine

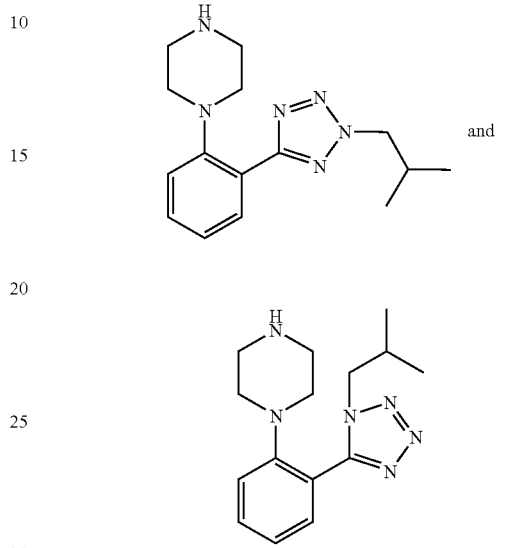

To a solution of N-boc-4-[2-(2H-tetrazole-5-yl-phenyl)-piperazine (330 mg, 1.0 mmol, 1.0 eq.) in DMF (10 mL) was added K₂CO₃ (331 mg, 2.4 mmol, 2.4 eq.) and isobutyl iodide (0.14 mL, 1.2 mmol, 1.2 eq.). The mixture was stirred at r.t. overnight. The mixture is diluted with ethyl acetate (50 mL) and washed with H₂O (20 mL) and brine (20 mL). The aqueous layers were extracted with EtOAc (2x). The combined organic extracts were dried (Na₂SO₄), filtered and concentrated to afford about 370 mg (96%, 0.96 mmol) of a mixture (60:40 by NMR) of Boc-protected title compounds favoring the 2H substituted tetrazole. LRMS (ESI+): 387.2 (M+1).

To a solution of the mixture of Boc-protected compounds from above (360 mg, 0.93 mmol, 1.0 eq.) in CH₂Cl₂ (10 mL) was added TPA (5 mL) and DMS (0.25 mL). The resulting mixture was stirred at r.t. for about 2 hours. The reaction mixture was concentrated and purified using SCX (10 g) ion-exchange chromatography to afford a mixture of the title compounds (240 mg, 0.84 mmol, 90%). LRMS (ESI+): 287.1 (M+1).

C Domain Preparations:

The protected amino acid derivatives corresponding to the B and C domains are, in many cases, commercially available. Other protected amino acid derivatives can be prepared by following known literature methods (See Williams, R. M. *Synthesis of Optically Active α-Amino Acids*, Pergamon Press: Oxford, 1989). The following provides the preparation of C domains.

Preparation 1C

1-Methoxycarbonylmethyl-1,3-dihydro-isoindole-2-carboxylic acid tert-butyl ester

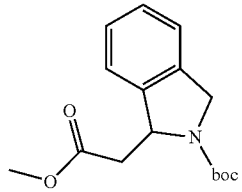

Step A: (2-Bromo-benzyl)-carbamic acid tert-butyl ester

To a mixture of 125.0 g (561.8 mmol) of 2-bromobenzylamine hydrochloride and 170.7 g (1236.0 mmol) of potassium carbonate in 300 mL of 50% THF/water was added 134.9 g (618.0 mmol) of di-tert-butyl dicarbonate in four portions over 20 minutes. The mixture was stirred at r.t. for about 16 hours and then diluted with 300 mL of ethyl acetate and 300 mL of water. The organic portion was separated and the aqueous portion was extracted three times with 200 mL each of ethyl acetate. The combined ethyl acetate portions were washed once with 250 mL of 10% aqueous sodium bisulfate. The organic portion was dried (MgSO$_4$), filtered and concentrated to dryness to afford about 161 g of Step A compound.

Step B: 3-[2-(tert-Butoxycarbonylamino-methyl)-phenyl]-acrylic acid methyl ester To compound of Step A (161.0 g, 561.8 mmol) in DMF (800 mL) was added methyl acrylate (58.0 g, 674.2 mmol), TEA (170.5 g, 1685.4 mmol) and dichlorobis(triphenylphosphine) palladium(II) (7.9 g, 11.2 mmol). The mixture was heated at 80° C. for about 32 hours. The mixture was cooled, diluted with 1000 mL of EtOAc and washed with 10% aqueous sodium bisulfate. The aqueous portion was extracted three times with EtOAc and the combined organics were dried (Na$_2$SO$_4$) and concentrated to dryness. The residue was dissolved in a small amount of DCM and filtered through 7 inches of silica gel in a 2 L sintered glass funnel eluting with 25% EtOAc/hexanes. The eluent was concentrated to dryness and recrystallized from EtOAc/hexanes to afford about 116.9 g (71%) of Step B compound.

Step C: To a 0° C. solution of (116.9 g, 401.2 mmol) material from Step B in DCM (800 mL) was added 200 mL of TFA dropwise over 15 minutes. After removing the cooling bath, the mixture was stirred for about 2.5 hours and then concentrated to dryness. The residue was dissolved in 500 mL of DCM and saturated aqueous sodium bicarbonate is slowly added until the mixture was slightly basic. The organic portion was separated and the aqueous portion is extracted two times with DCM. The combined organic portions were dried (Na$_2$SO$_4$) and concentrated to dryness. The residue was dissolved in 800 mL of DCM and DIPEA (57.0 g, 441.4 mmol) was added. To the mixture was added di-tert-butyl dicarbonate (96.3 g, 441.4 mmol) in five portions over 45 minutes and then stirred at r.t. for 16 hours. The mixture was washed with 10% aqueous sodium bisulfate, and the organic portion was separated and the aqueous portion is extracted two times with DCM. The combined organic extracts were dried ((Na$_2$SO$_4$) and concentrated to dryness. The resulting residue was dissolved in a small amount of DCM and filtered through 7 inch silica gel in a 2L sintered glass funnel eluting with 25% EtOAc/hexanes. The eluent was concentrated to dryness and the enantiomers were separated by chiral chromatography. The first eluting isomer was labeled as isomer #1 and the second eluting is labeled as isomer #2, which afforded about 52.6 g (45%) of the final compound (isomer 2). EIS-MS 292 [M+1].

Preparation 2C

1-Carboxymethyl-1,3-dihydro-isoindole-2-carboxylic acid tert-butyl ester

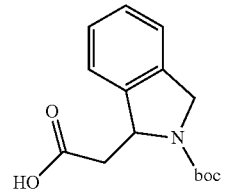

To 1-methoxycarbonylmethyl-1,3-dihydro-isoindole-2-carboxylic acid tert-butyl ester (52.6 g, 180.5 mmol) in MeOH (500 mL) was added 1 N NaOH (199 mL, 199.0 mmol). The mixture is stirred at r.t. for about 48 hours and then concentrated to dryness. The resulting residue was dissolved in water (300 mL) and extracted with diethyl ether (2×). The aqueous portion was acidified to pH 2 with 10% aqueous sodium bisulfate and extracted with EtOAc. The combined organic extracts were dried (MgSO$_4$) and concentrated to dryness to afford about 49.8 g of the final compound (99%). EIS-MS 276 [M−1].

Preparation 3C (2-isopropyl-2,3-dihydro-1H-isoindol-1-yl)-acetic acid

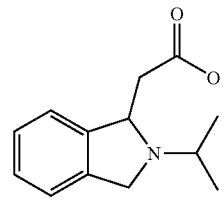

Step A: (2,3-dihydro-1H-isoindol-1-yl)-acetic acid methyl ester:

To the compound prepared in Preparation C1 (11.75 g., 40.41 mmol) in DCM (50 mL) was added TFA (50 mL) dropwise. After about 2 hours, the mixture was concentrated to dryness and the resulting residue was partitioned with saturated aqueous sodium bicarbonate (200 mL) and EtOAc (300 mL). The organic portion was separated and the aqueous layer was extracted with DCM (4×500 mL). The combined DCM extracts were combined, dried (Na$_2$SO$_4$), and concentrated to dryness to afford about 3.97 g (51%).

Step B: (2-isopropyl-2.3-dihydro-1H-isoindol-1-yl)-acetic acid methyl ester:

To the compound obtained from Step A (0.50 g, 2.61 mmol) in dichloroethane (46 mL) was added acetone (1.76 mL, 24.01 mmol) and sodium triacetoxyborohydride (2.48 g., 11.74 mmol). After 6 hours, the mixture was diluted with 1.0N NaOH (100 mL), and the organic portion was separated. The aqueous layer was extracted with DCM (3×100 mL). The combined DCM extracts were dried (MgSO$_4$) and concentrated to dryness to afford about 0.60 g (99%). EIS-MS 235 [M+1].

Step C: To the compound of Step B (0.53 g., 2.30 mmol) in MeOH (5.1 mL) was added 1.0N NaOH (2.53 mL, 2.53 mmol). After two days, the solution was concentrated to dryness. The resulting residue was diluted with 1.0N HCl and water was loaded onto a strong cation exchange resin. The resin was washed with water, TBF/water (1:1) and then water. The product was then eluted from the resin with pyridine/water (1:9). The eluent was concentrated to dryness to afford about 0.43 g (85%) of the final compound. EIS-MS 220 [M+1].

Preparation 4C (2-Methyl-2,3-dihydro-1H-isoindol-1-yl)-acetic acid

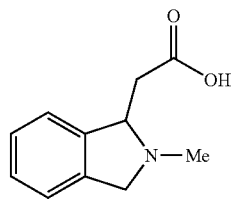

Step A: (2-Methyl-2,3-dihydro-1H-isoindol-1-yl)-acetic acid methyl ester:

The compound from preparation C1 was deprotected with TFA in a manner similar to preparation 3C of Step A. To the deprotected compound (0.50 g, 2.61 mmol), in dichloroethane (46 mL), was added 37% aqueous formaldehyde solution (1.80 mL, 24.01 mmol) and sodium triacetoxyborohydride (2.48 g., 11.74 mmol). After 3 days, the mixture was diluted with 1.0N NaOH (100 mL). The organic portion was separated and the aqueous layer was extracted with DCM (3×100 mL). The combined DCM extracts were dried (Na₂SO₄) and concentrated to dryness. The resulting residue was purified by flash chromatography (SiO₂, eluting with 100% EtOAc) affording about 0.43 g (79%) of the alkylated isoindole. EIS-MS 206 [M+1].

Step B: To the compound of Step A (0.34 g., 1.66 mmol) in MeOH (3.7 mL) was added 1.0N NaOH (1.82 mL, 1.82 mmol). After 2 days, the solution was concentrated to dryness. The resulting residue was diluted with 1.0N HCl and water was then loaded onto a strong cation exchange resin. The resin was washed with water, THF/water(1:1) and water, and the product was eluted from the resin with pyridine/water(1:9). The eluent was concentrated to dryness to afford about 0.31 g (98%) of the final compound. EIS-MS 192 [M+1].

Preparation 5C

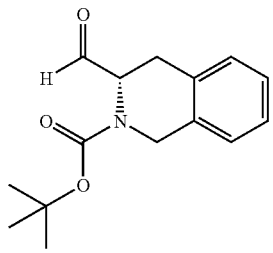

The above compound was prepared from Boc-L-Tic-OH as described in Preparation 6C below, except that the Weinreb amide was made by a similar procedure to that described in *Synthesis*, 676, 1983.

Preparation 6C

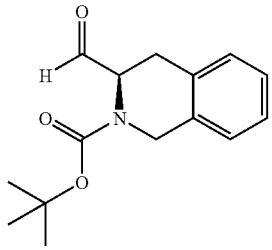

Boc-D-Tic-OH (14.9 g, 53.7 mmol), methoxymethylamine hydrochloride (5.24 g, 53.7 mmol), EDC (11.3 g, 59.1 mmol), HOBT (7.98 g, 59.1 mmol), DIEA (9.83 ml, 59.1 mmol) and THF (500 ml) were combined, and the resulting mixture was stirred for about 18 hours at r.t. under nitrogen. The reaction mixture was concentrated and the residue was taken up in ethyl acetate. The resulting mixture was washed with 1M HCl, saturated NaHCO₃ and brine, which was then dried via filtration through phase separator paper. Removal of solvent gives a residue, which was chromatographed on silica gel using (1:1 ethylacetate /hexane) to give about 12.3 g of Boc-D-Tic-NMeOMe (Weinreb amide).

Lithium aluminum hydride (1.0M in THF, 5.1 ml, 5.00 mmol) was slowly added to the Weinreb amide prepared above (1.28 g, 4.00mmol) in THF (35 ml) at 0° C. The reaction mixture was stirred at 0° C. for about 15 minutes. Aqueous KHSO₄ (970 mg in 20 ml H₂O) was slowly added followed by diethylether. The organic layer was separated and the aqueous layer was extracted with diethylether. The organic phases were combined and washed with aqueous 1M HCl, saturated aqueous NaHCO₃ and brine, which was then dried over Na₂SO₄. Removal of solvent afforded about 780 mg of the final compound. MS: MH+262.

Preparation 7C (2-Butyl-2.3-dihydro-1H-isoindol-1-yl)-acetic acid methyl ester

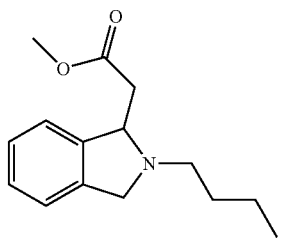

The compound from preparation C1 was deprotected with TFA in a manner similar to preparation 3C of Step A. To the deprotected compound (0.50 g, 2.61 mmol) and butryaldehyde (2.16 mL, 24.01 mmol) in dichloroethane (46 mL) was added sodium triacetoxyborohydride (2.48 g., 11.74 mmol).

After reacting about 3 hours, the mixture was diluted with 1.0 N NaOH (100 mL) and partitioned. The aqueous layer was extracted with DCM (3×75 mL). The DCM layers were combined, dried over sodium sulfate, filtered and concentrated under reduced pressure to give a brown residue. The residue was purified via silica gel chromatography (eluent: ethyl acetate/hexanes (1:3). The purified fractions were combined and concentrated to give the title compound as a brown oil (0.51 g, 77%). MS ES 249.2 (M+H)

Preparation 8C (2-Butyl-2,3-dihydro-1H-isoindol-1-yl)-acetic acid

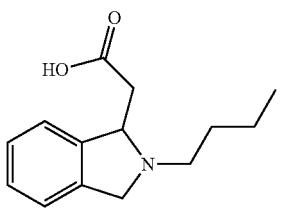

To a solution containing the compound 7C (0.47 g, 1.89 mmol) in methanol (4.2 mL) was added 1.0 N NaOH (2.08 mL, 2.08 mmol). After reacting about 2 hours, the solution was concentrated under reduced pressure. The residue was diluted with 1.0 N HCl, and water was loaded onto a strong cation exchange resin. The resin was washed with water and THF/water (1:1), and the product was eluted from the resin with pyridine/water (1:9). The pyridine washes were concentrated under reduced pressure, and azeotroped with acetone to give the tide compound as brown solids (0.28 g., (64%)) MS ES 234.19 (M+H)

Preparation 9C

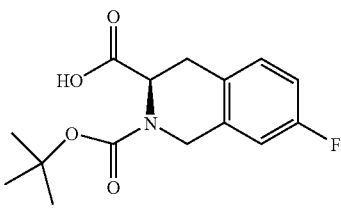

Step A: To a solution of N-Boc-4-Fluoro-D-Phe (2.37 g, 8.366 mmol) in methanol, 3 mL of concentrated sulfuric acid was added. The mixture was heated to reflux overnight and then concentrated in vacuo. MS M+1 198.1

Step B: To an ice cold mixture of 1.65 g (8.367 mmol) of compound from Step A, 1.353 mL of pyridine and ethyl chloroformate (0.848 mL, 8.869 mmol) is added slowly with stirring for about 30 minutes giving white solid. The mixture was partitioned between water and ethyl acetate. The aqueous layer was extracted with EtOAc (2×). The combined organic solution was dried over $MgSO_4$, filtered, and concentrated in vacuo to give about 2.17 g of yellow oil (96%). MS M+1 270.1.

Step C: A mixture containing 2.17 g (8.06 mmol) of the compound from Step B, paraformaldehyde (0.254 g, 8.46 mmol), and 10 mL of 3:1 glacial acetic acid/conc. sulfuric acid was stirred at r.t. for about 48 hours. The mixture was partitioned between water and ethyl acetate. The aqueous layer was extracted with EtOAc (3×). The combined EtOAc solution was dried over magnesium sulfate, filtered, and concentrated in vacuo. The desired product was purified by column chromatography eluting with 25% EtOAc in Hexane to give about 1.31 g (58%) of colorless oil. MS: M+1 282.1

Step D: A solution of 1.31 g (4.656 mmol) of material from Step C in 20 mL of 5N HCl was heated to reflux for about 24 hours. The solution was concentrated in vacuo. The resulting white solid was washed with ether to afford about 0.87 g (81%). MS M+1 196.1.

Step E: To a solution of 0.87 g (3.755 mmol) of material from Step D in 20 ml of 1:1 dioxane/water, di-t-butyl-dicarbonate (0.901 g, 4.131 mmol) and 2.355 mL (16.90 mmol) of TEA were added. The mixture was allowed to stir at r.t. overnight. The mixture was diluted with EtOAc, and the separated aqueous layer was extracted with EtOAc (3×). The combined organic solution was dried over magnesium sulfate, filtered and concentrated in vacuo to give about 0.64 g (58%) of the final compound. MS M-1 294.1.

Preparation 10C

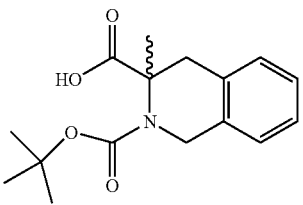

Step A: By following a procedure of Preparation 28C, Step A and 1.0 g (5.58 mmol) of □-methyl-DL-phenylanaline, about 1.4 g of ester was prepared. MS M+1 194.1

Step B: By following a procedure of Preparation 28C, Step B and 1.08 g (5.59 mmol) of material from Step A, about 1.48 g (100%) of product was prepared. MS M+1 266.1

Step C: By following a procedure of Preparation 28C, Step C and 1.48 g (5.59 mmol) of material from Step B, about 1.55 g (100%) of product was prepared. MS M+1 278.1

Step D: By following a procedure of Preparation 28C, Step D and 1.55 g (5.59 mmol) of material from Step C, about 1.33 g of product was prepared. MS M+1 192.1

Step E: By following a procedure of Preparation 28C, Step E and 1.33 g (5.84 mmol) of material from Step D, about 1.70 g (100%) of the final compound was prepared. MS M+1 292.2

Preparation 11C

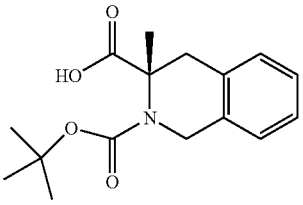

Step A: By following a procedure of Preparation 28C, Step A and 2.0 g (11.16 mmol) of □-methyl-D-phenylanaline, about 2.15 g of ester was prepared. MS M+1 194.1

Step B: By following a procedure of Preparation 28C, Step B and 2.15 g (11.16 mmol) of material from Step A, about 1.46 g (49%) of product was prepared. MS M+1 266.1

Step C: By following a procedure of Preparation 28C, Step C and 1.46 g (5.503 mmol) of material from Step B, about 0.74 g (48%) of product was prepared. MS M+1 278.1

Step D: By following a procedure of Preparation 28C, Step D and 0.74 g (2.67 mmol) of material from Step C, about 0.54 g (89%) of product was prepared. MS M+1192.1

Step E: By following a procedure of Preparation 28C, Step E and 0.54 g (2.37 mmol) of material from Step D, about 0.54 g (78%) of the final compound was prepared. MS M+1 292.2

Preparation 12C

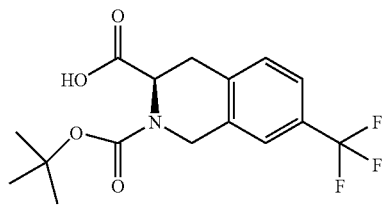

Step A: By following a procedure of Preparation 28C, Step A and 0.65 g (1.95 mmol) of N-Boc-4-trifluoromethyl-D-phenylanaline, about 0.48 g of ester was prepared. MS M+1 248.0

Step B: By following a procedure of Preparation 28C, Step B and 0.48 g (1.95 mmol) of material from Step A, about 0.60 g (96%) of product was prepared. MS M+1 320.1

Step C: By following a procedure of Preparation 28C, Step C and 0.6 g (1.879 mmol) of material from Step B, about 0.37 g (59%) of product was prepared. MS M+1 332.1

Step D: By following a procedure of Preparation 28C, Step D and 0.37 g (1.117 mmol) of material from Step C, about 0.11 g (35%) of product was prepared. MS M+1 246.1

Step E: By following a procedure of Preparation 28C, Step E and 1.11 g (0.391 mmol) of material from Step D, about 0.234 g (>100%) of the final compound is prepared. MS M−1 344.1

Preparation 13C

Lithium; (2-tert-butoxycarbonyl-1,2,3,4-tetrahydro-isoquinolin-1-yl)-acetate

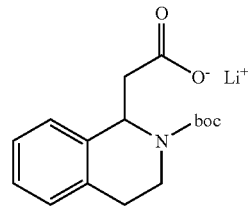

Step 1: (1,2,3,4-tetrahydro-isoquinolin-1-yl)-acetic acid methyl ester

To a solution 100.4 g (52 mol) of Boc-tetrahydo isoquinoline-1-acetic (100.4 g 520.0 mmol) in 200 mL methanol was added 400 mL of 2.3 M HCl in methanol. The mixture was stirred overnight and concentrated in vacuo. The residue was dissolved in ethyl acetate and washed with saturated sodium bicarbonate, brine, and then dried (Na$_2$SO$_4$) and concentrated in vacuo to afford about 109.5 g (100%) of the title compound. EIS-MS: 206 (M+1).

Step 2: 1-methoxycarbonylmethyl-3,4-dihydro-1H-isoguinoline-2-carboxylic acid tert-butyl ester To a 0° C. solution of material from Step 1 (50.5 g, 240.0 mmol) in 250 mL dry THF was added di-tert-butyl dicarbonate (59.3 g, 270.0 mmol) in 50 mL dropwise. After stirring for about 45 minutes, the mixture was concentrated in vacuo. The residue was dissolved in ethyl acetate, washed with saturated sodium bicarbonate and brine, and then dried (Na$_2$SO$_4$) and concentrated in vacuo. Chromatography of the residue afforded both enantiomers of the title compound. EIS-MS: 306 (M+1).

Step 3: To a solution of material from Step 2 (10.2 g, 33.4 mmol) in 220 mL of dioxane was added a solution of lithium hydroxide monohydrate (1.67 g, 39.8 mmol) in 110 mL water in portions to maintain a temperature below 30° C. The mixture was stirred for about 16 hours and concentrated in vacuo to afford about 11.2 g of the final compound. EIS-MS: 292 (M+1).

Preparation 14C

Lithium; (2-methyl-1,2,3,4-tetrahydro-isoquinolin-1-yl)-acetate

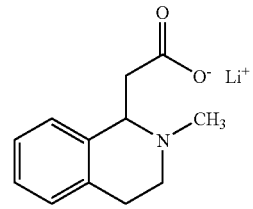

Step 1: (1,2,3,4-Tetrahydro-isoquinolin-1-yl)-acetic acid methyl ester

The material from Preparation of 13C Step 2 (9.98 g, 32.7 mmol) was mixed with 500 mL cold 4M HCl/dioxane and stirred at r.t. for about an hour. The mixture was concentrated in vacuo. The residue was dissolved in ethyl acetate and then washed with saturated sodium bicarbonate and brine. The organic portion was dried (Na$_2$SO$_4$), filtered and concentrated in vacuo to afford about 6.9 g (100%) of the title compound. EIS-MS: 206 (M+1).

Step 2: (2-methyl-1,2,3,4-tetrahydro-isoquinolin-1-yl)-acetic acid methyl ester

To a solution of material from Step 1 (6.71 g, 32.0 mmol) in 175 mL of dichloroethane was added 37% aqueous formaldehyde (22.6 mL, 300 mmol). After about 10 minute, sodium triacetoxyborohydride (31.2 g, 147.0 mmol) was added in 2 to 3 g portions with some cooling to maintain ambient temperature. The mixture was stirred for about 16 hours and DCM and water was added. The mixture was adjusted to pH 9-10 with 5N sodium hydroxide. The organic layer was separated, washed with brine, and then dried (Na$_2$SO$_4$) and concentrated in vacuo. Chromatography (silica gel, 5% (2N ammonia in methanol)/DCM) of the residue afforded about 6.9 g (96%) of the title compound. EIS-MS: 220 (M+1).

Step 3: To a solution of material from Step 2 (4.45 g, 18.9 mmol) in 120 mL dioxane was added lithium hydroxide monohydrate (1.02 g, 22.7 mmol) in 65 mL water in portions keeping the temperature below 30° C. After about 16 hours, the mixture was concentrated in vacuo to afford about 8.12 g of the final compound. EIS-MS: 206 (M+1).

Preparation 15C

1,1-Dimethyl-6-methoxy-1,2,3,4-tetrahydroisoquinoline-3-carboxylic acid ethyl ester

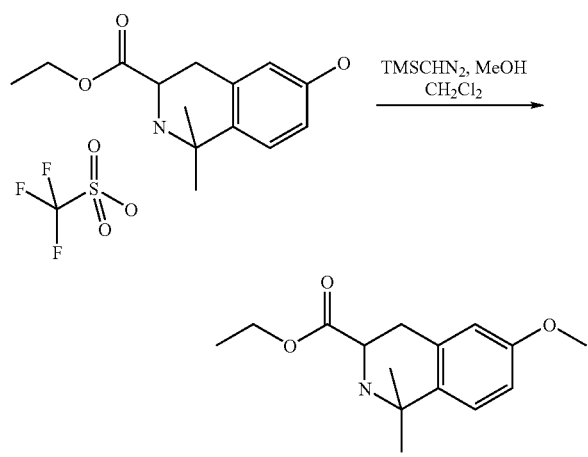

To a solution of the triflate salt of 1,1-dimethyl-1,2,3,4-tetrahydroisoquinoline-3-carboxylic acid ethyl ester (1.5 g, 3.76 mmol, 1.0 eq.) in MeOH (20 mL) and $CH_2Cl_2$ (2 mL) at 0° C. was added a solution of (trimethylsilyl)diazomethane (2.0 M in hexane, 3.7 mL, 2.0 eq.). The resulting mixture was warmed to r.t. and stirred overnight, and then the solution was concentrated. Purification by flash chromatography (125 g $SiO_2$ linear gradient, 40 mL/min, 1:1 EtOAc/hexane for 33 minutes) afforded about 900 mg of the final compound (96%). LRMS (electrospray): 250.2 (M+1).

"A Domain" and "B Domain" Combination

Preparation 1AB and 2AB 1-(D-p-Cl-Phe)-4-(2-methanesulfonyl-phenyl)piperazine and 1-(D-p-Cl-Phe)-4-(2-methanesulfinyl-phenyl)-piperazine

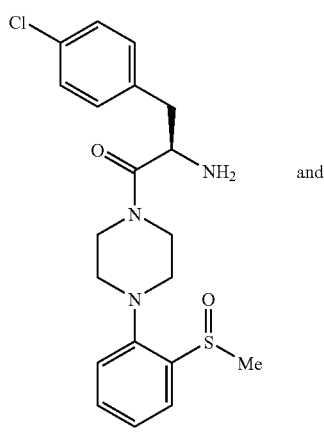

and

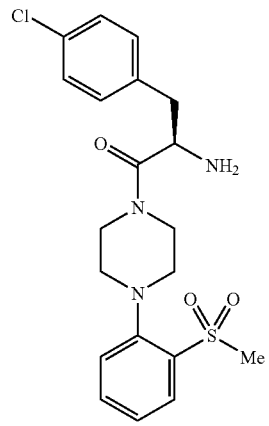

Commercially available 1-(2-methylthiophenyl) piperazine was coupled to Boc-p-Cl-D-Phe-OH in a manner substantially similar to that described in coupling procedure 1. To a solution of the coupled product (100 mg, 0.204 mmol) in 5 mL of $CH_2Cl_2$ cooled to −78° C. was added m-chloroperbenzoic acid (49 mg, 0.204 mmol). After stirring for about 30 minutes, the reaction was quenched with 1 M $Na_2S_2O_3$ and extracted with $CH_2Cl_2$. The combined organic solutions were washed with saturated sodium bicarbonate, dried ($Na_2SO_4$), filtered and concentrated. Purification by flash chromatography (10 g $SiO_2$, linear gradient 0-10% methanol/$CH_2Cl_2$, 30 mL/minute, over 30 minutes) afforded about 46 mg (0.090 mmol, 43%) of the sulfoxide and 60 mg (0.115 mmol, 56%) of the sulfone. Each of these is separately deprotected in manner substantially similar to that described in coupling procedure 1.

Preparation 3AB

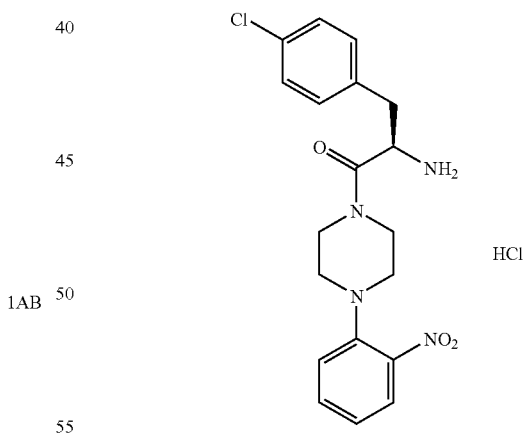

1-(2-Nitrophenyl)piperazine (3.13 g, 15.1 mmol), Boc-D-4-chlorophenylalanine (4.52 g, 15.1 mmol), EDC (3.19 g, 16.6 mmol), HOBT (2.21 g, 16.7 mmol) and DIBA (2.63 ml, 15.1 mmol) were added to THF. The resulting mixture was stirred overnight at r.t. under a nitrogen. The reaction mixture was then concentrated in vacuo. The residue was taken up in ethyl acetate and washed with 1M HCl, diluted with $NaHCO_3$ and brine and then dried with $Na_2SO_4$. Removal of the solvent gave a residue, which was chromatographed on normal phase (ethyl acetate/hexane 1:1) to give about 6.8 g of the Boc-protected compound.

The Boc-protected compound (6.88 g, 14.1 mmol) was dissolved in 4M HCl/dioxane (230 ml), and the resulting mixture was stirred at r.t. for about an hour. The mixture was concentrated in vacuo to give about 5.1 g of the final compound.

Preparation 4AB

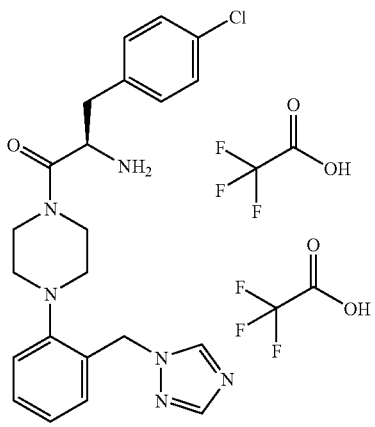

The mixture of piperazine from Preparation 54A (6.99 g, 28.76 mmol), N-Boc-D-Cl-Phe (8.624 g, 28.76 mmol), HATU (10.94 g, 28.76 mmol) and DIEA (25.05 mL, 143.8 mmol) in 160 mL of DCM was stirred at r.t. overnight. The mixture was partitioned between water and $CH_2Cl_2$. The aqueous layer was extracted with $CH_2Cl_2$ (2×). The combined organic solution was dried over $MgSO_4$, filtered and concentrated in vacuo. The residue was Purified through silica gel column using 10% MeOH in EtOAc to give Boc protected product. The Boc protected compound was treated with 1:1 $TFA/CH_2Cl_2$. The mixture was stirred at r.t. for about 2 hours and then concentrated in vacuo to afford the final compound (13.9 g, 74%). MS M+1 425.2.

Preparation 5AB 1-(D-p-Cl-Phe)-4-1-[(2-aminosulfonyl)phenyl]piperazine

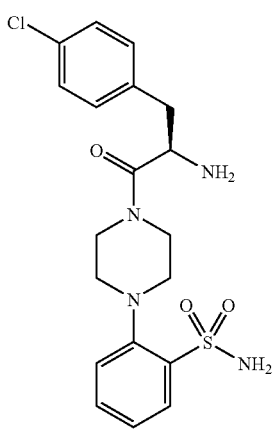

1-[(2-aminosulfonyl)phenyl]piperazine from preparation 19A was coupled to Boc-p-Cl-D-Phe-OH followed by deprotection and HCl salt formation in a manner similar to coupling procedure 1, Steps 1 and 4.

"B Domain" and "C Domain" Combination

Preparation 1BC

N-Boc-D-Tic-D-p-Cl-phe-OH

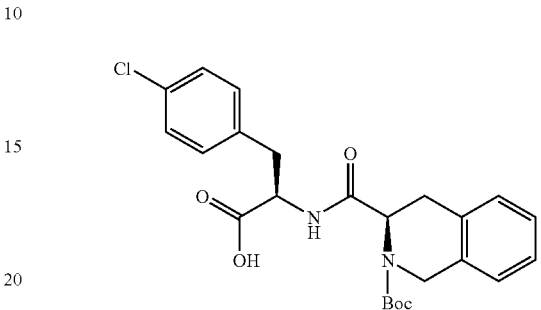

Step 1: The HCl salt of H-D-p-Cl-Phe-OMe (35.8 g, 129 mmol) was dissolved in water (200 mL). Ethyl acetate (200 mL) was added followed by addition of a saturated sodium bicarbonate solution. The mixture was stirred for about 5 minutes, and then the organic layer was separated, washed with water (200 mL) and dried over magnesium sulfate. Concentration of the mixture under reduced pressure produces a white solid (32.2 g). The solid was then dissolved in methylene chloride (200 mL), D-Boc-Tic (35.8 g, 129 mmol) and 4-dimethylaminopyridine (75 mg). The mixture was cooled to 0° C. and EDC (24.7 g, 129 mmol) was added in two portions. After stirring for about 20 minutes, the ice bath was removed and the solution was allowed to warm to r.t. The solution was stirred for about 4 hours and then diluted with water (400 mL). The organic layer was washed with water (3×), dried over magnesium sulfate and concentrated under reduced pressure to give a clear oil (70 g). Column chromatography (35% ethyl acetate/heptane) afforded about 55.6 g of the intermediate Boc-D-Tic-D-p-Cl-Phe-OMe (85%).

$^1$H NMR(DMSO) (Two rotamers observed) δ8.26(d, 1H), 8.19(d, 0.5 H), 7.24(d, 2H), 7.00-7.19(m, 8H), 4.68(m, 0.5H), 4.20-4.60(m, 4.5H), 3.58(s, 3H), 3.51(s, 1.5H), 2.77-3.10(m, 6H), 1.42(s, 3H), 1.21(s, 9H). MS(ES) 473.0(M$^+$), 471.1(M$^-$).

Step 2: The compound of Step 1 (54.3 g, 114 mmol) was dissolved in methanol (170 mL). The solution was cooled to 0° C. with an ice bath and 1N NaOH (290 mL) is added dropwise. After vigorous stirring for about 20 minutes, the mixture was warmed to about 25° C. The solution was concentrated under reduced pressure to give yellow oil. The oil was dissolved in water (200 mL) and the pH is adjusted to about 1. Ethyl acetate (200 mL) was added, and the organic layer was separated and dried over magnesium sulfate. Concentration of the organics produced about 46.3 g of the final compound.

1H NMR(DMSO) (Two rotamers observed) δ7.98(d, 1H), 7.82(d, 0.5 H), 6.90-7.41(m, 16H), 4.20-4.70(m, 8.5H), 2.60-3.20(m, 8.5H), 1.32-1.41(m, 19H). MS(ES) 459.1 m/z (M$^+$), 457.1(M$^-$).

Preparation 2BC

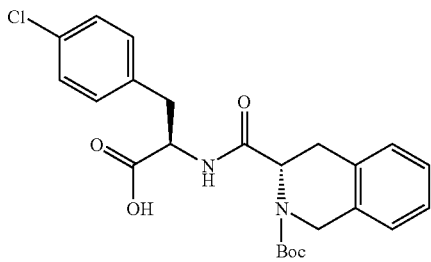

The above compound was prepared using N-Boc-L-Tic-OH as described in Preparation 1BC.

$^1$H NMR(DMSO) (Two rotomers observed) δ7.98(d, 1H), 7.72(d, 0.5 H), 6.90-7.41(m, 16H), 4.0-4.70(m, 8.5H), 2.60-3.20(m, 8.5H), 1.32-1.41(m, 19H). MS (ES) 459.1 m/z(M$^+$), 457.1(M$^-$).

Preparation 3BC

Lithium; 2-[(2-tert-butoxycarbonyl-1,2,3,4-tetrahydro-isoquinolin-3-ylmethyl)-amino]-3-(4-chloro-phenyl)-propionate

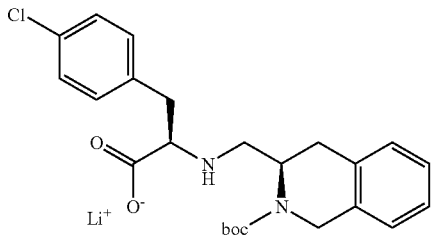

Step A: 3-{[2-(4-Chloro-phenyl)-1-methoxycarbonyl-ethylamino]-methyl}-3,4-dihydro-1H-isoguinoline-2-carboxylic acid tert-butyl ester To a 0° C. solution of 4-Cl-D-Phe-OMe (6.27 g, 25.1 mmol) and sodium acetate (8.23 g, 100.0 mmol), in 850 ml dry MeOH, was added the aldehyde from Prearation 6C (9.8 g, 37.6 mmol) in 50 ml MeOH. The mixture was stirred for about 15 minutes and then sodium cyanoborohydride (2.37 g, 37.6 mmol) was added. The cooling bath was removed and the reaction stirred for 16 hours at r.t. The mixture was concentrated to dryness and the resulting residue taken up in water and 1 ml of 1M HCl. The mixture was extracted with EtOAc, and the organics were washed with saturated sodium bicarbonate and brine, and then dried (Na$_2$SO$_4$) and concentrated to dryness. The resulting residue was purified by flash chromatography (SiO$_2$, eluting with 2:1 hexane/EtOAc) affording about 8.62 g (75%). EIS-MS 459 [M+1].

Step B: To a 12° C. solution of material from Step A (1.11 g, 2.42 mmol) in dioxane (15 ml) was added a solution of lithium hydroxide (0.10 g, 2.42 mmol) in water (7.5 mL). The mixture was stirred for about 16 hours and then concentrated to dryness affording about 1.08 g (100%) of the final compound. EIS-MS 445 [M+1].

Preparation 4BC

Lithium; 2-[(2-tert-butoxycarbonyl-1,2,3,4-tetrahydro-isoquinolin-3-ylmethyl)-amino]-3-(4-chloro-phenyl)-propionate

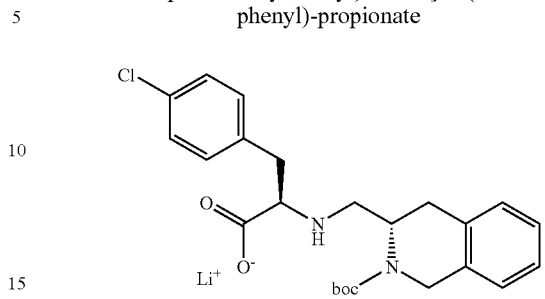

The above compound was Prepared in a manner similar to the preparation 3BC above except that aldehyde from Preparation 5C was used.

Preparation 5BC

Preparation of Lithium 2-[(2-tert-butoxycarbonyl-1,2,3,4-tetrahydro-isoquinolin-3-ylmethyl)-methyl-amino]-3-(4-chloro-phenyl)-propionate

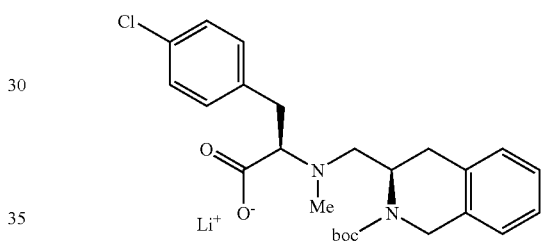

Step A: To a solution of 3-{[2-(4-Chloro-phenyl)-1-methoxycarbonyl-ethylamino]-methyl}-3,4-dihydro-1H-isoquinoline-2-carboxylic acid tert-butyl ester from preparation 3BC Step A (0.60 gm, 1.31 mmol) in anhydrous methanol, was added sodium acetate (0.54 gm, 6.54 mmol). The solution was brought to pH 5-6 with 3-4 drops of glacial acetic acid. Aqueous formaldehyde (37% by wt., 0.49 mL) was added. The solution was put under a nitrogen atmosphere and cooled to 0° C. After about 15 minutes, sodium cyanoborohydride (0.25 gm, 3.92 mmol) was added and rinsed into the reaction with anhydrous methanol (5 mL). The mixture was stirred at r.t. overnight, and then concentrated in vacuo and reconstituted in aqueous sodium bicarbonate and ethyl acetate. After separation of phases, the aqueous phase was extracted with ethyl acetate (2x), and all organics were combined, dried (magnesium sulfate), filtered, and concentrated to an opaque white oil (0.64 gm). Chromatography (0 to 20% ethyl acetate in hexane) gave about 0.6 g of methylated product as a clear oil (97%). MS (m/z, ES+): 473.2.

Step B: A solution of LiOH.H$_2$O (0.05 gm, 1.27 mmol) in distilled water (4 mL) was added to a solution of the material from Step A in 1,4-dioxane (8 mL), and the reaction was cooled slightly in an ice water bath. The mixture was stirred under a nitrogen atmosphere at r.t. overnight. An additional 1.5 eq. of LiOH.H$_2$O (0.08 gm) were added as an aqueous solution (4 mL), and the mixture was stirred at r.t. over the weekend. The mixture was concentrated, and then combined with THF and concentrated (3x) to help dry the material. The resulting foam was dried at r.t. overnight in a vacuum oven to give about 0.67 g of final compound as a white foam (114%). MS (m/z, ES+): 459.2.

Preparation 6BC

Lithium 2-[(2-tert-butoxycarbonyl-1,2,3,4-tetrahydro-isoquinolin-3-ylmethyl)-(2-methoxy-ethyl)-amino]-3-(4-chloro-phenyl)-propionate

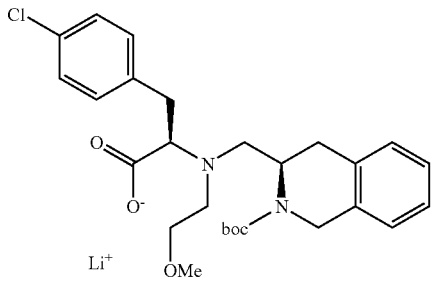

Step A: To a solution of methoxyacetaldehyde (0.15 gm, 2.03 mmol), 3-{[2-(4-Chloro-phenyl)-1-methoxycarbonyl-ethylamino]-methyl}-3,4dihydro-1H-isoquinoline-2-carboxylic acid tert-butyl ester from preparation 3BC Step C (0.31 gm, 0.68 mmol) in acetonitrile was added sodium triacetoxyborohydride (0.72 gm, 3.38 mmol). After stirring overnight under a nitrogen atmosphere at r.t., additional acetaldehyde (0.25 gm) dissolved in acetonitrile and sodium triacetoxyborohydride (0.21 gm) was added, and the mixture was stirred for about 8.5 hours. The mixture was quenched at r.t. with 5N NaOH (5 mL). The aqueous phase was separated from the organic and extracted with ethyl acetate (4x). The combined organics were washed with a brine solution, and then dried, filtered and concentrated. Chromatography (gradient of ethyl acetate in hexane, 0 to 12%) gives about 0.23 g of 3-{[[2-(4-Chloro-phenyl)-1-methoxycarbonyl-ethyl]-(2-methoxy-ethyl)-amino]-methyl}-3,4dihydro-1H-isoquinoline-2-carboxylic acid tert-butyl ester as a yellow oil (70%). MS (m/z, ES+): 517.2.

Step B: To a solution of the material from Step A in 1,4-dioxane was added a solution of lithium hydroxide monohydrate (0.05 gm, 1.11 mmol) in distilled water (2 mL). The mixture was stirred overnight at r.t. and then concentrated to a white residue. Addition of THF and concentration (3x) gives the lithium carboxylate as a foam. The foam was dried overnight under vacuum to afford about 0.25 g of crude solids (109%). MS (m/z, ES+): 503.3.

Preparation 7BC

1-{[1-Carboxy-2-(4-chloro-phenyl)-ethylcarbamoyl]-methyl}-1,3-dihydro-isoindole-2-carboxylic acid tert-butyl ester

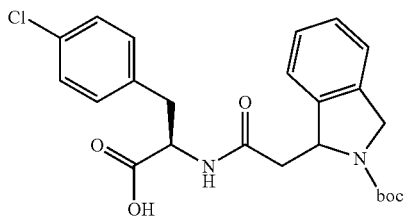

Step A: To a suspension of 4-Cl-D-Phe-OMe hydrochloride(40.4 g, 161.5 mmol) in DCM (250 mL) was added saturated aqueous sodium bicarbonate (250 mL), and the mixture was stirred at r.t. for about 1 hour. The organic portion was separated and the aqueous portion was extracted with DCM (2x). The combined organic portions were dried (Na$_2$SO$_4$) and concentrated to dryness. To the free amine, in DCM (400 mL) at 0° C., was added 1-Carboxymethyl-1,3-dihydro-isoindole-2-carboxylic acid tert-butyl ester from preparation 2C (isomer 2, 44.8 g, 161.5 mmol), EDC (31.0 g, 161.5 mmol) and 4-DMAP (2.0 g, 16.1 mmol). The mixture was stirred at 0° C. for about 30 minutes whereupon the cooling bath was removed and the mixture was stirred for another 5 hours at r.t. The mixture was then washed with saturated aqueous sodium bicarbonate (200 mL) and 10% aqueous sodium bisulfate (200 mL), and then dried (Na$_2$SO$_4$) and concentrated to dryness to afford about 76.4 g (100%) of the ester. EIS-MS 471 [M−1].

Step B: To the ester from Step A (76.4 g, 161.5 mmol) in MeOH (760 mL) was added 1 N NaOH (242.0 mL, 242.0 mmol), and the mixture was heated at 50° C. for 4 hours and then stirred for another 16 hours at r.t. After concentrating to dryness, the resulting residue was taken up in 500 mL of water and washed with diethyl ether (2x). The aqueous portion was acidified to pH 2 with 10% aqueous sodium bisulfate and extracted with EtOAc (4x200 mL). The combined organic extracts were dried (MgSO$_4$) and concentrated to dryness. The resulting solid was suspended in hexanes, filtered, and dried to afford about 67.7 g (91%) of the final compound. EIS-MS 457 [M−1].

Preparation 8BC 3-(4-Chloro-phenyl)-2-[(1,1-dimethyl-1,2,3,4-tetrahydro-isoquinoline-3-carbonyl)-amino]-propionic acid methyl ester

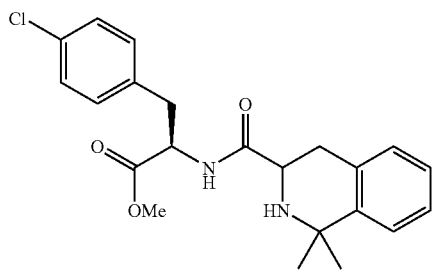

To a solution of 1,1-dimethyl Tic (240 mg, 1.17 mmol), 4-Cl-D-Phe-OMe (322 mg, 1.28 mmol), HOBT (197 mg, 1.46 mmol), and DIPEA (0.81 mL, 44.68 mmol) in DCM/DMF (1:1) was added EDC (280 mg, 1.46 mmol). The resulting mixture was stirred at r.t. overnight. The mixture was then diluted with EtOAc (100 mL), washed with saturated aqueous NaHCO$_3$ and brine, and then dried Na$_2$SO$_4$) and concentrated to dryness. Purification and separation of diastereomers by flash chromatography (35 g SiO$_2$, linear gradient, 40 mL/min 10-50% EtOAc/hexane for 25 minutes and 50% EtOAc/hexane for 7 minutes) afforded the final compound. LRMS (ESI+): 401.1 (M+H).

Preparation 9BC 3-(4-Chloro-phenyl)-2-[(1,1-dimethyl-1,2,3,4-tetrahydro-isoquinoline-3-carbonyl)-amino]-propionic acid

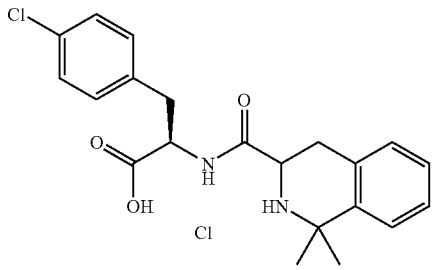

To the compound from preparation 8BC (5.95 g, 14.88 mmol) in a 1:1 mixture of THF/H$_2$O (50 mL) was added lithium hydroxide hydrate (0.75 g, 17.87 mmol). The mixture was stirred at r.t. for about 18 hours. The mixture was then concentrated to dryness. The resulting residue was dissolved in water (50 mL), made acidic with 1N HCl (25 mL) and washed with Et$_2$O (100 mL). The aqueous layer was evaporated to dryness to afford about 6.18 g of the final compound (98%). LRMS(EIS+): 387 [M+1].

Preparation 10BC

1-{[1-Carboxy-2-(4-methoxy-phenyl)-ethylcarbamoyl]-methyl}-1,3-dihydro-isoindole-2-carboxylic acid tert-butyl ester

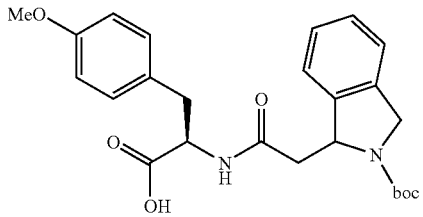

Step 1: To a solution of p-methoxy-D-Phe-OMe (1.72 g, 8.23 mmol) dissolved in TBF (45mL) and 1-carboxymethyl-1,3-dihydro-isoindole-2-carboxylic acid tert-butyl ester (2.51 g, 9.05 mmol) was added HOBT (1.22 g, 9.05 mmol), EDC (1.73 g, 9.05 mmol) and DIPEA (1.6 mL, 9.05 mmol). The reaction was stirred overnight at r.t. and then concentrated. The mixture was washed with 1M HCl, dilute NaHCO$_3$ and brine, and then dried with sodium sulfate. The mixture was chromatographed on silica gel eluting with 3% 2M NH$_3$ in MeOH/CH$_2$Cl$_2$ giving about 2.58 g as white solids. Mass MH$^+$ 469

Step 2: The white solid from Step 1 (2.58 g, 5.5 mmol) was dissolved in dioxane (37 mL) and lithium hydroxide hydrate (0.35 g, 8.3 mmol) dissolved in H$_2$O (19 mL) was added. The mixture was stirred for about 2.5 hours at r.t. and then concentrated. Ethyl acetate was added and the mixture was treated with 1M HCl, which was then washed with brine and concentrated to afford about 2.56 g of the final free acid. LRMS(ESI+): 455 (M+1)

Preparation 11BC

1-[1-Carboxy-2-(4-chloro-phenyl)-ethylcarbamoyl]-1,3-dihydro-isoindole-2-carboxylic acid tert-butyl ester

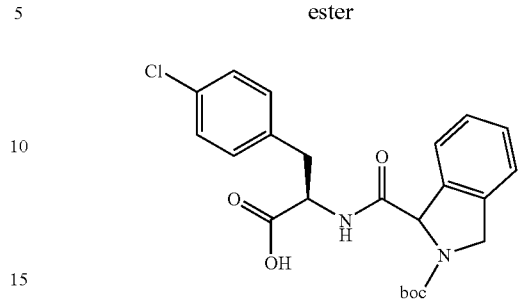

Step 1: About 2.0 g (7.60 mmol) of (R,S)-Boc-1,3-dihydro-2H isoindole carboxylic acid was dissolved in 100 ml THF and about 2.28 g (9.12 mmol) of 4-Cl-D-phe-methylester HCl, 1.25 g (9.12 mmol) of HOBT, 1.75 g (9.12 mmol) of EDC, and 1.6 ml (9.12 mmol) of DIEA were added. The mixture was stirred overnight at r.t., concentrated to dryness, washed with 1M HCl, dilute NaHCO$_3$ and brine, and then dried over sodium sulfate. The material was chromatographed on silica gel by eluting with ethyl acetate/hexane 1:2 to give about 1.05 g of isomer 1 and about 0.82 g of isomer 2, and about 1.61 g mixture of isomers 1 and 2. Mass MH$^+$ 459.

Step 2: About 0.82 g (1.79 mmol) of the isomer 2 obtained in Step 1 was dissolved in 11 ml of dioxane and 0.11 g (2.68 mmole) of LiOH-hydrate in 5.5 ml of H$_2$O was added. The mixture was stirred for about 4 hours at r.t. and then concentrated to dryness. Ethyl acetate was added, and the solution was washed with 1M HCl and brine, and then concentrated to dryness affording about 0.75 g of the free acid. Mass: 445 (MH$^+$).

EXAMPLE

Coupling Procedure 1

1-(D-TIC-4-Cl-D-Phe)-4-(2-methylphenyl)-piperazine, HCl

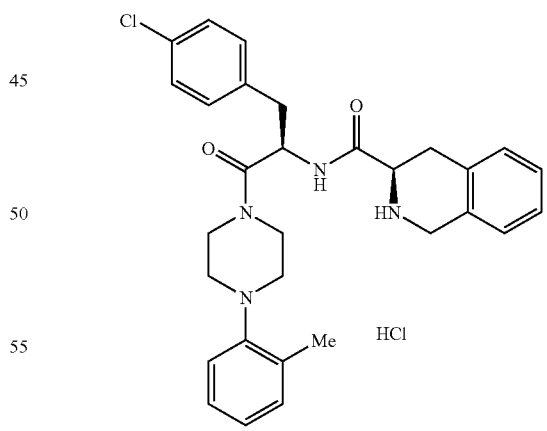

Step 1: To a solution of N-Boc-4-Cl-D-Phe (200 mg, 0.67 mmol, 1.0 eq.), 1-(2-methylphenyl)piperazine (140 mg, 0.79 mmol, 1.2 eq.), HOBT (113 mg, 0.84 mmol, 1.25 eq.), DIPEA (290 microliters, 1.66 mmol, 2.5 eq.), CH$_2$Cl$_2$ (4 mL), and DMP (1 mL) is added EDC (160 mg, 0.84 mmol, 1.25 eq.). The solution is stirred at r.t. overnight. The solution is diluted with ethyl acetate (30 mL) and washed with saturated aqueous sodium bicarbonate, 0.05 M phosphate buffer (pH 7, 2×) and brine, and then dried over Na$_2$SO$_4$, filtered, and concentrated. Purification by flash chromatography (10 g SiO$_2$, linear gradient 0-10% methanol/CH$_2$Cl$_2$, 30 mL/minute, over 15 minutes) affords about 293 mg (96%) of 1-(N-Boc-4-Cl-D-Phe)-4-(2-methylphenyl)piperazine. LRMS (ESI+): 458.2 (M+H).

Step 2: To a solution of 1-(N-Boc-4-Cl-D-Phe)-4-(2-methylphenyl)piperazine (293 mg, 0.64 mmol), CH$_2$Cl$_2$ (2 mL), and DMS (0.5 mL) is added TFA (2 mL). After stirring for about 1 hour, the solution is azeotroped from heptane (3×). The residue is dissolved in CH$_2$Cl$_2$ and washed with saturated sodium bicarbonate. The aqueous solution is extracted with CH$_2$Cl$_2$ (2×). The combined organic solutions were dried over Na$_2$SO$_4$, filtered, and concentrated to afford about 200 mg (87%) of 1-(4-Cl-D-Phe)-4-(2-methylphenyl)piperazine.

Step 3: To a solution of 1-(4-Cl-D-Phe)-4-(2-methylphenyl)piperazine (60 mg, 0.17 mmol, 1.0 eq.), N-Boc-D-TIC (56 mg, 0.20 mmol, 1.2 eq.), HOBT (28 mg, 0.21 mmol, 1.25 eq.), DIPEA (73 microliters, 0.42 mmol, 2.5 eq.), CH$_2$Cl$_2$ (2 mL) and DMF(0.5 mL) is added EDC (40 mg, 0.21 mmol, 1.25 eq.). The solution is stirred at r.t. overnight. The solution is diluted with ethyl acetate and washed with saturated aqueous sodium bicarbonate, 1 M NaHSO$_4$ and brine, and then dried over Na$_2$SO$_4$, filtered and concentrated. Purification by flash chromatography (10 g SiO$_2$, linear gradient 0 to 100% EtOAc/CH$_2$Cl$_2$, 30 mL/min, over 30 minutes) gives about 81 mg (0.13 mmol, 77%) of 1-(N-Boc-D-TIC-4-Cl-D-Phe)-4-(2-methylphenyl)piperazine. LRMS (ESI+): 617.2 (M+H).

Step4: To a solution of 1-(N-Boc-D-TIC-4-Cl-D-Phe)-4-(2-methylphenyl)piperazine (81 mg, 0.13 mmol), CH$_2$Cl$_2$ (2 mL), and DMS (0.5 mL) is added TFA (2 mL). After stirring for about 1 hour, the solution is azeotroped from heptane (3×). The residue is dissolved in CH$_2$Cl$_2$ and washed with saturated aqueous sodium bicarbonate. The aqueous solution is extracted with CH$_2$Cl$_2$ (2×). The combined organic solutions are dried over Na$_2$SO$_4$, filtered and concentrated. The residue is dissolved in 5% methanol/Et$_2$O and precipitated with 1 M HCl in Et$_2$O. The precipitate is washed with Et$_2$O (2×) to afford about 64 mg (0.12 mmol, 92%) of the title compound. HRMS (ESI+) calculated for C$_{30}$H$_{34}$ClN$_4$O$_2$: 517.2370. Found: 517.2383 (M+H).

Coupling Procedure 2

1-(D-TIC-4-Cl-D-Phe)-4-(2-methoxy-5-nitrophenyl)piperazine, HCl

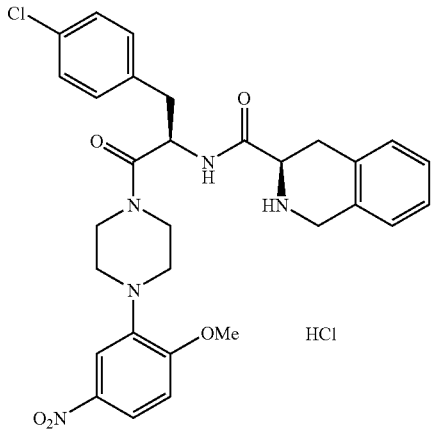

Step 1: To a solution of N-Boc-D-TIC-4-Cl-D-Phe-OH (348 mg, 0.76 mmol, 1.2 eq.), 1-(2-methoxy-5-nitrophenyl]piperazine (150 mg, 0.63 mmol, 1.0 eq.), HOAT (108 mg, 0.79 mmol, 1.25 eq), 2,6-lutidine (0.37 mL, 3.18 mmol, 5.0 eq.), CH$_2$Cl$_2$ (8 mL) and DMF (2 mL) is added HATU (300 mg, 0.79 mmol, 1.25 eq.). After stirring at r.t. overnight, the solution is diluted with ethyl acetate and washed with 1 M HCl (2×), saturated sodium bicarbonate and brine, and then dried over Na$_2$SO$_4$, filtered, and concentrated. Purification by flash chromatography (10 g SiO$_2$, linear gradient 0-5% methanol/CH$_2$Cl$_2$, 30 mL/minute, over 20 minutes) gives about 392 mg (0.58 mmol, 91%) of 1-(N-Boc-D-TIC-4-Cl-D-Phe)-4-(2-methoxy-5-nitrophenyl) piperazine. LRMS (ESI+): 678.5 (M+H).

Step 2: To a solution of 1-(N-Boc-D-TIC-4-Cl-D-Phe)-4-(2-methoxy-5-nitrophenyl)piperazine (53 mg, 0.078 mmol) in CH$_2$Cl$_2$ (2 mL) and DMS (0.2 mL) is added TFA (1 mL). After stirring for about 2 hours, the solution is azeotroped from heptane (2×). The residue is dissolved in CH$_2$Cl$_2$ and washed with saturated sodium bicarbonate. The aqueous solution is extracted with CH$_2$Cl$_2$ (3×). The combined organic solutions are dried over Na$_2$SO$_4$, filtered, and concentrated. Purification by flash chromatography (10 g SiO$_2$, linear gradient 0-10% methanol/CH$_2$Cl$_2$, 30 mL/minute, over 30 minutes) affords D-TIC-4-Cl-D-Phe-4-(2-methoxy-5-nitrophenyl)piperazine. The solid is dissolved in CH$_2$Cl$_2$ and precipitated with 1 M HCl in Et$_2$O. The solution is concentrated to afford about 40 mg (0.065 mmol, 84%) of the title compound. HRMS (ESI+) calculated for C$_{30}$H$_{34}$ClN$_4$O$_2$: 578.2170. Found: 578.2157 (M+H).

Coupling Procedure 3

1-(D-TIC-4-Cl-D-Phe)-4-(2-methanesulfonyl-phenyl)piperazine, HCl

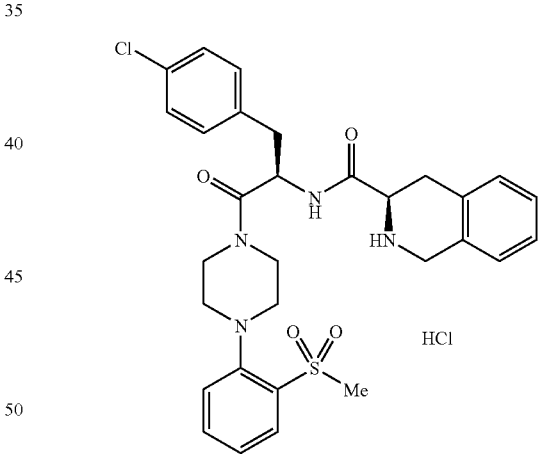

Step 1. To a solution of 1-(D-p-Cl-Phe)-4-(2-methanesulfinyl-phenyl)-piperazine (Preparation 1AB)(168 mg, 0.39 mmol, 1.0 eq.), N-Boc-D-TIC (132 mg, 0.47 mmol, 1.2 eq.), HOBT (69 mg, 0.49 mmol, 1.25 eq.), DIPEA (0.17 mL, 1.0 mmol, 2.5 eq.), CH$_2$Cl$_2$ (5 mL) and DMF (2 mL) is added EDC (95 mg, 0.49 mmol, 1.25 eq.). The solution is stirred at r.t. overnight. The solution is diluted with EtOAc and washed with saturated aqueous NaHCO$_3$ and brine, and then dried over Na$_2$SO$_4$, filtered and concentrated. Purification by flash chromatography (35 g SiO$_2$, 40 mL/min, linear gradient, 40-60% EtOAc/hexane over 15 min and 60% EtOAC/Hexane for 18 minutes) affords (256 mg, 0.39 mmol, 96%) 1-(N-Boc-D-TIC-4-Cl-D-Phe)-4-(2-methanesulfonyl-phenyl)piperazine. LRMS (ESI+): 681.2 (M+H).

Step 2. To a solution of 1-(N-Boc-D-TIC-4-Cl-D-Phe)-4-(2-methanesulfonyl-phenyl)piperazine (240 mg, 0.35 mmol), CH$_2$Cl$_2$ (2 mL) and DMS (0.25 mL) is added TFA (2 mL). After stirring for about 2 hours, the solution is azeotroped from heptane (3×). The residue is dissolved in CH$_2$Cl$_2$ and washed with saturated sodium bicarbonate. The aqueous layer is extracted with CH$_2$Cl$_2$ (2×). The combined organic extracts are dried (Na$_2$SO$_4$), filtered, and concentrated. The residue are dissolved in 5% MeOH/Et$_2$O and precipitated with 1 M HCl in Et$_2$O. The precipitates are washed with Et$_2$O (2×) to afford (191 mg, 0.31 mmol, 88%) the chloride salt of title compound. HRMS (ESI+) calcd. for C$_{30}$H$_{34}$ClSN$_4$O$_4$: 581.1989. Found: 581.1995.

Coupling Procedure 4

1-(D-TIC-4-Cl-D-Phe)-1-(5-isopropyl-2-pyrrolidin-1-ylmethyl-phenyl)-piperazine, 3HCl

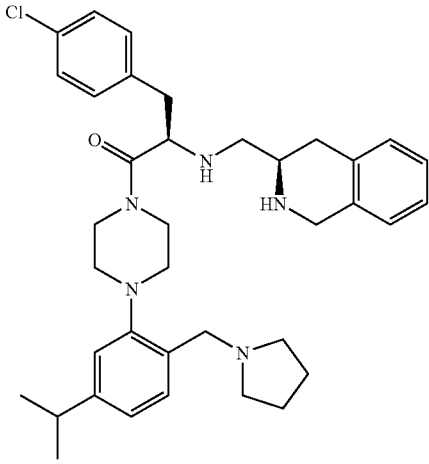

Step 1: 1-Boc-4-(5-isopropyl-2-pyrrolidin-1-ylmethyl-phenyl)-piperazine (162 mg, 0.42 mmol, 1.0 eq.) is deprotected with TFA and freebased using SCX ion exchange chromatography. To a solution of the deprotected piperazine, the BC domain from Preparation 3BC (245 mg, 0.54 mmol, 1.3 eq.), HOBT (68 mg, 0.50 mmol, 1.2 eq.), Et$_3$N (140 microliters, 1.0 mmol, 2.4 eq.), CH$_2$Cl$_2$ (4 mL) and DMF (4 mL) is added 1-(3-dimethylaminopropyl)-3-ethylcarbodiimide hydrochloride (96 mg, 0.5 mmol, 1.2 eq). The solution is stirred at r.t. overnight. The solution is diluted with ethyl acetate (30 mL) and washed with saturated sodium bicarbonate, water and brine, and then dried over Na$_2$SO$_4$, filtered and concentrated. Purification by flash chromatography (35 g SiO$_2$, linear gradient 0-10% 2 M NH$_3$ in methanol/CH$_2$Cl$_2$, 35 mL/minute, over 30 minutes) affords about 250 mg (0.35 mmol, 84%) of 2-Boc-3-({1-(4-chloro-benzyl)-2-[4-(5-isopropyl-2-pyrrolidin-1-ylmethyl-phenyl)-piperazin-1-yl]-2-oxo-ethylamino}-methyl)-3,4-dihydro-1H-isoquinoline. LRMS (ESI+): 714.2 (M+H).

Step 2: To a solution of the compound from Step 1 (240 mg, 0.035 mmol) in CH$_2$Cl$_2$ (2 mL) and DMS (0.2 mL) is added TFA (1 mL). After stirring for about 2 hours, the solution is azeotroped from heptane (2×). The residue is dissolved in CH$_2$Cl$_2$ and washed with saturated sodium bicarbonate. The aqueous solution is extracted with CH$_2$Cl$_2$ (3×). The combined organic solutions are dried over Na$_2$SO$_4$, filtered, and concentrated. Purification by flash chromatography (35 g SiO$_2$, linear gradient 0-10% 2M NH$_3$ in methanol/CH$_2$Cl$_2$, 35 mL/minute, over 30 minutes) affords the title compound. The solid is dissolved in CH$_2$Cl$_2$ and precipitated with 1 M HCl in Et$_2$O. The solution is concentrated to afford about 235 mg (0.325 mmol, 93%) of the title compound. HRMS (ESI+) calculated for C$_{37}$H$_{49}$ClN$_5$O: 614.3626. Found: 614.3627 (M+H).

Coupling Procedure 5

N-{1-(4-Chloro-benzyl)-2-oxo-2-[4-(2-pyrrolidin-1-ylmethyl-phenyl)-piperazin-1-yl]-ethyl}-2-(2-methyl-2,3-dihydro-1H-isoindol-1-yl)-acetamide, 2HCl

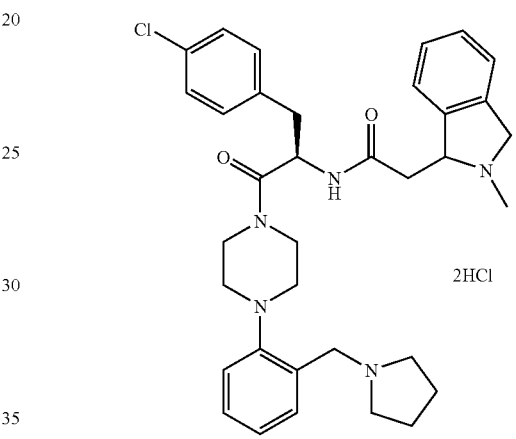

To a room temperature, stirred solution of 2-amino-3-(4-chlorophenyl)-1-[4-((2-pyrrolidin-1-yl)methylphenyl)-piperazin-1-yl]-propan-1-one(0.49 g., 1.15 mmol), (2-methyl-2,3-dihydro-1H-isoindol-1-yl)-acetic acid (0.17 g., 0.1.15 mmol) and HATU (0.43 g., 1.15 mmol) in DCM is added N,N-diisopropylethylamine (0.40 mL, 2.31 mmol). After about an hour, the solution is concentrated under reduced pressure, and the residue is purified by silica gel chromatography (eluent: 5 to 10% 2.0 M NH$_3$ in MeOH)/DCM). The purified fractions are combined and concentrated to give Boc protected compound as a yellow film (0.15 g, 22%) LRMS (ESI+): 600.2 (M+H)

To a flask containing (R)-N-{1-(4-chlorobenzyl)-2-oxo-2-[4-((2-pyrrolidin-1-yl)methylphenyl)-piperazin-1-yl]-ethyl}-2-(2-methyl-2,3-dihydro-1H-isoindol-1-yl)-acetamide is added 1.0 N HCl (7 mL). After about 1 hour, the solution is solidified at −78° C. and the solid is lyophilized to give the title compound as purple solids (0.10 g.) LRMS (ESI+): 600.2 (M+H)

Examples 1-83

The compounds of Examples 1-83 are prepared from an appropriate A domain piperazine by following a substantially similar coupling procedure as described in Procedures 1-5.

| Example | Z | Coupling Procedure | MS (ESI) |
|---|---|---|---|
| 1 | 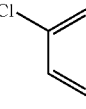 | 1 | 582.2 (M + H) |
| 2 | 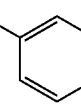 | 1 | 548.2 (M + H) |
| 3 | 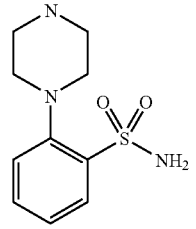 | 1 | 616.2 (M + H) |
| 4 | 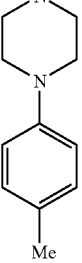 | 2 | 567.2 (M + H) |
| 5 | 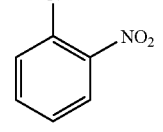 | 2 | 562.2 (M + H) |
-continued
| Example | Z | Coupling Procedure | MS (ESI) |
|---|---|---|---|
| 6 | 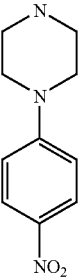 | 1 | 517.2 (M + H) |
| 7 | 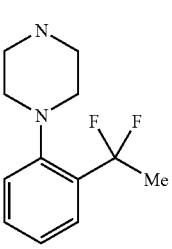 | 1 | 548.2 (M + H) |
| 8 | 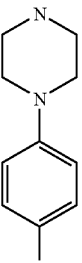 | 1 | 571.2 (M + H) |
| 9 | 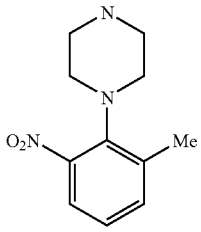 | 1 | 531.3 (M + H) |

| Example | Z | Coupling Procedure | MS (ESI) |
|---|---|---|---|
| 10 | 1-(2-methylthiophenyl)piperazine | 1 | 549.2 (M + H) |
| 11 | 1-(2-ethylphenyl)piperazine | 2 | 531.5 (M + H) |
| 12 | 1-(2,4-dimethylphenyl)piperazine | 1 | 531.3 (M + H) |
| 13 | 1-(4-cyanophenyl)piperazine | 1 | 528.2 (M + H) |
| 14 | 1-(2-cyanophenyl)piperazine | 2 | 528.0 (M + H) |

| Example | Z | Coupling Procedure | MS (ESI) |
|---|---|---|---|
| 15 | 1-(2-hydroxyphenyl)piperazine | 2 | 519.2 (M + H) |
| 16 | 1-(4-fluorophenyl)piperazine | 2 | 521.2 (M + H) |
| 17 | 1-(4-chlorophenyl)piperazine | 2 | 537.2 (M + H) |
| 18 | 1-(2-fluorophenyl)piperazine | 2 | 521.2 (M + H) |
| 19 | 1-(3-methylphenyl)piperazine | 2 | 517.2 (M + H) |

-continued
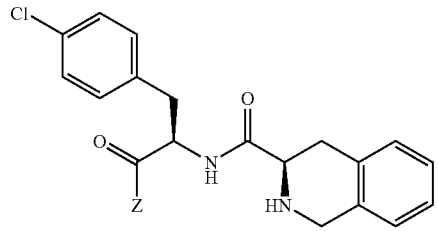
| Example | Z | Coupling Procedure | MS (ESI) |
|---|---|---|---|
| 20 | 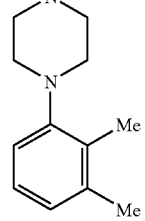 | 2 | 531.3 (M + H) |
| 21 | 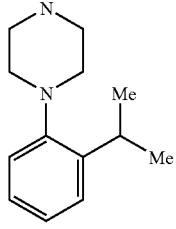 | 2 | 545.3 (M + H) |
| 22 | 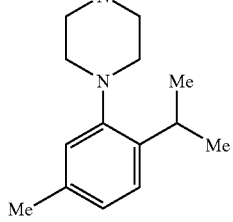 | 2 | 559.0 (M + H) |
| 23 | 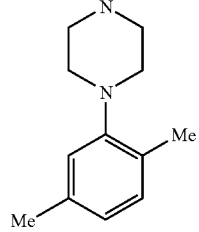 | 1 | 531.3 (M + H) |
| 24 | 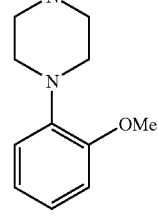 | 1 | 533.2 (M + H) |
-continued
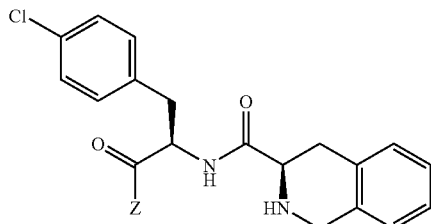
| Example | Z | Coupling Procedure | MS (ESI) |
|---|---|---|---|
| 25 | 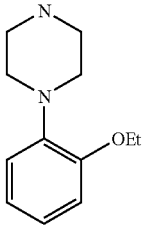 | 1 | 547.2 (M + H) |
| 26 | 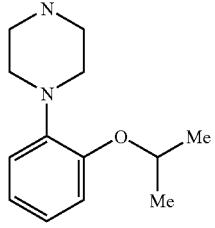 | 2 | 561.3 (M + H) |
| 27 | 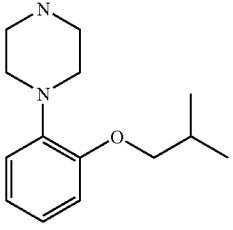 | 2 | 575.3 (M + H) |
| 28 | 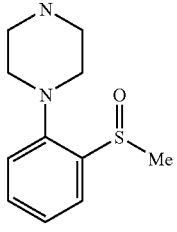 | 3 | 565.2 (M + H) |
| 29 | 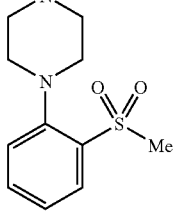 | 3 | 581.2 (M + H) |

-continued
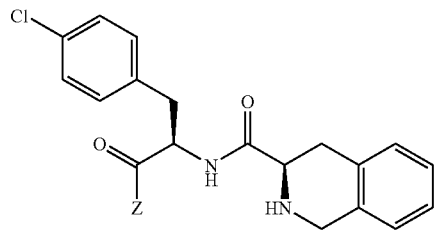
| Example | Z | Coupling Procedure | MS (ESI) |
|---|---|---|---|
| 30 | 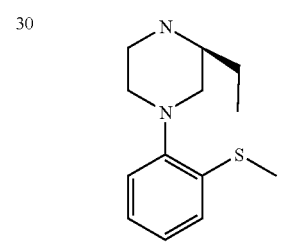 | 2 | 577.1 (M + 1) |
| 31 | 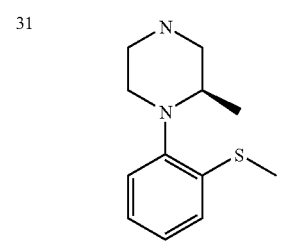 | 2 | 563.2 (M + 1) |
| 32 | 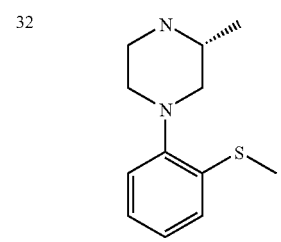 | 2 | 563.3 (M + 1) |
| 33 | 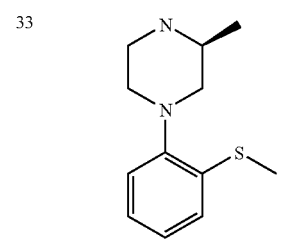 | 2 | 563.3 (M + 1) |
| 34 | 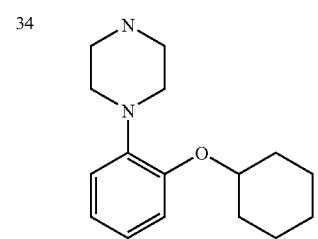 | 2 | 601.3 (M + 1) |
-continued
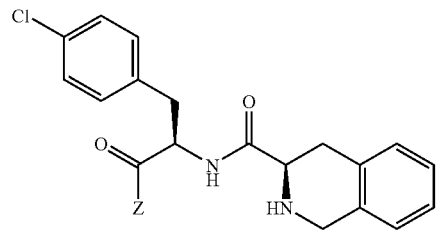
| Example | Z | Coupling Procedure | MS (ESI) |
|---|---|---|---|
| 35 | 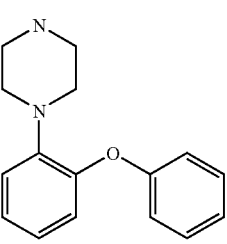 | 2 | 595.2 (M + 1) |
| 36 | 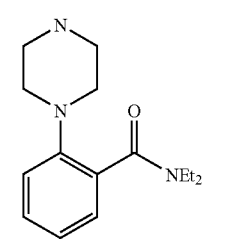 | 2 | 602.2 (M + 1) |
| 37 | 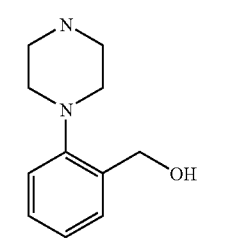 | 2 | 533.2 (M + 1) |
| 38 | 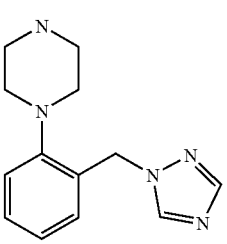 | 2 | 584.3 (M + 1) |
| 39 | 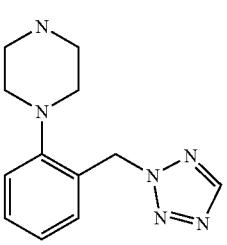 | 2 | 585.2 (M + 1) |

-continued

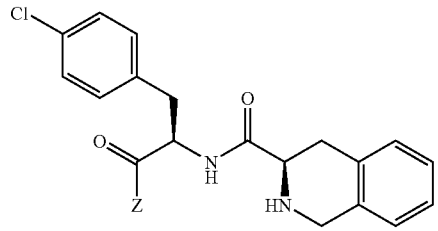

| Example | Z | Coupling Procedure | MS (ESI) |
|---|---|---|---|
| 40 | (piperazine-phenyl-CH2-imidazole) | 2 | 583.3 (M + 1) |
| 41 | (piperazine-phenyl-CH2-pyrrolidine-NMe2) | 2 | 629.3 (M + 1) |
| 42 | (piperazine-phenyl-CH2-pyrrolidine-NMe2) | 2 | 629.3 (M + 1) |
| 43 | (piperazine-phenyl-CH2-pyrrolidine) | 2 | 586.1 (M + 1) |
| 44 | (piperazine-phenyl-CH2-piperidine) | 2 | 600.0 (M + 1) |

-continued

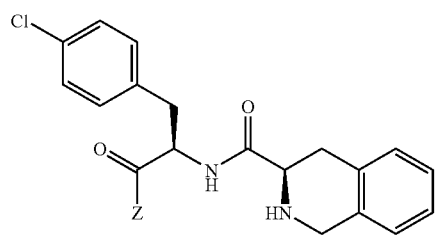

| Example | Z | Coupling Procedure | MS (ESI) |
|---|---|---|---|
| 45 | (piperazine-phenyl-CH2-morpholine) | 2 | 602.0 (M + 1) |
| 46 | (piperazine-phenyl-CH2-2-methylimidazole) | 2 | 597.3 (M + 1) |
| 47 | (piperazine-phenyl-CH2-2-isopropylimidazole) | 2 | 625.3 (M + 1) |
| 48 | (piperazine-phenyl-CH2-2-ethylimidazole) | 2 | 611.3 (M + 1) |
| 49 | (piperazine-phenyl-CH2-2-SEt-imidazole) | 2 | 643.3 (M + 1) |

-continued
| Example | Z | Coupling Procedure | MS (ESI) |
|---|---|---|---|
| 50 | 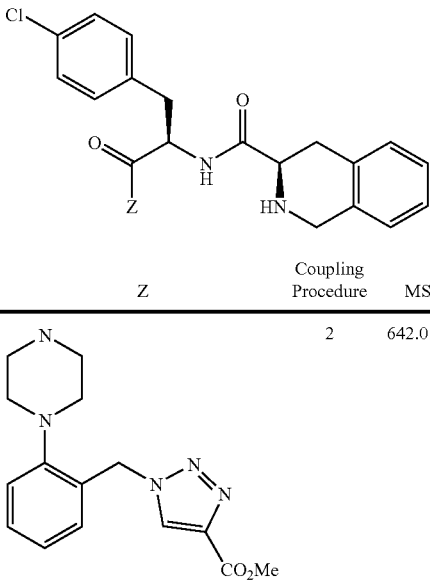 | 2 | 642.0 (M + 1) |
| 51 | 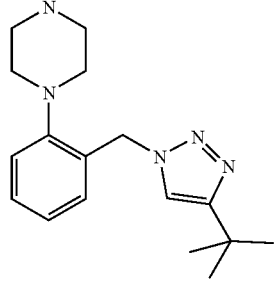 | 2 | 640.0 (M + 1) |
| 52 | 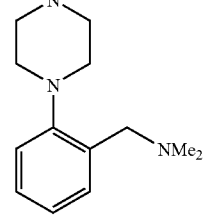 | 2 | 560.2 (M + 1) |
| 53 | 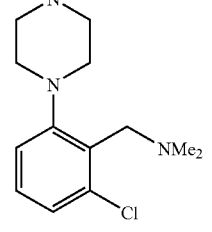 | 2 | 594.0 (M + 1) |
| 54 | 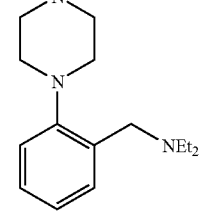 | 2 | 588.0 (M + 1) |
-continued
| Example | Z | Coupling Procedure | MS (ESI) |
|---|---|---|---|
| 55 | | 2 | 616.0 (M + 1) |
| 56 | | 2 | 610.0 (M + 1) |
| 57 | | 2 | 624.0 (M + 1) |
| 58 | | 2 | 638.0 (M + 1) |
| 59 | | 2 | 672.0 (M + 1) |

-continued

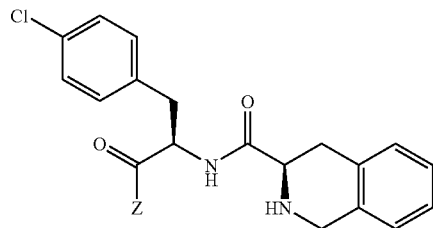

| Example | Z | Coupling Procedure | MS (ESI) |
|---|---|---|---|
| 60 | piperazinyl-phenyl-CH2-N(Me)(SO2Me) | 2 | 624.0 (M + 1) |
| 61 | piperazinyl-phenyl-CH2-N(Et)(SO2Me) | 2 | 638.0 (M + 1) |
| 62 | piperazinyl-phenyl-CH2-N(CH2Ph)(SO2Me) | 2 | 700.0 (M + 1) |
| 63 | piperazinyl-phenyl-CH2-NHAc | 2 | 575.0 (M + 1) |
| 64 | piperazinyl-phenyl-CH2-N(Me)(Ac) | 2 | 588.0 (M + 1) |

-continued

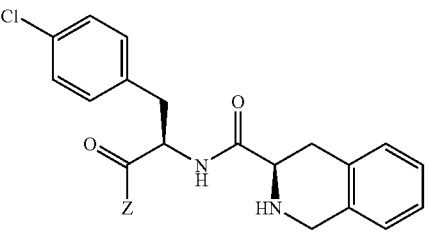

| Example | Z | Coupling Procedure | MS (ESI) |
|---|---|---|---|
| 65 | piperazinyl-phenyl-CH2-N(Et)(Ac) | 2 | 602.0 (M + 1) |
| 66 | piperazinyl-phenyl-CH2-N(CH2Ph)(Ac) | 2 | 664.0 (M + 1) |
| 67 | piperazinyl-phenyl-CH2-NHC(O)Ph | 4 | 636.0 (M + 1) |
| 68 | piperazinyl-phenyl-CH2-NHC(O)iPr | 4 | 602.0 (M + 1) |
| 69 | piperazinyl-phenyl-CH2-NHC(O)Et | 4 | 588.0 (M + 1) |

-continued
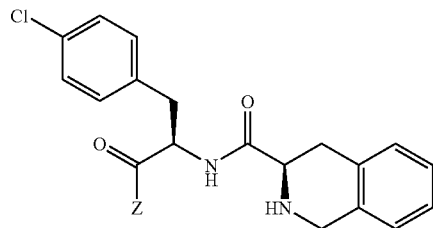
| Example | Z | Coupling Procedure | MS (ESI) |
|---|---|---|---|
| 70 | 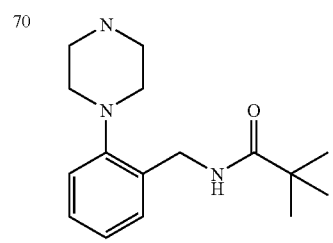 | 4 | 616.0 (M + 1) |
| 71 | 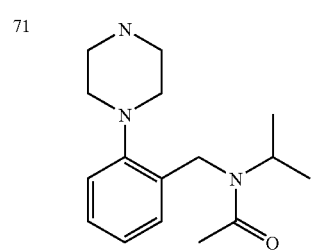 | 2 | 616.0 (M + 1) |
| 72 | 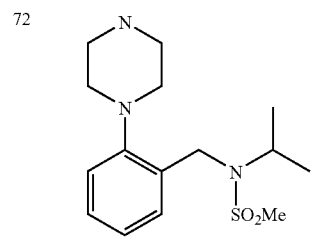 | 2 | 652.0 (M + 1) |
| 73 | 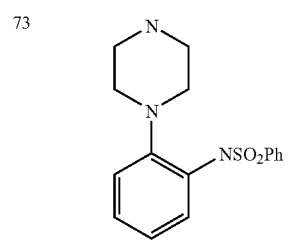 | 2 | 658.2 (M + 1) |
| 74 | 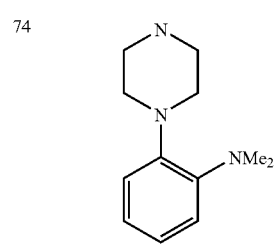 | 2 | 546.3 (M + 1) |
-continued
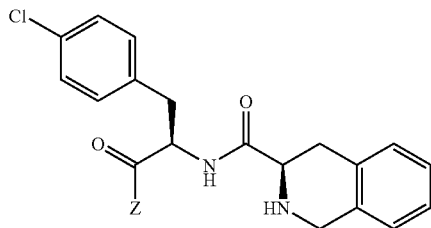
| Example | Z | Coupling Procedure | MS (ESI) |
|---|---|---|---|
| 75 | 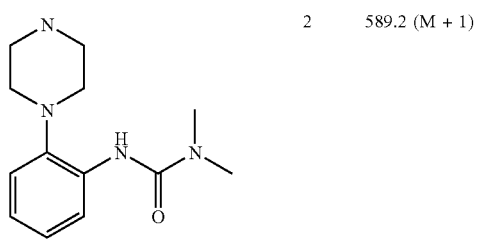 | 2 | 589.2 (M + 1) |
| 76 | 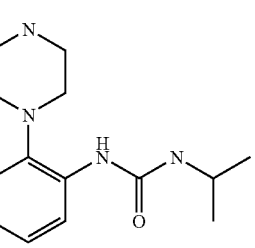 | 2 | 603.3 (M + 1) |
| 77 | 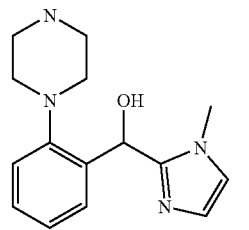 | 2 | 635.3 (M + 1) |
| 78 | 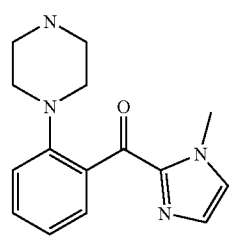 | 2 | 611.2 (M + 1) |
| 79 | 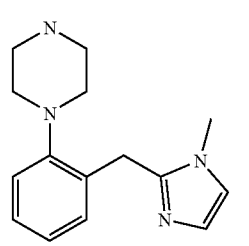 | 2 | 597.3 (M + 1) |

-continued

| Example | Z | Coupling Procedure | MS (ESI) |
|---|---|---|---|
| 80 | [2-(piperazin-1-yl)phenyl]-NH-CH2-(1-methylimidazol-2-yl) | 2 | 612.3 (M + 1) |
| 81 | [2-(piperazin-1-yl)phenyl]-O-CH2-(1-methylimidazol-2-yl) | 2 | 613.3 (M + 1) |
| 82 | [2-(piperazin-1-yl)phenyl]-O-CH2-phenyl | 2 | 609.3 (M + 1) |
| 83 | [2-(1,4-diazepan-1-yl)phenyl]-CH2-NMe2 | 2 | 574.0 (M + 1) |

Examples 84–86

The compounds of Examples 84-85 are prepared from an appropriate A domain piperazine by following a substantially similar coupling procedure as described in Procedures 1-5.

| Example | Z | Coupling Procedure | MS |
|---|---|---|---|
| 84 | [2-(piperazin-1-yl)phenyl]-CH2-(1,2,4-triazol-1-yl) | 2 | 584.2 (M + H) |
| 85 | [2-(piperazin-1-yl)phenyl]-CH2-(pyrrolidin-1-yl) | 2 | 586.1 (M + H) |

Example 86

Example 86 is prepared by following a substantially similar coupling procedure as described in Procedure 2.

MS: 624.2 (M + H)

Examples 87–100

The compounds of Examples 87-100 are prepared from an appropriate A domain piperazine by following a substantially similar coupling procedure as described in Procedures 1-5.

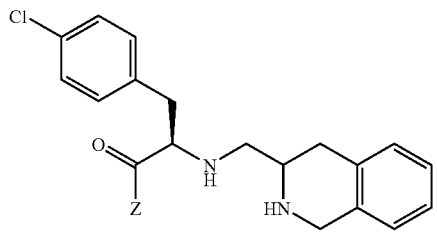
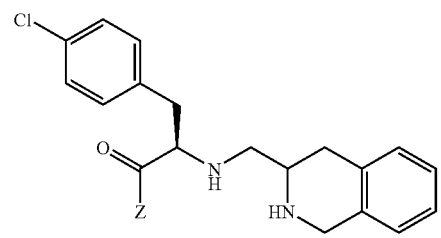
-continued
| Example | Z | Coupling Procedure | Found MS (ESI) |
|---|---|---|---|
| 87 | 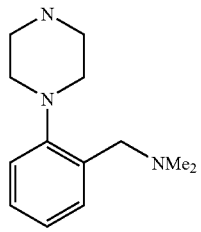 | 4 | 546.3 (M + H) |
| 88 | 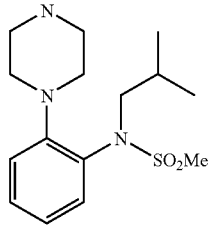 | 4 | 638.3 (M + H) |
| 89 | 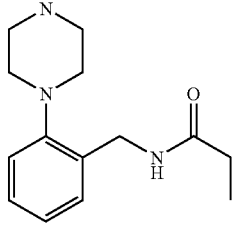 | 4 | 574.3 (M + H) |
| 90 | 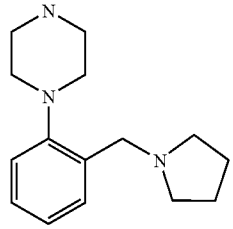 | 4 | 572.3 (M + H) |
| 91 | 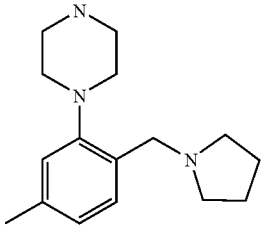 | 4 | 586.3 (M + H) |
| Example | Z | Coupling Procedure | Found MS (ESI) |
|---|---|---|---|
| 92 | 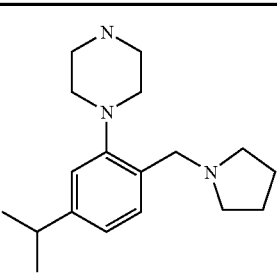 | 4 | 614.4 (M + H) |
| 93 | 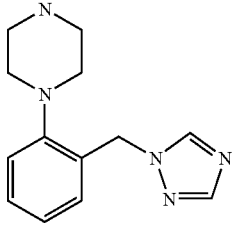 | 4 | 570.3 (M + H) |
| 94 | 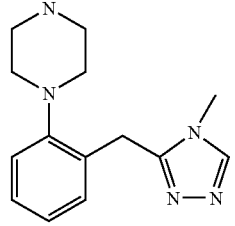 | 4 | 584.3 (M + H) |
| 95 | 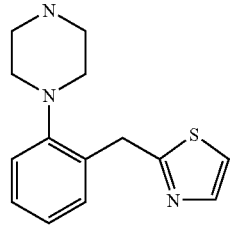 | 4 | 586.2 (M + H) |
| 96 | 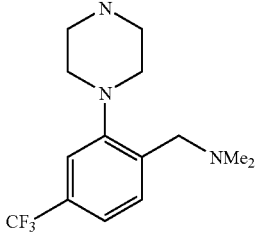 | 4 | 614.3 (M + H) |

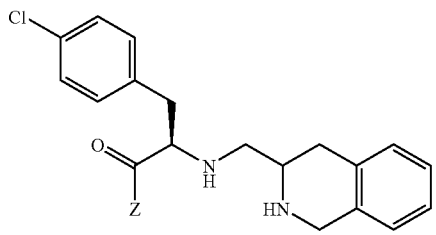

| Example | Z | Coupling Procedure | Found MS (ESI) |
|---|---|---|---|
| 97 | 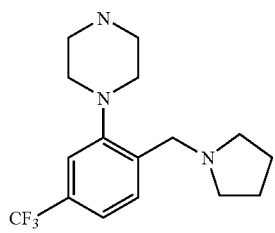 | 4 | 640.3 (M + H) |
| 98 | 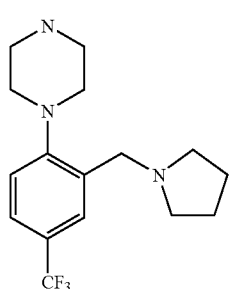 | 4 | 640.3 (M + H) |
| 99 | 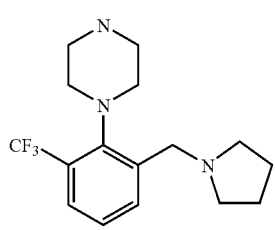 | 4 | 640.3 (M + H) |
| 100 | 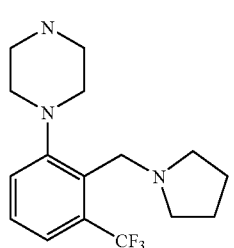 | 4 | 640.3 (M + H) |

Examples 101-102

The compounds of Examples 101 and 102 are prepared from an appropriate A domain piperazine by following a substantially similar coupling procedure as described in Procedures 1-5.

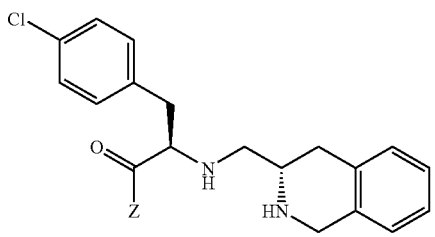

| Example | Z | Coupling Procedure | Found MS (ESI) |
|---|---|---|---|
| 101 | 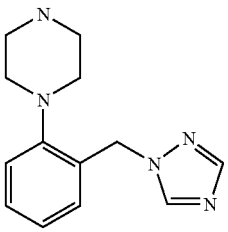 | 4 | 570.1 (M + H) |
| 102 | 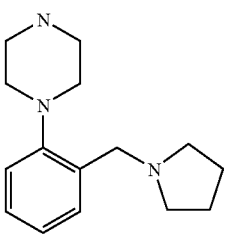 | 4 | 572.1 (M + H) |

Examples 103-146

The compounds of Examples 103-146 are prepared from an appropriate A domain piperazine by following a substantially similar coupling procedure as described in Procedures 1-5.

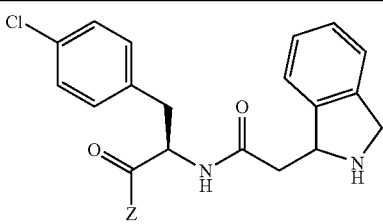

| Example | Z | Coupling Procedure | Found MS (ESI) |
|---|---|---|---|
| 103 | 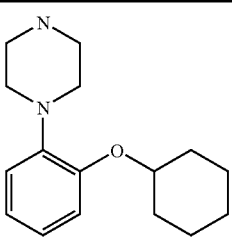 | 2 | 601.3 (M + H) |

-continued
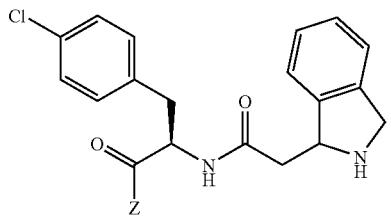
| Example | Z | Coupling Procedure | Found MS (ESI) |
|---|---|---|---|
| 104 | 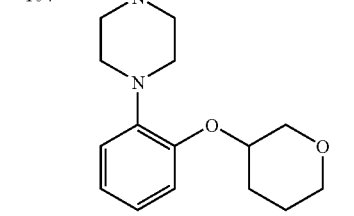 | 2 | 603.3 (M + H) |
| 105 | 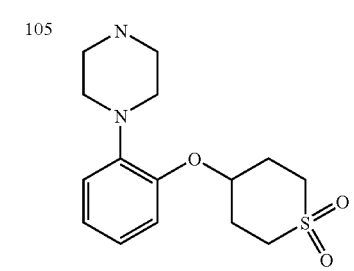 | 2 | 651.1 (M + H) |
| 106 | 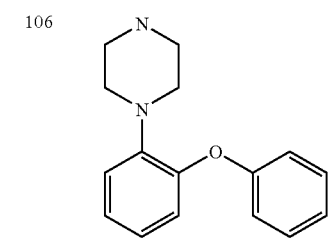 | 2 | 595.2 (M + H) |
| 107 | 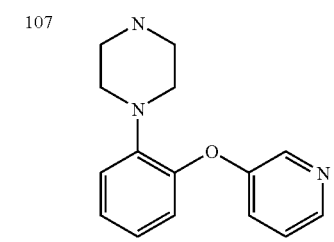 | 2 | 601.1 (M + H) |
| 108 | 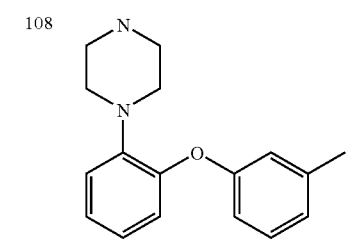 | 2 | 609.3 (M + H) |
-continued
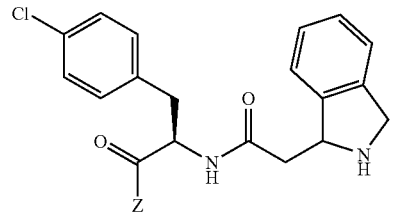
| Example | Z | Coupling Procedure | Found MS (ESI) |
|---|---|---|---|
| 109 | 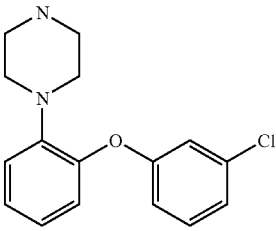 | 2 | 668.3 (M + H) |
| 110 | 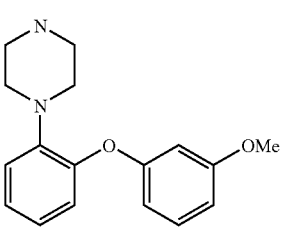 | 2 | 625.3 (M + H) |
| 111 | 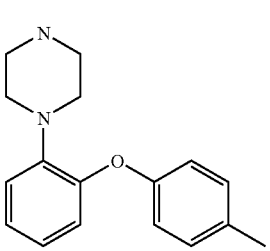 | 2 | 609.3 (M + H) |
| 112 | 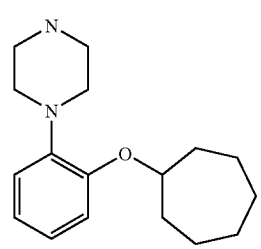 | 2 | 615.2 (M + H) |
| 113 | 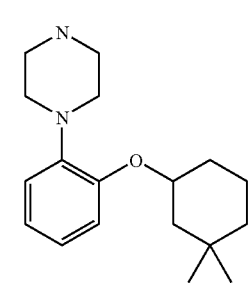 | 2 | 629.2 (M + H) |

-continued

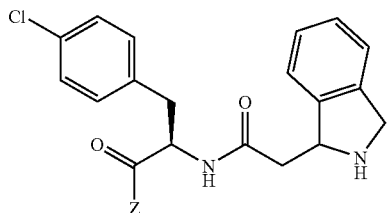

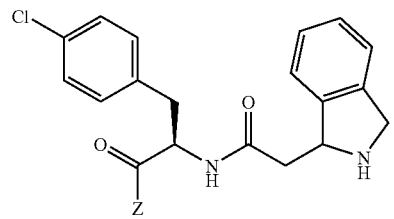

| Example | Z | Coupling Procedure | Found MS (ESI) | Example | Z | Coupling Procedure | Found MS (ESI) |
|---|---|---|---|---|---|---|---|
| 114 | piperazinyl-2-(cyclopentyloxy)phenyl | 2 | 587.2 (M + H) | 119 | piperazinyl-2-cyclohexylphenyl | 2 | 585.3 (M + H) |
| 115 | piperazinyl-2-(tetrahydrothiopyran-3-yloxy)phenyl | 2 | 619.2 (M + H) | 120 | piperazinyl-2-[N-methyl-N-(methylsulfonyl)amino]phenyl | 1 | 610.2 (M + H) |
| 116 | piperazinyl-2-(isobutoxy)phenyl | 2 | 675.3 (M + H) | 121 | piperazinyl-2-[N-ethyl-N-(methylsulfonyl)amino]phenyl | 1 | 624.2 (M + H) |
| 117 | piperazinyl-2-(isobutylsulfonyl)phenyl | 2 | 623.3 (M + H) | 122 | piperazinyl-2-[N-isobutyl-N-(methylsulfonyl)amino]phenyl | 1 | 652.3 (M + H) |
| 118 | piperazinyl-2-(NHSO₂Me)phenyl | 2 | 596.2 (M + H) | 123 | piperazinyl-2-[N-(cyclohexylmethyl)-N-(methylsulfonyl)amino]phenyl | 1 | 692.3 (M + H) |

-continued

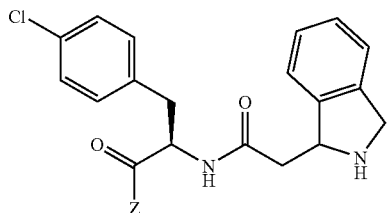

| Example | Z | Coupling Procedure | Found MS (ESI) |
|---|---|---|---|
| 124 | piperazine-phenyl-N(CH2-cyclobutyl)SO2Me | 2 | 664.3 (M + H) |
| 125 | piperazine-phenyl-N(CH2-cyclopropyl)SO2Me | 2 | 650.3 (M + H) |
| 126 | piperazine-phenyl-N(n-butyl)SO2Me | 2 | 652.3 (M + H) |
| 127 | piperazine-phenyl-N(isopentyl)SO2Me | 2 | 666.3 (M + H) |
| 128 | piperazine-phenyl-N(2-ethylbutyl)SO2Me | 2 | 680.3 (M + H) |

-continued

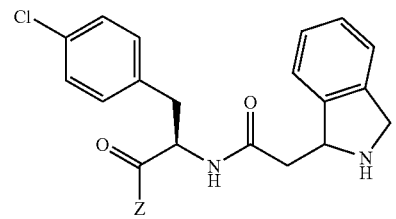

| Example | Z | Coupling Procedure | Found MS (ESI) |
|---|---|---|---|
| 129 | piperazine-phenyl-NH-isobutyl | 2 | 574.3 (M + H) |
| 130 | piperazine-phenyl-N(isobutyl)C(O)Me | 2 | 616.3 (M + H) |
| 131 | piperazine-phenyl-N(isobutyl)C(O)OMe | 2 | 632.3 (M + H) |
| 132 | piperazine-phenyl-N(isobutyl)C(O)OiPr | 2 | 660.3 (M + H) |
| 133 | piperazine-phenyl-N(isobutyl)C(O)OiBu | 2 | 674.3 (M + H) |

-continued
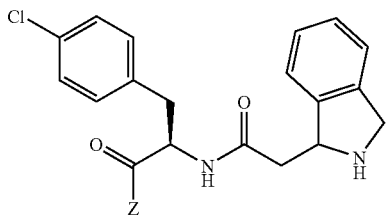
| Example | Z | Coupling Procedure | Found MS (ESI) |
|---|---|---|---|
| 134 | 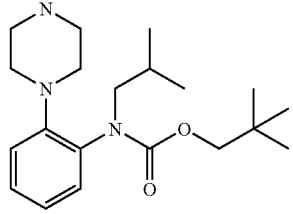 | 2 | 688.4 (M + H) |
| 135 | 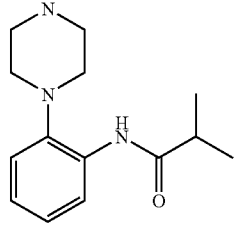 | 2 | 588.3 (M + H) |
| 136 | 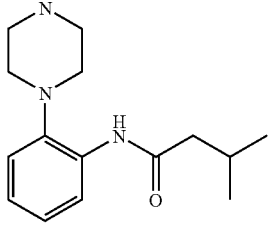 | 2 | 602.3 (M + H) |
| 137 | 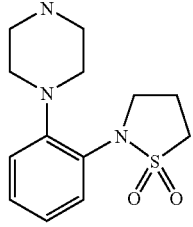 | 1 | 622.2 (M + H) |
| 138 | 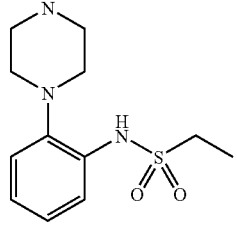 | 2 | 610.0 (M + H) |
-continued
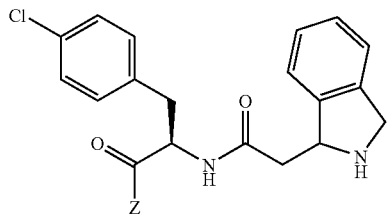
| Example | Z | Coupling Procedure | Found MS (ESI) |
|---|---|---|---|
| 139 | 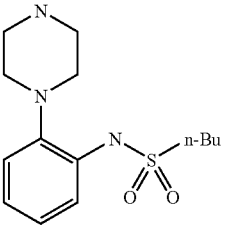 | 2 | 638.0 (M + H) |
| 140 | 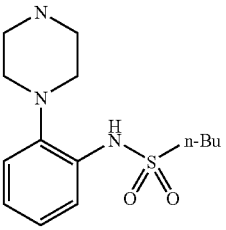 | 2 | 624.2 (M + H) |
| 141 | 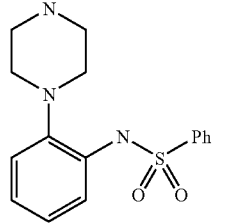 | 2 | 658.2 (M + H) |
| 142 | 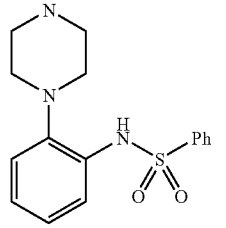 | 2 | 672.0 (M + H) |
| 143 | 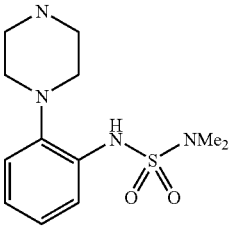 | 2 | 625.2 (M + H) |

-continued

| Example | Z | Coupling Procedure | Found MS (ESI) |
|---|---|---|---|
| 144 | 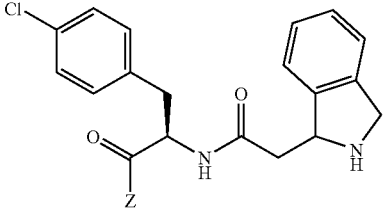 | 2 | 614.2 (M + H) |
| 145 | 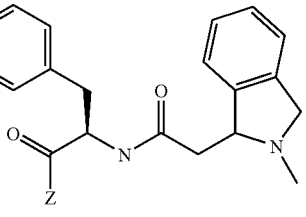 | 2 | 615.2 (M + H) |
| 146 | 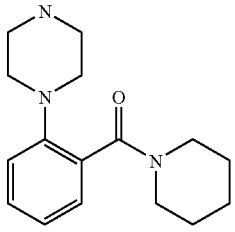 | 2 | 584.0 (M + H) |
| 147 | 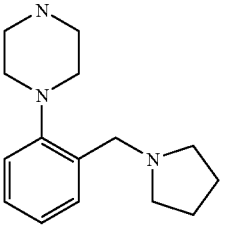 | 5 | 600.2 (M + H) |
| 148 | 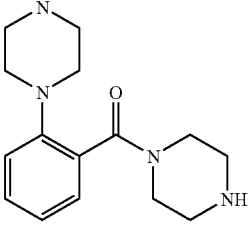 | 5 | — |

Examples 147-148

The compounds of Examples 150-151 are prepared from an appropriate A domain piperazine by following a substantially similar coupling procedure as described in Procedures 1-5.

Example 149-150

N-(1-(4-Chloro-benzyl)-2-{4-[2-(2-isobuyl-2H-tetrazol-5-yl)-phenyl]-piperazin-1-yl}-2-oxo-ethyl)-2-(2,3-dihydro-1H-isoindol-1-yl)-acetamide and N-(1-(4-Chloro-benzyl)-2-{4-[2-(1-isobutyl-1H-tetrazol-5-yl)-phenyl]-piperazin-1-yl}-2-oxo-ethyl)-2-(2,3-dihydro-1H-isoindol-1-yl)-acetamide

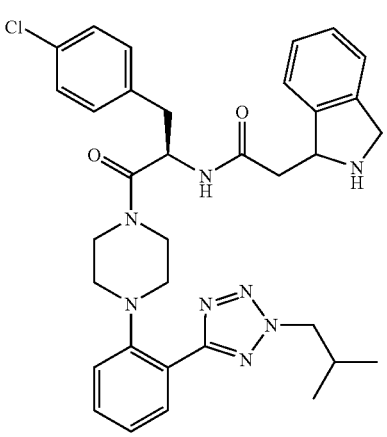

and

-continued

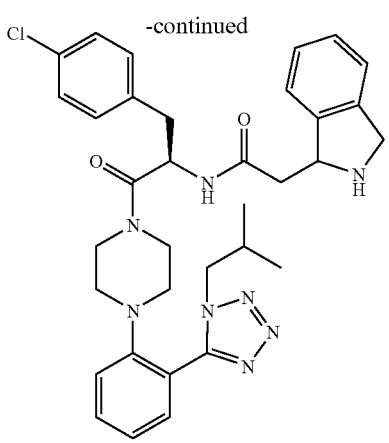

The mixture of 4-[2-(2-isobutyl-2H-tetrazol-5-yl)-phenyl]piperazine and 4-[2-(1-isobutyl-1H-tetrazol-5-yl)-phenyl]piperazine (60:40 by NMR favoring the 2H substituted tetrazole, 230 mg, 0.8 mmol, 1.0 eq) was coupled in a similar manner as described in coupling procedure 2. The regioisomers were separated using silica gel chromatography. The separated compounds were deprotected using TFA followed by purification and HCl salt formation.

2H substituted tetrazole: HRMS (ES+) calculated for $C_{34}H_{40}N_8O_2Cl$: 627.2963. Found: 627.2946.

1H substituted tetrazole: HREMS (ES+) calculated for $C_{34}H_{40}N_8O_2Cl$: 627.2963. Found: 627.2961.

Example 151

6-Hydroxy-1,1-dimethyl-1,2,3,4-tetrahydro-isoquinoline-3-carboxylic acid {1-(4-chloro-benzyl)-2-oxo-2-[4-(2-[1,2,4]triazol-1-ylmethyl-phenyl)-piperazin-1-yl]-ethyl}-amide

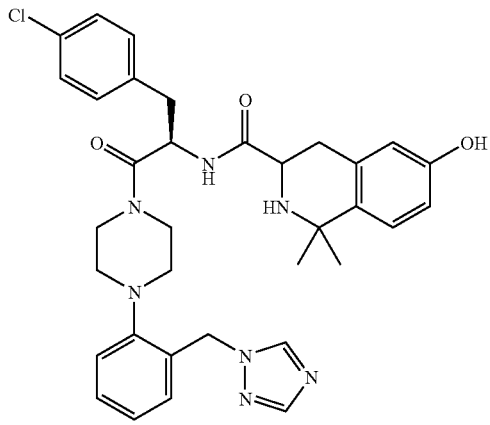

1-Boc-4-(2-[1,2,4]triazol-1-ylmethyl-phenyl)-piperazine was deprotected and coupled to Boc-D-p-Cl-Phe-OH in a manner similar to coupling procedure 1. The coupled product was deprotected and prepared as the chloride salt. To a solution of the chloride salt (1.16 g, 2.52 mmol), 6-hydroxy-1,1-dimethyl-1,2,3,4-tetrahydro-isoquinoline-3-carboxylic acid (714 mg), DIEA (1.75 mL), HOBt (408 mg), and DMAP (62 mg) in 2.52 mL of $CH_2Cl_2$ was added EDC (579 mg). After stirring overnight, the mixture was extracted with EtOAc, washed with water, saturated bicarbonate and brine, and then dried over $Na_2SO_4$, filtered and evaporated to dryness. The mixture was chromatographed with 5% MeOH/EtOAc. The diastereomers were separated on a waters symmetry C18 column 80:20 to 50:50 water (0.05% TFA) acetonitrile over 40 minutes detecting at 230 nm. LRMS (ESI+): 628.3 (M+1).

Example 152

1-(D-TIC-4-Cl-D-Phe)-4-(2-methanesulfonatephenyl)piperazine

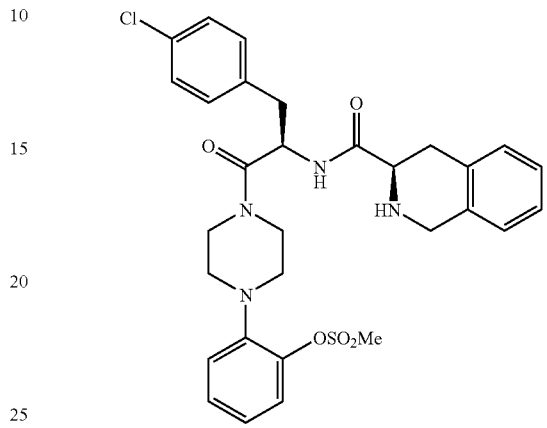

To a solution of 1-(N-Boc-D-TIC-4-Cl-D-Phe)-4-(2-hydroxy-phenyl)piperazine (150 mg, 0.242 mmol) and $Et_3N$ (50 mL, 0.36 mmol) in 6 mL of $CH_2Cl_2$ cooled to 0° C. was added methanesulfonyl chloride (19 microliters, 0.24 mmol). After stirring for 2 hours, the reaction was quenched with saturated sodium bicarbonate and extracted with $CH_2Cl_2$. The combined organic solutions were washed with 1 M HCl, saturated sodium bicarbonate, brine, dried ($Na_2SO_4$), filtered, and concentrated. Without further purification, the product was deprotected with TFA by following the procedure as described in Coupling Procedure 1, Step 4. HRMS (ESI+) calculated for $C_{30}H_{34}ClN_4O_5S$: 597.1938. Found: 597.1954 (M+H).

Example 153

1-(D-TIC-4-Cl-D-Phe)-4-(2-aminophenyl)piperazine

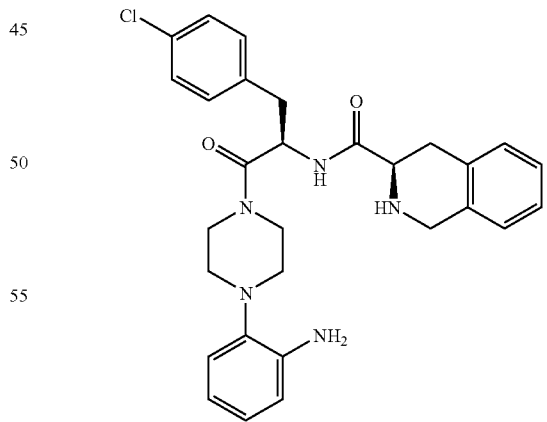

A solution of 1-(N-Boc-D-TIC-4-Cl-D-Phe)-4-(2-nitrophenyl)piperazine (260 mg, 0.4 mmol), $PtO_2$ (70 mg) in 30 mL of isopropanol was shaken in a Parr hydrogenation apparatus under 45 psi of $H_2$ for about 1 hour. The solution was filtered through celite and concentrated to yield about 263 mg (0.4 mmol, 100%) of the amine which was used without further purification. The amine was deprotected with TFA by following the procedure as described in Coupling Procedure 1, Step 4. HRMS (ESI+) calculated for $C_{29}H_{33}ClN_5O_2$: 518.2323. Found: 518.2338 (M+H).

Example 154

1-(D-TIC-4-Cl-D-Phe)-4-(2-sulfonamide)piperazine

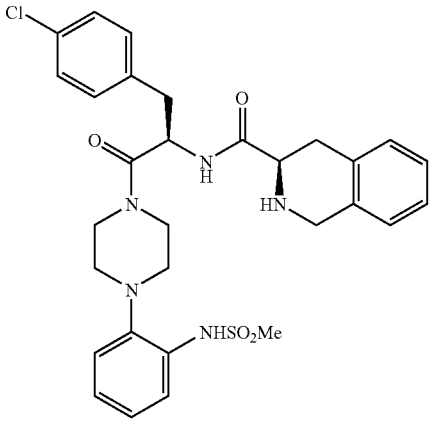

To a solution of 1-(N-Boc-D-TIC-4-Cl-D-Phe)-4-(2-aminophenyl)piperazine (120 mg, 0.19 mmol) and $Et_3N$ (27 microliters, 0.19 mmol) in 6 mL of $CH_2Cl_2$ cooled to 0° C. was added methanesulfonyl chloride (15 microliters, 0.19 mmol). After stirring for 2 hours, the reaction was quenched with saturated sodium bicarbonate and extracted with $CH_2Cl_2$. The combined organic solutions were washed with 1 M HCl, saturated sodium bicarbonate and brine, and then dried ($Na_2SO_4$), filtered and concentrated. Without further purification, the product was deprotected with TFA by following the procedure as described in Coupling Procedure 1, Step 4. HRMS (ESI+) calculated for $C_{30}H_{35}ClN_5O_4S$: 596.2098. Found: 596.2104 (M+H).

Example 155

N-[2-(4-{3-D-(4-chloro-phenyl)-2-D-[(1,2,3,4-tetrahydro-isoquinolin-3-ylmethyl)-amino]-propionyl}-piperazin-1-yl]-methanesulfonamide trihydrochloride

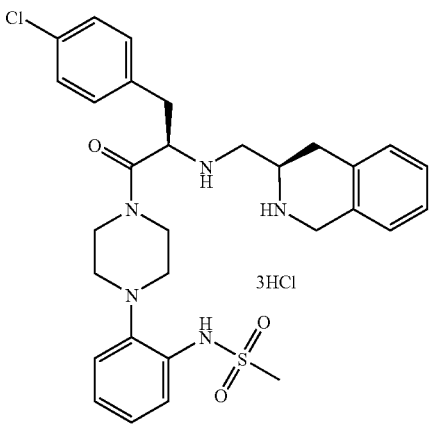

Step 1: 1-(2-Nitrophenyl)piperazine (3.13 g, 15.1 mmol) was coupled with Boc-D-4-chloro-phenyl alanine (4.52 g, 15.1 mmoles) in the presence of EDC/HOBT. The crude product was chromatographed on silica gel (EtOAc/hexane 1:1) to give yellow solids (6.88 g). Mass: MH⁺ 489

Step 2: {1-4-Chloro-phenyl)-2-[4-2-nitro-phenyl)-piperazin-1-yl]-2-oxo-ethyl}-carbamic acid tert-butyl ester made above (6.88 g, 14.1 mmol) was mixed with 4 M HCl in dioxane (230 ml) and stirred at r.t. for about an hour and then concentrated to give yellow solids (5.1 g). Mass: MH⁺ 389

Step 3: 2-Amino-3-(4-chloro-phenyl)-1-[4-(2-nitro-phenyl)-piperazin-1-yl]-propan-1-one hydrochloride made above (2.5 g, 5.88 mmol) and NaOAc (1.7 g, 20.7 mmol) were dissolved in MeOH (175 ml) and cooled in an ice-water bath. The aldehyde from Preparation 6C (2.02 g, 7.7 mmol) was added and stirred for several minutes and then $NaBH_3CN$ (0.48 g, 7.6 mmol) was added. The mixture was stirred at r.t. overnight. More NaOAc (0.57 g, 7.0 mmol), the aldehyde (0.67 g, 2.6 mmol) and $NaBH_3CN$ (0.16 g, 2.5 mmol) were added with bath in place. The mixture was stirred at r.t. for about 4 hours, and then stripped to dryness. 1 M HCl and EtOAc were added followed by washing with $NaHCO_3$ and brine, and then dried over $Na_2SO_4$. Removal of solvent gave a residue, which was chromatographed on silica gel (2% $MeOH/CH_2Cl_2$) to give yellow solids (2.53 g). Mass: MH⁺ 634

Step 4: 3-({1-(4-Chloro-benzyl)-2-[4-(2-nitro-phenyl)-piperazin-1-yl]-2-oxo-ethylamino}-methyl)-3,4-1H-isoquinoline-2-carboxylic acid tert-butyl ester made above (2.5 g, 3.94 mmol) was dissolved in $CH_2Cl_2$ (10 ml) and cooled to 0° C. TEA (0.4 g, 4.0 mmoles) and Boc anhydride (0.86 g, 3.94 mmol) dissolved in $CH_2Cl_2$ (10 ml) was added to the mixture dropwise. Additional TEA (0.4 g, 4.0 mmol) was added and the mixture was stirred for about 1.5 hours. The mixture was concentrated to remove $Et_3N$ and $CH_2Cl_2$ was added. The mixture was stirred over the weekend. Additional DMAP (0.096 g, 0.79 mmol) and TEA (0.4 g, 4.0 mmol) were added and the mixture was stirred for about 5 hours. The mixture was stripped to dryness and chromatographed with ethyl acetate/hexane (2:8) to afford about 1.06 g of product. Mass: MH⁺ 734

Step 5: 3-[tert-Butoxycarbonyl-{1-(4-chloro-benzyl)-2-[4-2-nitro-phenyl)-piperazin-1-yl]-2-oxo-ethyl}-amino)-methyl]-3,4-dihydro-1H-isoquinoline-2-carboxylic acid tert-butyl ester made above (0.50 g, 0.68 mmol) was dissolved in isopropyl alcohol (100 ml) and $Pt_2O$ (0.13 g, 0.59 mmol) was added. The hydrogenation was carried out on Parr shaker at 45 psi for about an hour at r.t. The mixture was filtered, stripped to dryness to give a white solid (0.46 g). Mass: MH⁺ 704

Step 6: 3-({[2-[4-(2-Amino-phenyl)-piperazin-1-yl]-(4-chloro-benzyl)-2-oxo-ethyl]-tert-butoxycarbonyl-amino}-methyl)-3,4dihydro-1H-isoquinoline-2-carboxylic acid tert-butyl ester made above (0.46 g, 0.65 mmol) was dissolved in $CH_2Cl_2$ (10 ml). The mixture was cooled with an ice bath under nitrogen, and then TEA (0.13 g, 1.31 mmoles) was added followed by slow addition of MsCl (0.075 g, 0.65 mmol) in $CH_2Cl_2$ (1 ml). After about 30 minutes, an additional amount of MsCl (0.025 g, 0.22 mmol) was added. The mixture was cooled, diluted with ethyl acetate, extracted with saturated $Na_2CO_3$, washed with brine, dried and evaporated in vacuo. The material was chromatographed on ion exchange chromatography (0.35 g). Mass: MH⁺ 782

Step 7: 3-[tert-Butoxycarbonyl-{1-(4-chloro-benzyl)-2-[4-(2-methanesulfonylamino-phenyl)-piperazin-1-yl]2-oxo-ethyl}-amino)-methyl]-3,4-dihydro-1H-isoquinoline-2-carboxylic acid t-butyl ester made above (0.35 g, 0.65 mmol) was stirred with 4M HCl in dioxane (30 ml) at r.t. for about an hour. The mixture was stripped to dryness and saturated sodium bicarbonate was added. The mixture was then extracted with ethyl acetate, washed with brine and dried. The material was chromatographed on silica gel using 5% MeOH/CH$_2$Cl$_2$. The residue was dissolved in methanol (40 ml) and 2M HCl in ether (3 ml) was added, which was then stripped to dryness affording about 0.23 g of the final compound. Calculated exact mass: 582.2305. Found exact mass: 582.2286

Example 156

2-(4-{3-D-(4-chloro-phenyl)-2-D-[(1,2,3,4-tetrahydro-isoquinolin-3-ylmethyl)-amino]-propionyl}-piperazin-1-yl)-benzenesulfonamide trihydrochloride

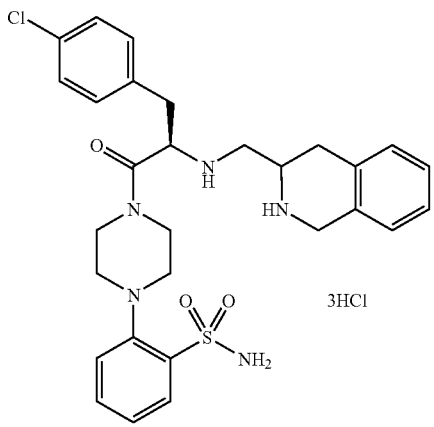

The aldehyde from Preparation 6C was reacted with 2-{4-[2-Amino-3-D-(4-chloro-phenyl)-propionyl]-piperazin-1-yl}-benzenesulfonamide hydrochloride by following the procedure described in Example 158, Step 3 and then Step 7. Deprotection of Boc group in the presence of 4M HCl/dioxane gave the title compound. Exact mass calculated: 568.2419; Found: 568.2158.

Example 157

3-(4-Chloro-phenyl)-2-[methyl-(1,2,3,4-tetrahydro-isoquinolin-3-ylmethyl)-amino]-1-[4-(2-pyrrolidin-1-ylmethyl-phenyl)-piperazin-1-yl]-propan-1-one tetrahydrochloride

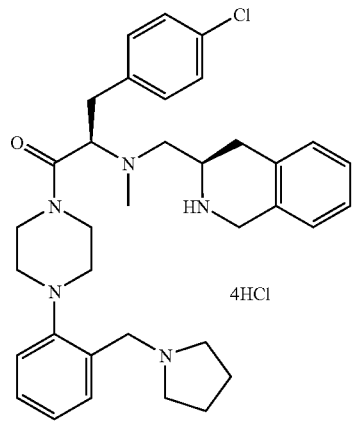

Step A: A 4M solution of HCl in dioxane (20 mL) was added to a solution of 4-(2-Pyrrolidin-1-ylmethyl-phenyl)-piperazine-1-carboxylic acid t-butyl ester (2.01 gm, 5.82 mmol). The solution was stirred at r.t. overnight under a nitrogen and then concentrated to remove dioxane. Diethyl ether was added and the solution was concentrated (2×). Diethyl ether was added and the product was isolated by suction filtration and then washed with diethyl ether. Vacuum drying at 50° C. overnight gave 1-(2-Pyrrolidin-1-ylmethyl-phenyl)-piperazine 2HCl (1.62 g, 87.6%). MS (m/z, ES+): 246.1.

Step B: Lithium 2-[(2-tert-butoxycarbonyl-1,2,3,4-tetrahydro-isoquinolin-3-ylmethyl)-methyl-amino]-3-(4-chloro-phenyl)-propionate (0.59 gm, 1.27 mmol), the compound of Step A (0.27 gm, 0.85 mmol), EDC (0.24 gm, 1.27 mmol) and HOBt (0.17 gm, 1.27 mmol) were combined and dissolved in anhydrous DMF (5 mL). DIPEA was added (440 microliter, 2.54 mmol), and the reaction was stirred under nitrogen overnight at room temperature. The reaction was concentrated and reconstituted in CH$_2$Cl$_2$ and then diluted with NaHCO$_3$. After separation of the organic phase, the aqueous layer was extracted with CH$_2$Cl$_2$ (2×). The combined organics were dried (Na$_2$SO$_4$), filtered and concentrated. Chromatography (EtOAc to 5% MeOH/EtOAc) gave about 100 mg of 3-[({1-(4-Chloro-benzyl)-2-oxo-2-[4-(2-pyrrolidin-1-ylmethyl-phenyl)-piperazin-1-yl]-ethyl}-methyl-amino)-methyl]-3,4-dihydro-1H-isoquinoline-2-carboxylic acid t-butyl ester. MS (m/z, ES+): 686.4.

Step C: The material from Step B was taken up in a 4M solution of HCl in dioxane (30 mL). The reaction was stirred at r.t. overnight under nitrogen. The mixture was concentrated to remove dioxane, and the resulting film was triturated with diethyl ether and then concentrated (2×). Trituration with diethyl ether, isolation by suction filtration, and drying at r.t. under vacuum gave about 0.103 g of the final compound as yellow solids (97%). MS (m/z, ES+): 586.3.

Example 158

3-(4-Chloro-phenyl)-2-[(2-methoxy-ethyl)-(1,2,3,4-tetrahydro-isoquinolin-3-ylmethyl)-amino]-1-[4-(2-pyrrolidin-1-ylmethyl-phenyl)-piperazin-1-yl]-propan-1-one tetrahydrochloride

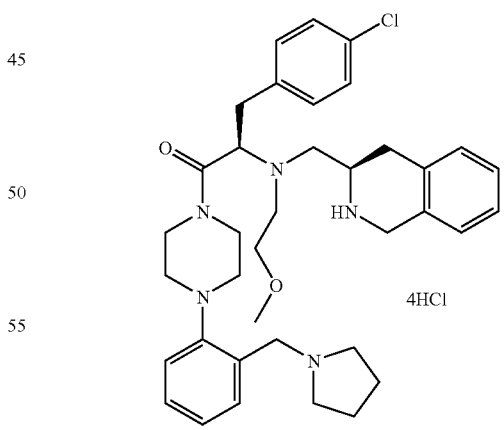

4-(2-Pyrrolidin-1-ylmethyl-phenyl)-piperazine-1-carboxylic acid t-butyl ester was deprotected and then the resulting amine hydrochloride (0.10 gm, 0.30 mmol) was coupled with lithium 2-[(2-tert-butoxycarbonyl-1,2,3,4-tetrahydro-isoquinolin-3-ylmethyl)-(2-methoxy-ethyl)-amino]-3-(4-chloro-phenyl)-propionate (0.23 gm, 0.45 mmol). The mixture was chromatographed to obtain the

Example 159

(R)-N-{1-(4-Chlorobenzyl)-2-oxo-2-[4-(2-([1,2,4]triazol-1-yl)methylphenyl)-piperazin-1-yl]-ethyl}-2-(2-isopropyl-2,3-dihydro-1H-isoindol-1-yl)-acetamide (isomer 1)

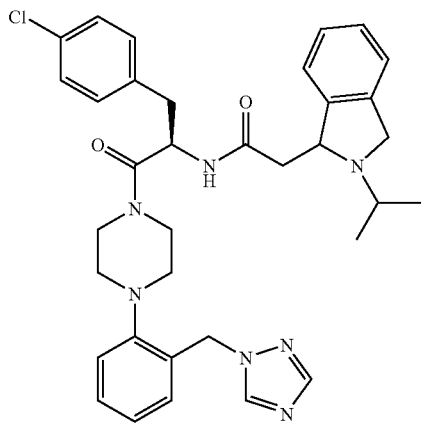

To a solution of 2-amino-3-(4-chloro-phenyl)-1-[4-(2-[1,2,4]triazol-1-ylmethyl-phenyl)-piperazin-1-yl]-propan-1-one trifluoroacetyl carboxylate salt(0.30 g, 0.55 mmol), (2-isopropyl-2,3-dihydro-1H-isoindol-1-yl)-acetic acid (0.12 g, 0.55 mmol), HATU (0.21 g, 0.55 mmol) in DCM was added DIPEA (0.19 mL, 1.13 mmol). After about 3 hours, the solution was purified by silica gel chromatography (eluent: 3% 2.0M NH$_3$ in MeOH/DCM). The purified fractions were combined and concentrated under reduced pressure to give the final compound as white foam (0.06 g, 18%). ES MS 626.3 (M+H)

Example 160

(R)-N-{1-(4-Chlorobenzyl)-2-oxo-2-[4-(2-([1,2,4]triazol-1-yl)methylphenyl)-piperazin-1-yl]-ethyl}-2-(2-isopropyl-2,3-dihydro-1H-isoindol-1-yl)-acetamide dihydrochloride salt (isomer 1)

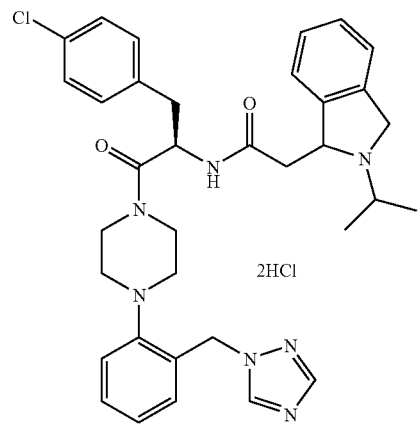

Into a flask containing (R)-N-{1-(4-chlorobenzyl)-2-oxo-2-[4-(2-([1,2,4]triazol-1-yl)methylphenyl)-piperazin-1-yl]-ethyl}-2-(2-isopropyl-2,3-dihydro-1H-isoindol-1-yl)-acetamide (Example 162) was added 1.0 N HCl (5 mL). After about an hour, the solution was solidified at −78° C., and the solid lyophilized to give about 0.06 g of the final compound as tan solids. ES MS 626.3 (M+H)

Example 161

2-(2-Butyl-2,3-dihydro-1H-isoindol-1-yl)-N-{1-(4-chlorobenzyl)-2-oxo-2-[4-((2-[1,2,4]triazol-1-yl)methylphenyl)-piperazin-1-yl]-ethyl}-acetamide (isomer 1)

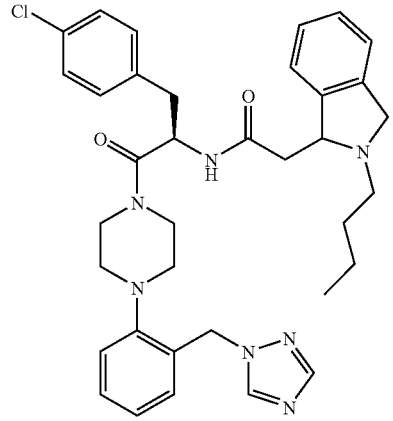

To a solution prepared from Preparation 4AB (0.30 g., 0.45 mmol), (2-butyl-2,3-dihydro-1H-isoindol-1-yl)-acetic acid (Preparation 8C) (0.10 g, 0.45 mmol), HATU (0.17 g., 0.45 mmol) in DCM (5.1 mL) was added DIPEA (0.16 mL, 0.91 mmol). After about 3 hours, the solution was purified by silica gel chromatography (eluent: 2-4% 2.0M NH$_3$ in MeOH)/DCM). The purified fractions were combined and concentrated under reduced pressure to give about 0.07 g of the final compound as off-white foam (26%). ES MS 640.3 (M+H)

Example 162

2-(2-Butyl-2,3-dihydro-1H-isoindol-1-yl)-N-{1-(4-chlorobenzyl)-2-oxo-2-[4-((2-[1,2,4]triazol-1-yl)methylphenyl)-piperazin-1-yl]-ethyl}-acetamide dihydrochloride salt (isomer 1)

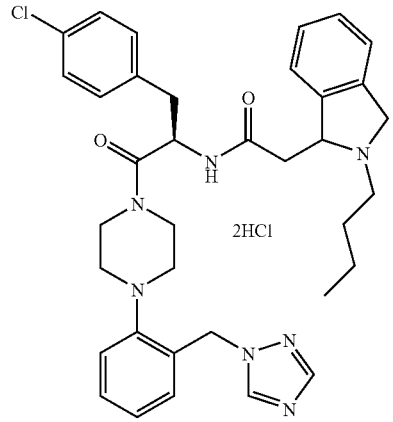

To a flask containing 2-(2-butyl-2,3-dihydro-1H-isoindol-1-yl)-N-{1-(4-chlorobenzyl)-2-oxo-2-[4-((2-[1,2,4]triazol-1-yl)methylphenyl)-piperazin-1-yl]-ethyl}-acetamide (Example 166)(0.07 g, 0.11 mmol) was added 1.0 N HCl (5 mL). After about an hour, the solution was solidified at −78° C., and the solid lyophilized to give about 0.06 g of the final compound as green solids. ES MS 640.3 (M+H)

Examples 163-166

The Examples 163 to 166 were prepared as follows. The mixture of 4AB-2TFA salts or 4AB-HCl salts (Preparation 4AB) (1.0 eq.), N-Boc-substituted-D-Tic-OH or N-Boc-substituted-DL-Tic-OH (1.0 eq.), HATU (1.0 eq.) and DIEA (5.0-10.0 eq.) in DCM was stirred at r.t. overnight. The mixture was partitioned between water and $CH_2Cl_2$. The aqueous layer was extracted with $CH_2Cl_2$ (2×). The combined organic solution was dried over $MgSO_4$, filtered and concentrated in vacuo. The mixture purified by silica gel column using 10% MeOH in EtOAc to give N-Boc product.

The N-Boc product was mixed with 5 mL of saturated HCl in EtOAc and stirred at r.t. overnight. Diethylether was added, and the resulting white solid was filtered and washed with ether (3×) to give the final compound as HCl salt.

Example 163

3-Methyl-1,2,3,4-tetrahydro-isoquinoline-3-carboxylic acid {1-(4-chloro-benzyl)-2-oxo-2-[4-(2-[1,2,4]triazol-yl-methyl-phenyl)-piperazin-1-yl]-ethyl}-amide, HCl Salt

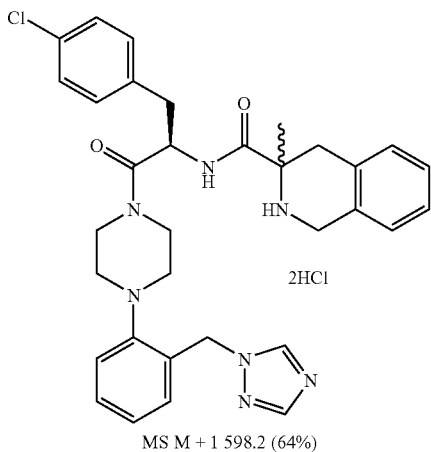

MS M + 1 598.2 (64%)

Example 164

7-Fluoro-1,2,3,4-tetrahydro-isoquinoline-3-carboxylic acid {1-(4-chloro-benzyl)-2-oxo-2-[4-(2-[1,2,4]triazol-1-ylmethyl-phenyl)-piperazin-1-yl]-ethyl}-amide, HCl Salt

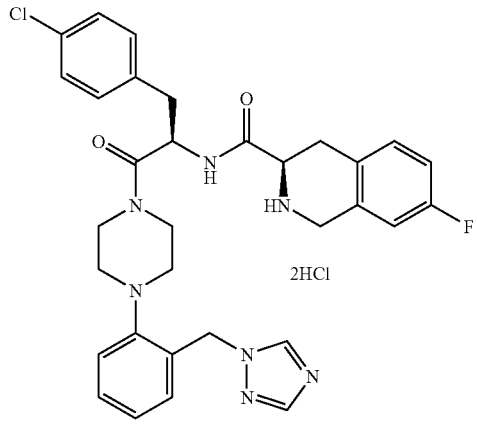

MS M + 1 602.2 (86%)

Example 165

7-Trifluoromethyl-1,2,3,4-tetrahydro-isoquinoline-3-carboxylic acid {1-(4-chloro-benzyl)-2-oxo-2-[4-(2-[1,2,4]triazol-1-ylmethyl-phenyl)-piperazin-1-yl]-ethyl}-amide, HCl Salt

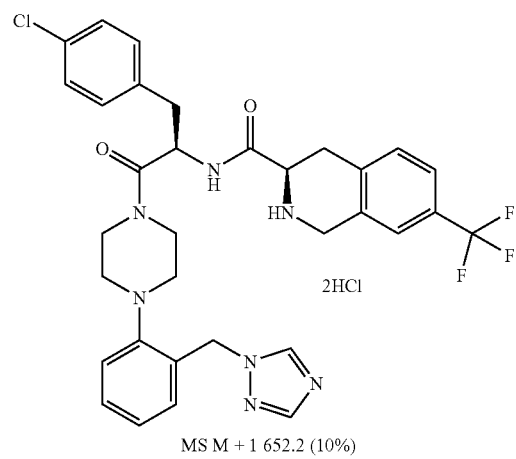

MS M + 1 652.2 (10%)

Example 166

3-Methyl-1,2,3,4-tetrahydro-isoquinoline-3-carboxylic acid {1-(4-chloro-benzyl)-2-oxo-2-[4-(2-[1,2,4]triazol-1-ylmethyl-phenyl)-piperazin-1-yl]ethyl}-amide, HCl Salt

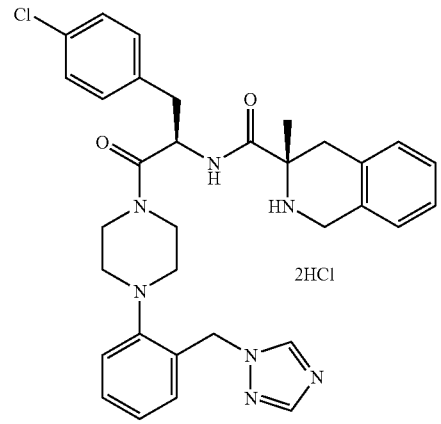

MS M + 1 598.3 (58%)

Example 167

1,2,3,4-Tetrahydro-isoquinoline-3-carboxylic acid [2-{4-[2-(isobutyl-methanesulfonyl-amino)-phenyl]-piperazin-1-yl}-1-(4-methoxy-benzyl)-2-oxo-ethyl]-amide, 2HCl Salt (isomer 2)

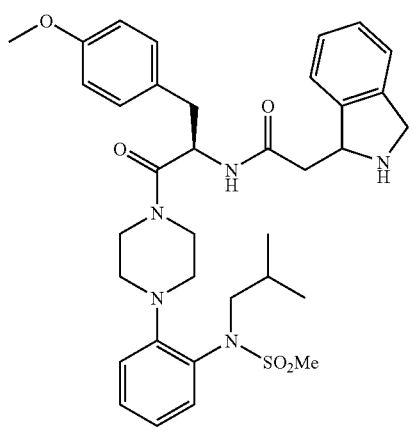

The above compound is prepared from the A domain 98A (Preparation 98A) and the BC domain from Preparation 11BC following a procedure substantially similar to Coupling Procedure 2. LRMS (ESI+): 648.3 (M+H)

Example 168

2-(2,3-Dihydro-1H-isoindol-1-yl)-N-(1-(4-fluoro-benzyl)-2-{4-[2-(isobutyl-methanesulfonyl-amino)-phenyl]-piperazin-1-yl}-2-oxo-ethyl)-acetamide, HCl Salt

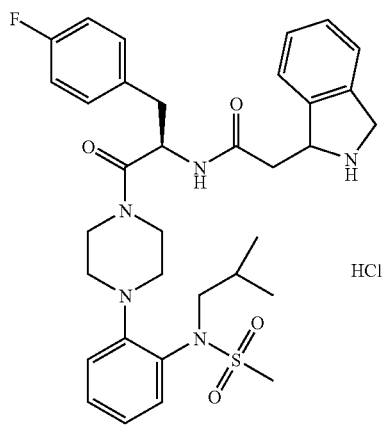

The above compound was prepared by following substantially similar procedure as described in Example 167. MS M+1 636.3 (90%).

Example 169

3-(4-Chloro-phenyl)-1-[4-(2-dimethylaminomethyl-phenyl)-piperazin-1-yl]-2-[methyl-(1,2,3,4-tetrahydro-isoquinolin-3-ylmethyl)-amino]-propan-1-one tri-hydrochloride salt

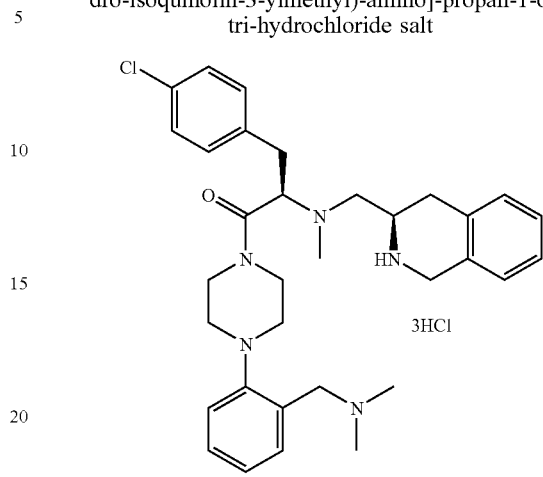

The Boc protected compound of Example 90 (0.19 g, 0.29 mmol) was dissolved in MeOH and stirred under $N_2$ at room temperature. NaOAc (0.12 g, 1.5 mmol) was added to the mixture followed by aqueous HCHO (0.11 ml, 1.5 mmol). The mixture was stirred at r.t. for about 30 minutes. $NaBH_3CN$ (0.06 g, 88 mmol) in MeOH (2 ml) was added dropwise at 0° C. The mixture was stirred at r.t. for about an hour. The mixture was concentrated, taken up in EtOAc and washed with dilute $NaHCO_3$ and brine. The mixture was dried over $Na_2SO_4$ and solvent was evaporated. The resulting residue was purified by flash chromatography (silica gel, 6% 2M $NH_3/MeOH/CH_2Cl_2$) to give about 0.3 g of Boc protected amine compound (2) as white solids. Mass: $MH^+$ 660

To the compound obtained above (0.18 g) was added 4M HCl/dioxane (15 ml) and the mixture was stirred at r.t. for about 20 minutes. The mixture was stripped to dryness and triturated with $Et_2O$ to afford about 0.24 g of the final compound as white solids (92%). LC-MS: $MH^+$ 560; Exact mass calculated: 560.3156; Pound: 560.3170.

Example 170

1-(D-TIC-4-Cl-D-Phe)-4-[(2-(1-S hydroxyethyl) phenyl] piperazine

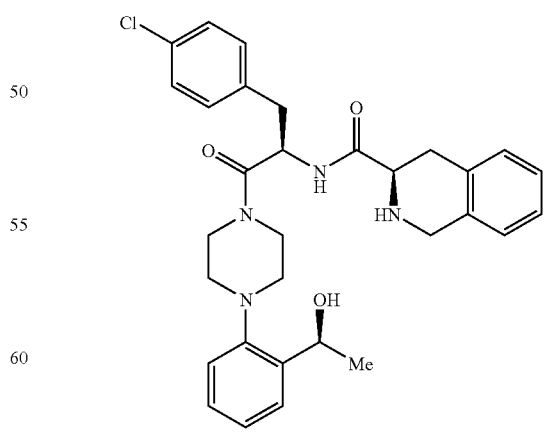

The A domain piperazine of Preparation 11A was coupled to Boc-D-TIC-4-Cl-D-Phe-OH in a manner substantially similar to that describe in Coupling Procedure 2. To a solution of the protected product (100 mg, 0.131 mmol) in 2 mL CH$_2$Cl$_2$ was added 1 drop of H$_2$O, and 1 mL of TFA. After stirring at r.t. for about 3 hours, the solution is azeotroped from heptane (3×). To a solution of the residue in THF at 0° C. was added 1 mL of HF-pyr. After stirring overnight, the solution was diluted with CH$_2$Cl$_2$, washed with saturated sodium bicarbonate (2×) and brine, and then dried (Na$_2$SO$_4$), filtered and concentrated. After purification by flash chromatography (10 g SiO$_2$, linear gradient 0-10% methanol/CH$_2$Cl$_2$, 30 mL/minute over 30 minutes), the product was dissolved in CH$_2$Cl$_2$ and precipitated with 1 M HCl in Et$_2$O to afford about 63 mg (0.11 mmol, 82%) of the final compound. HRMS (electrospray) calculated for C$_{31}$H$_{36}$ClN$_4$O$_3$: 547.2476. Found: 547.2485 (M+H).

Example 171

1-(D-TIC-4-Cl-D-Phe)-4-[(2-(1-R hydroxyethyl)phenyl] piperazine

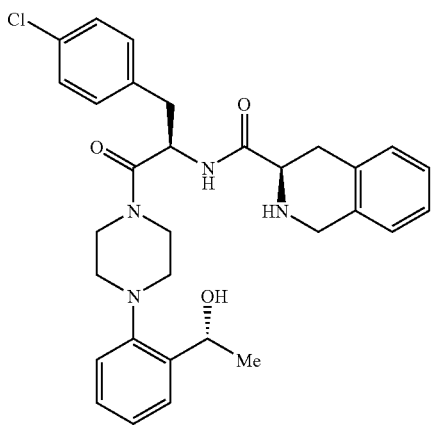

The A domain piperazine of Preparation 12A was coupled to Boc-D-TIC-4-Cl-D-Phe-OH and deprotected in a manner substantially similar to that describe in Example 171 above. HRMS (electrospray) calculated for C$_{31}$H$_{36}$ClN$_4$O$_3$: 547.2476. Found: 547.2480 (M+H).

The following Examples 172-174 are prepared from an appropriately substituted A domain piperazine by following a substantially similar coupling procedure as described in Coupling Procedures 1.

Example 172

Isoquinoline-3-carboxylic acid {1-(4-chloro-benzyl)-2-oxo-2-[4-(2-[1,2,4]triazol-1-ylmethyl-phenyl)-piperazin-1-yl]-ethyl}-amide

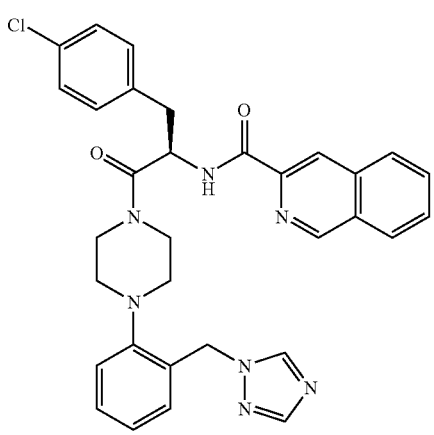

The above compound is prepared by following a Coupling Procedure 1. Found MS (ESI) 580.2 (M+H)

Example 173

Isoquinoline-3-carboxylic acid (1-(4-chloro-benzyl)-2-oxo-2-{4-[2-(propionylamino-methyl)-phenyl]-piperazin-1-yl}-ethyl)-amide

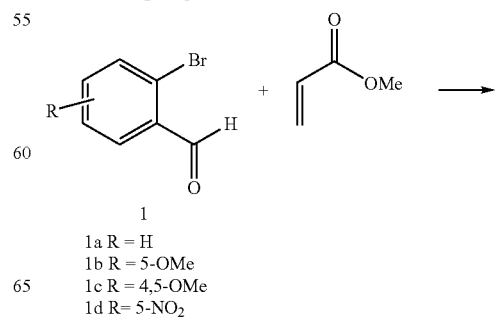

The above compound is prepared by following a Coupling Procedure 1. Found MS (ESI) 584.3 (M+H)

Example 174

Isoquinoline-3-carboxylic acid (1-(4-chloro-benzyl)-2-{4-[2-(N-isobutyl-hydrazino)-phenyl]-piperazin-1-yl}-2-oxo-ethyl)-amide The above compound was prepared by following a Coupling Procedure 1. Found MS (ESI) 648.0 (M+H)

Preparation of Novel C-Domain Pieces

Heck Coupling:

1
1a R = H
1b R = 5-OMe
1c R = 4,5-OMe
1d R = 5-NO$_2$

-continued

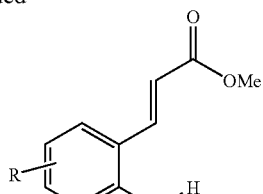

2
2a R = H
2b R = 5-OMe
2c R = 4,5-OMe
2d R= 5-NO₂

Preparation PP1

Synthesis of Compound (2a) by a Heck Coupling of 2-bromobenzaldehyde (1a) with methyl acrylate (Pd(OAc)₂/PPh₃ as the catalyst): A mixture of 2-bromobenzaldehye (1a) (24.5 g, 132 mmol), methyl acrylate (17.9 mL, 199 mmol), Pd(OAc)₂ (590 mg, 2.65 mmol, 2 mol %), PPh₃ (1.39 g, 5.30 mmol, 4 mol %) and Et₃N (46 mL, 331 mmol) was stirred at 80° C. for 15 h. Large amount of yellow solid was formed after the reaction was done. The mixture was cooled to rt, concentrated, and mixed with H₂O (200 mL). The organic solid was collected by filtration, and then applied to a plug of silica gel (25 g) (EtOAc/hexane 1:1) to give a dark yellow solid. The solid was purified by crystallization (100 mL EtOAc bottom layer, 120 mL hexane top layer) to provide 17.57 g (70%) (100% pure by NMR) of the first crop and 5.23 g (21%) (95% by NMR) of the second crop of 2a.

Preparation PP2

Synthesis of Compound (2a) by a Heck Coupling of 2-bromobenzaldehyde (1a) with Methyl Acrylate (R═H) (Pd(OAc)₂/P(O-Tolyl)₃ as the catalyst): The compound 1a (9.998 g, 54.04 mmol) was dissolved in toluene (20 mL) at r.t. Methylacrylate (5.996 g, 69.65 mmol, 1.29 eq.), NEt₃ (15 mL), Pd(OAc)₂ and P(O-Tolyl)₃ were successively added and the mixture was stirred under reflux. After 2 hours, the reaction mixture was allowed to cool to r.t. Then the precipitated yellow catalyst was removed by filtration. The catalyst was rinsed with toluene (2×10 mL) and the filtrates were concentrated to dryness under reduced pressure. The residual oil was dried under vacuum over the weekend to give a crude solid (11.449 g). The solid was taken-up with isopropanol (25 mL) and stirred overnight at r.t. Then, the precipitate was filtered and rinsed with isopropanol (5 mL). The wet cake (8.240 g) was dried overnight at RT affording the highly pure 2-carboxaldehyde-methyl-cinnamate with 74% yield (7.627 g, 40.1 mmol).

Preparation PP3

Heck Coupling of 1b and methyl acrylate to form 2b (R=5-OMe): A mixture of 2-bromo-5-methoxybenzaldehyde (1b) (4.5 g, 20.9 mmol, Aldrich), methyl acrylate (2.7 g, 1.5 eq, 2.83 mL), Et₃N (7.4 g, 3.5 eq, 10.2 mL), Pd(OAc)₂ (93 mg, 0.02 eq), and P(O-Tol)₃ was stirred and heated to 80° C. over 2-3 days. The reaction mixture was cooled to r.t., partitioned between EtOAc (50 mL) and brine (50 mL). The aqueous was extracted with EtOAc (2×50 mL). The combined organic was washed with brine (1×50 mL), dried over MgSO₄, filtered, concentrated to yield a yellow brown oil (5.01 g, 109%). This crude oil was purified in a hot solvent Hex/EtOAc (80 mL/15 mL) to yield 2b as a pale yellow solid (3.5 g, 76%).

Preparation PP4

Heck Coupling of 1c and Methyl Acrylate to Form 2c (R=4,5-OMe): To a solution of 1c (906 mg, 3.70 mmol) in toluene (2 mL) was added Pd(OAc)₂ (17 mg, 0.074 mmol, 2 mol %), P(O-Tolyl)₃ (45 mg, 0.148 mmol, 4 mol %), methyl acrylate (0.5 mL, 5.55 mmol) and Et₃N (1.5 mL, 11.1 mmol). The mixture was stirred at 80° C. for 21 h, cooled to rt, and mixed with H₂O (40 mL). The organic compounds were extracted with EtOAc (50 mL), washed with brine (40 mL), dried (Na₂SO₄), and concentrated. The residue was purified by flash chromatography to provide 466 mg (47%) of recovered 1c followed by 450 mg (49%) of 2c (4,5-Ome).

Preparation PP5

Heck Coupling of 1d and Methyl Acrylate to Form 2d (R=5-NO₂): The procedure is same as that of 2c, yielding 82% of 2d after purification.

Preparation PP6

Reductive Amination

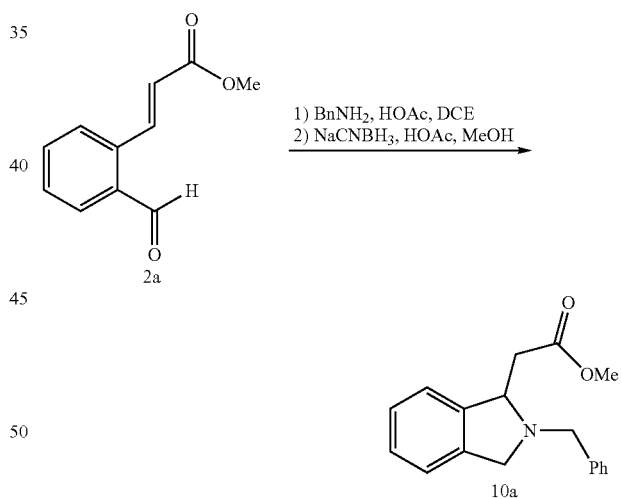

Reductive amination of (2a) with benzyl amine to form isoindoline (10a). To a solution of 2a (11.27 g, 59.2 mmol) in ClCH₂CH₂Cl (60 mL) was added BnNH₂ (6.47 mL, 59.2 mmol), followed by HOAc (5.1 mL, 89 mmol). The mixture was stirred at rt for 1 h. NaCNBH₃ (5.58 g, 88.8 mmol) and MeOH (30 mL) were then added to the above solution. The resulting mixture was stirred at rt for another 2 h and quenched with sat. NaHCO₃ solution (150 mL). The mixture was extracted with EtOAc (2×100 mL) and the combined organic layers were washed with brine (150 mL), dried (Na₂SO₄), and concentrated to provide 15.3 g of crude product of 10a which was carried out for the next hydrogenolysis reaction.

Preparation PP7

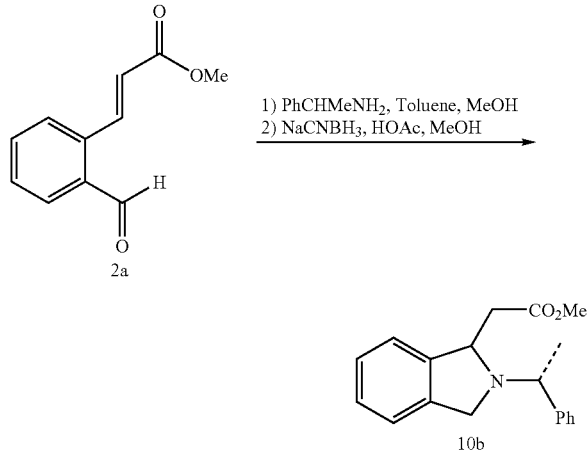

One-pot process from 2-carboxaldehyde-methyl-cinnamate to target cyclized isoindoline product using NaBH$_3$CN. 2-carboxaldehyde-methyl-cinnamate 2a (3.254 g, 17.1 mmol) was dissolved in a 1:1 MeOH:PhCH$_3$ mixture (20 mL) at r.t. R-(+)-phenethylamine (2.073 g, 17.1 mmol) was added and the solution was heated under reflux for 2 hours. HPLC in process control indicated that the imine formation was completed. Then, AcOH (2.055 g, 34.2 mmol) and NaBH$_3$CN (2.15 g, 34.2 mmol) were successively added at RT, the reaction mixture being cooled with a water-bath. The reaction mixture was post-agitated overnight. Water (10 mL), MeOH (20 mL) and 37% HCl (2.8 mL) were successively added and the organic layer was extracted. The aqueous layer was washed with PhCH$_3$ (10 mL). Then, the aqueous layer was made basic with 5N NaOH (20 mL) and MeOH was concentrated to partly remove MeOH. Extraction with EtOAc (2×25 mL) was performed. The combined organic layers were dried over MgSO4, filtered and rinsed with EtOAc (10 mL). The filtrates were concentrated under reduced pressure and the residual oil was dried under vacuum overnight at RT to afford the target cyclized isoindoline product 10b with 92% yield (4.642 g, 15.7 mmol). HPLC % area indicated that the 2 diastereomers were produced in a 55:45 ratio. $^1$H NMR confirmed this result by integration of the methyl group of the phenethyl substituent. Note: The Heck or Heck-type coupling was performed in toluene with a slight excess of methylacrylate which was removed by distillation before the MeOH and the R-(+)-phenethylamine addition.

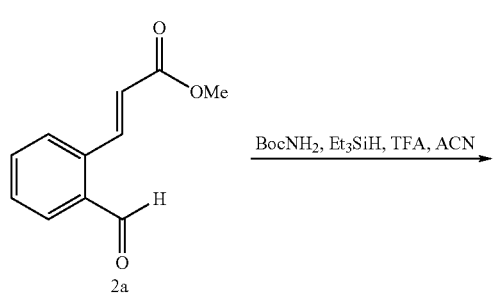

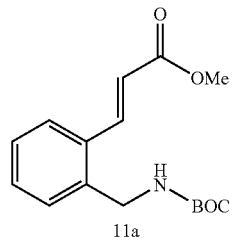

Reductive amination of (2a) with t-butyl carbamate to form (11a): To a solution of aldehyde 2a (238 mg, 1.25 mmol) in CH$_3$CN (8 mL) was added t-butyl carbamate (439 mg, 3.75 mmol), followed by triethylsilane (0.6 mL, 3.75 mmol) and TFA (0.19 mL, 2.5 mmol). The mixture was stirred at rt overnight, quenched with sat. NaHCO$_3$ solution (20 mL) and extracted with EtOAc (2×30 mL). The combined organic layers were washed with brine (30 mL), dried (Na$_2$SO$_4$) and concentrated. The residue was purified by flash chromatography (hexane/EtOAc 3:1) to provide 317 mg (87%) of 11a.

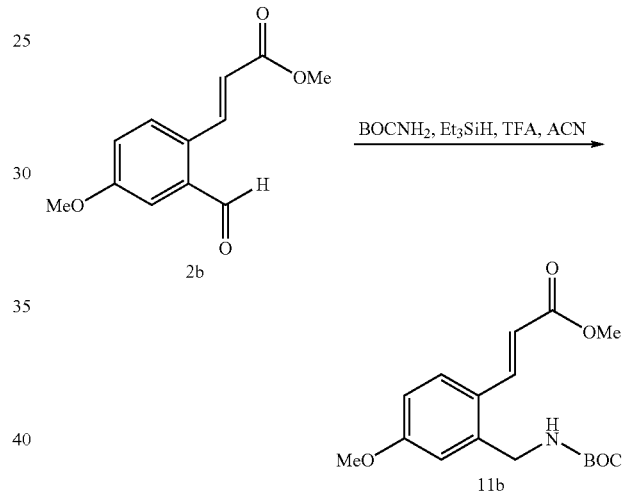

Reductive amination of 2b with t-butyl carbamate to form 11b: A mixture of aldehyde 2b (600 mg, 2.72 mmol) Et$_3$SiH (955 mg, 3 eq, 1.31 mL), TFA (620 mg, 2 eq, 420 uL), t-butyl carbamate (980 mg, 3 eq) in acetonitrile (15 mL) was stirred at room temperature over 2 days. Removed the solvent on a Rotary evaporator and purified the crude residue on a flash column (100 g SiO$_2$, 7:1→6:1 Hex/EtOAc). Collected 307 mg good desired product 11b (35%); 195 mg product contaminated with aldehyde SM (22%).

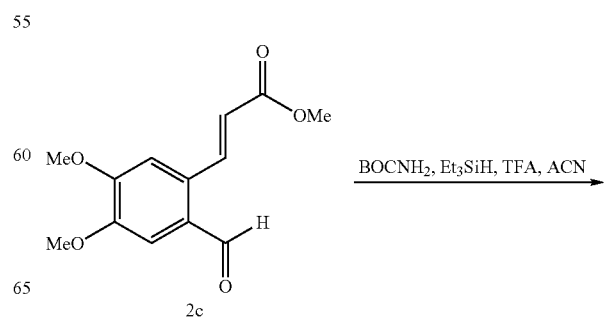

-continued

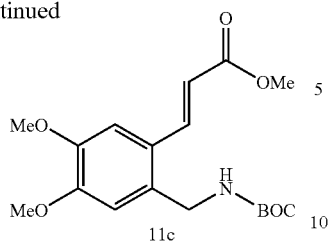

11c

Reductive amination of (2c) with t-butyl carbamate to form (11c): To a solution of aldehyde 2c (411 mg, 1.64 mmol) in CH$_3$CN (10 mL) was added t-butyl carbamate (580 mg, 4.93 mmol), followed by triethylsilane (0.8 mL, 4.93 mmol) and TFA (0.25 mL, 3.28 mmol). The mixture was stirred at rt overnight, quenched with sat. NaHCO$_3$ solution (30 mL) and extracted with EtOAc (2×30 mL). The combined organic layers were washed with brine (30 mL), dried (Na$_2$SO$_4$) and concentrated. The residue was purified by flash chromatography (hexane/EtOAc 3:1, hexane/EtOAc 1:1) to provide 535 mg (93%) of 11c.

Preparation PP11

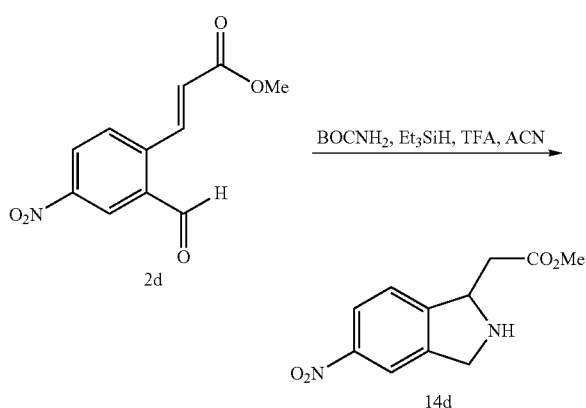

14d

To a solution of 2d (1.02 g, 4.34 mg) in CH$_2$Cl$_2$/CH$_3$CN (1:1 24 mL) was added BocNH$_2$ (1.5 g, 13.02 mmol), Et$_3$SiH (2.1 mL, 13.02 mmol), and TFA (0.67 mL, 8,67 mmol). The mixture was stirred at rt for 7 h. A precipitate was formed during the reaction. The reaction mixture was quenched with sat. NaHCO$_3$ solution (30 mL), and diluted with CH$_2$Cl$_2$ (40 mL). The organic layer was washed with brine (30 mL), dried (Na$_2$SO$_4$), and concentrated. The residue was purified by flash chromatography (hexane/EtOAc 3:1, then CH$_2$Cl$_2$/EtOAc 10:1) to provide 2.08 g yellow solid which still containing BocNH$_2$. The product is not the desired Boc-carbamate 14c. LC-MS result showed that the product is the Schiff base intermediate.

To the above product (420 mg) in CH$_2$Cl$_2$ (10 mL) was added Et$_3$SiH (1 mL) and TFA (0.4 mL). The mixture was stirred at rt for 1 h and small amount of sample was taken for NMR. NMR analysis demonstrated that the starting material was consumed and the product was 14c. TFA (0.7 mL) was then added to the above mixture and the resultant solution was stirred at rt for another 5 h and concentrated. The residue was dissolved in EtOAc (20 mL) and washed with H$_2$O (10 mL). The aqueous layer was basified with sat. NaHCO$_3$ (30 mL) and the organic compounds were extracted with CH$_2$Cl$_2$ (2×25 mL). The combined organic layers were washed with brine (20 mL), dried (Na$_2$SO$_4$) and concentrated to provide 218 mg of the cyclized compound 14c.

Preparation PP12

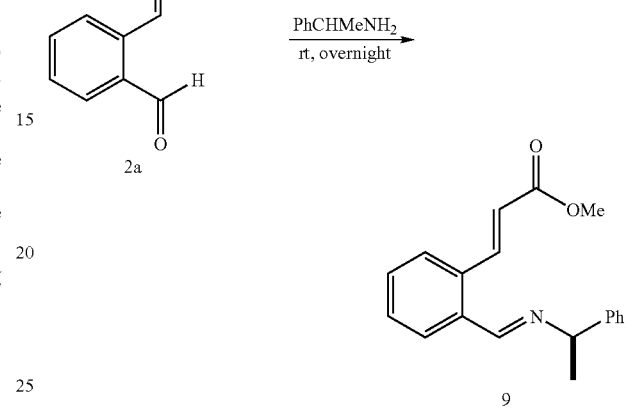

Condensation of 2a with alpha-methylbenzylamine to Form Imine 9. 2-carboxaldehyde-methyl-cinnamate 2a (0.897 g, 4.72 mmol) was dissolved in MeOH (10 mL) at r.t. R-(+)-phenethylamine (0.577 g, 4.76 mmol) was added and the solution was heated under reflux for 2 hours. HPLC in process control indicated that the imine formation was completed. The solvent was stripped on a rotary evaporator and the resulting oil was dried at RT under vacuum overnight. The Schiff base 9 was obtained almost quantitatively (1.412 g, 4.81 mmol).

Preparation PP13

Michael Addition:

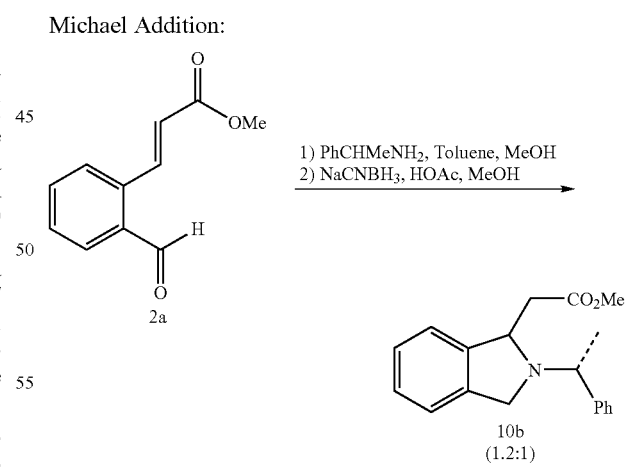

The compound of alpha-methyl benzylamine was applied as the auxiliary. As shown above, the one-pot reaction of aldehyde 2a and alpha-methyl benzylamine gave 90% of 10b with a ratio of 1.2:1.

Step-wise Reduction, Amination and Cyclization:

Condensation of aldehyde 2a with alpha-methylbenzylamine in acetonitrile, methanol, methanol/toluene(1:1) or toluene afforded imine 9 in excellent yield. Reduction of the imine was initially carried out at RT with NaCNBH$_3$/HOAc. As a result, a poor ee ratio (1.2:1) was obtained, similarly to the previous described one-pot procedure. But when the reaction was carried out with NaBH$_4$/TFA at RT, the ratio was elevated to 2:1. By lowering the reaction temperature to −78° C., the ratio was increased to 5 to 6:1.

Preparation PP14

Cyclization of t-Butyl carbamate (11a): The N-Boc isoindoline methyl ester 12 was originally synthesized from 11a via deprotection of Boc with TFA, followed by basic workup, and protection with a Boc group. This procedure has been greatly improved by a one-step procedure.

Preparation PP15

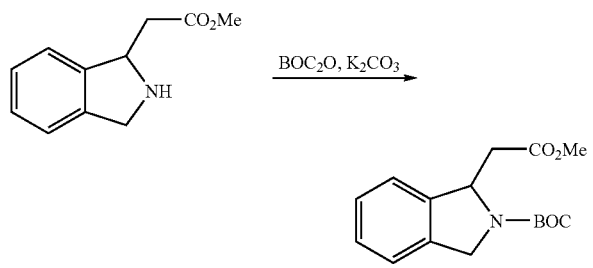

In a 3 L 3-neck round bottom flask equipped with a nitrogen inlet, thermocouple and mechanical stirrer, a solution of 160 g (1.15 moles) of K$_2$CO$_3$ in 180 mL of water was stirred at ρ.τ. Solid BOC anhydride 120 g (0.55 moles) was added in one portion forming a semi-solution. To the reaction mixture, a solution of the crude amino ester starting material, 87 g (0.46 moles) in 120 mL of THF was added slowly at such a rate to keep the internal temperature below 35° C. A mild effervescence was observed. The reaction mixture was stirred for 18 hours at ρ.τ. Analysis of a reaction aliquot via NMR (DMSO$_6$) indicates the desired product. The reaction was diluted with brine and the product extracted with EtOAc. The organic layer was dried over Na$_2$SO$_4$, filtered, and concentrated to yield a dark oil, 150.1 g, >100% yield. The crude material was taken on to the next step.

Preparation PP16

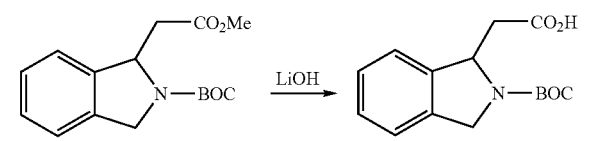

In a 3-L 3-neck round bottom flask equipped with a mechanical stirrer, thermocouple, and reflux condenser, a solution of 150 g (approx. 0.46 moles) of crude N-BOC ester starting material in 750 mL of methanol was stirred at ρ.τ. To the solution, 750 mL of water was added and the cloudy mixture was stirred vigorously. Solid LiOH 25 g (1.03 moles) was added in small portions at such a rate to maintain the internal temperature below 45° C. Upon completion of addition, the reaction was stirred overnight at rt becoming a dark green color. After 18 hours the reaction was concentrated to yield a thick semisolid. The crude product was dissolved in EtOAc and washed with 1 N HCl quickly, followed by two brine washes. The organic layer was dried with Na$_2$SO$_4$, filtered and concentrated to yield 81 g of a dark green solid. The aqueous layers were combined and back extracted with methylene chloride, dried over Na$_2$SO$_4$, filtered, and concentrated to yield 6 g of a dark green solid. Both solids were combined to yield 87 g of desired product confirmed via NMR (DMSO$_6$).

Preraration PP17

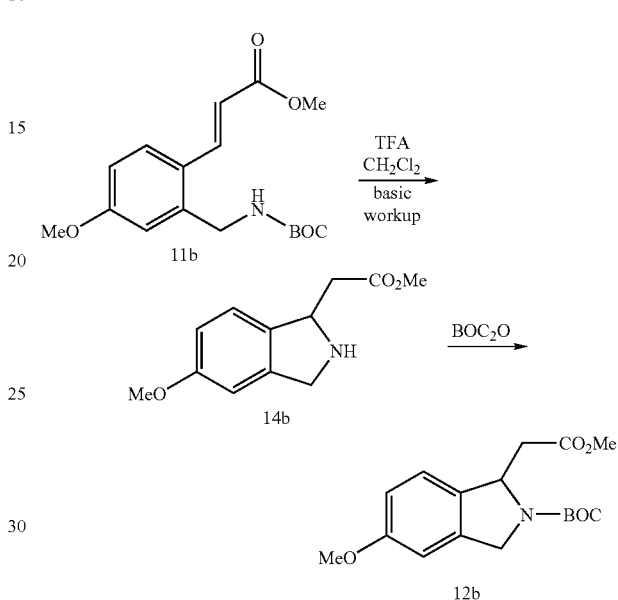

Synthesis of 14b: Dissolved the N-boc compound 11b (200 mg, 0.62 mmol) in CH$_2$Cl$_2$ (1.0 mL). Cooled the clear light yellow solution to 0° C. Added slowly TFA (~710 mg, 10 eq, ~500 microliter) via a syringe. Removed the cooling bath and stirred the clear light brown solution at RT overnight. TLC (3:1 Hex/EtOAc, UV) confirmed a complete reaction. Removed the TFA on a rotavapor. Added EtOAc and concentrated again (twice). The crude residue was partitioned between EtOAc (10-15 mL) and a sat. NaHCO$_3$ (10-15 mL). The aqueous was extracted with EtOAc (2×10 mL). The combined organic was dried over MgSO$_4$, filtered, and concentrated to yield a light brown wet solid (212 mg, 138%). NMR (CD$_3$OD) confirmed the desired isoindoline 14b. This crude isoindoline was used in the next protection step without purification.

Preparation PP18

Synthesis of 12b: To a mixture of the isoindoline 14b (190 mg, 0.859 mmol), K$_2$CO$_3$ (189 mg, 1.5 eq) in a solvent 1:1 TFH/H$_2$O (1.0 mL) at RT was added BOC$_2$O (210 mg, 1.1 eq). The reaction mixture was stirred at RT overnight. TLC (3:1 Hex/EtOAc, UV) confirmed a complete reaction. Diluted the mixture with EtOAc (15 mL), and washed with H$_2$O (1×20 mL). The aqueous was extracted with EtOAc (1×20 mL). The combined organic was washed with brine (1×20 mL), dried over MgSO$_4$, filtered, concentrated to yield a clear brown oil (340 mg, 123%). This crude oil was purified on a prep TLC plate (2×1,000 micron, solvent 2:1.5:0.5 CHCl$_3$/Hex/EtOAc) to yield 12b a clear yellow oil (190 mg, 69%). $^1$H and $^{13}$C NMR (CDCl$_3$) were obtained.

Procedure PP19

Synthesis of 12d (5-NO₂) by Boc-protection. The compound was prepared by following the same procedure as described for 12b.

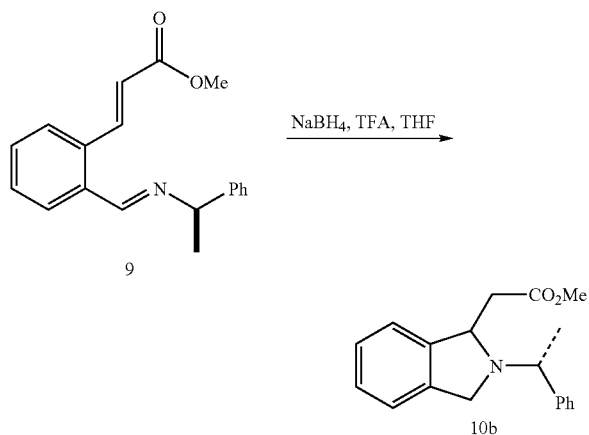

The imine 9 (1.412 g, 4.81 mmol) was dissolved in anhydrous THF (10 mL) at RT and TFA (5 mL) was added. The black solution was then cooled to −78° C. (dry ice bath) and NaBH₄ (0.893 g, 23.6 mmol, 5 eq.) was added in 2 portions over 5 minutes. Then, the reaction mixture was post-agitated at −78° C. for 3 hours and allowed to gently warm at RT overnight. Water (20 mL), cyclohexane (10 mL) and EtOH (20 mL) were successively added and the organic layer was extracted and discarded. The aqueous layer was made basic with 5N NaOH (20 mL) and extracted two times with a 2:1 EtOAC/PhCH₃ mixture (30 mL). The combined organic layers were dried over MgSO4, filtered and rinsed with EtOAc (10 mL). The filtrates were concentrated under reduced pressure and the residual oil was dried under vacuum overnight at RT to afford the target cyclized isoindoline product 10b (1.273 g, 4.31 mmol) with 91.4% yield. HPLC % area indicated that the 2 diastereomers were produced in a 84:16 ratio (de 68%). ¹H NMR confirmed this result by integration of the methyl group of the phenethyl substituent.

Preparation PP20

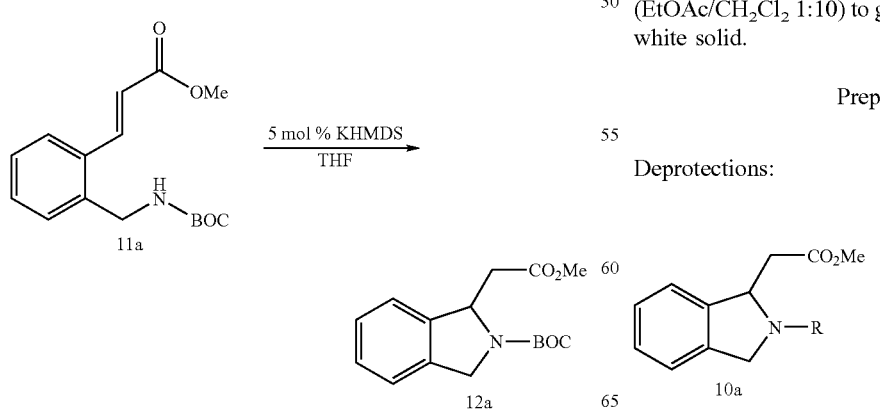

N-Boc methyl ester 11a (36.3 g, 0.125 mol) was dissolved in THF (250 mL), and the solution was cooled to about 0° C. A solution of potassium bis(trimethylsilyl) amide (1.24 g, 0.05 mol. Eq.) was added slowly via a syringe under nitrogen atmosphere. The temperature was raised about 8 degrees during the addition. The cooling bath was removed and the solution was stirred at r.t. for 30-45 min. The clear brown solution was poured into a separation funnel containing about 100 mL of a saturated NH₄Cl. The layers were separated. The aqueous layer was extracted with EtOAc (2×50 mL). The combined organic was washed with brine (1×100 mL), dried over Na₂SO₄, filtered, concentrated on a Rotary evaporator to a clear yellow oil (37.3 g). This crude oil was purified on a flash column (600 g SiO₂), with a gradient solvent 6:1 Hex/EtOAc (2.1 L), 5:1 Hex/EtOAc (1.2 L), 4:1 Hex/EtOAc (1.5 L) to yield 12a as a clean yellow oil (34.5 g, 95%).

Preparation PP21

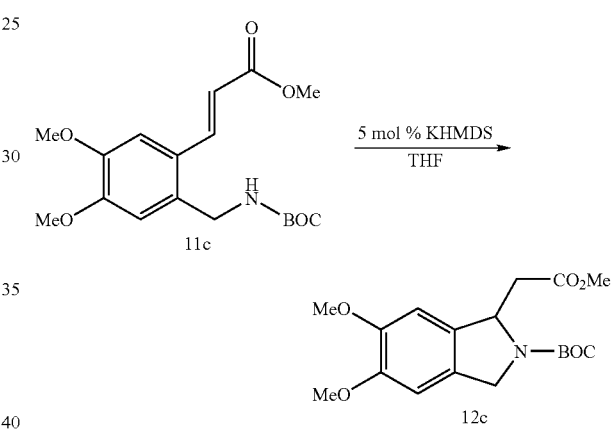

To a solution of 11c (535 mg, 1.52 mmol) in THF (10 mL) was added KHMDS (0.5 M in toluene, 0.1 mL, 0.05 mmol, 2 mol %). The mixture was stirred at r.t. for 20 min, quenched with sat. NH₄Cl solution (20 mL), and diluted with EtOAc (20 mL). The organic layer was separated, washed with brine (20 mL), dried (Na₂SO₄) and concentrated. The residue was filtered through a plug of silica gel (EtOAc/CH₂Cl₂ 1:10) to give 530 mg (99%) of 12c as an off white solid.

Preparation PP22

Deprotections:

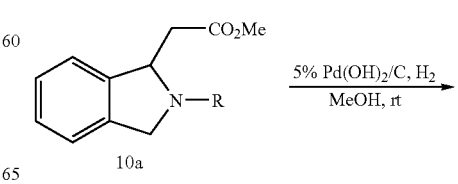

-continued

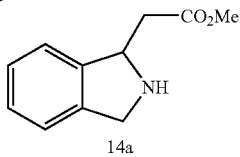
14a

Hydrogenolysis of 10a (R=Bn) to Form (14a): To a solution of crude 10a (15.3 g, 54.4 mmol) in MeOH (100 mL) was added Pd(OH)$_2$/C (Pearlman's catalyst, 1.02 g, 6 mol %) in a par-shaker bottle. The suspension was shaken under 30 psi H$_2$ pressure overnight in the par-shaker, and filtered through a plug of celite. The filtrate was concentrated to provide 10.1 g of crude 14a as brown oil. (The procedure is same for the methyl benzylamine isoindoline substrate 10b).

Preparation PP23

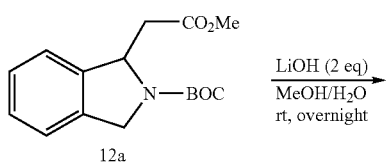
12a

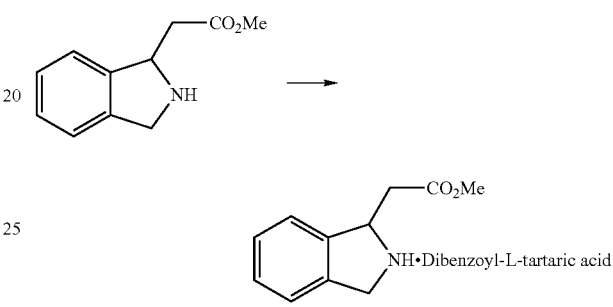
16a

In a typical reaction a mixture of the isoindoline ester 12a (92 mg, 0.316 mmol) in 1:1 MeOH/H$_2$O (2 ml) was treated with LiOH (15 mg, 2 eq) at RT overnight. Diluted the mixture with CH$_2$Cl$_2$ (5 ml) and water (5 ml). Adjusted the pH of the reaction mixture to 1-3 with a 10% NaHSO$_4$ solution. Separated the layers. The aqueous was extracted with CH$_2$Cl$_2$ (1×10 ml). The combined organic was dried over Na$_2$SO$_4$, filtered, concentrated to yield 16a as a pale yellow foam (76 mg, 87%). NMR (CDCl$_3$) showed a clean desired acid product.

It is noted that he reaction time must be more than 6 hours. The crude foam can be purified by slurry in warm hexane and then filter to yield a tan solid. Hydrolysis using KOH (2-5 eq) in 1:1 MeOH/H$_2$O overnight would give the same result.

Preparation PP24

Resolution:

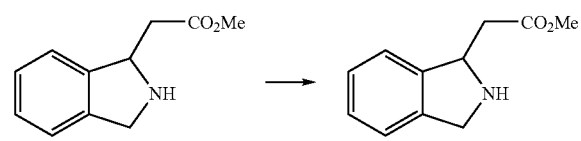

Purification of Partially Resolved Isoindoline-caboxylic acid methyl ester: A solution of the crude material (97.62 g) isoindolinecaboxylic acid methyl ester in CH$_2$Cl$_2$ (350 mL) was extracted with 1M HCl (400 mL, 200 mL). The combined aqueous portions were washed with CH$_2$Cl$_2$ (4×250 mL) and then made basic with K$_2$CO$_3$ solution (85 g in 150 mL of water). The mixture was extracted with CH$_2$Cl$_2$ (6×100 mL) and the combined organic extracts were dried (Na$_2$SO$_4$) and concentrated to give partially resolved Isoindolinecaboxylic acid methyl ester as an oil (33.2 g). 60% ee by chiral CE.

Preparation PP25

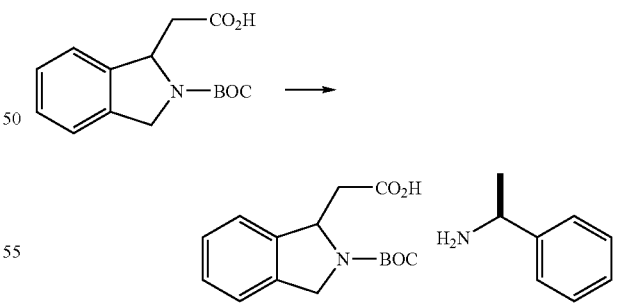

Resolution of Partially Resolved Isoindoline-caboxylic acid methyl ester: A solution of partially resolved isoindoline-caboxylic acid methyl ester (33.24 g, 0.174 mol) in EtOH (130 mL) was treated slowly with a solution of dibenzoyl-L-tartaric acid (56.06 g, 0.156 mol) in EtOH (200 mL). The solution was seeded with seeded with product and stirred at RT for 4 hours. Pure product was collected by filtration, washed with EtOH (30 mL) and dried to off-white crystals (60.49 g). 96.5% ee by chiral CE.

Preparation PP26

Resolution of N-BOC Isoindolinecaboxylic acid: A solution/slurry of racemic N-BOC Isoindolinecaboxylic acid (114.5 g, 0.413 mol) in EtOAc (1000 mL) was treated slowly with triethylamine (28.8 mL, 0.206 mol), followed by (S)-(−)-alpha-methylbenzylamine. The solution was seeded with product and stirred at RT overnight. The product was collected by filtration, washed with EtOAc (200 mL) and dried to a white powder (62.98 g). 97.6% ee by chiral CE.

Asymmetric Hydrogenation Routes

Part I: Synthesis of the Z-isomer (Precursor of Asymmetric Hydrogenation)

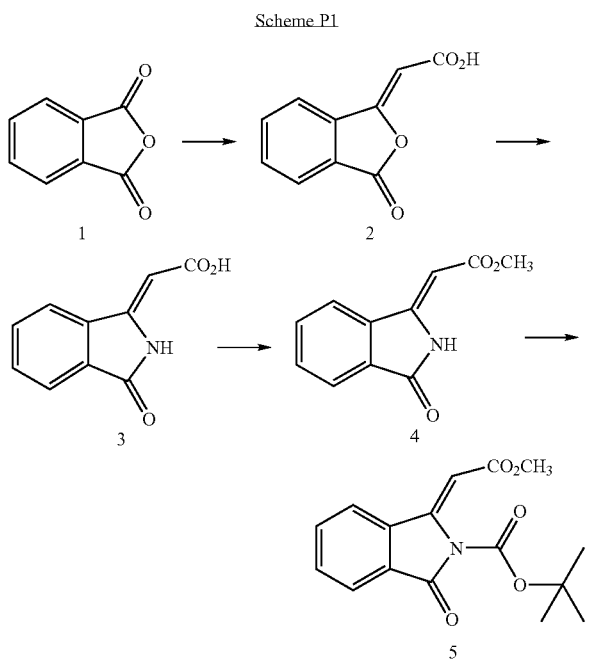

Scheme P1

Preparation PP27

Z-isomer 5 was synthesized as outlined in Scheme P1. Compound 5 was shown to be a single isomer by HPLC and H-1 nmr. The double bond stereochemistry was derived from comparative NOE data using the purported E-isomer (Scheme P1). The best chiral induction was achieved using compound 8/Ferrotane/MeOH-THF. With regard to the conversion of 9 to 10, which would constitute a formal asymmetric synthesis of isoindolene 10, this has been achieved using Super hydride-BF$_3$.OEt$_2$. However, the product was a mixture of 10 and the corresponding de-BOC (deprotected) compound.

Preparation PP28

Compound 2 (Scheme P1)

Phthalic anhydride (751.5 g, 5.014 mole), potassium acetate (498 g, 5.014 mole) and acetic anhydride (1L) were stirred together under nitrogen. The mixture was slowly warmed to 145-150° C. and stirred for 10 minutes, then at 140° C. for 20 minutes. The mixture was allowed to slowly cool to 80° C. over 1 hour. Three volumes of water were added causing precipitation of a solid. After filtration, the filtered solid was washed with warm water and pulled as dry as possible for 30 minutes. The solid was then washed with ethanol and acetone respectively. If required further purification could be achieved by slurring the solid in acetone, at room temperature, for 15 minutes, then filtration. Drying in vacuo at 50° C. for 20 hours gave compound 2 as an off-white solid, 470 g (48%) with an NMR purity of approx. 90%.

Preparation PP29

Compound 3 (Scheme P1)

Compound 2 (470 g, 2.47 mole) was added to stirred aqueous ammonia (470 ml conc. NH$_3$ in 4.7L water). The resultant mixture was stirred at room temperature for 1 hour then filtered. The filtered solid was washed with water. The combined aqueous filtrate and washings were carefully acidified with 6M aq. HCl (2.35L). The precipitate was removed by filtration and dried in vacuo at 50° C. to give compound 3 as a yellow solid, 259 g (52%).

Preparation PP30

Compound 4 (Scheme P1)

Compound-3 (511 g, 2.7 mole) was slurried in toluene (10 vol). Thionyl chloride (385 g, 3.24 mole) was added over 10 minutes to the stirred mixture, which was then heated to reflux for 1.5 hours. H-1 NMR analysis indicated approx. 80% conversion to acid chloride). DMF (3.7 ml) was added and the mixture refluxed an additional 3 hours. The resultant mixture was allowed to cool to 35° C. and methanol (1.27L) added at such a rate that the reaction temperature was maintained at 30-35° C. The reaction mixture was kept at this temperature a further 15 minutes then concentrated in vacuo to give compound 4 as a brown solid, 536 g (quantitative).

Preparation PP31

Compound 5 (Scheme P1)

Compound 4 (750 g, 3.65 mole) was dissolved in acetonitrile (15L). The stirred mixture was cooled to 0-5° C. and DMAP (624 g, 5.11 mole) added in one portion. After 10 minutes BOC anhydride (1115 g, 5.11 mole) was added in one portion: there was a slight exotherm accompanied by gas evolution. The mixture was stirred at room temperature for 5 hours, and then concentrated in vacuo. The residue was dissolved in EtOAc and washed with 10% aqueous citric acid, satd. aq. Na$_2$CO$_3$ and water respectively. After drying, concentration of the organics gave a thick syrup. This material was run through a plug of silica gel (1.5 kg) eluting with 1:1 EtOAc-hexane. Compound 5 was isolated as a dark solid, 619 g (55%). Careful chromatography on silica gel eluting with 20% EtOAc-hexane gave 5 as a fluffy white solid.

Scheme P2

Part II: Synthesis of the E-isomer (Precursor of asymmetric hydrogenation)

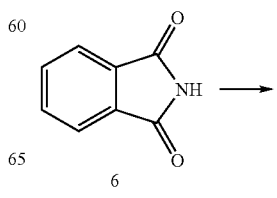

-continued

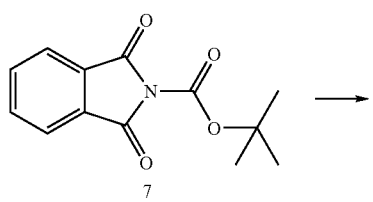

7

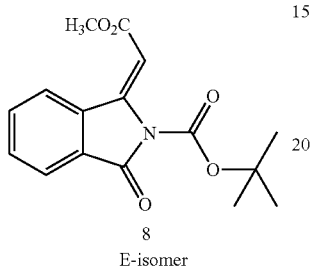

8
E-isomer

Preparation PP32

The E-isomer of Compound 8 (Scheme P2) was prepared as shown in Scheme P2.

Preparation PP33

Compound 7 (Scheme P2)

The compound 7 was prepared according to the procedure of Einhorn et al, *Synth. Commun.* 2001, 31(5), 741-748.

Preparation PP34

Compound 8 (Scheme P2)

Compound 7 (15.00 g, 60.7 mmole) and methyl(triphenyl phosphoranylidene) acetate (41.40 g, 121.3 mmole) were slurred in toluene (150 ml). The mixture was stirred at reflux and monitored for reaction of 7 by GC. After 1.5 hours the reaction appears complete by GC. After cooling to room temperature, the mixture was filtered. The solid on the filter was washed with toluene until colorless. The combined filtrate/washings were concentrated in vacuo to leave a tan solid. This material was coated on silica gel and chromatographed on silica gel (1 kg) eluting with 10% EtOAc-hexane. Compound 8 was isolated as a white or pale yellow powder, 5.52 g (30%).

Scheme P3

Asymmetric hydrogenation:

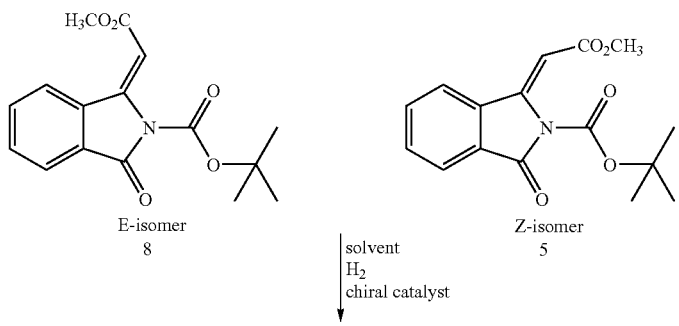

E-isomer
8 solvent
H$_2$
chiral catalyst

Z-isomer
5

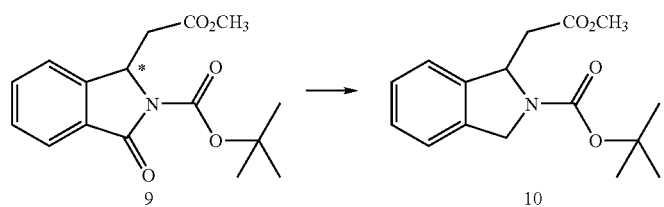

9 → 10

Preparation PP35

Screening of chiral hydrogenation conditions indicated that the best chiral induction was achieved using compound 8/Ferrotane/MeOH-THF. With regard to the conversion of 9 to 10, which would constitute a formal asymmetric synthesis of isoindolene 10, this has been achieved using Super hydride-BF$_3$.OEt$_2$. However, the product was a mixture of 10 and the corresponding de-BOC (deprotected) compound.

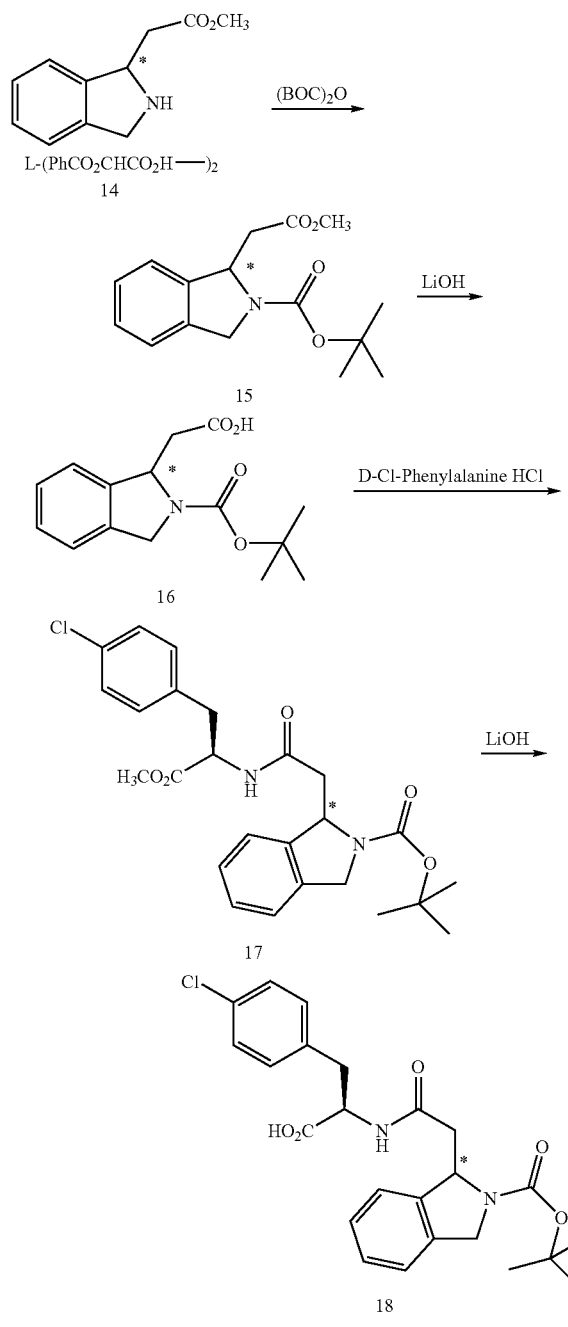

Preparation PP36

Compound 15 (Scheme P4)

Tartrate salt 14 (58.00 g, 100.27 mmole) was slurried in water (580 ml). Solid NaHCO$_3$ (25.27 g, 300.8 mmole) was carefully added. BOC anhydride (22.98 g, 105.28 mmole) was added in one portion and the progress of the reaction monitored by reverse phase HPLC. After 1 hour additional BOC anhydride (2.18 g, 10.00 mmole) was added. The reaction was complete (by HPLC) after 3 hours. The mixture was extracted with EtOAc (2×250 ml). The combined organic extracts were washed with water (250 ml) and dried (MgSO$_4$). Filtration and concentration in vacuo gave 15 as a clear light brown oil (31.33 g) contaminated with a small amount of t-BuOH and BOC anhydride. This material was used directly in the next reaction.

Preparation PP37

Compound 16 (Scheme P4)

Ester 15 (29.21 g, 100.26 mmole) was dissolved in 3:1 THF-water (100 ml). LiOH (6.00 g, 250.65 mmole) was added in 1 portion to the stirred solution. After 17 hours, the mixture was stripped to dryness and the residue dissolved in water (500 ml). EtOAc (250 ml) was added and solid NaHSO$_4$ added to the stirred mixture until the pH=3. The organic layer was separated and the aqueous layer extracted with EtOAc (250 ml). The combined EtOAc layers were dried (MgSO$_4$). Filtration and concentration in vacuo gave acid 16 as a light tan solid, 27.10 g (97%).

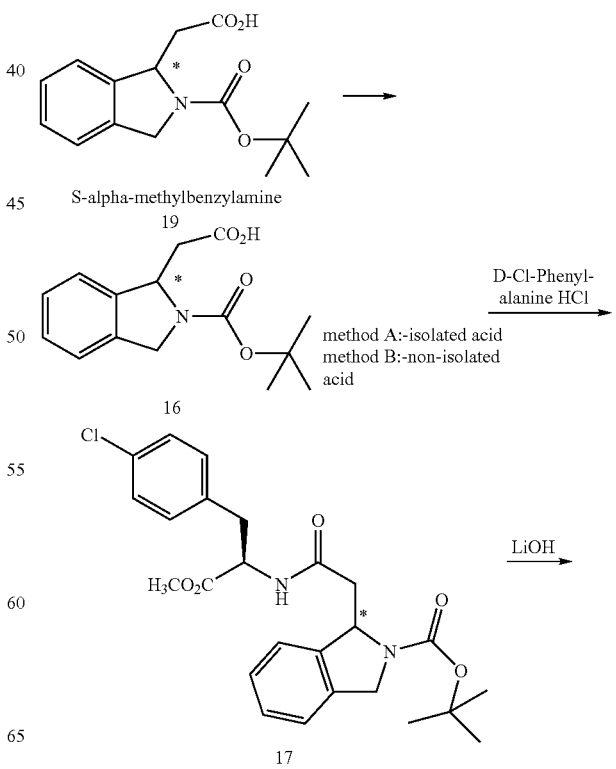

-continued

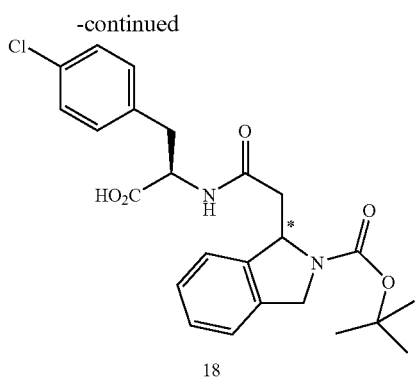

18

The chemistry used is shown in Scheme P5. Two protocols were used: method A used isolated 16, method B used a solution of 16 derived from resolved salt 19.

Preparation PP38

Compound 17 (Scheme P5, Method A)

Acid 16 (24.18 g, 87.2 mmole) and D-chloro-phenylalanine hydrochloride (21.81 g, 87.2 mmole) were dissolved in $CH_2Cl_2$ (100 ml) and DMF (25 ml). The mixture was stirred at ambient temperature. HOBT (13.55 g, 100.3 mmole) and Hunig's base (45.6 ml, 33.81 g, 261.6 mmole) were added. HATU (38.13 g, 100.3 mmole) was added in 1 portion (there was a rapid exotherm to 50° C.). The mixture was stirred for 90 minutes then diluted with EtOAc (750 ml). The resulting mixture was washed with water, 5% $KHSO_4$, brine and satd. $NaHCO_3$ respectively, then dried. Filtration and concentration in vacuo gave crude 17 as a brown foam. The product was purified by chromatography on silica gel (1 kg) eluting with 1:1 EtOAc-hexane. Ester 17 was isolated as a tan powder, 38.85 g (94%).

Preparation PP39

Compound 17 (Scheme P5, Method B)

Resolved salt 19 (96.27 g, 232.5 mmole) was partitioned between water (500 ml) and $CH_2Cl_2$ (250 ml) Solid $KHSO_4$ was added portion wise until pH=2.5. Separate the organic layer and extract the aqueous layer with $CH_2Cl_2$ (150 ml). The combined organic layers were dried ($MgSO_4$) then filtered. To this solution was added 4-chloro-D-phenylalanine (58.16 g, 232.5 mmole), HOBT (34.57 g, 255.8 mmole), Hunig's base (93.2 ml, 69.13 g, 534.9 mmole) and finally HATU (97.26 g, 255.8 mmole). The resultant mixture was stirred at room temperature for 18.5 hours, and then poured onto a plug of silica gel (1 kg). This was washed with 1:1 EtOAc-hexane until no more product elutes. Ester 17 was isolated as a pink foam, 101.79 g (93%): contains about 1% unreacted 16.

Preparation PP40

Compound 18 (Scheme P5)

Ester 17 (38.64 g, 81.7 mmole) was dissolved in 3:1 THF-water (200 ml). LiOH (2.15 g, 89.9 mmole) was added to the mixture, which was stirred at room temperature for 2 hours. The solvent was then removed in vacuo and the residual solid taken up in water (600 ml). This was extracted with MTBE (250 ml). The aqueous layer was separated and stirred with EtOAc (250 ml), and solid $KHSO_4$ was added portion wise until pH=3. The layers were separated and the aqueous extracted with EtOAc (250 ml). The combined organic layers were dried over $MgSO_4$. Filtration and concentration in vacuo gave acid 18 as a light pink foam, 38.41 g (35.71 g corrected for residual solvent, 95%).

Preparation PP41

Step 1: Esterification

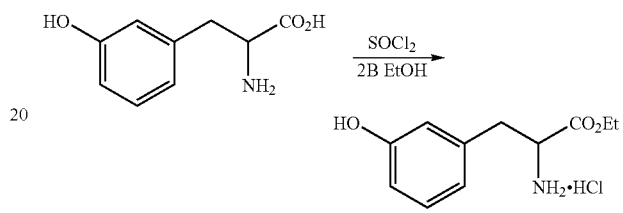

In a 22 L 4-neck round bottom flask equipped with a reflux condenser, thermocouple and nitrogen inlet, a slurry of 1000 g (5.4 moles) of m-tyrosine in 10 L of 2B-3 EtOH was cooled to 5° C. To the slurry, 350 mL (12.4 moles) of thionyl chloride were added dropwise via an addition funnel at such a rate to maintain the reaction temperature below 20° C. Upon completion of addition, the reaction was heated to reflux temperature and stirred for 18 hrs. The reaction was concentrated to one-third the volume and 8 L of MTBE were charged. The resulting thick slurry was stirred for 14 hrs in a rotary evaporator at p.т. The resulting solid was isolated on a filter pad and dried at 40° C. for 48 hrs yielding 1288 g (95%). NMR (DMSOd6) indicated desired material.

Preparation PP42

Step 2: Pictet-Spengler

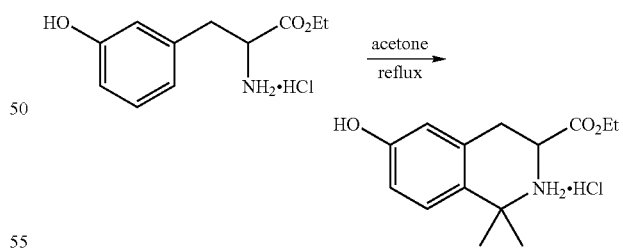

In a 22L 4 neck round bottom flask equipped with a mechanical stirrer, thermocouple, and reflux condenser placed on top of a Soxhlet extractor charged with 4° A sieves, a semi-solution of m-tyrosine ethyl ester hydrochloride 1288 g (5.26 moles) in 13 L of acetone was heated to reflux temperature. The condensate was filtered through the sieves to remove water. The reaction was stirred vigorously at reflux for 48 hrs. An NMR sample in $DMSOd_6$ indicated the absence of starting material. The reaction was cooled to rt and concentrated to yield an off-white solid, 1411 g (94%).

Preparation PP43

Step 3: Triflation

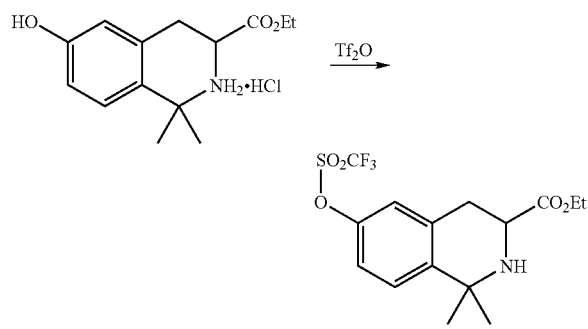

In a 22 L 4 neck round bottom flask equipped with a reflux condenser, mechanical stirrer, nitrogen inlet, and a thermocouple, 1240 g (4.35 moles) of the starting material salt in 12.4 L of methylene chloride was cooled to 4° C. To the mixture, 1452 mL (10.4 moles) of triethylamine were added and stirred into solution. Triflic anhydride, 1472 mL (5.22 moles) was added dropwise to the reaction at such a rate to maintain the internal temperature below 10° C. The ice bath was removed and the reaction warmed to р.т. and stirred for 18 hrs. The reaction was concentrated to a oil then dissolved in 4 L of EtOAc and concentrated again to an oil in an effort to remove excess triflic anhydride The crude residue was dissolved in 4 L of EtOAc and washed with water and saturated sodium bicarbonate solution. The organic layer was isolated and dried with sodium sulfate, filtered and concentrated to yield 1720 g (>100%) of a crude dark oil which was used without further purification.

Preparation PP44

Step 4: Deoxygenation

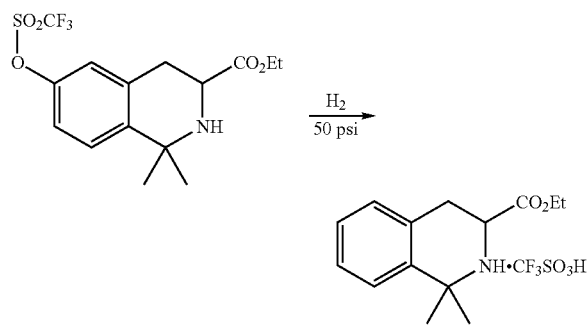

A solution of 1720 g (4.35 moles) of crude starting material in 14 L of acetone was charged to a 10 gallon stainless steel autoclave. To the solution, a slurry of 5% Pd/C in 1.2 L of toluene was added. The reaction mixture was evacuated and purged with $H_2$ gas at 50 psi two times. The reaction was stirred overnight at 50° C. with $H_2$ at 50 psi. A sample aliquot indicated no reaction had occurred. The mixture was filtered and concentrated to a thick oil and resubjected to reaction conditions. After 18 hrs, NMR of a sample aliquot indicated absence of starting material. The reaction mixture was filtered and the filtrate concentrated to yield 1581 g of an off-white solid (95%).

Preparation PP45

Step 5: Hydrolysis/Salt Formation

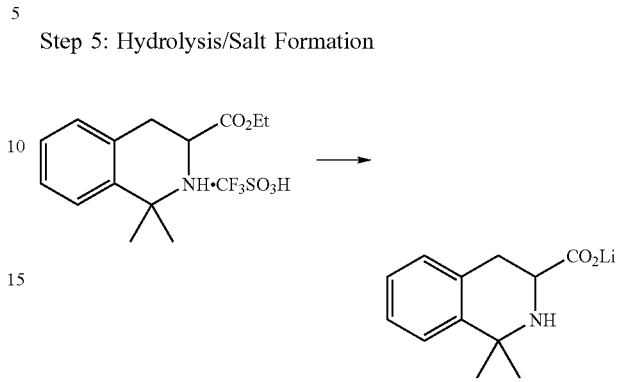

To a 2 L 3 neck round bottom flask equipped with a mechanical stirrer, thermocouple, and nitrogen inlet, a mixture of 700 g (1.83 moles) of the triflate salt starting material was charged. A solution of 427 g. (1.83 moles) of the starting material free base in 13.3 L of THF was added followed by 700 mL of water. The semi-solution was stirred vigorously at r.t. To the reaction flask, 43.7 g (1.83 moles) of solid LiOH were added in small portions at such a rate to maintain the internal temperature below 35° C. The reaction was stirred for 18 hrs at r.t and concentrated to yield a thick oil. THF (4 L) was added and the semi-solution was concentrated. This was repeated with toluene and the semi-solid was placed under house vacuum on the roto vap with stirring for 18 hrs to yield 650 g of a crude solid. The solid was reslurred in EtOAc, filtered, isolated and dried to yield 525 g (68%) of the lithium salt as an off-white solid.

Preparation PP46

Step 6: Coupling

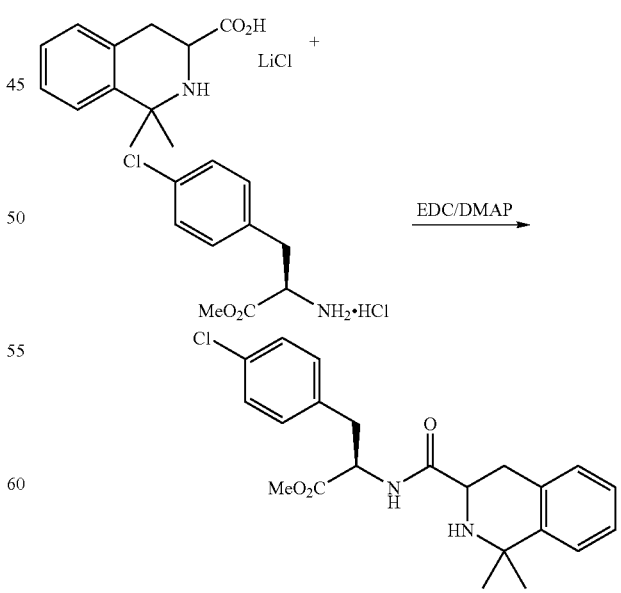

Solid d-chloro-phenylalanine 446 g (1.78 moles) was added to the semi-solution followed by 20 g (0.162 moles)

of DMAP. The resulting mixture was stirred for 15 minutes then solid EDCl (1-(3-dimethylaminopropyl)-3-ethylcarbodiimide hydrochloride) 390 g (2.03 moles) was added. The reaction mixture was heated to 80° C. and stirred for 18 hours. Thin layer chromatography (1:1 EtOAc:Hex) indicated very little starting material present. The reaction was cooled to rt and concentrated to yield a thick oil. The crude oil was dissolved in EtOAc and washed with water, and brine. The solution was dried with sodium sulfate, filtered and concentrated to yield a thick oil, 426 g. The crude oil was chromatographed in several lots using a Waters Prep 500 chromatography apparatus. The eluent consisted of a gradient system, 5%-80% EtOAc in heptane at a flow rate of 240 ml/min over 38 minutes. The two diasteromers were separated and isolated to yield 119.04 g for the top spot and 111.3 g for the bottom spot. Conformation of both desired diastereomers was achieved via NMR (DMSO$_6$).

Preparation PP47

Resolution of tetrahydroisoquinolinecarboxylic acid ethyl ester to prepare l-tartaric acid salt:

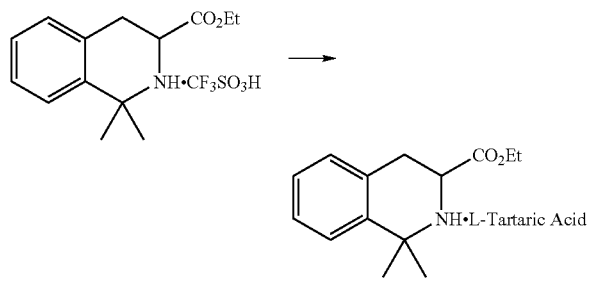

Preparation of free-base: A racemic mixture of tetrahydroisoquinolinecarboxylic acid (7.43 g) in EtOAc (60 mL) was treated with saturated NaHCO$_3$ solution (60 mL) and saturated Na$_2$CO$_3$ solution (10 mL). The mixture was agitated and the layers were separated. The organic phase was dried (Na$_2$SO$_4$) and concentrated to give the corresponding free-base as an oil (4.85 g)

Resolution: A mixture of the above free base (467 mg, 2.0 mmol), and L-tartaric acid (300 mg, 2.0 mmol) in acetone (4 mL) was stirred at RT overnight. The title L-tartaric acid salt was collected by filtration, washed with acetone (about 2 mL) and dried to a white powder (367 mg). 100% ee by chiral CE.

Preparation PP48

Resolution of N-BOC tetrahydroisoquinolinecarboxylic acid

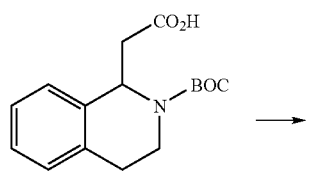

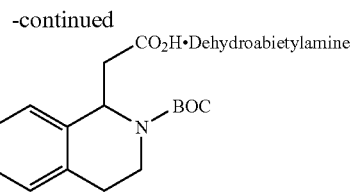

2-{2-[(tert-butyl)oxycarbonyl]-1,2,3,4-tetrahydroisoquinolyl}acetic acid dehydroabietylamine salt: Racemic 2-{2-[(tert-butyl)oxycarbonyl]-1,2,3,4-tetrahydroisoquinolyl}acetic acid (30.15 g, 103.5 mmol) was dissolved in i-PA (300 mL). Dehydroabietylamine (22.11 g, 52.7 mmol of a 68 weight % mixture) was added to the solution, which was then agitated on a multi-arm shaker for 63 h. The resultant thick paste was filtered and rinsed with i-PA (50 mL, 25 mL). Dried in a 50° C. vacuum oven to obtain a white solid (27.73 g, 52% ee by chiral CE analysis). The product was reslurried in i-PA (266 mL) and agitated on a multi-arm shaker for 23.5 h. Filtered the thick slurry and rinsed with cold i-PA (50 mL, 30 mL). Dried the cake in a 50° C. vacuum oven and obtained the product as a white solid (23.63 g, 40% yield, 94% ee by chiral CE analysis).

Scheme P6

Asymmetric Hydrogenation:

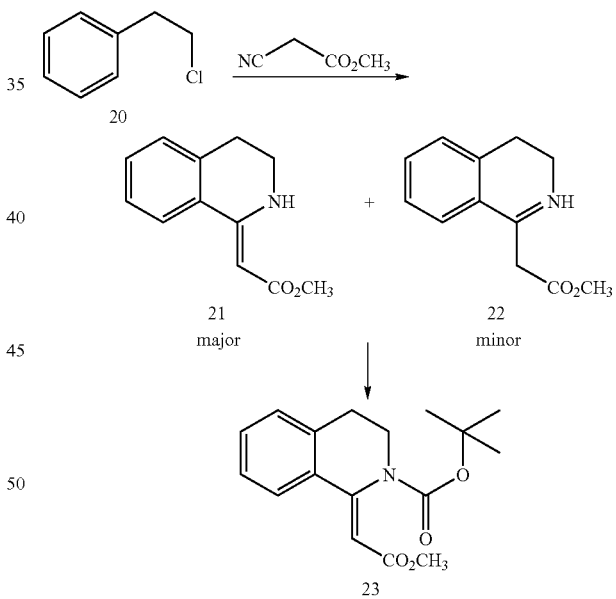

Preparation PP49

Enamine 21 (Scheme P6) was prepared as a substrate for asymmetric hydrogenation screening studies. It is formed as an approx. 10:1 mixture with imine 22. The enamine (21) may be NH-protected i.e., by a Boc protecting group. The resulting compound 23 may be subjected to asymmetric hydrogenation to afford the acetic acid or methylacetate substituted isoquinoline, which may be processed into a compound of formula I as demonstrated previously.

Preparation PP50

Compound 21 (Scheme P6)

Prepared as published W Sobotka et al, *J. Org. Chem.*, 1965, 30, 3667

Scheme P7

Synthesis of Gem-dimethyl TIC:

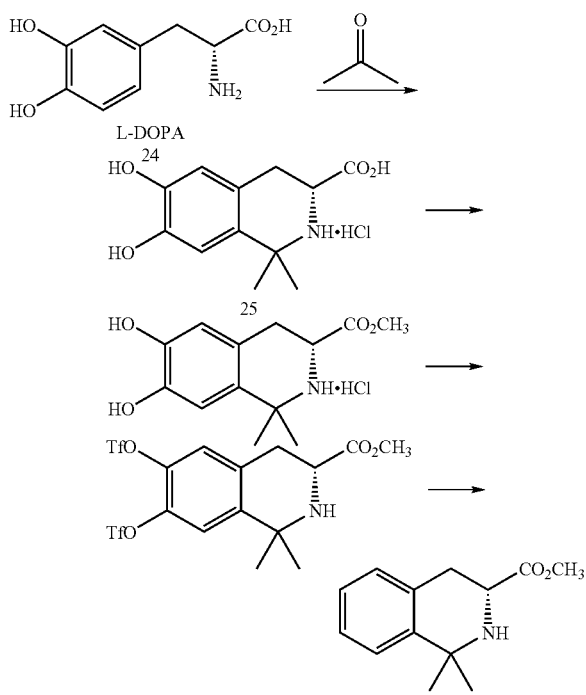

Preparation PP51

The chiral synthesis of gem-dimethyl TIC using L-Dopa as the starting material instead of tyrosine was successfully demonstrated up to the Pictet-Spengler reaction with L-DOPA and acetone. The product is a mixture of starting material 24 and product 25 (major component). The product was isolated by using common isolation procedures. An alternative isolation method is to react the mixture (24 and 25) with BOC anhydride wherein the less hindered N—H in 24 leads to preferential BOC protection of 24, allowing for ready separation of 25. Chemistry for the rest of the sequence i.e., deoxygenation reaction, has been demonstrated herein.

What is claimed is:

1. A compound of formula I:

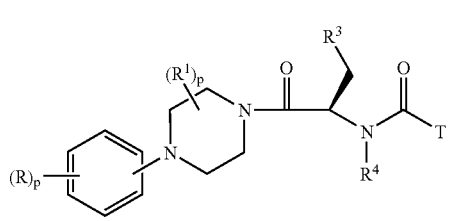

or a pharmaceutically acceptable salts or stereoisomers thereof, wherein

T is:

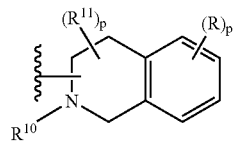

R is independently:
  hydroxy,
  cyano,
  nitro,
  halo,
  $C_1$-$C_8$ alkyl,
  $C_1$-$C_8$ alkoxy,
  $C_1$-$C_4$ haloalkyl,
  $NH_2$,
  $NHSO_2(C_1$-$C_4$ alkyl),
  $OSO_2R^9$,
  $SR^9$,
  $SOR^9$,
  $SO_2R^9$, or
  $SO_2N(R^9)_2$;

$R^1$ is independently:
  Hydrogen or $C_1$-$C_2$ alkyl;

$R^3$ is: phenyl optionally substituted with one to three substituents selected from the group consisting of:
  cyano, halo, $C_1$-$C_8$ alkyl, $C_3$-$C_7$ cycloalkyl, $C_1$-$C_4$ alkoxy, $C_1$-$C_4$ haloalkyl, benzyloxy, and $OCF_3$;

$R^4$ is independently:
  hydrogen, $C_1$-$C_8$ alkyl, $C(O)R^9$, $C(O)OR^9$, $C_3$-$C_7$ cycloalkyl or $(CH_2)_nO(C_1$-$C_8$ alkyl), wherein n is 2-8;

each $R^9$ is independently:
  hydrogen, or $C_1$-$C_8$ alkyl;

each $R^{10}$ is independently:
  hydrogen; or $(C_1$-$C_8)$alkyl;

each $R^{11}$ is independently:
  hydrogen, or $C_1$-$C_8$ alkyl; and p is 0.

2. The compound of claim 1, wherein $R^3$ is phenyl optionally para-substituted with chloro, bromo, fluoro, iodo, methoxy, benzyloxy or methyl.

3. The compound of claim 2, wherein $R^3$ is phenyl para-substituted with chloro, fluoro or methoxy.

4. The compound of claim 3, wherein $R^4$ is hydrogen.

5. The compound of claim 4, wherein —$(CH_2)_n$-T is:

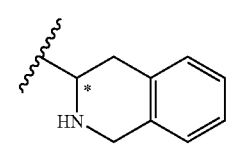

where * denotes a chiral carbon atom having a R or S configuration.

6. The compound of claim 5, wherein the chiral carbon has an R configuration.

7. A compound of formula II,

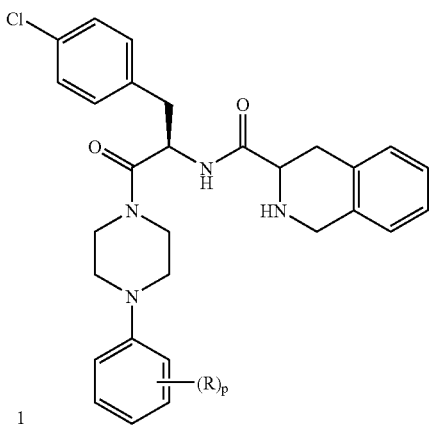

or a pharmaceutically acceptable salts or stereoisomers thereof, wherein
p is 0;
R is independently:
  hydroxy,
  cyano,
  nitro,
  halo,
  $C_1$-$C_8$ alkyl,
  $C_1$-$C_8$ alkoxy,
  $C_1$-$C_4$ haloalkyl,
  $NH_2$,
  $NHSO_2(C_1$-$C_8$ alkyl,
  $OSO_2R^9$,
  $SR^9$,
  $SOR^9$,
  $SO_2N(R^9)_2$; and
each $R^9$ is independently:
  hydrogen, or $C_1$-$C_8$ alkyl.

8. A compound of formula TV,

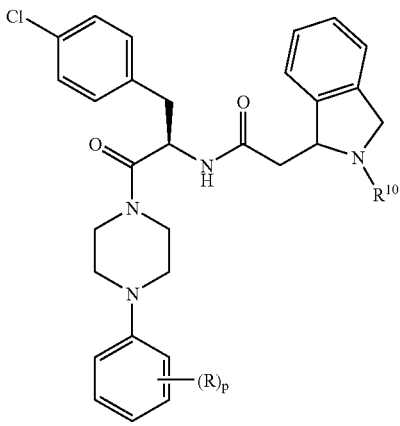

or a pharmaceutically acceptable salts or stereoisomers thereof, wherein
p is 0-5;
n is 0-8;
q is 0-1;
D is a bond or —$CH_2)_n$—, R is independently:
  hydrogen,
  hydroxy,
  cyano,
  nitro,
  halo,
  $C_1$-$C_8$ alkyl,
  $C_1$-$C_8$ alkoxy,
  $C_1$-$C_4$ haloalkyl,
  (D)C(O)$SR^9$,
  (D)C(O)heteroaryl,
  (D)$NH_2$,
  $NHSO_2(C_1$-$C_8$ alkyl),
  (D)$OR^9$,
  $OSO_2R^9$,
  (D)[O]$_q$($C_3$-$C_7$ cycloalkyl),
  (D)[O]$_q$($CH_2)_n$aryl,
  (D)[O]$_q$($CH_2)_n$heteroaryl,
  (D)[O]$_q$($CH_2)_n$heterocyclyl, wherein heterocyclyl excludes a heterocyclyl containing a single nitrogen when q=1,
  (D)$SR^9$,
  (D)$SOR^9$,
  (D)$SO_2R^9$, or
  (D)$SO_2N(R^9)_2$;
wherein $C_1$-$C_8$ alkyl, $C_1$-$C_8$ alkoxy, $C_3$-$C_7$ cycloalkyl, aryl, heterocyclyl and heteroaryl are optionally substituted with one to five substituents independently selected from $R^8$;
each $R^8$ is independently:
  hydrogen,
  halo,
  $C_1$-$C_8$ alkyl,
  (D)$C_3$-$C_7$ cycloalkyl,
  $C_1$-$C_4$ haloalkyl,
  $C_1$-$C_4$ alkoxy,
  hydroxy,
  phenyl,
  (D)CO($C_1$-$C_8$ alkyl),
  (D)C(O)O($C_1$-$C_8$ alkyl)$R^9$
  (D)O($C_1$-$C_8$ alkyl),
  (D)OCO($C_1$-$C_8$ alkyl),
  (D)OCO$_2$($C_1$-$C_8$ alkyl),
  (D)S($C_1$-$C_8$ alkyl),
  (D)SO($C_1$-$C_8$ alkyl), or
  (D)$SO_2$($C_1$-$C_8$ alkyl);
each $R^9$ is independently:
  hydrogen,
  $C_1$-$C_8$ alkyl,
  $C_1$-$C_4$ haloalkyl,
  (D)$C_3$-$C_7$ cycloalkyl,
  (D)aryl, wherein aryl being phenyl or naphthyl
  heteroaryl or
  heterocyclyl; wherein heterocyclyl excludes a heterocyclyl containing a single nitrogen; and
  wherein aryl, heteroaryl, heterocyclyl, alkyl or cycloalkyl is optionally substituted with one to three substituents selected from the group consisting of oxo, $C_1$-$C_8$ alkyl, $OR^{10}$, $SR^{10}$; and
each $R^{10}$ is independently:
  hydrogen, ($C_1$-$C_8$)alkyl, or C(O)$C_1$-$C_8$ alkyl.

9. The compound of claim 8, wherein $R^{10}$ is hydrogen or ($C_1$-$C_8$)alkyl.

10. A compound selected from the group consisting of:

| Name of Compounds | Structure of Compounds |
|---|---|
| 1-(D-Tic-4-Cl-D-Phe)-4-(2-methanesulfonylamino-phenyl)-piperazine | 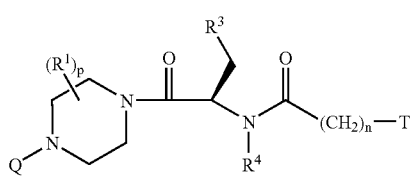 |

11. A pharmaceutical composition which comprises a pharmaceutical carrier and at least one compound of formula I or its pharmaceutically acceptable salts or stereoisomers thereof as recited in claim 1.

12. A process of making a pharmaceutical composition comprising admixing a compound of formula I or its pharmaceutically acceptable salt or stereoisomers thereof as recited in claim 1 and a pharmaceutically acceptable carrier.

13. A method of treating obesity in a mammal comprising the administration of a therapeutically effective amount of the compound of formula I as recited in claim 1.

14. A process for preparing a compound of formula I:

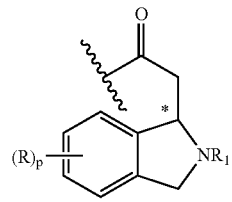

(I)

or a pharmaceutically acceptable salts or stereoisomers thereof, wherein $C(O)(CH_2)_nT$ is:

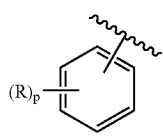

wherein $R^1$ is hydrogen, $C_1$-$C_8$ alkyl, Boc, CBZ, phenyl, FMOC or ($C_1$-$C_8$ alkyl)phenyl;

Q represents a moiety:

R is independently:
hydrogen,
hydroxy,
cyano,
nitro,
halo,
$C_1$-$C_8$ alkyl,
$C_1$-$C_8$ alkoxy,
$C_1$-$C_4$ haloalkyl,
(D)C(O)$SR^9$,
(D)C(O)heteroaryl,
(D)$NH_2$,
(D)$NHSO_2$($C_1$-$C_8$ alkyl),
(D)$OR^9$,
$OSO_2R^9$,
(D)$[O]_q$($C_3$-$C_7$ cycloalkyl),
(D)$[O]_q$($CH_2$)$_n$aryl,
(D)$[O]_q$($CH_2$)$_n$heteroaryl,
(D)$[O]_q$($CH_2$)$_n$heterocyclyl, wherein heterocyclyl excludes a heterocyclyl containing a single nitrogen when q=1,
(D)$SR^9$,
(D)$SOR^9$,
(D)$SO_2R^9$, or
(D)$SO_2N(R^9)_2$;
wherein $C_1$-$C_8$ alkyl, $C_1$-$C_8$ alkoxy, $C_3$-$C_7$ cycloalkyl, aryl, heterocyclyl and heteroaryl are optionally substituted with one to five substituents independently selected from $R^8$;

$R^1$ is independently:
hydrogen, CONH($C_1$-$C_8$ alkyl), $C_1$-$C_8$ alkyl, (D)phenyl, (D)$C_3$-$C_7$ cycloalkyl or oxo, provided that oxo is not attached to a carbon atom to provide a secondary amide moiety;

$R^3$ is aryl optionally substituted with one to three substituents selected from the group consisting of:
cyano, halo, $C_1$-$C_8$ alkyl, (D)$C_3$-$C_7$ cycloalkyl, $C_1$-$C_4$ alkoxy, $C_1$-$C_4$ haloalkyl benzyloxy, and $C_1$-$C_4$ haloalkyloxy;

$R^4$ is independently:
hydrogen, $C_1$-$C_8$ alkyl, C(O)$R^9$, C(O)O$R^9$, $C_3$-$C_7$ cycloalkyl or ($CH_2$)$_n$O($C_1$-$C_8$ alkyl), wherein n is 2-8;

each $R^8$ is independently:
hydrogen,
halo,
$C_1$-$C_8$ alkyl,
(D)$C_3$-$C_7$ cycloalkyl,
$C_1$-$C_4$ haloalkyl,
$C_1$-$C_4$ alkoxy,
hydroxy,
phenyl,
(D)CO($C_1$-$C_8$ alkyl),
(D)C(O)O($C_1$-$C_8$ alkyl),
(D)O($C_1$-$C_8$ alkyl),
(D)OCO($C_1$-$C_8$ alkyl),
(D)OCO$_2$($C_1$-$C_8$ alkyl),
(D)S($C_1$-$C_8$ alkyl),
(D)SO($C_1$-$C_8$ alkyl), or
(D)$SO_2$($C_1$-$C_8$ alkyl);

each $R^9$ is independently:
hydrogen,
C$_1$-$C_8$ alkyl,
$C_1$-$C_4$ haloalkyl,
(D)$C_3$-$C_7$ cycloalkyl,
(D)aryl, wherein aryl being phenyl or naphthyl,
(D)heteroaryl or (D)heterocyclyl; wherein heterocyclyl excludes a heterocyclyl containing a single nitrogen; and wherein aryl, heteroaryl, heterocyclyl, alkyl or cycloalkyl is optionally substituted with one to three substituents selected from the group consisting of oxo, $C_1$-$C_8$ alkyl, $OR^{10}$, and $SR^{10}$;

each $R^{10}$ is independently:

hydrogen, ($C_1$-$C_8$)alkyl, C(O)$C_1$-$C_8$ alkyl, aryl or $C_3$-$C_7$ cycloalkyl;

D is a bond or —(CH$_2$)$_n$—, n is 0-8;

p is 0-5;

q is 0-1; and r is 1-2;

comprising the steps of:

a) reacting a compound having a structural formula 1,

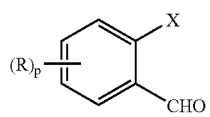

(1)

with CH$_2$CH=C(O)OR$^a$ wherein R$^a$ is hydrogen or $C_1$-$C_8$ alkyl and X is halo, in the presence of a catalyst and a base in a suitable organic solvent to give the compound of formula 2,

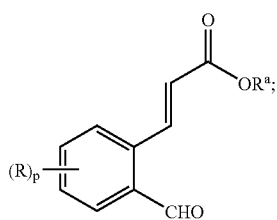

(2)

b) reductively aminating the compound of formula 2 in the presence of amine in an acidic condition to give a compound of formula 3,

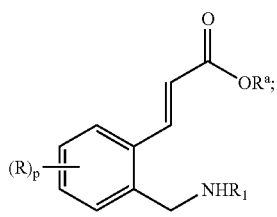

(3)

c) cyclizing the compound of formula 3 by Michael addition to give a compound of formula 4 or stereoisomers thereof,

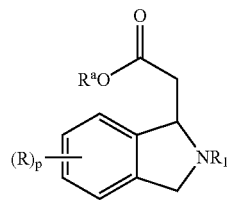

(4)

d) coupling the compound of formula 4 or stereoisomers thereof, wherein R$^a$ of compound 4 is K with a compound of formula 5,

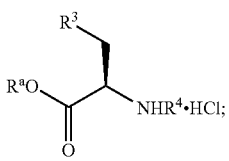

(5)

wherein R$^a$ of compound 5 is $C_1$-$C_8$ alkyl, to give a compound of formula 6;

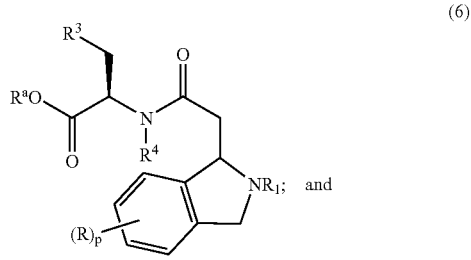

(6)

e) coupling the compound of formula 6, wherein R$^a$ is H with a compound having a structural,

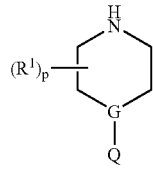

to afford the compound of formula 1.

15. The process of claim 14, wherein X is 2-Br for

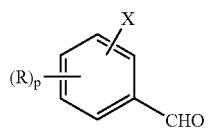

in Step (a).

16. The process of claim 15, wherein CH$_2$CH=C(O)OR in Step (a) is methylacrylate.

17. The process of claim 16, wherein the catalyst in Step (a) is selected from the group consisting of: Pd(Ph$_3$P)$_2$Cl$_2$, Pd(Ph$_3$P)$_4$Cl$_2$, Pd(Ph$_3$P)$_4$, Pd(Ph$_3$P)$_2$Cl$_2$/CuI, Pd(OAc)$_2$/Ph$_3$P-Bu$_4$NBr, Pd(Ph$_3$P)$_4$Cl$_2$/H$_2$ and Pd(OAc)$_2$/P(O-tol)$_3$; and wherein the base in Step (a) is NR$^3$ wherein R is hydrogen or $C_1$-$C_8$ alkyl.

18. The process of claim 17, wherein the amine in Step (b) is selected from the group consisting of: benzylamine, alpha-methylbenzylamine and BocNH$_2$.

19. The process of claim 18, wherein the Step (b) further comprises reducing of intermediate imine compound in the presence of reducing agent, the reducing agent being selected from the group consisting of: $NaCNBH_3$, $Na(OAc)_3BH$, $NaBH_4/H^+$, and a combination of $Et_3SiH$ and TFA in $CH_3CN$ or $CH_2Cl_2$.

20. The process of claim 19, wherein the stereoisomer of compound of formula 4 in Step (c) is a compound of formula 4a

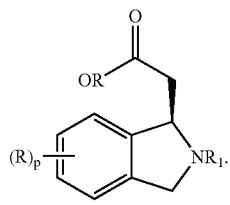

(4a)

21. The process of claim 20, wherein the compound of formula 4a is prepared by asymmetric hydrogenation of a compound having structural formula,

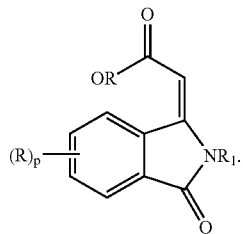

22. The process of claim 21, wherein the Michael addition in Step (c) is carried out in a basic workup condition.

23. The process of claim 14, wherein the Step (e) further comprises deprotecting or protecting of the compound of formula (6) at $NR_1$.

* * * * *